US008933103B2

(12) United States Patent
Ohki et al.

(10) Patent No.: US 8,933,103 B2
(45) Date of Patent: Jan. 13, 2015

(54) PYRIDONE DERIVATIVES

(71) Applicant: Daiichi Sankyo Company, Limited, Tokyo (JP)

(72) Inventors: Hitoshi Ohki, Tokyo (JP); Masahiro Ota, Tokyo (JP); Kosuke Takeuchi, Tokyo (JP); Hideaki Watanabe, Tokyo (JP); Akitake Yamaguchi, Tokyo (JP); Yoshihiro Shibata, Tokyo (JP); Yuichi Tominaga, Tokyo (JP); Takeshi Jimbo, Tokyo (JP); Keijiro Kobayashi, Kanagawa (JP); Katsuhiro Kobayashi, Kanagawa (JP); Daisuke Fukatsu, Kanagawa (JP)

(73) Assignee: Daiichi Sankyo Company, Limited, Tokyo (JP)

( * ) Notice: Subject to any disclaimer, the term of this patent is extended or adjusted under 35 U.S.C. 154(b) by 0 days.

(21) Appl. No.: 13/753,926

(22) Filed: Jan. 30, 2013

(65) Prior Publication Data
US 2013/0281428 A1 Oct. 24, 2013

Related U.S. Application Data

(60) Provisional application No. 61/746,039, filed on Dec. 26, 2012.

(30) Foreign Application Priority Data

Jan. 31, 2012 (JP) ................. 2012-017971

(51) Int. Cl.
*C07D 401/12* (2006.01)
*C07D 413/14* (2006.01)
*A61K 31/44* (2006.01)
*A61P 35/00* (2006.01)
*C07D 213/82* (2006.01)
*C07D 401/14* (2006.01)
*C07D 405/14* (2006.01)
*C07D 451/02* (2006.01)

(52) U.S. Cl.
CPC ............ *C07D 213/82* (2013.01); *C07D 401/14* (2013.01); *C07D 405/14* (2013.01); *C07D 413/14* (2013.01); *C07D 401/12* (2013.01); *C07D 451/02* (2013.01)
USPC ............ 514/332; 514/335; 546/256; 546/261

(58) Field of Classification Search
USPC ........................... 546/256, 261; 514/332, 335
See application file for complete search history.

(56) References Cited

U.S. PATENT DOCUMENTS

| | | |
|---|---|---|
| 2007/0142402 A1 | 6/2007 | Ding et al. |
| 2009/0111816 A1 | 4/2009 | Singh et al. |
| 2009/0274693 A1 | 11/2009 | Gilmer et al. |
| 2010/0069369 A1 | 3/2010 | Ding et al. |
| 2010/0168416 A1 | 7/2010 | Goff et al. |
| 2010/0204221 A1 | 8/2010 | Vankayalapati et al. |

FOREIGN PATENT DOCUMENTS

| | | |
|---|---|---|
| WO | WO 2007/030680 A2 | 3/2007 |
| WO | WO 2007/057399 A2 | 5/2007 |
| WO | WO 2007/066187 A2 | 6/2007 |
| WO | WO 2007/070872 A1 | 6/2007 |
| WO | WO 2008/025820 A1 | 3/2008 |
| WO | WO 2008/045978 A1 | 4/2008 |
| WO | WO 2008/074997 A1 | 6/2008 |
| WO | WO 2008/083353 A1 | 7/2008 |
| WO | WO 2008/083354 A1 | 7/2008 |
| WO | WO 2008/083356 A1 | 7/2008 |
| WO | WO 2008/083357 A1 | 7/2008 |
| WO | WO 2008/083367 A2 | 7/2008 |
| WO | WO 2008/128072 A2 | 10/2008 |
| WO | WO 2009/007390 A2 | 1/2009 |
| WO | WO 2009/024825 A1 | 2/2009 |
| WO | WO 2009/047514 A1 | 4/2009 |
| WO | WO 2009/053737 A2 | 4/2009 |
| WO | WO 2009/054864 A1 | 4/2009 |
| WO | WO 2009/058801 A1 | 5/2009 |
| WO | WO 2009/094417 A1 | 7/2009 |
| WO | WO 2009/094427 A1 | 7/2009 |
| WO | 2009/127417 A1 | 10/2009 |
| WO | 2009/138799 A1 | 11/2009 |
| WO | 2010/005876 A2 | 1/2010 |
| WO | 2010/005879 A1 | 1/2010 |
| WO | 2010/090764 A1 | 8/2010 |

(Continued)

OTHER PUBLICATIONS

Angelillo-Scherrer, A., et al., "Deficiency or inhibition of Gas6 causes platelet dysfunction and protects mice against thrombosis," *Nature Medicine*, vol. 7, No. 2, pp. 215-221 (2001).

Berclaz, G., et al., "Estrogen dependent expression of the receptor tyrosine kinase axl in normal and malignant human breast," *Annals of Oncology*, vol. 12, pp. 819-824 (2001).

Chung, B.I., et al., "Expression of the Proto-Oncogene Axl in Renal Cell Carcinoma," *DNA and Cell Biology*, vol. 22, No. 8, pp. 533-540 (2003).

Craven, R.J., et al., "Receptor Tyrosine Kinases Expressed in Metastatic Colon Cancer," *Int. J. Cancer*, vol. 60, pp. 791-797 (1995).

(Continued)

*Primary Examiner* — Bruck Kifle
(74) *Attorney, Agent, or Firm* — Dorsey and Whitney LLP

(57) ABSTRACT

Novel compounds or salts thereof, or crystals thereof, which inhibit Axl and are useful for treating diseases caused by Axl hyperfunction, diseases associated with Axl hyperfunction and/or diseases accompanied by Axl hyperfunction are provided. Pyridone derivatives represented by the formula (1) having various substituents or salts thereof, or crystals thereof (where $R^1$, $R^2$, $R^3$, $R^5$, $R^6$, A, W, X and n in the formula (1) are as defined in the specification, respectively) are provided.

28 Claims, 8 Drawing Sheets

(56) References Cited

FOREIGN PATENT DOCUMENTS

| WO | 2011/045084 A1 | 4/2011 |
|---|---|---|
| WO | 2012/121939 A2 | 9/2012 |

OTHER PUBLICATIONS

Illig, C.R., et al., "Discovery of novel FMS kinase inhibitors as anti-inflammatory agents," *Bioorganic & Medicinal Chemistry Letters*, vol. 18, pp. 1642-1648 (2008).

Ito, T., et al., "Expression of the Axl Receptor Tyrosine Kinase in Human Thyroid Carcinoma," *Thyroid*, vol. 9, No. 6, pp. 563-567 (1999).

Kim, K.S., et al., "Discovery of Pyrrolopyridine—Pyridone Based Inhibitors of Met Kinase: Synthesis, X-ray Crystallographic Analysis, and Biological Activities," *J. Med. Chem.*, vol. 51, pp. 5330-5341 (2008).

Lai, D., et al., "9,10-Secosteroids, protein kinase inhibitors from the Chinese gorgonian *Astrogorgia* sp.," *Bioorganic & Medicinal Chemistry*, vol. 19, pp. 6873-6880 (2011).

Linger, R.M.A., et al., "Taking aim at Mer and Axl receptor tyrosine kinases as novel therapeutic targets in solid tumors," *Expert Opinion Ther. Targets*, vol. 14, No. 10, pp. 1073-1090 (2010).

Lu, Q., et al., "Tyro-3 family receptors are essential regulators of mammalian spermatogenesis," *Nature*, vol. 398, pp. 723-728 (1999).

Lu, Q., et al., "Homeostatic Regulation of the Immune System by Receptor Tyrosine Kinases of the Tyro 3 Family," *Science*, vol. 293, pp. 306-311 (2001).

Mahadevan, D., et al., "A novel tyrosine kinase switch is a mechanism of imatinib resistance in gastrointestinal stromal tumors," *Oncogene*, vol. 26, pp. 3909-3919 (2007).

Mollard, A., et al., "Design, Synthesis, and Biological Evaluation of a Series of Novel AXL Kinase Inhibitors," *ACS Med. Chem. Lett.*, vol. 2, pp. 907-912 (2011).

Nakano, T., et al., "Vascular Smooth Muscle Cell-derived, Gla-containing Growth-potentiating Factor for $Ca^{2+}$-mobilizing Growth Factors," *The Journal of Biological Chemistry*, vol. 270, No. 11, pp. 5702-5705 (1995).

Nemoto, T., et al., "Overexpression of Protein Tyrosine Kinases in Human Esophageal Cancer," *Pathobiology*, vol. 65, pp. 195-203 (1997).

O'Bryan, J.P., et al., "*axl*, a Transforming Gene Isolated from Primary Human Myeloid Leukemia Cells, Encodes a Novel Receptor Tyrosine Kinase," *Molecular and Cellular Biology*, vol. 11, No. 10, pp. 5016-5031 (1991).

Quong, R.Y.Y., et al., "Protein kinases in normal and transformed melanocytes," *Melanoma Research*, vol. 4, pp. 313-319 (1994).

Sawabu, T., et al., "Growth Arrest-Specific Gene 6 and Axl Signaling Enhances Gastric Cancer Cell Survival via Akt Pathway," *Molecular Carcinogenesis*, vol. 46, pp. 155-164 (2007).

Schroeder, G.M., et al., "Discovery of *N*-(4-(2-Amino-3-chloropyridin-4-yloxy)-3-fluorophenyl)-4-ethoxy-1-(4-fluorophenyl)-2-oxo-1,2-dihydropyridine-3-carboxamide (BMS-777607), a Selective and Orally Efficacious Inhibitor of the Met Kinase Superfamily," *J. Med. Chem.*, vol. 52, pp. 1251-1254 (2009).

Son, B., et al., "Gas6/Axl-PI3K/Akt pathway plays a central role in the effect of statins on inorganic phosphate-induced calcification of vascular smooth muscle cells," *European Journal of Pharmacology*, vol. 556, pp. 1-8 (2007).

Sun, W.S., et al., "Coexpression of growth arrest-specific gene 6 and receptor tyrosine kinases Axl and Sky in human uterine endometrial cancers," *Annals of Oncology*, vol. 14, pp. 898-906 (2003).

Sun, W., et al., "Coexpression of Gas6/Axl in Human Ovarian Cancers," *Oncology*, vol. 66, pp. 450-457 (2004).

Yanagita, M., et al., "Essential role of Gas6 for glomerular injury in nephrotoxic nephritis," *The Journal of Clinical Investigation*, vol. 110, No. 2, pp. 239-246 (2002).

Zhang, Y., et al., "Axl Is a Potential Target for Therapeutic Intervention in Breast Cancer Progression," *Cancer Research*, vol. 68, No. 6, pp. 1905-1915 (2008).

PYRIDONE DERIVATIVES

BACKGROUND OF THE INVENTION

1. Field of the Invention

The present invention relates to pyridone derivatives or salts thereof, or crystals thereof, which have Axl inhibitory activity.

2. Description of the Related Art

Axl is a receptor tyrosine kinase of the Tyro3-Axl-Mer (TAM) receptor tyrosine kinase family, which has the growth arrest-specific gene 6 (Gas6) protein as a ligand. Axl has initially been identified as a transforming gene in chronic myelogenous leukemia (O'Bryan et al., Mol. Cell. Biol., 1991, 11, 5031).

The Gas6/Axl signaling pathway has been reported to modulate various cellular responses such as cell survival, cell division, autophagy, cell migration, angiogenesis, platelet aggregation and NK cell differentiation (Rachel M A Linger et al., Expert Opin. Ther. Targets, 2010, 14, 1073). Axl also has often been reported to be overexpressed in cancer tissues such as tissues of primary colon cancer (Craven et al., Int. J. Cancer., 1995, 60, 791), gastric cancer (Sawabu et al., Mol. Carcinog., 2007, 46, 155), esophageal cancer (Nemoto et al., Pathobiology, 1997, 65, 195), melanoma (Quong et al., Melanoma Res., 1994, 4, 313), ovarian cancer (Sun et al., Oncology, 2004, 66, 450), renal cancer (Chung et al., DNA Cell Biol., 2003, 22, 533), endometrial cancer (Sun et al., Ann. Oncol., 2003, 14, 898) and thyroid cancer (Ito et al., Thyroid, 1999, 9, 563). It has also been demonstrated that the presence of Axl is greatly related to the lymph node status and the stage in lung cancer, and the ER expression in breast cancer (Berclaz et al., Ann. Oncol., 2001, 12, 819).

It has further been demonstrated that Axl has a role in immunity (Lu et al., Science, 2001, 293, 306), platelet function (Angelillo-Scherrer et al., Nat. Med., 2001, 7, 215), spermatogenesis (Lu et al., Nature, 1999, 398, 723), vascular calcification (Son et al., Eur. J. Pharmacol., 2007, 556, 1), thrombin-induced vascular smooth muscle cell (VSMC) growth (Nakano et al., J. Biol. Chem., 1995, 270, 5702), and various renal diseases such as acute and chronic glomerulonephritis, diabetic nephropathy and chronic allograft rejection (Yanagita et al., J. Clin. Invest., 2002, 110, 239). Axl inhibitors are expected to be useful not only for the treatment of cancer (including solid tumors such as carcinoma and sarcoma, leukemia, and lymphoid malignancy) but also for the treatment of many diseases such as vascular diseases (including, but not limited to, thrombosis, atherosclerosis and restenosis), renal diseases (including, but not limited to, acute and chronic glomerulonephritis, diabetic nephropathy, and transplant rejection), and diseases with significant chaotic angiogenesis (including, but not limited to, diabetic retinopathy, retinopathy, psoriasis, rheumatoid arthritis, atheroma, Kaposi's sarcoma and hemangioma).

Compounds reported to inhibit Axl include compounds having a sulfonamide structure (WO 2008/128072), compounds having a pyrrolopyrimidine structure (US Patent Application Publication No. 20100204221 and WO 2010/090764), compounds having pyridine and pyrazine structures (WO 2009/053737), compounds having a pyrazine structure (WO 2009/007390), compounds having a pyrazinylbenzimidazole structure (WO 2009/024825), compounds having an indolinone structure (WO 2007/057399), compounds having triazolopyridine and triazolopyrimidine structures (WO 2009/047514), compounds having an imidazole structure (WO 2009/058801), compounds having a triazole structure (WO 2008/083367, WO 2008/083353, WO 2010/005879, WO 2008/083357, WO 2008/083356, WO 2008/083354, WO 2007/030680, WO 2009/054864, WO 2010/005876, WO 2009/054864, US Patent Application Publication No. 20090111816 and US Patent Application Publication No. 20100168416), compounds having a pyrimidinediamine structure (WO 2008/045978), compounds having a pyrimidine structure (WO 2007/070872, Alexis Mollard et al., Med. Chem. Lett., 2011, 2, 907 and D Mahadevan et al., Oncogene, 2007, 26, 3909), compounds having a quinolinyloxyphenylsulfonamide structure (WO 2011/045084), compounds having a quinoline structure (WO 2009/127417, US Patent Application Publication No. 20090274693 and Yi-Xiang Zhang et al., Cancer Res., 2008, 68, 1905), compounds having a pyridine structure (WO 2007/066187 and Gretchen M. Schroeder et al., J. Med. Chem., 2009, 52, 1251), compounds having a urea structure (WO 2009/138799), compounds having a 2,4-disubstituted arylamide structure (Carl R. Illig et al., Bioorg. Med. Chem. Lett., 2008, 18, 1642), compounds having a secosteroid structure (Daowan Lai et al., Bioorg. Med. Chem., 2011, 19, 6873), compounds having a bicyclic pyrimidine structure (US Patent Application Publication No. 20100069369 and US Patent Application Publication No. 20070142402) and compounds having aminopyrazine and aminopyridine structures (WO 2012/121939).

SUMMARY OF THE INVENTION

The present invention provides novel Axl-inhibiting compounds or salts thereof, or crystals thereof. The present invention also provides a therapeutic agent for a disease caused by Axl hyperfunction, a disease associated with Axl hyperfunction and/or a disease accompanied by Axl hyperfunction, e.g., an anticancer agent, comprising such Axl-inhibiting compounds or salts thereof, or crystals thereof.

As a result of extensive studies, the present inventors have found that a compound having a structure represented by the following general formula (1) or a salt thereof, or crystals thereof, has high Axl inhibitory activity. This finding has led to the completion of the present invention.

Specifically, the present invention relates to the following [1] to [59].

[1] A compound represented by the general formula (1):

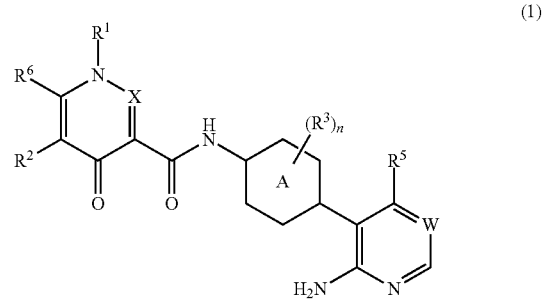

(1)

wherein in the formula (1),
A represents a phenylene group or a six-membered heteroarylene group, where the amino group bonded to A and the nitrogen-containing heterocycle are para-positioned relative to each other;
$R^1$ represents a $C_1$-$C_6$ alkyl group which may have one or more substituents selected from Group 1, an aryl group which may have one or more substituents selected from Group 2, a heteroaryl group which may have one or more substituents selected from Group 2, or a hydrogen atom;

$R^2$ represents a $C_1$-$C_6$ alkyl group which may have one or more substituents selected from Group 1, a $C_1$-$C_6$ alkoxy group which may have one or more substituents selected from a halogen atom and a hydroxyl group, —$CONR^AR^B$ (where $R^A$ and $R^B$ each independently represent a $C_1$-$C_6$ alkyl group which may have one or more substituents selected from a halogen atom, a $C_1$-$C_6$ alkoxy group and a hydroxyl group, or a hydrogen atom, or $R^A$ and $R^B$ together with the nitrogen atom to which they are bonded may form a three- to seven-membered heterocycloalkyl group which may have one or more substituents selected from a halogen atom, a $C_1$-$C_6$ alkyl group, a $C_1$-$C_6$ alkoxy group and a hydroxyl group), a cycloalkyl group which may have one or more substituents selected from Group 2, a phenyl group which may have one or more substituents selected from Group 2, a heteroaryl group which may have one or more substituents selected from Group 2, or a hydrogen atom;

$R^3$ is a substituent on A (where n represents an integer of 0 to 4, and each $R^3$ may be identical to or different from one another when n is two or more), and represents a $C_1$-$C_6$ alkyl group which may have one or more substituents selected from Group 1, a $C_1$-$C_6$ alkoxy group which may have one or more substituents selected from a halogen atom and a hydroxyl group, a $C_1$-$C_6$ alkylthio group which may have one or more substituents selected from a halogen atom and a hydroxyl group, a halogen atom, or a hydroxyl group;

$R^5$ represents a $C_1$-$C_6$ alkyl group which may have one or more substituents selected from Group 1, —$OR^C$ (where $R^C$ represents a $C_1$-$C_6$ alkyl group which may have one or more substituents selected from a $C_1$-$C_6$ alkoxy group, a halogen atom and a hydroxyl group, a three- to seven-membered heterocycloalkyl group which may have one or more substituents selected from a halogen atom, a $C_1$-$C_6$ alkyl group and a hydroxyl group, or a hydrogen atom), a $C_1$-$C_6$ alkylthio group which may have one or more substituents selected from a halogen atom and a hydroxyl group, or a hydrogen atom;

$R^6$ represents a hydrogen atom, or a $C_1$-$C_6$ alkyl group which may have one or more substituents selected from Group 1;

W represents C—$R^4$ or a nitrogen atom (where $R^4$ represents a $C_1$-$C_6$ alkyl group which may have one or more substituents selected from Group 1, a $C_1$-$C_6$ alkoxy group which may have one or more substituents selected from a $C_1$-$C_6$ alkoxy group, a heterocycloalkyl group, a halogen atom and a hydroxyl group, a cycloalkyl group which may have one or more substituents selected from Group 3, a cycloalkenyl group which may have one or more substituents selected from Group 3, a heterocycloalkyl group which may have one or more substituents selected from Group 3, a heterocycloalkenyl group which may have one or more substituents selected from Group 3, an aryl group which may have one or more substituents selected from Group 3, a heteroaryl group which may have one or more substituents selected from Group 3, a halogen atom, or a hydrogen atom); and X represents CH or a nitrogen atom]
or a salt thereof.

Group 1 includes the following:
a halogen atom;
—$NR^AR^B$ and —$CONR^AR^B$ (where $R^A$ and $R^B$ each independently represent a $C_1$-$C_6$ alkyl group which may have one or more substituents selected from a halogen atom, a $C_1$-$C_6$ alkoxy group and a hydroxyl group, or a hydrogen atom, or $R^A$ and $R^B$ together with the nitrogen atom substituted with them may form a three- to seven-membered heterocycloalkyl group which may have one or more substituents selected from a halogen atom, a $C_1$-$C_6$ alkyl group, a $C_1$-$C_6$ alkoxy group and a hydroxyl group);

—$OR^C$ (where $R^C$ represents a $C_1$-$C_6$ alkyl group which may have one or more substituents selected from a $C_1$-$C_6$ alkoxy group, a halogen atom and a hydroxyl group, a three- to seven-membered heterocycloalkyl group which may have one or more substituents selected from a halogen atom, a $C_1$-$C_6$ alkyl group and a hydroxyl group, or a hydrogen atom);
an aryl group which may have one or more substituents selected from a $C_1$-$C_6$ alkyl group which may have one or more substituents selected from a halogen atom and a hydroxyl group, a $C_1$-$C_6$ alkoxy group, an oxo group and a halogen atom;
a heteroaryl group which may have one or more substituents selected from a $C_1$-$C_6$ alkyl group which may have one or more substituents selected from a halogen atom and a hydroxyl group, a $C_1$-$C_6$ alkoxy group, an oxo group, a hydroxyl group and a halogen atom;
a three- to seven-membered cycloalkyl group which may have one or more substituents selected from a $C_1$-$C_6$ alkyl group which may have one or more substituents selected from a halogen atom and a hydroxyl group, a $C_1$-$C_6$ alkoxy group, an oxo group, a hydroxyl group and a halogen atom; and
a three- to seven-membered heterocycloalkyl group which may have one or more substituents selected from a $C_1$-$C_6$ alkyl group which may have one or more substituents selected from a halogen atom and a hydroxyl group, a $C_1$-$C_6$ alkoxy group, an oxo group, a hydroxyl group and a halogen atom.

Group 2 includes the following:
a $C_1$-$C_6$ alkyl group which may have one or more substituents selected from a halogen atom and a hydroxyl group, a $C_1$-$C_6$ alkoxy group, an oxo group, a hydroxyl group and a halogen atom.

Group 3 includes the following:
a $C_1$-$C_6$ alkyl group which may have one or more substituents selected from Group 1, a $C_1$-$C_6$ acyl group,
a $C_1$-$C_6$ alkylthio group which may have one or more substituents selected from a halogen atom and a hydroxyl group;
—$CONR^AR^B$ (where $R^A$ and $R^B$ each independently represent a $C_1$-$C_6$ alkyl group which may have one or more substituents selected from a halogen atom, a $C_1$-$C_6$ alkoxy group and a hydroxyl group, or a hydrogen atom, or $R^A$ and $R^B$ together with the nitrogen atom substituted with them may form a three- to seven-membered heterocycloalkyl group which may have one or more substituents selected from a halogen atom, a $C_1$-$C_6$ alkyl group, a $C_1$-$C_5$ alkoxy group and a hydroxyl group);
—$OR^C$ (where $R^C$ represents a $C_1$-$C_6$ alkyl group which may have one or more substituents selected from a $C_1$-$C_6$ alkoxy group, a halogen atom, a three- to seven-membered heterocycloalkyl group and a hydroxyl group, a three- to seven-membered heterocycloalkyl group which may have one or more substituents selected from a halogen atom, a $C_1$-$C_6$ alkyl group and a hydroxyl group, or a hydrogen atom); and
a heterocycloalkyl group which may have one or more substituents selected from Group 2.

[2] The compound or salt thereof according to [1], wherein A is a phenylene group.

[3] The compound or salt thereof according to [1] or [2], wherein W is C—$R^4$.

[4] The compound or salt thereof according to any one of [1] to [3], wherein n is 0.

[5] The compound or salt thereof according to any one of [1] to [4], wherein $R^5$ is a hydrogen atom.

[6] Any one compound selected from the following group, or a salt thereof:

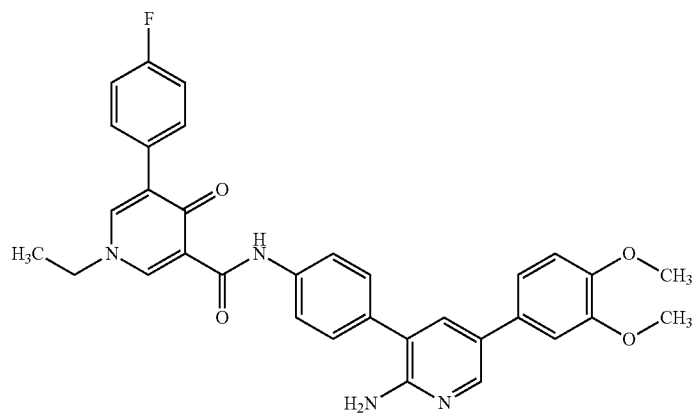
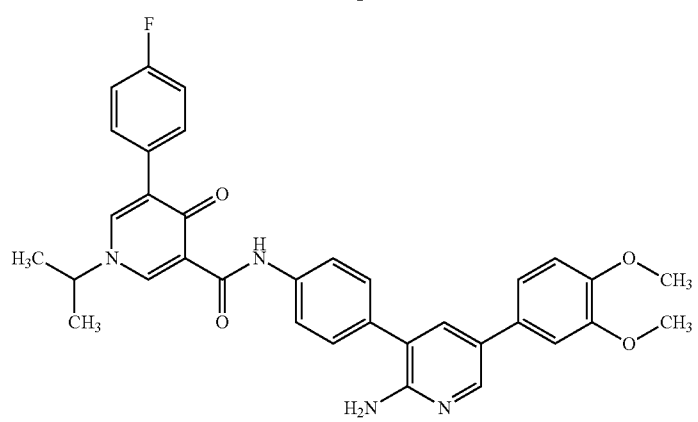
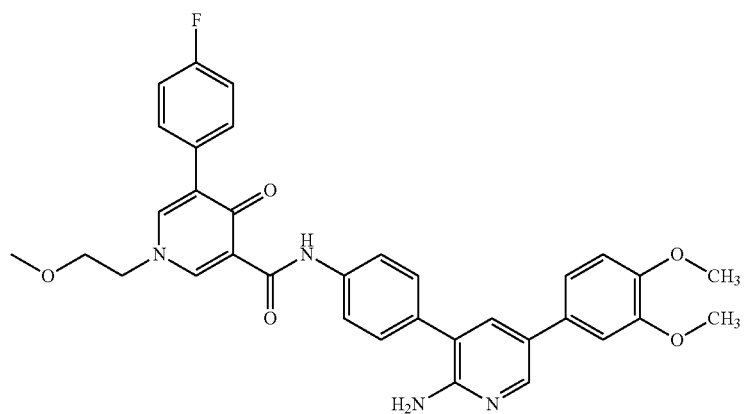
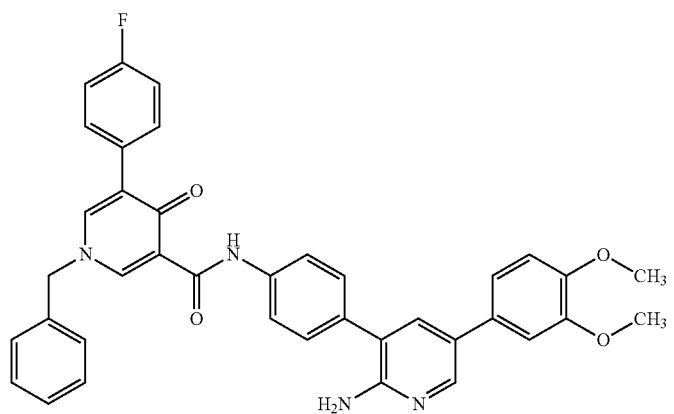

-continued
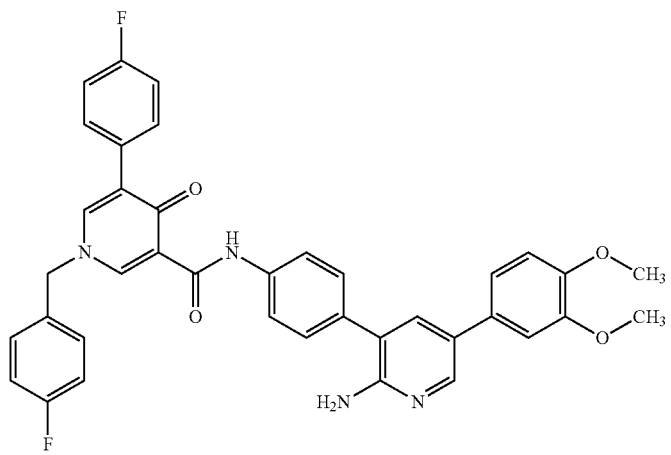
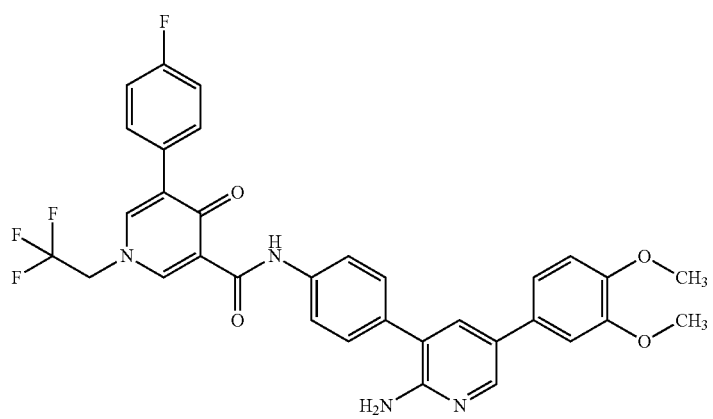
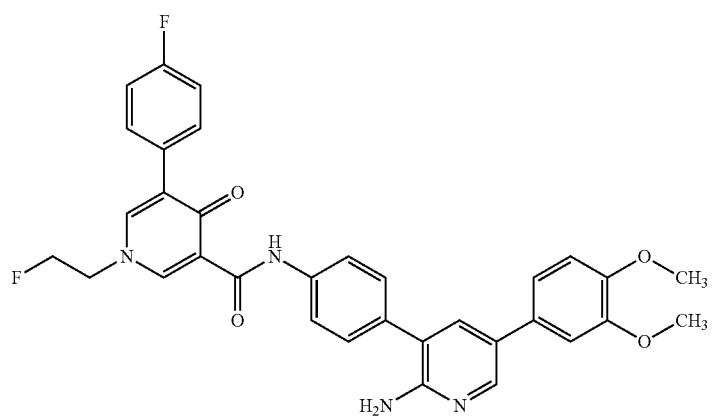
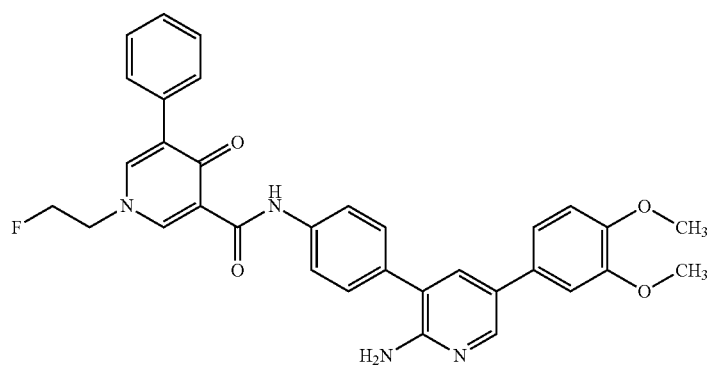

-continued
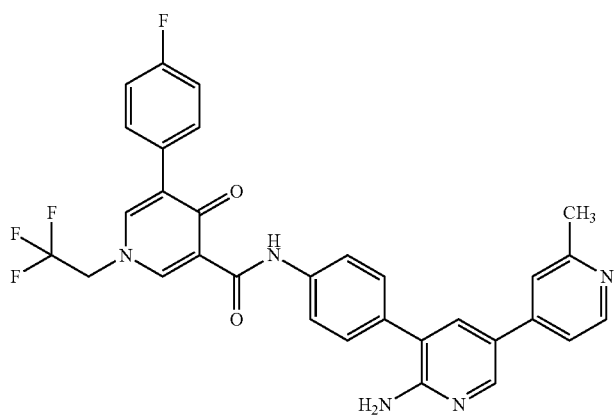
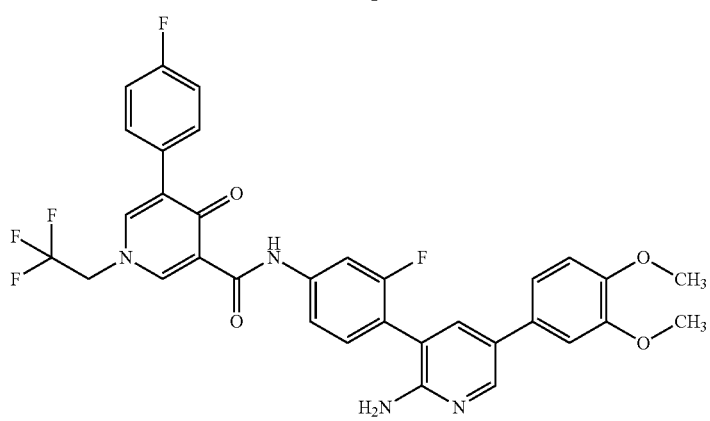
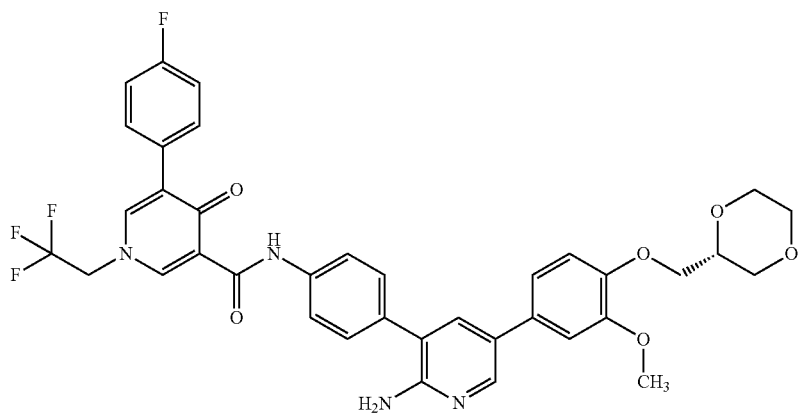
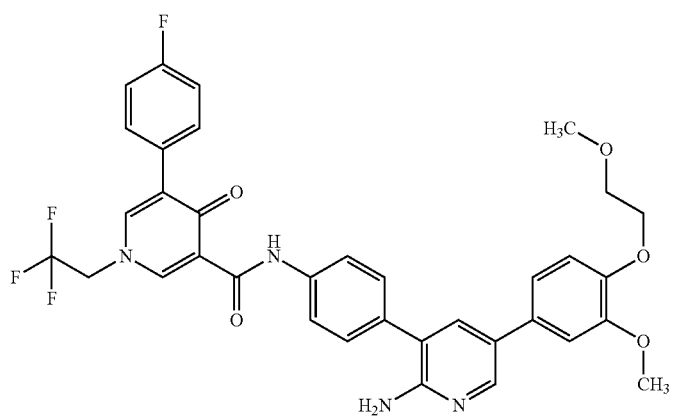

-continued
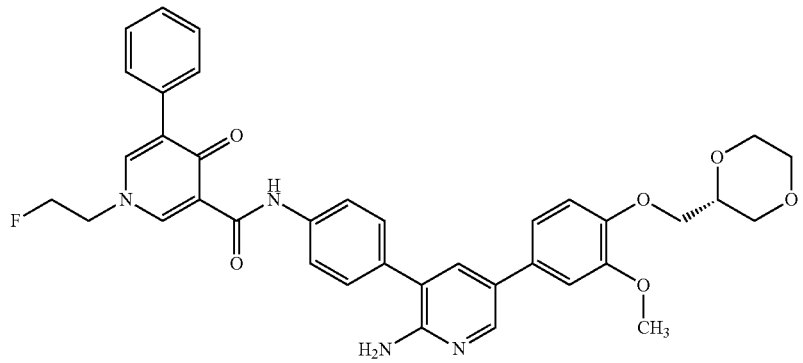
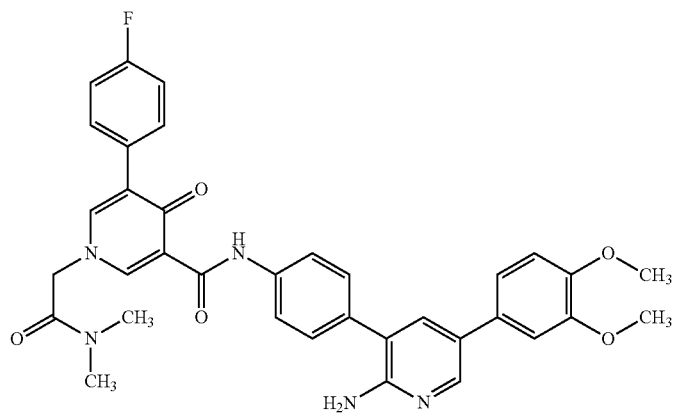
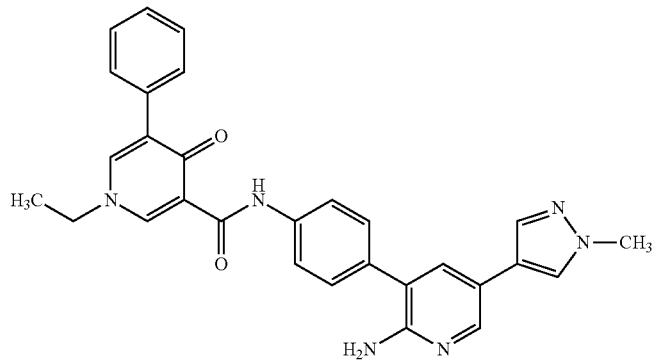
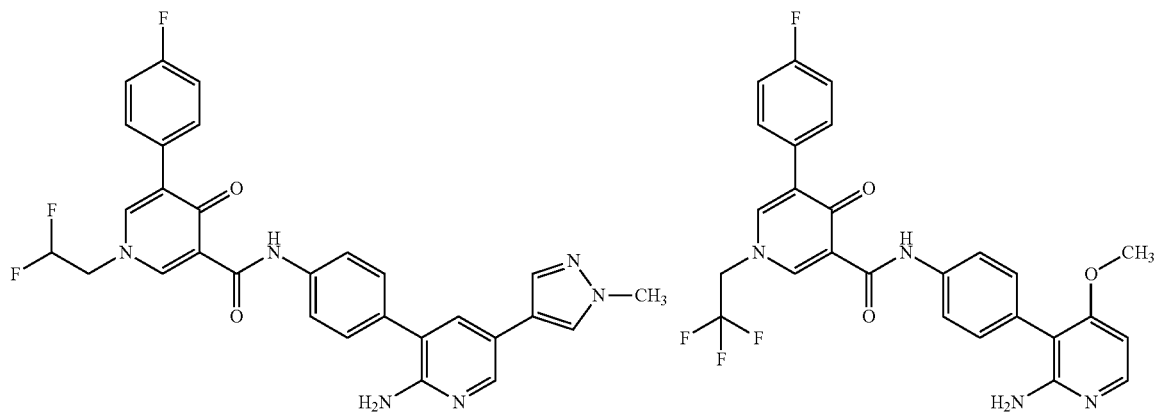

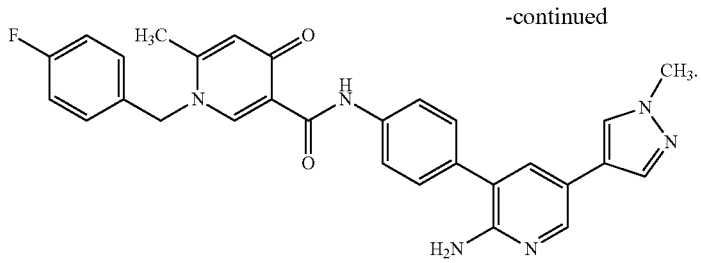

[7] N-{4-[2-Amino-5-(3,4-dimethoxyphenyl)pyridin-3-yl]phenyl}-5-(4-fluorophenyl)-4-oxo-1-(2,2,2-trifluoroethyl)-1,4-dihydropyridine-3-carboxamide or a salt thereof.

[8] N-{4-[2-Amino-5-(3,4-dimethoxyphenyl)pyridin-3-yl]phenyl}-5-(4-fluorophenyl)-4-oxo-1-(2,2,2-trifluoroethyl)-1,4-dihydropyridine-3-carboxamide hydrochloride.

[9] A crystal of N-{4-[2-amino-5-(3,4-dimethoxyphenyl)pyridin-3-yl]phenyl}-5-(4-fluorophenyl)-4-oxo-1-(2,2,2-trifluoroethyl)-1,4-dihydropyridine-3-carboxamide hydrochloride.

[10] The crystal according to [9], which has an X-ray diffraction pattern shown in FIG. 1 in a powder X-ray diffraction diagram obtained by irradiation with copper Kα radiation (wavelength λ=1.54 Å).

[11] The crystal according to [9], which has an X-ray diffraction pattern shown in FIG. 2 in a powder X-ray diffraction diagram obtained by irradiation with copper Kα radiation (wavelength λ=1.54 Å).

[12] The crystal according to [9], which has an X-ray diffraction pattern shown in FIG. 3 in a powder X-ray diffraction diagram obtained by irradiation with copper Kα radiation (wavelength λ=1.54 Å).

[13] The crystal according to [9], which has an X-ray diffraction pattern shown in FIG. 4 in a powder X-ray diffraction diagram obtained by irradiation with copper Kα radiation (wavelength λ=1.54 Å).

[14] The crystal according to [9], which has an X-ray diffraction pattern shown in FIG. 5 in a powder X-ray diffraction diagram obtained by irradiation with copper Kα radiation (wavelength λ=1.54 Å).

[15] The crystal according to [9], which has an X-ray diffraction pattern shown in FIG. 6 in a powder X-ray diffraction diagram obtained by irradiation with copper Kα radiation (wavelength λ=1.54 Å).

[16] The crystal according to [9], which has an X-ray diffraction pattern shown in FIG. 7 in a powder X-ray diffraction diagram obtained by irradiation with copper Kα radiation (wavelength λ=1.54 Å).

[17] The crystal according to [9], which has an X-ray diffraction pattern shown in FIG. 8 in a powder X-ray diffraction diagram obtained by irradiation with copper Kα radiation (wavelength λ=1.54 Å).

[18] The crystal according to [9], which has an X-ray diffraction pattern shown in FIG. 9 in a powder X-ray diffraction diagram obtained by irradiation with copper Kα radiation (wavelength λ=1.54 Å).

[19] The crystal according to [9], which has an X-ray diffraction pattern shown in FIG. 10 in a powder X-ray diffraction diagram obtained by irradiation with copper Kα radiation (wavelength λ=1.54 Å).

[20] The crystal according to [9], which has an X-ray diffraction pattern shown in FIG. 11 in a powder X-ray diffraction diagram obtained by irradiation with copper Kα radiation (wavelength λ=1.54 Å).

[21] The crystal according to [9], which has an X-ray diffraction pattern shown in FIG. 12 in a powder X-ray diffraction diagram obtained by irradiation with copper Kα radiation (wavelength λ=1.54 Å).

[22] The crystal according to [9], which has an X-ray diffraction pattern shown in FIG. 13 in a powder X-ray diffraction diagram obtained by irradiation with copper Kα radiation (wavelength λ=1.54 Å).

[23] The crystal according to [9], which has an X-ray diffraction pattern shown in FIG. 14 in a powder X-ray diffraction diagram obtained by irradiation with copper Kα radiation (wavelength λ=1.54 Å).

[24] The crystal according to [9], which has an X-ray diffraction pattern shown in FIG. 15 in a powder X-ray diffraction diagram obtained by irradiation with copper Kα radiation (wavelength λ=1.54 Å).

[25] The crystal according to [9], which has an X-ray diffraction pattern shown in FIG. 16 in a powder X-ray diffraction diagram obtained by irradiation with copper Kα radiation (wavelength λ=1.54 Å).

[26] The crystal according to [9], which has characteristic peaks at diffraction angles 2θ of 7.44, 10.00, 13.48, 14.86, 16.10, 19.30, 20.30, 22.62, 23.02, 23.70, 24.54, 25.92 and 28.46 in a powder X-ray diffraction diagram obtained by irradiation with copper Kα radiation (wavelength λ=1.54 Å).

[27] The crystal according to [9], which has characteristic peaks at diffraction angles 2θ of 4.32, 9.10, 15.52, 18.32, 18.54, 19.22, 20.54, 20.70, 23.54, 24.14, 25.34 and 27.02 in a powder X-ray diffraction diagram obtained by irradiation with copper Kα radiation (wavelength λ=1.54 Å).

[28] The crystal according to [9], which has characteristic peaks at diffraction angles 2θ of 13.86, 15.04, 19.76, 20.58, 22.26, 22.58, 23.82, 24.10, 24.36 and 24.88 in a powder X-ray diffraction diagram obtained by irradiation with copper Kα radiation (wavelength λ, =1.54 Å).

[29] The crystal according to [9], which has characteristic peaks at diffraction angles 2θ of 5.34, 7.22, 8.20, 11.68, 14.54, 15.74, 17.54, 23.24, 23.72, 25.12 and 26.16 in a powder X-ray diffraction diagram obtained by irradiation with copper Kα radiation (wavelength λ=1.54 Å).

[30] The crystal according to [9], which has characteristic peaks at diffraction angles 2θ of 11.02, 11.86, 15.56, 18.20, 22.12, 24.70, 25.80, 26.04, 26.26 and 28.62 in a powder X-ray diffraction diagram obtained by irradiation with copper Kα radiation (wavelength λ=1.54 Å).

[31] The crystal according to [9], which has characteristic peaks at diffraction angles 2θ of 3.58, 4.56, 6.60, 6.72, 7.20, 9.62, 10.28, 13.06 and 24.52 in a powder X-ray diffraction diagram obtained by irradiation with copper Kα radiation (wavelength λ=1.54 Å).

[32] The crystal according to [9], which has characteristic peaks at diffraction angles 2θ of 7.78, 8.14, 8.88, 12.54, 15.68, 16.36, 18.76, 19.34, 20.08, 22.36, 24.66, 25.74, 26.70 and 28.02 in a powder X-ray diffraction diagram obtained by irradiation with copper Kα radiation (wavelength λ=1.54 Å).

[33] The crystal according to [9], which has characteristic peaks at diffraction angles 2θ of 5.78, 8.90, 13.66, 14.42, 16.84, 17.56, 19.26, 20.74, 22.42, 24.66, 25.12, 25.60 and 26.96 in a powder X-ray diffraction diagram obtained by irradiation with copper Kα radiation (wavelength λ=1.54 Å).

[34] The crystal according to [9], which has characteristic peaks at diffraction angles 2θ of 11.12, 14.82, 18.86, 20.32, 20.66, 21.64, 22.36, 22.68, 23.00, 24.10, 25.26 and 27.00 in a powder X-ray diffraction diagram obtained by irradiation with copper Kα radiation (wavelength λ=1.54 Å).

[35] The crystal according to [9], which has characteristic peaks at diffraction angles 2θ of 7.80, 12.18, 12.78, 16.20, 16.82, 19.20, 19.66, 20.20, 21.20, 24.52, 25.68 and 26.78 in a powder X-ray diffraction diagram obtained by irradiation with copper Kα radiation (wavelength λ=1.54 Å).

[36] The crystal according to [9], which has characteristic peaks at diffraction angles 2θ of 2.80, 6.86, 7.88, 11.60, 13.68, 14.86, 17.40, 22.40, 23.78 and 25.74 in a powder X-ray diffraction diagram obtained by irradiation with copper Kα radiation (wavelength λ=1.54 Å).

[37] The crystal according to [9], which has characteristic peaks at diffraction angles 2θ of 5.32, 7.98, 10.68, 11.70, 14.84, 16.02, 19.78, 21.76, 23.08, 25.30 and 25.68 in a powder X-ray diffraction diagram obtained by irradiation with copper Kα radiation (wavelength λ=1.54

[38] The crystal according to [9], which has characteristic peaks at diffraction angles 2θ of 8.10, 10.60, 12.06, 14.16, 14.58, 15.60, 18.16, 20.72, 20.94, 22.86, 23.90, 24.32 and 27.14 in a powder X-ray diffraction diagram obtained by irradiation with copper Kα radiation (wavelength λ=1.54 Å).

[39] The crystal according to [9], which has characteristic peaks at diffraction angles 2θ of 3.60, 6.22, 9.56, 10.42, 14.04, 14.66, 15.30, 16.40, 19.52, 22.12 and 26.42 in a powder X-ray diffraction diagram obtained by irradiation with copper Kα radiation (wavelength λ=1.54 Å).

[40] The crystal according to [9], which has characteristic peaks at diffraction angles 2θ of 5.46, 7.98, 9.54, 11.00, 14.00, 15.36, 16.56, 22.00, 23.54, 24.00 and 26.56 in a powder X-ray diffraction diagram obtained by irradiation with copper Kα radiation (wavelength λ=1.54 Å).

[41] The crystal according to [9], which has characteristic peaks at diffraction angles 2θ of 5.64, 6.92, 8.06, 11.32, 14.40, 16.18, 17.04, 21.84, 22.50, 23.82 and 24.28 in a powder X-ray diffraction diagram obtained by irradiation with copper Kα radiation (wavelength λ=1.54 Å).

[42] An Axl inhibitor comprising the compound or salt thereof according to any one of [1] to [6], or a crystal thereof.

[43] A medicine comprising the compound or salt thereof according to any one of [1] to [6], or a crystal thereof, as an active ingredient.

[44] A medicine for treating a disease caused by Axl kinase hyperfunction, a disease associated with Axl kinase hyperfunction and/or a disease accompanied by Axl kinase hyperfunction, comprising the compound or salt thereof according to any one of [1] to [6], or a crystal thereof, as an active ingredient.

[45] A medicine for treating hyperproliferative disease, comprising the compound or salt thereof according to any one of [1] to [6], or a crystal thereof, as an active ingredient.

[46] A medicine for treating cancer, comprising the compound or salt thereof, according to any one of [1] to [6], or a crystal thereof as an active ingredient.

[47] A medicine for preventing cancer metastasis, comprising the compound or salt thereof according to any one of [1] to [6], or a crystal thereof, as an active ingredient.

[48] A medicine for overcoming drug resistance, comprising the compound or salt thereof according to any one of [1] to [6], or a crystal thereof, as an active ingredient.

[49] The medicine according to [46] or [47], wherein the cancer is selected from breast cancer, colon cancer, prostate cancer, lung cancer, gastric cancer, ovarian cancer, endometrial cancer, renal cancer, hepatocellular carcinoma, thyroid cancer, uterine cancer, esophageal cancer, squamous cell carcinoma, leukemia, osteosarcoma, melanoma, glioblastoma, neuroblastoma and pancreatic cancer.

[50] A pharmaceutical composition comprising the compound or salt thereof according to any one of [1] to [6], or a crystal thereof, and a pharmaceutically acceptable carrier.

[51] A method for treating a disease caused by Axl kinase hyperfunction, a disease associated with Axl kinase hyperfunction and/or a disease accompanied by Axl kinase hyperfunction, comprising using the compound or salt thereof according to any one of [1] to [6], or a crystal thereof.

[52] A method for treating hyperproliferative disease, comprising using the compound or salt thereof according to any one of [1] to [6], or a crystal thereof.

[53] A method for treating cancer, comprising using the compound or salt thereof according to any one of [1] to [6], or a crystal thereof.

[54] A method for preventing cancer metastasis, comprising using the compound or salt thereof according to any one of [1] to [6], or a crystal thereof.

[55] A method for overcoming drug resistance, comprising using the compound or salt thereof according to any one of [1] to [6], or a crystal thereof.

[56] The method according to [53] or [54], wherein the cancer is selected from breast cancer, colon cancer, prostate cancer, lung cancer, gastric cancer, ovarian cancer, endometrial cancer, renal cancer, hepatocellular carcinoma, thyroid cancer, uterine cancer, esophageal cancer, squamous cell carcinoma, leukemia, osteosarcoma, melanoma, glioblastoma and neuroblastoma.

[57] Use of the compound or salt thereof according to any one of [1] to [6], or a crystal thereof, for manufacturing a medicine.

[58] Use of the compound or salt thereof according to any one of [1] to [6], or a crystal thereof, for treating cancer.

[59] Use of the compound or salt thereof according to any one of [1] to [6], or a crystal thereof, for preventing cancer metastasis.

The present invention provides novel pyridone derivatives represented by the above formula (1) having Axl inhibitory activity. Such novel compounds are useful as therapeutic agents for a disease caused by Axl hyperfunction, a disease associated with Axl hyperfunction and/or a disease accompanied by Axl hyperfunction, e.g., anticancer agents.

DETAILED DESCRIPTION OF THE PREFERRED EMBODIMENTS

Figure 1:
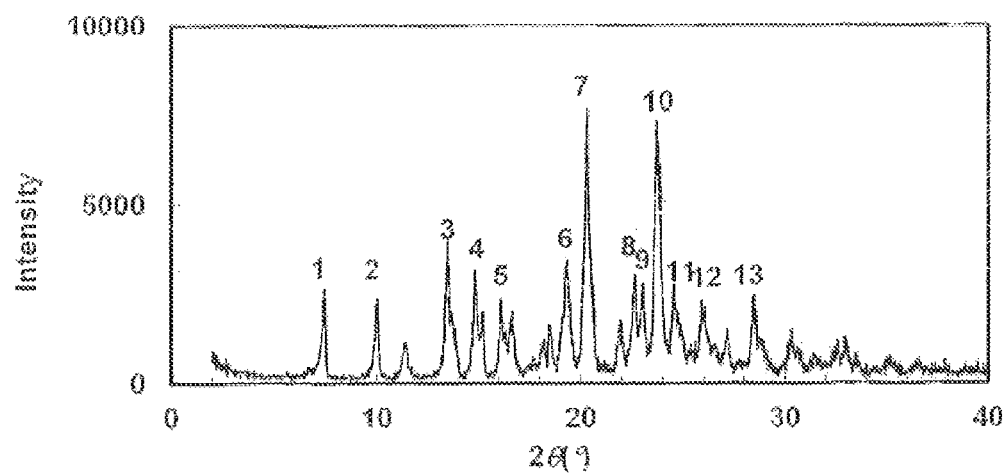
FIG. 1 is a powder X-ray diffraction diagram of the crystals obtained in Example 90, where the vertical axis represents diffraction intensity in counts per seconds (cps), and the horizontal axis represents values of diffraction angles 2θ.

In the present invention, Axl refers to a protein encoded by an Axl gene. "Axl" includes Axl proteins encoded by full-length Axl genes or Axl proteins encoded by Axl gene mutants (including deletion mutants, substitution mutants or addition mutants). In the present invention, "Axl" refers to homologs derived from various animal species.

In the present invention, the "Axl inhibitor" refers to an agent inhibiting functions of Axl as a tyrosine kinase.

In the present invention, the terms "tumor" and "cancer" are used interchangeably. In the present invention, tumor, malignant tumor, cancer, malignant neoplasm, carcinoma, sarcoma and the like may be collectively referred to as "tumor" or "cancer."

In the present invention:

The "$C_1$-$C_6$ alkyl group" refers to a linear or branched alkyl group having 1 to 6 carbon atoms. Examples of the "$C_1$-$C_6$ alkyl group" include a methyl group, an ethyl group, a propyl group, an isopropyl group, a butyl group and a tert-butyl group.

The "$C_1$-$C_6$ alkoxy group" refers to an alkoxy group having a linear or branched alkyl group having 1 to 6 carbon atoms. Examples of the "$C_1$-$C_6$ alkoxy group" include a methoxy group, an ethoxy group, a propoxy group, an isopropoxy group and a butoxy group.

Examples of the "halogen atom" include a fluorine atom, a chlorine atom, a bromine atom and an iodine atom.

The "oxo group" refers to a group represented by "=O" unless otherwise stated.

The "cycloalkyl group" refers to a cyclic alkyl group having 3 to 8 carbon atoms unless otherwise stated. Examples of the group include a cyclopropyl group, a cyclobutyl group, a cyclopentyl group and a cyclohexyl group.

The "heterocycloalkyl group" refers to a monovalent saturated heterocyclic group and includes a saturated heterocyclic group having a nitrogen atom on the ring and a saturated heterocyclic group having an oxygen atom on the ring. Examples of the group include monovalent groups derived from pyrrolidine, imidazoline, piperidine, piperazine, azetidine, morpholine, dioxane, oxetane, tetrahydropyran and quinuclidine.

The "cycloalkenyl group" includes the above "cycloalkyl group" having one or more unsaturated bonds such as double bonds. Examples of the group include a cyclopentenyl group and a cyclohexenyl group.

The "heterocycloalkenyl group" includes the above "heterocycloalkyl group" having one or more unsaturated bonds such as double bonds. Examples of the group include a tetrahydropyridinyl group and a dihydropyranyl group.

The "aryl group" refers to a monovalent substituent derived from an aromatic hydrocarbon. Examples of the aryl group include a phenyl group, an indenyl group, a naphthyl group, a fluorenyl group, an anthranyl group and a phenanthrenyl group.

The "heteroaryl group" refers to a monovalent aromatic heterocyclic group. Examples of the group include a pyrrolyl group, a pyrazolyl group, a triazolyl group, an oxazolyl group, an oxadiazolyl group, a thiophenyl group, a thiazolyl group, a thiadiazolyl group, a pyridinyl group, a pyrimidinyl group, a pyridazinyl group, a pyrazinyl group, a benzimidazolyl group, a benzotriazolyl group, a benzofuranyl group, a benzothiophenyl group, a quinolyl group, a carbazolyl group and a dibenzofuranyl group.

The "heteroarylene group" refers to a divalent aromatic heterocyclic group. Examples of the group include divalent groups derived from pyridine, pyrimidine, pyrazine, pyridazine and triazine.

Each substituent in formula (1) will be described below.
In the following general formula (1):

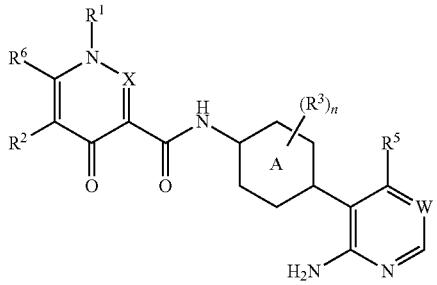

A represents a phenylene group or a six-membered heteroarylene group. The amino group bonded to the ring A and the nitrogen-containing heterocycle are para-positioned relative to each other.

When A is a heteroarylene group, A is preferably a group containing a nitrogen atom, and particularly preferably a group derived from pyridine. The position of a heteroatom in the ring A is not particularly limited.

A is more preferably a phenylene group.

$R^1$ represents a $C_1$-$C_6$ alkyl group which may have one or more substituents selected from the above Group 1, an aryl group which may have one or more substituents selected from the above Group 2, a heteroaryl group which may have one or more substituents selected from the above Group 2, or a hydrogen atom.

Here, when $R^1$ is a "$C_1$-$C_6$ alkyl group which may have one or more substituents selected from the above Group 1," the $C_1$-$C_6$ alkyl group is preferably a methyl group, an ethyl group, a propyl group, an isopropyl group, a butyl group or an isobutyl group.

The halogen atom as a substituent for the $C_1$-$C_6$ alkyl group is preferably a fluorine atom, a chlorine atom or a bromine atom. The $C_1$-$C_6$ alkyl group may be substituted with a plurality of identical or different halogen atoms, and the number of substitutions is preferably 1 to 3 if it is substituted with a halogen atom(s).

Each of —$NR^AR^B$ and —$CONR^AR^B$ as substituents for the $C_1$-$C_6$ alkyl group (where $R^A$ and $R^B$ each independently represent a $C_1$-$C_6$ alkyl group which may have one or more substituents selected from a halogen atom, a $C_1$-$C_6$ alkoxy group and a hydroxyl group, or a hydrogen atom, or $R^A$ and $R^B$ together with the nitrogen atom substituted with them may form a three- to seven-membered heterocycloalkyl group which may have one or more substituents selected from a halogen atom, a $C_1$-$C_6$ alkyl group, a $C_1$-$C_6$ alkoxy group and a hydroxyl group) is preferably an amino group which may be substituted with a $C_1$-$C_6$ alkyl group which may have one or more substituents selected from a halogen atom, a $C_1$-$C_6$ alkoxy group and a hydroxyl group, or a carbamoyl group which may be substituted with a $C_1$-$C_6$ alkyl group which may have one or more substituents selected from a halogen atom, a $C_1$-$C_6$ alkoxy group and a hydroxyl group, more preferably an amino group which may be substituted with a $C_1$-$C_6$ alkyl group(s), or a carbamoyl group which may be substituted with a $C_1$-$C_6$ alkyl group(s), still more preferably an amino group which may be substituted with a $C_1$-$C_3$ alkyl group(s), or a carbamoyl group which may be substituted with a $C_1$-$C_3$ alkyl group(s), and particularly preferably an amino group, a carbamoyl group, a monomethylamino group, a dimethylamino group, a monomethylcarbamoyl group, a dimethylcarbamoyl group, a monoethylamino group, a diethylamino group, a methylethylamino group, a monoethylcarbamoyl group, a diethylcarbamoyl group or a methylethylcarbamoyl group.

In —$OR^C$ as a substituent for the $C_1$-$C_6$ alkyl group (where $R^C$ represents a $C_1$-$C_6$ alkyl group which may have one or more substituents selected from a $C_1$-$C_6$ alkoxy group, a halogen atom and a hydroxyl group, a three- to seven-membered heterocycloalkyl group which may have one or more substituents selected from a halogen atom, a $C_1$-$C_6$ alkyl group and a hydroxyl group, or a hydrogen atom), $R^C$ is preferably a $C_1$-$C_6$ alkyl group, a three- to seven-membered heterocycloalkyl group or a hydrogen atom, and $R^C$ is more preferably a $C_1$-$C_3$ alkyl group, a tetrahydropyranyl group or a hydrogen atom.

The "aryl group which may have one or more substituents selected from a $C_1$-$C_6$ alkyl group which may have one or more substituents selected from a halogen atom and a hydroxyl group, a $C_1$-$C_6$ alkoxy group, an oxo group and a halogen atom" as a substituent for the $C_1$-$C_6$ alkyl group is preferably a phenyl group which may have one or more substituents selected from a $C_1$-$C_6$ alkyl group which may have one or more substituents selected from a halogen atom and a hydroxyl group, a $C_1$-$C_6$ alkoxy group, an oxo group and a halogen atom, more preferably a phenyl group which may have one or more substituents selected from a $C_1$-$C_6$ alkyl group which may have 1 to 3 substituents selected from 1 to 3 halogen atoms and 1 to 3 hydroxyl groups, a $C_1$-$C_3$ alkoxy group, an oxo group and 1 to 3 halogen atoms, and still more preferably a phenyl group unsubstituted or substituted with 1 to 3 halogen atoms or a $C_1$-$C_3$ alkoxy group.

The "heteroaryl group" in the "heteroaryl group which may have one or more substituents selected from a $C_1$-$C_6$ alkyl group which may have one or more substituents selected from a halogen atom and a hydroxyl group, a $C_1$-$C_6$ alkoxy group, an oxo group, a hydroxyl group and a halogen atom" as a substituent for the $C_1$-$C_6$ alkyl group is preferably a heteroaryl group containing a nitrogen atom.

The "heteroaryl group which may have one or more substituents selected from a $C_1$-$C_6$ alkyl group which may have one or more substituents selected from a halogen atom and a hydroxyl group, a $C_1$-$C_6$ alkoxy group, an oxo group, a hydroxyl group and a halogen atom" is preferably a pyridinyl group which may have one or more substituents selected from a $C_1$-$C_6$ alkyl group which may have one or more substituents selected from a halogen atom and a hydroxyl group, a $C_1$-$C_6$ alkoxy group, an oxo group, a hydroxyl group and a halogen atom, a pyrimidinyl group which may have one or more substituents selected from a $C_1$-$C_6$ alkyl group which may have one or more substituents selected from a halogen atom and a hydroxyl group, a $C_1$-$C_6$ alkoxy group, an oxo group, a hydroxyl group and a halogen atom, a pyrazinyl group which may have one or more substituents selected from a $C_1$-$C_6$ alkyl group which may have one or more substituents selected from a halogen atom and a hydroxyl group, a $C_1$-$C_6$ alkoxy group, an oxo group, a hydroxyl group and a halogen atom, a pyridazinyl group which may have one or more substituents selected from a $C_1$-$C_6$ alkyl group which may have one or more substituents selected from a halogen atom and a hydroxyl group, a $C_1$-$C_6$ alkoxy group, an oxo group, a hydroxyl group and a halogen atom, or a thiophenyl group which may have one or more substituents selected from a $C_1$-$C_6$ alkyl group which may have one or more substituents selected from a halogen atom and a hydroxyl group, a $C_1$-$C_6$ alkoxy group, an oxo group, a hydroxyl group and a halogen atom, and particularly preferably a pyridinyl group which may have one or more substituents selected from a $C_1$-$C_6$ alkyl group which may have one or more substituents selected from a halogen atom and a hydroxyl group, a $C_1$-$C_6$ alkoxy group, an oxo group, a hydroxyl group and a halogen atom. The position at which each heteroaryl group is bonded to the $C_1$-$C_6$ alkyl group is not limited, but the pyridinyl group is preferably bonded at the 2-position, the pyrimidinyl group is preferably bonded at the 2-position, the pyrazinyl group is preferably bonded at the 2-position, the pyridazinyl group is preferably bonded at the 3-position, and the thiophenyl group is preferably bonded at the 2-position.

The "heteroaryl group which may have one or more substituents selected from a $C_1$-$C_6$ alkyl group which may have one or more substituents selected from a halogen atom and a hydroxyl group, a $C_1$-$C_6$ alkoxy group, an oxo group, a hydroxyl group and a halogen atom" as a substituent for the $C_1$-$C_6$ alkyl group is particularly preferably an unsubstituted pyridinyl group, a pyridinyl group substituted with a $C_1$-$C_3$ alkoxy group, or a pyridinyl group substituted with a halogen atom.

The "three- to seven-membered cycloalkyl group which may have one or more substituents selected from a $C_1$-$C_6$ alkyl group which may have one or more substituents selected from a halogen atom and a hydroxyl group, a $C_1$-$C_6$ alkoxy group, an oxo group, a hydroxyl group and a halogen atom" as a substituent for the $C_1$-$C_6$ alkyl group is preferably an unsubstituted three- to seven-membered cycloalkyl group or a three- to seven-membered cycloalkyl group substituted with a plurality of halogen atoms, and more preferably an unsubstituted three- to seven-membered cycloalkyl group.

The "three- to seven-membered heterocycloalkyl group which may have one or more substituents selected from a $C_1$-$C_6$ alkyl group which may have one or more substituents selected from a halogen atom and a hydroxyl group, a $C_1$-$C_6$ alkoxy group, an oxo group, a hydroxyl group and a halogen atom" as a substituent for the $C_1$-$C_6$ alkyl group is preferably a three- to seven-membered heterocycloalkyl group unsubstituted or substituted with a $C_1$-$C_6$ alkyl group or an oxo group. Here, the "three- to seven-membered heterocycloalkyl group" is preferably a tetrahydropyranyl group, a tetrahydrofuranyl group, a pyrrolidinyl group, an imidazolidinyl group, a pyrazolidinyl group, a piperidino group, a morpholino group, a dioxanyl group or an oxetanyl group, and more preferably a pyrrolidinyl group, a tetrahydropyranyl group or a dioxanyl group. The position at which each heterocycloalkyl group is bonded to the $C_1$-$C_6$ alkyl group is not limited, but the dioxanyl group is preferably bonded at the 2-position, the tetrahydrofuranyl group is preferably bonded at the 2-position, and the pyrrolidinyl group is preferably bonded at the 2-position.

When $R^1$ is an "aryl group which may have one or more substituents selected from the above Group 2," the "aryl group" is preferably a phenyl group. The substituent for the phenyl group is preferably a $C_1$-$C_6$ alkyl group which may have 1 to 3 substituents selected from a fluorine atom, a chlorine atom and a hydroxyl group, a $C_1$-$C_6$ alkoxy group, a hydroxyl group, a fluorine atom or a chlorine atom.

When $R^1$ is a "heteroaryl group which may have one or more substituents selected from the above Group 2," the "heteroaryl group" is preferably a heteroaryl group containing a nitrogen atom, more preferably a pyridinyl group, a pyrimidinyl group, a pyridazinyl group or a pyrazinyl group, and particularly preferably a pyridinyl group. The substituent for the heteroaryl group is preferably a $C_1$-$C_6$ alkyl group which may have 1 to 3 substituents selected from a fluorine atom, a chlorine atom and a hydroxyl group, a $C_1$-$C_6$ alkoxy group, a hydroxyl group, a fluorine atom or a chlorine atom.

$R^1$ is particularly preferably a $C_1$-$C_6$ alkyl group substituted with 1 to 3 halogen atoms, a methoxyethyl group, an ethoxyethyl group, a benzyl group, or a benzyl group having a benzene ring substituted with 1 to 3 halogen atoms. Here, the halogen atom is preferably a fluorine atom.

$R^2$ represents a $C_1$-$C_6$ alkyl group which may have one or more substituents selected from the above Group 1, a $C_1$-$C_6$ alkoxy group which may have one or more substituents selected from a halogen atom and a hydroxyl group, —CON$R^A R^B$ (where $R^A$ and $R^B$ each independently represent a $C_1$-$C_6$ alkyl group which may have one or more substituents selected from a halogen atom, a $C_1$-$C_6$ alkoxy group and a hydroxyl group, or a hydrogen atom, or $R^A$ and $R^B$ together with the nitrogen atom substituted with them may form a three- to seven-membered heterocycloalkyl group which may have one or more substituents selected from a halogen atom, a $C_1$-$C_6$ alkyl group, a $C_1$-$C_6$ alkoxy group and a hydroxyl group), a cycloalkyl group which may have one or more substituents selected from the above Group 2, a phenyl group which may have one or more substituents selected from the above Group 2, a heteroaryl group which may have one or more substituents selected from the above Group 2, or a hydrogen atom.

When $R^2$ is a "$C_1$-$C_6$ alkyl group which may have one or more substituents selected from the above Group 1," preferred examples thereof are the same as those of the "$C_1$-$C_6$ alkyl group which may have one or more substituents selected from the above Group 1" in the above $R^1$. When $R^2$ is a "$C_1$-$C_6$ alkyl group which may have one or more substituents selected from the above Group 1," it is more preferably an unsubstituted $C_1$-$C_6$ alkyl group.

When $R^2$ is a "$C_1$-$C_6$ alkoxy group which may have one or more substituents selected from a halogen atom and a hydroxyl group," it is preferably an unsubstituted $C_1$-$C_6$ alkoxy group, and more preferably a methoxy group or an ethoxy group.

When $R^2$ is "—CON$R^A R^B$ (where $R^A$ and $R^B$ each independently represent a $C_1$-$C_6$ alkyl group which may have one or more substituents selected from a halogen atom, a $C_1$-$C_6$ alkoxy group and a hydroxyl group, or a hydrogen atom, or $R^A$ and $R^B$ together with the nitrogen atom substituted with them may form a three- to seven-membered heterocycloalkyl group which may have one or more substituents selected from a halogen atom, a $C_1$-$C_6$ alkyl group, a $C_1$-$C_6$ alkoxy group and a hydroxyl group)," it is preferred that $R^A$ and $R^B$ each independently be an unsubstituted $C_1$-$C_6$ alkyl group or a hydrogen atom, or $R^A$ and $R^B$ together with the nitrogen atom substituted with them form a three- to six-membered heterocycloalkyl group which may have one or more substituents selected from a halogen atom, a $C_1$-$C_6$ alkyl group, a $C_1$-$C_6$ alkoxy group and a hydroxyl group. Here, the "three- to six-membered heterocycloalkyl group" is preferably a pyrrolidinyl group, a morpholino group or an azetidinyl group.

When $R^2$ is a "cycloalkyl group which may have one or more substituents selected from the above Group 2," the "cycloalkyl group" is preferably a cyclopropyl group or a cyclohexyl group. Here, $R^2$ is preferably an unsubstituted cyclohexyl group.

When $R^2$ is a "phenyl group which may have one or more substituents selected from the above Group 2," the substituents for the phenyl group are preferably 1 to 3 groups selected from a $C_1$-$C_6$ alkyl group, a fluorine atom, a chlorine atom and a bromine atom.

When $R^2$ is a "heteroaryl group which may have one or more substituents selected from the above Group 2," the "heteroaryl group" is preferably a pyridinyl group, a pyrimidinyl group, a pyrazinyl group, a pyridazinyl group, a thiophenyl group, a furanyl group or an oxadiazolyl group, and more preferably a pyridinyl group, a thiophenyl group or an oxadiazolyl group. The substituents for the heteroaryl group are preferably 1 to 3 groups selected from a $C_1$-$C_6$ alkyl group, a fluorine atom, a chlorine atom and a bromine atom.

$R^2$ is preferably a phenyl group substituted with 1 to 3 groups selected from a $C_1$-$C_6$ alkyl group substituted with 1 to 3 halogen atoms, and a halogen atom, an unsubstituted phenyl group, a hydrogen atom, a methyl group or a methoxy group. It is more preferably an unsubstituted phenyl group or a phenyl group substituted with 1 to 3 fluorine atoms.

$R^3$ is a substituent on A (where n represents an integer of 0 to 4, and each $R^3$ may be identical to or different from one another when n is two or more), and represents a $C_1$-$C_6$ alkyl group which may have one or more substituents selected from Group 1, a $C_1$-$C_6$ alkoxy group which may have one or more substituents selected from a halogen atom and a hydroxyl group, a $C_1$-$C_6$ alkylthio group which may have one or more substituents selected from a halogen atom and a hydroxyl group, a halogen atom, or a hydroxyl group.

When $R^3$ is a "$C_1$-$C_6$ alkyl group which may have one or more substituents selected from the above Group 1," preferred examples thereof are the same as those of the "$C_1$-$C_6$ alkyl group which may have one or more substituents selected from the above Group 1" in the above $R^1$. When $R^3$ is a "$C_1$-$C_6$ alkyl group which may have one or more substituents selected from the above Group 1," it is preferably a $C_1$-$C_6$ alkyl group which may be substituted with 1 to 3 fluorine atoms, chlorine atoms, bromine atoms or hydroxyl groups, and more preferably an unsubstituted $C_1$-$C_6$ alkyl group.

When $R^3$ is a "$C_1$-$C_4$ alkoxy group which may have one or more substituents selected from a halogen atom and a hydroxyl group," it is preferably a $C_1$-$C_3$ alkoxy group which may be substituted with 1 to 3 fluorine atoms, chlorine atoms, bromine atoms or hydroxyl groups, and more preferably an unsubstituted $C_1$-$C_3$ alkoxy group.

When $R^3$ is a "$C_1$-$C_6$ alkylthio group which may have one or more substituents selected from a halogen atom and a hydroxyl group," it is preferably a $C_1$-$C_3$ alkylthio group which may be substituted with 1 to 3 fluorine atoms, chlorine atoms, bromine atoms or hydroxyl groups, and more preferably an unsubstituted $C_1$-$C_3$ alkylthio group.

When $R^3$ is a "halogen atom," it is preferably a fluorine atom, a chlorine atom or a bromine atom.

In $R^3$, n is preferably 0 to 3, n is more preferably 0 or 1, and n is still more preferably 0. When n is 1 to 3, $R^3$ is still more preferably a fluorine atom, a chlorine atom, a bromine atom, a $C_1$-$C_6$ alkyl group or a $C_1$-$C_6$ alkoxy group.

$R^5$ represents a $C_1$-$C_6$ alkyl group which may have one or more substituents selected from Group 1, —$OR^C$ (where $R^C$ represents a $C_1$-$C_6$ alkyl group which may have one or more substituents selected from a $C_1$-$C_6$ alkoxy group, a halogen atom and a hydroxyl group, a three- to seven-membered heterocycloalkyl group which may have one or more substituents selected from a halogen atom, a $C_1$-$C_6$ alkyl group and a hydroxyl group, or a hydrogen atom), a $C_1$-$C_6$ alkylthio group which may have one or more substituents selected from a halogen atom and a hydroxyl group, or a hydrogen atom.

When $R^5$ is a "$C_1$-$C_6$ alkyl group which may have one or more substituents selected from the above Group 1," preferred examples thereof are the same as those of the "$C_1$-$C_6$ alkyl group which may have one or more substituents selected from the above Group 1" in the above $R^1$. When $R^5$ is a "$C_1$-$C_6$ alkyl group which may have one or more substituents selected from the above Group 1," it is preferably an unsubstituted $C_1$-$C_6$ alkyl group or a $C_1$-$C_6$ alkyl group substituted with 1 to 3 halogen atoms, and more preferably an unsubstituted $C_1$-$C_6$ alkyl group.

When $R^5$ is "—$OR^C$ (where $R^C$ represents a $C_1$-$C_6$ alkyl group which may have one or more substituents selected from a $C_1$-$C_6$ alkoxy group, a halogen atom and a hydroxyl group, a three- to seven-membered heterocycloalkyl group which may have one or more substituents selected from a halogen atom, a $C_1$-$C_6$ alkyl group and a hydroxyl group, or a hydrogen atom)," it is preferably a hydrogen atom, an unsubstituted $C_1$-$C_6$ alkoxy group or a $C_1$-$C_6$ alkoxy group substituted with 1 to 3 halogen atoms, and more preferably an unsubstituted $C_1$-$C_6$ alkoxy group.

When $R^5$ is a "$C_1$-$C_6$ alkylthio group which may have one or more substituents selected from a halogen atom and a hydroxyl group," it is preferably an unsubstituted $C_1$-$C_6$ alkylthio group.

$R^5$ is preferably a $C_1$-$C_6$ alkyl group, a $C_1$-$C_6$ alkoxy group or a hydrogen atom, and more preferably a methoxy group, an ethoxy group, a trifluoromethoxy group, a difluoromethoxy group or a hydrogen atom.

$R^6$ represents a hydrogen atom, or a $C_1$-$C_6$ alkyl group which may have one or more substituents selected from Group 1.

When $R^6$ is a "$C_1$-$C_6$ alkyl group which may have one or more substituents selected from the above Group 1," preferred examples thereof are the same as those of the "$C_1$-$C_6$ alkyl group which may have one or more substituents selected from the above Group 1" in the above $R^1$. When $R^6$ is a "$C_1$-$C_6$ alkyl group which may have one or more substituents selected from the above Group 1," it is preferably an unsubstituted $C_1$-$C_6$ alkyl group or a $C_1$-$C_6$ alkyl group substituted with 1 to 3 halogen atoms, and more preferably an unsubstituted $C_1$-$C_6$ alkyl group.

$R^6$ is preferably a $C_1$-$C_6$ alkyl group or a hydrogen atom, and more preferably a methyl group, an ethyl group, a propyl group, a butyl group or a hydrogen atom.

W represents C—$R^4$ or a nitrogen atom, where $R^4$ represents a $C_1$-$C_6$ alkyl group which may have one or more substituents selected from the above Group 1, a $C_1$-$C_6$ alkoxy group which may have one or more substituents selected from a $C_1$-$C_6$ alkoxy group, a heterocycloalkyl group, a halogen atom and a hydroxyl group, a cycloalkyl group which may have one or more substituents selected from the above Group 3, a cycloalkenyl group which may have one or more substituents selected from Group 3, a heterocycloalkyl group which may have one or more substituents selected from Group 3, a heterocycloalkenyl group which may have one or more substituents selected from Group 3, an aryl group which may have one or more substituents selected from Group 3, a heteroaryl group which may have one or more substituents selected from Group 3, a halogen atom, or a hydrogen atom.

When $R^4$ is a "$C_1$-$C_6$ alkyl group which may have one or more substituents selected from the above Group 1," preferred examples thereof are the same as those of the "$C_1$-$C_6$ alkyl group which may have one or more substituents selected from the above Group 1" in the above $R^1$. When $R^4$ is a "$C_1$-$C_6$ alkyl group which may have one or more substituents selected from the above Group 1," it is preferably an unsubstituted $C_1$-$C_6$ alkyl group or a $C_1$-$C_6$ alkyl group substituted with 1 to 3 halogen atoms, and more preferably an unsubstituted $C_1$-$C_6$ alkyl group.

When $R^4$ is a "$C_1$-$C_6$ alkoxy group which may have one or more substituents selected from a $C_1$-$C_6$ alkoxy group, a heterocycloalkyl group, a halogen atom and a hydroxyl group," it is preferably an unsubstituted $C_1$-$C_6$ alkoxy group or a $C_1$-$C_6$ alkoxy group substituted with 1 to 3 halogen atoms, and more preferably an unsubstituted $C_1$-$C_6$ alkoxy group.

When $R^4$ is a "cycloalkyl group which may have one or more substituents selected from the above Group 3," the "cycloalkyl group" is preferably a cyclopropyl group, a cyclobutyl group, a cyclopentyl group or a cyclohexyl group. When $R^4$ is a "cycloalkenyl group which may have one or more substituents selected from the above Group 3," the "cycloalkenyl group" is preferably a cyclopentenyl group or a cyclohexenyl group. When $R^4$ is a "heterocycloalkyl group which may have one or more substituents selected from the above Group 3," the "heterocycloalkyl group" is preferably an azetidinyl group, a pyrrolidinyl group, a piperidinyl group, a piperazinyl group or a morpholinyl group. When $R^4$ is a "heterocycloalkenyl group which may have one or more substituents selected from the above Group 3," the "heterocycloalkenyl group" is preferably a tetrahydropyridyl group or a dihydropyranyl group. When $R^4$ is an "aryl group which may have one or more substituents selected from the above Group 3," the aryl group is preferably a phenyl group. When $R^4$ is a "heteroaryl group which may have one or more substituents selected from the above Group 3," the "heteroaryl group" is preferably a pyridinyl group, a pyrazinyl group, a pyrimidinyl group, a pyrrolyl group, a pyrazolyl group, an imidazolyl group, a thiophenyl group, a thiazolyl group, an isothiazolyl group, a furanyl group, an oxazolyl group or a triazolyl group.

The number of substituents for such a cycloalkyl, cycloalkenyl, heterocycloalkyl, heterocycloalkenyl, aryl or heteroaryl group is preferably 0 to 3.

When the substituent for such a cycloalkyl, cycloalkenyl, heterocycloalkyl, heterocycloalkenyl, aryl or heteroaryl group is a "$C_1$-$C_6$ alkyl group which may have one or more substituents selected from the above Group 1," preferred examples thereof are the same as those of the "$C_1$-$C_6$ alkyl group which may have one or more substituents selected from the above Group 1" in the above $R^1$. More preferable examples thereof are a $C_1$-$C_6$ alkyl group substituted by —$OR^C$ (where $R^C$ represents a $C_1$-$C_6$ alkyl group which may have one or more substituents selected from a $C_1$-$C_6$ alkoxy group, a halogen atom and a hydroxyl group, a three- to seven-membered heterocycloalkyl group which may have one or more substituents selected from a halogen atom, a $C_1$-$C_6$ alkyl group and a hydroxyl group, or a hydrogen atom) or a heterocycloalkyl group which may have a substituent, and a $C_1$-$C_6$ alkyl group which may be substituted with an unsubstituted heterocycloalkyl group or a $C_1$-$C_6$ alkoxy group, or an unsubstituted $C_1$-$C_6$ alkyl group is further preferable.

When the substituent for such a cycloalkyl, cycloalkenyl, heterocycloalkyl, heterocycloalkenyl, aryl or heteroaryl group is a "$C_1$-$C_6$ acyl group," it is preferably an acetyl group. When the substituent is a "$C_1$-$C_6$ alkylthio group which may have one or more substituents selected from a halogen atom and a hydroxyl group," it is preferably an unsubstituted $C_1$-$C_6$ alkylthio group. When the substituent is "—$CONR^AR^B$ (where $R^A$ and $R^B$ each independently represent a $C_1$-$C_6$ alkyl group which may have one or more substituents selected from a halogen atom, a $C_1$-$C_6$ alkoxy group and a hydroxyl group, or a hydrogen atom, or $R^A$ and $R^B$ together with the nitrogen atom substituted with them may form a three- to seven-membered heterocycloalkyl group which may have one or more substituents selected from a halogen atom, a $C_1$-$C_6$ alkyl group, a $C_1$-$C_6$ alkoxy group and a hydroxyl group)," it is preferred that $R^A$ and $R^B$ each independently be an unsubstituted $C_1$-$C_6$ alkyl group or a hydrogen atom, or $R^A$ and $R^B$ together with the nitrogen atom substituted with them form a three- to six-membered heterocycloalkyl group which may have one or more substituents selected from a halogen atom, a $C_1$-$C_6$ alkyl group, a $C_1$-$C_6$ alkoxy group and a hydroxyl group. Here, the "three- to six-membered heterocycloalkyl group" is preferably a pyrrolidinyl group, a morpholino group, an azetidinyl group or a piperidinyl group.

When the substituent for such a cycloalkyl, cycloalkenyl, heterocycloalkyl, heterocycloalkenyl, aryl or heteroaryl group is "—$OR^C$ (where $R^C$ represents a $C_1$-$C_6$ alkyl group which may have one or more substituents selected from a $C_1$-$C_6$ alkoxy group, a halogen atom, a three- to seven-membered heterocycloalkyl group and a hydroxyl group, a three- to seven-membered heterocycloalkyl group which may have one or more substituents selected from a halogen atom, a $C_1$-$C_6$ alkyl group and a hydroxyl group, or a hydrogen atom)," "$R^C$" is preferably a $C_1$-$C_6$ alkyl group which may have one or more substituents selected from a $C_1$-$C_6$ alkoxy group, a halogen atom, a three- to seven-membered heterocycloalkyl group and a hydroxyl group, or a hydrogen atom, and more preferably an unsubstituted $C_1$-$C_6$ alkyl group or a $C_1$-$C_6$ alkyl group substituted with a $C_1$-$C_6$ alkoxy group or a three- to seven-membered heterocycloalkyl group. Here, the "three- to seven-membered heterocycloalkyl group" is preferably a pyrrolidyl group, an imidazolidinyl group, a pyrazolidinyl group, a piperidinyl group, a piperazinyl group, a tetrahydropyranyl group, a dioxanyl group or a tetrahydrofuranyl group. "$R^C$" is particularly preferably a methyl group, an ethyl group, a methyl group substituted with a dioxanyl group, or an ethyl group substituted with a methoxy group.

When the substituent for such a cycloalkyl, cycloalkenyl, heterocycloalkyl, heterocycloalkenyl, aryl or heteroaryl group is a "heterocycloalkyl group which may have one or more substituents selected from Group 2," it is preferably a heterocycloalkyl group which may be substituted with a $C_1$-$C_6$ alkyl group, a $C_1$-$C_6$ alkoxy group, an oxo group, a hydroxyl group or a halogen atom, and more preferably a heterocycloalkyl group substituted with a $C_1$-$C_6$ alkyl group, a halogen atom or an oxo group, or an unsubstituted heterocycloalkyl group.

When $R^4$ is a "halogen atom," it is preferably a fluorine atom, a chlorine atom or a bromine atom.

$R^4$ is preferably a phenyl group substituted with 1 to 3 $C_1$-$C_6$ alkoxy groups, a five- or six-membered nitrogen-containing heteroaryl group substituted with 1 to 3 $C_1$-$C_6$ alkyl groups, or a group represented by any of the following formulas:

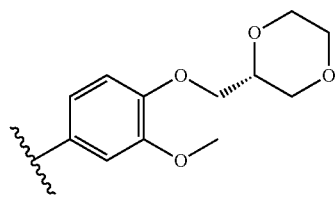

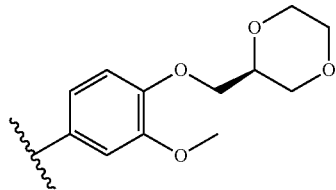

-continued
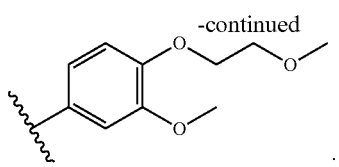
Here, the nitrogen-containing heteroaryl group is preferably a pyridyl group or a pyrazolyl group.
W is preferably C—R$^4$.
X represents CH or a nitrogen atom and, is preferably CH.
Further, the compound represented by the general formula (1) according to the present invention is preferably one compound selected from the following group:
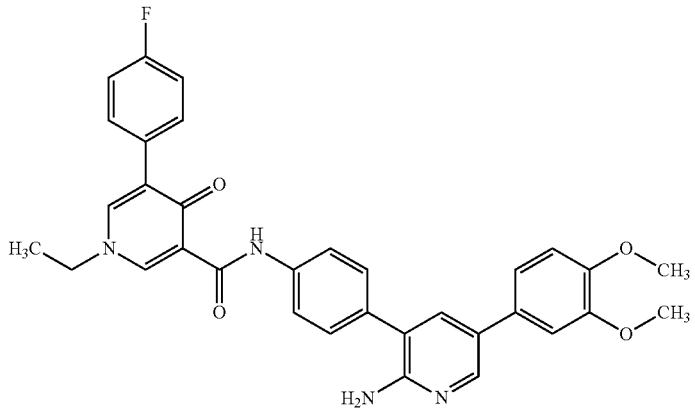
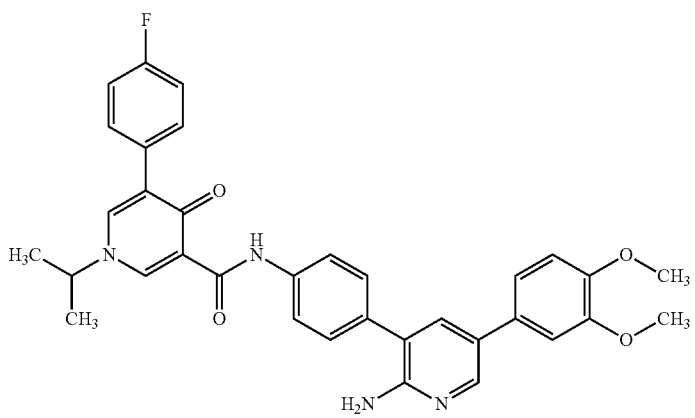
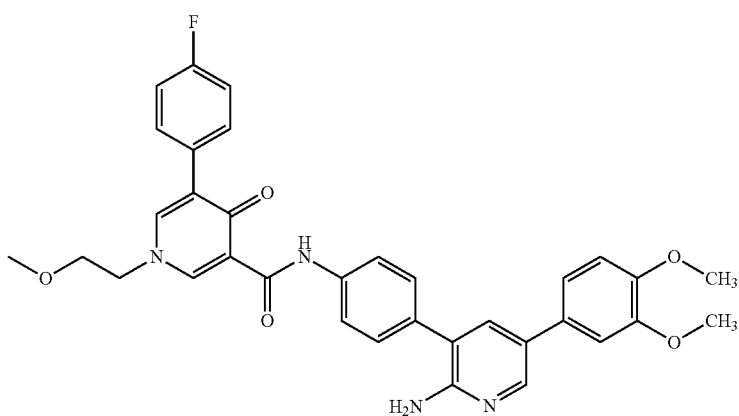

-continued
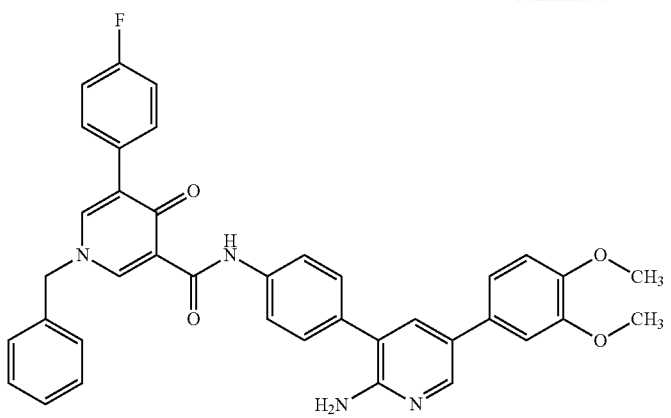
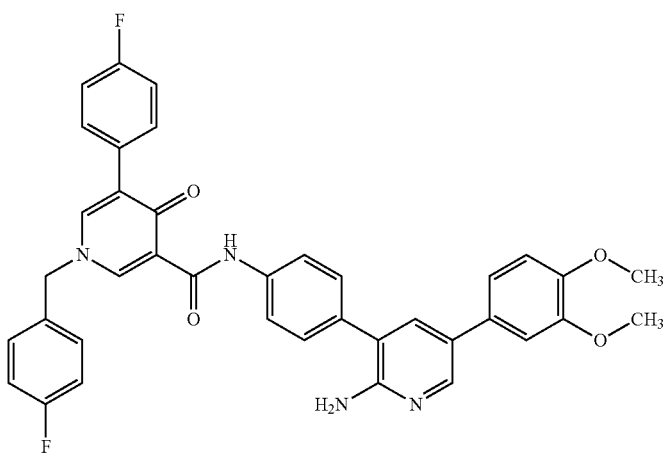
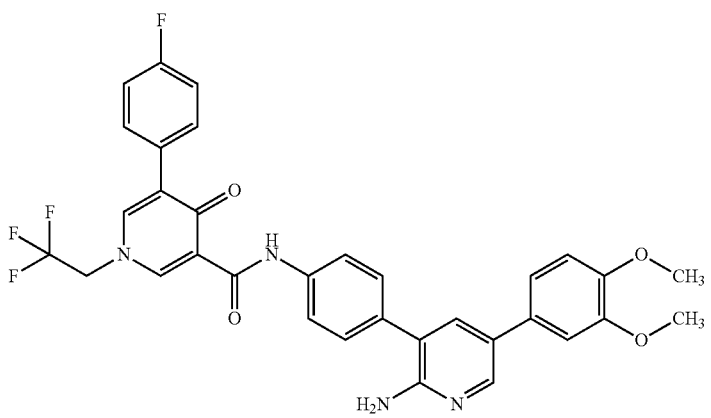
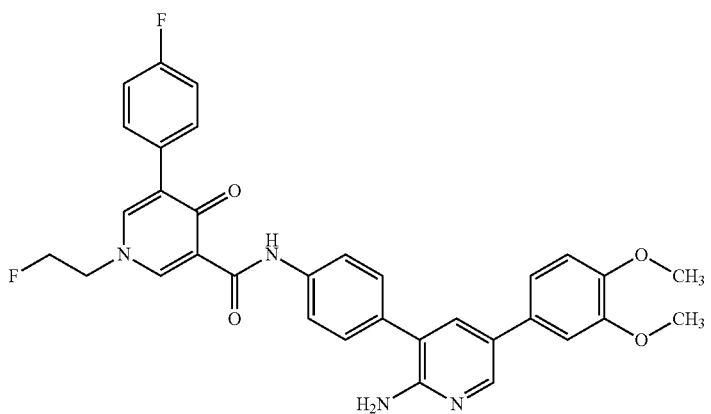

-continued
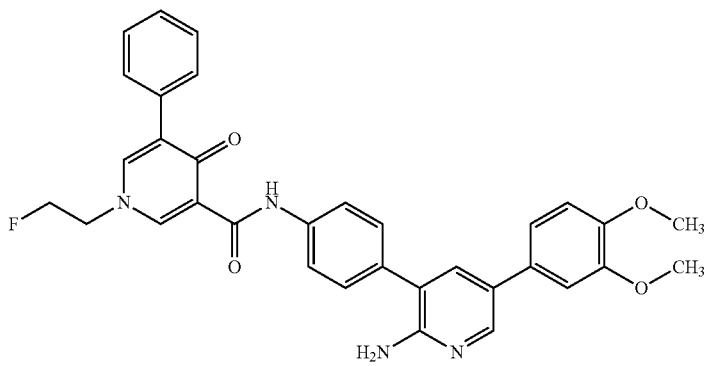
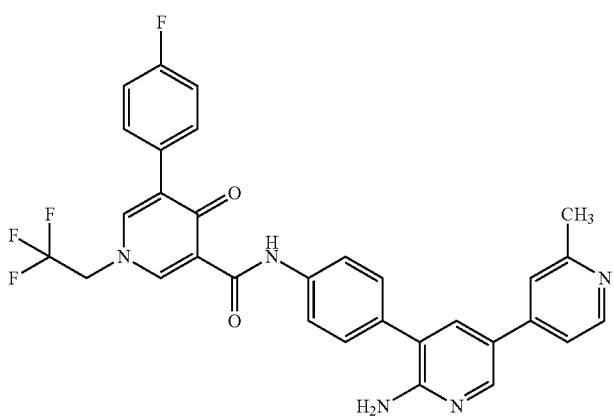
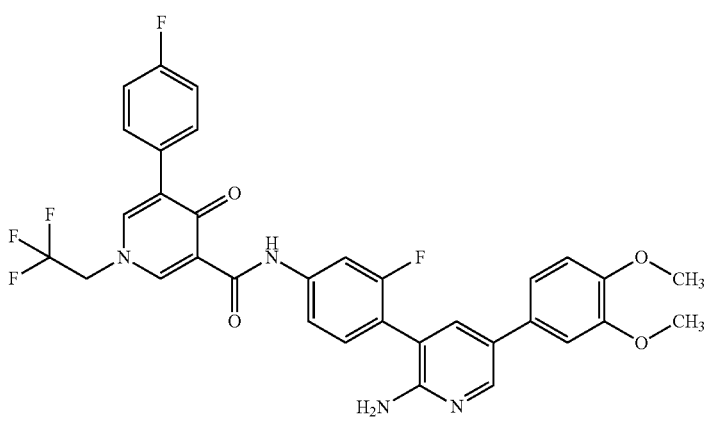
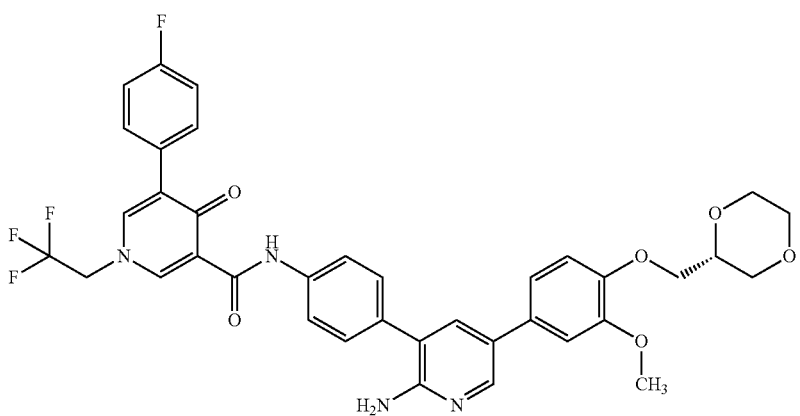

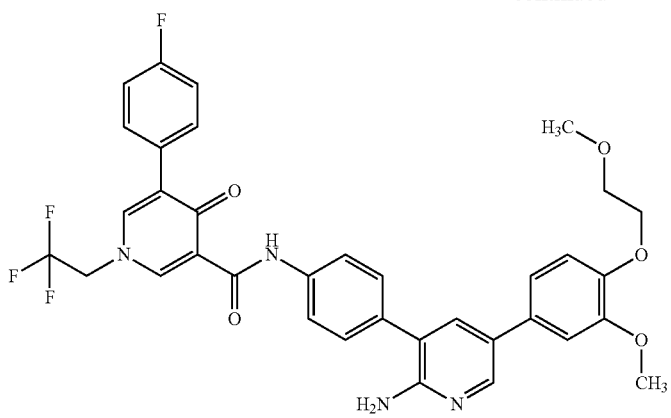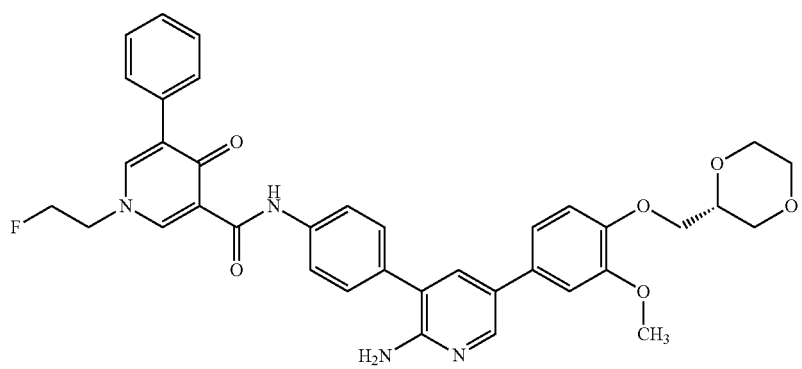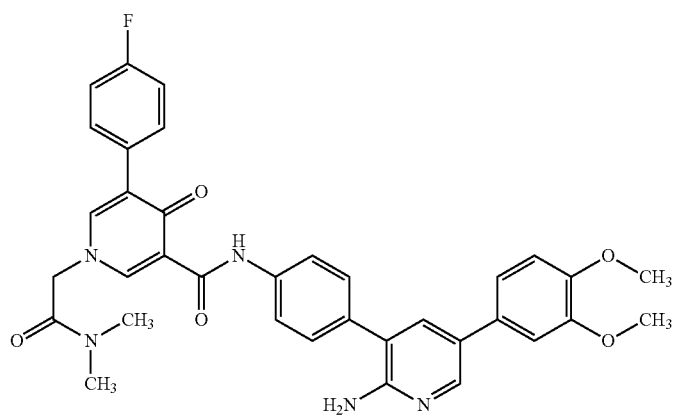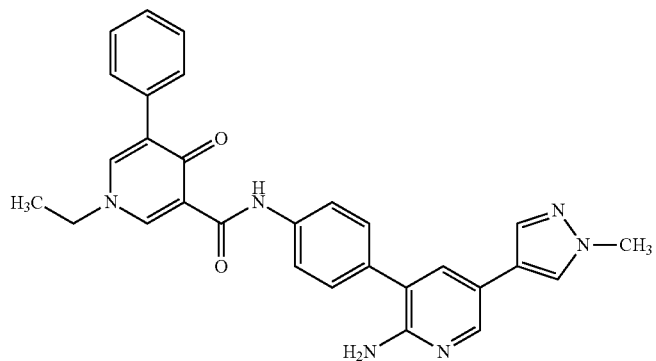

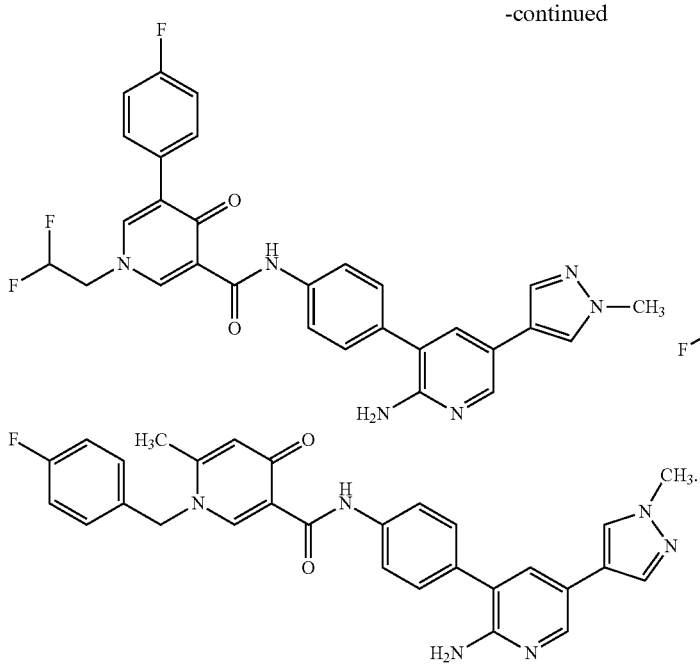
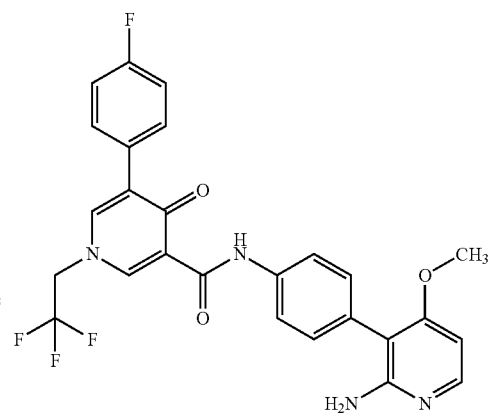

The compounds represented by formula (1) according to the present invention may exist as stereoisomers, or optical isomers derived from asymmetric carbon atoms. Such stereoisomers and optical isomers and mixtures thereof are all encompassed by the present invention.

When the compounds represented by the general formula (1) according to the present invention have a basic group such as an amino group, they can be converted to pharmaceutically acceptable salts as desired. Examples of such salts include hydrohalic acid salts such as hydrochlorides and hydroiodides; inorganic acid salts such as nitrates, perchlorates, sulfates and phosphates; lower alkanesulfonates such as methanesulfonates, trifluoromethanesulfonates and ethanesulfonates; arylsulfonates such as benzenesulfonates and p-toluenesulfonates; organic acid salts such as formates, acetates, malates, fumarates, succinates, citrates, tartrates, oxalates and maleates; and amino acid salts such as ornithinates, glutamates and aspartates. Hydrohalic acid salts and organic acid salts are preferred.

When the compounds represented by the general formula (1) according to the present invention have an acidic group such as a carboxy group, base addition salts can generally be formed. Examples of pharmaceutically acceptable salts include alkali metal salts such as sodium salts, potassium salts and lithium salts; alkaline earth metal salts such as calcium salts and magnesium salts; inorganic salts such as ammonium salts; and organic amine salts such as dibenzylamine salts, morpholine salts, phenylglycine alkyl ester salts, ethylenediamine salts, N-methylglucamine salts, diethylamine salts, triethylamine salts, cyclohexylamine salts, dicyclohexylamine salts, N,N'-dibenzylethylenediamine salts, diethanolamine salts, N-benzyl-N-(2-phenylethoxy)amine salts, piperazine salts, tetramethylammonium salts and tris(hydroxymethyl)aminomethane salts.

The compounds represented by the general formula (1) or salts thereof according to the present invention may also exist as free forms or solvates. They may also exist as solvates due to absorption of moisture in the air, for example. Solvates are not particularly limited if pharmaceutically acceptable, but hydrates (such as monohydrates or dihydrates) and ethanolates are specifically preferred. When nitrogen atoms are present in the inventive compounds represented by the general formula (1), N-oxides may be formed. These solvates and N-oxides are also encompassed within the scope of the present invention.

The compounds represented by the general formula (1) according to the present invention may exist as various isomers including geometric isomers such as cis and trans isomers, tautomers, or optical isomers such as d- and l-isomers depending on the types and combinations of the substituents. The compounds of the present invention include all of these isomers and stereoisomers, and mixtures of any proportions of these isomers and stereoisomers, unless otherwise specified.

The compounds represented by the general formula (1) according to the present invention may also contain unnatural proportions of atomic isotopes at one or more of the atoms that constitute the compounds. Examples of atomic isotopes include deuterium ($^2H$), tritium ($^3H$), iodine-125 ($^{125}I$) and carbon-14 ($^{14}C$). These compounds are useful as therapeutic or prophylactic agents, research reagents such as assay reagents, and diagnostic agents such as in vivo diagnostic imaging agents. All isotopic variants of the compounds represented by the general formula (1), whether radioactive or not, are encompassed within the scope of the present invention.

The present invention also encompasses compounds that are active ingredients of the pharmaceutical compositions of the present invention and are converted to the compounds represented by the general formula (1) by reactions by enzyme, gastric acid or the like under physiological conditions in vivo. Specifically, the compounds are "pharmaceutically acceptable prodrug compounds" that are, for example, enzymically oxidized, reduced or hydrolyzed and thus are converted to the compounds represented by the general formula (1), or are hydrolyzed by gastric acid or the like and thus are converted to the compounds represented by the general formula (1).

Examples of the prodrugs of the compounds represented by the general formula (1) in which an amino group is present include compounds in which the amino group is acylated, alkylated or phosphorylated (for example, compounds in which the amino group is eicosanoylated, alanylated, pentylaminocarbonylated, (5-methyl-2-oxo-1,3-dioxolen-4-yl)methoxycarbonylated, tetrahydrofuranylated, pyrrolidylmethylated, pivaloyloxymethylated or tert-butylated). Examples of the prodrugs of the compounds represented by the general formula (1) in which a hydroxyl group is present include compounds in which the hydroxyl group is acylated, alkylated, phosphorylated or borated (for example, compounds in which the hydroxyl group is acetylated, palmitoylated, propanoylated, pivaloylated, succinylated, fumarylated, alanylated or dimethylaminomethylcarbonylated). Examples of the prodrugs of the compounds represented by the general formula (1) in which a carboxy group is present include compounds in which the carboxy group is esterified or amidated (for example, compounds in which the carboxy group is ethyl esterified, phenyl esterified, carboxymethyl esterified, dimethylaminomethyl esterified, pivaloyloxymethyl esterified, ethoxycarbonyloxyethyl esterified, amidated or methylamidated).

Prodrugs of the compounds of the present invention can be produced from the compounds represented by the general formula (1) by known methods. Prodrugs of the compounds of the present invention also include those converted to the compounds represented by the general formula (1) under physiological conditions as described in "Iyakuhin No Kaihatsu," Development of Pharmaceuticals, Vol. 7, Bunshi Sekkei, Molecular Design, Hirokawa Shoten, 1990, pp. 163-198.

Next, representative production processes for the compounds represented by the general formula (1) will be described. The compounds of the present invention can be produced by various production processes. The production processes illustrated below are merely examples, and the present invention should not be construed to be limited thereto. The reactions can be performed with substituents protected by appropriate protecting groups as required, and the type of the protecting group is not particularly limited.

In the following formulas, A, $R^1$, $R^2$, $R^3$, $R^4$, $R^5$, $R^6$, $R^A$, $R^B$, W and X are as described above, $M^1$ to $M^4$ each represent a boronic acid or boronate ester, an alkyltin or the like, and $L^1$ to $L^3$ each represent a halogen atom or the like.

Compound 1a illustrated below, which is a compound represented by formula (1), can be produced according to the following reaction formula, for example.

[Production Process 1]

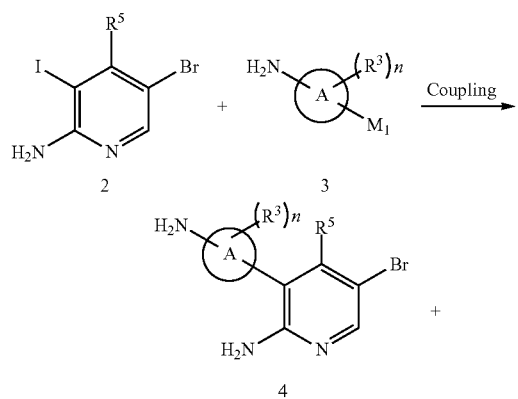

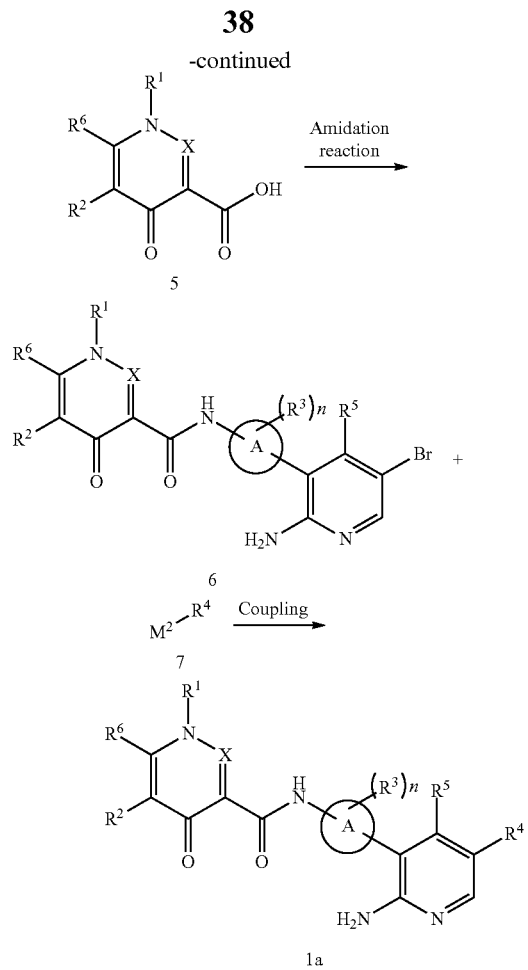

(1) Conversion of Compound 2 to Compound 4

Compound 2 is converted to Compound 4 by a coupling reaction of Compound 2 with a compound that has a partial structure containing A (such as Compound 3) using a known organic chemistry technique.

The reaction is performed by adding to Compound 2 an organic or inorganic base (such as sodium carbonate, potassium carbonate, tripotassium phosphate or diisopropylethylamine), a ligand (such as triphenylphosphine) and a known reaction-promoting additive (such as lithium chloride or copper iodide) as required in the presence of an appropriate organoboronic acid, organotin, organozinc or organomagnesium derivative or the like (such as Compound 3) and an appropriate transition metal catalyst (such as a palladium compound).

The above coupling reaction is performed using an appropriate solvent not adversely affecting the reaction (such as N,N-dimethylformamide, tetrahydrofuran, toluene, 1,4-dioxane or water) or a mixed solvent thereof. The reaction is performed at a temperature of preferably 0° C. to 300° C., and more preferably at room temperature to 200° C. The optimum temperature is 80° C. to 100° C. The above reaction can also be performed by treatment in a sealed tube or under microwave irradiation. The organoboronic acid or the like and the base are each preferably used in an amount of one to excess molar equivalents in relation to Compound 2. The organoboronic acid or the like is more preferably used in an amount of 1 to 1.5 molar equivalents and the base is more preferably used in an amount of 1 to 5 molar equivalents, each as in relation to Compound 2. The reaction time is preferably 1 minute to 60 hours, and more preferably 5 minutes to 24 hours.

(2) Conversion of Compound 4 to Compound 6

Compound 4 is converted to Compound 6 by an amidation reaction of Compound 4 using a known organic chemistry technique. The reaction is performed by reacting Compound 5 with a separately synthesized carboxylic acid. The reaction is performed in an appropriate solvent not adversely affecting the reaction (such as benzene, toluene, diethyl ether, dichloromethane, tetrahydrofuran or N,N-dimethylformamide) or a mixed solvent thereof. The reaction is performed at −30° C. to the boiling point of the solvent used for the reaction, and preferably at 0° C. to 50° C., in the presence of an appropriate condensing agent such as N,N-dicyclohexylcarbodiimide, 1-ethyl-3-(3-dimethylaminopropyl)carbodiimide, diethyl cyanophosphate, (1-cyano-2-ethoxy-2-oxoethylideneaminooxy)dimethylamino-morpholino-carbenium hexafluorophosphate (COMU) or N,N,N',N'-tetramethyl-O-(7-azabenzotriazol-1-yl)uronium hexafluorophosphate (HATU).

The condensing agent may be used in an amount of excess molar equivalents, and preferably 1 to 5 molar equivalents, in relation to Compound 4. The reaction may also be performed with the addition of a base (such as triethylamine, diisopropylethylamine, N-methylmorpholine or 4-dimethylaminopyridine) as required. The base can be used in a catalytic amount or in an excess amount.

The reaction time is preferably 10 minutes to 72 hours, and more preferably 30 minutes to 24 hours. The reaction is performed using a known reaction-promoting additive (such as 1-hydroxybenzotriazole or 1-hydroxy-7-azabenzotriazole) as required. The reaction-promoting additive can be used in a catalytic amount to an excess amount.

The reaction can also be performed by reacting Compound 4 with a carboxylic halide derived from the carboxylic acid Compound 5. The reaction is performed in an appropriate solvent not adversely affecting the reaction (such as benzene, toluene, diethyl ether, dichloromethane, tetrahydrofuran or N,N-dimethylformamide) or a mixed solvent thereof. The reaction is performed at −30° C. to the boiling point of the solvent used for the reaction, and preferably at 0° C. to 100° C., in the presence of an appropriate base (such as triethylamine, diisopropylethylamine, N-methylmorpholine or 4-dimethylaminopyridine). The base can be used in a catalytic amount or in an excess amount.

The reaction time is preferably 10 minutes to 72 hours, and more preferably 30 minutes to 24 hours.

Alternatively, the reaction can be performed by reacting Compound 4 with the carboxylic acid Compound 5 in an acidic solvent (such as polyphosphoric acid) at 0° C. to the boiling point of the solvent used for the reaction, and preferably at 10° C. to 120° C. The reaction time is preferably 10 minutes to 72 hours, and more preferably 30 minutes to 24 hours.

(3) Conversion of Compound 6 to Compound 1a

Compound 6 is converted to Compound 1a by a coupling reaction of Compound 6 with a compound that has a partial structure containing $R^4$ (such as Compound 7) using a known organic chemistry technique. A common coupling reaction similar to the coupling reaction described in (1) can be applied.

For example, the reaction is performed by adding to Compound 6 an organic or inorganic base (such as sodium carbonate, potassium carbonate, tripotassium phosphate or diisopropylethylamine), a ligand (such as triphenylphosphine) and a known reaction promoting additive (such as lithium chloride or copper iodide) as required in the presence of an appropriate organoboronic acid, organotin, organozinc or organomagnesium derivative or the like (such as Compound 7) and an appropriate transition metal catalyst (such as a palladium compound).

The above coupling reaction is performed using an appropriate solvent not adversely affecting the reaction (such as N,N-dimethylformamide, tetrahydrofuran, toluene, 1,4-dioxane or water) or a mixed solvent thereof. The reaction is performed at a temperature of preferably 0° C. to 300° C., and more preferably at room temperature to 200° C. The optimum temperature is 80° C. to 120° C. The above reaction can also be performed by treatment in a sealed tube or under microwave irradiation. The organoboronic acid or the like and the base may each be used in an amount of one to excess molar equivalents, and preferably 1 to 5 molar equivalents, in relation to Compound 6. The reaction time is preferably 1 minute to 60 hours, and more preferably 5 minutes to 24 hours.

[Production Process 2]

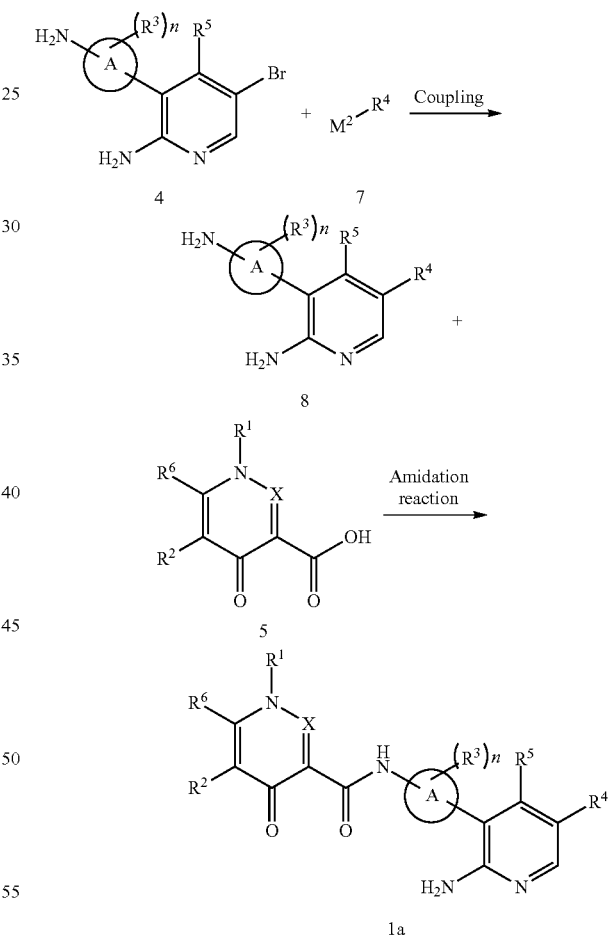

Compound 1a can also be obtained by performing the amidation reaction (2) and the coupling reaction (3) in the reverse order for Compound 4 of the above Production Process 1.

(1) Conversion of Compound 4 to Compound 8

Compound 4 can be converted to Compound 8 by a common coupling reaction similar to the method described in (1) of the above Production Process 1.

(2) Conversion of Compound 8 to Compound 1a

Compounds 8 and 5 can be converted to Compound 1a by a common amidation reaction similar to the method described in the above Production Process 1.

[Production Process 3]

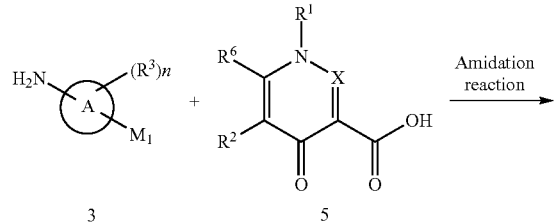

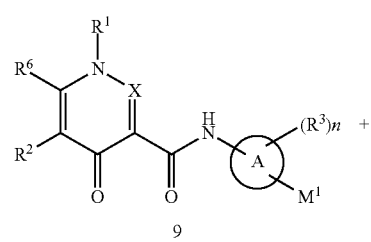

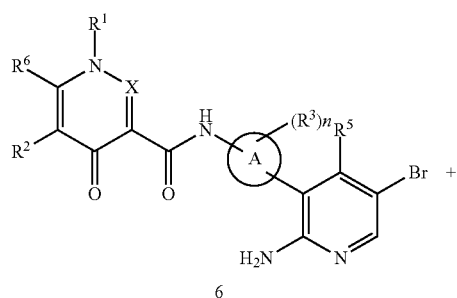

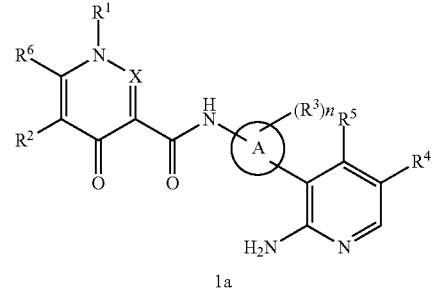

Compound 1a can also be obtained by first synthesizing Compound 9, which has a partial structure containing A, and then performing coupling reaction of Compound 9 with Compound 2.

(1) Conversion of Compound 3 to Compound 9

Compounds 3 and 5 are converted to Compound 9 by an amidation reaction of Compound 3 using a known organic chemistry technique. The details of the reaction are similar to those of the method (2) described in Production Process 1 (a common amidation reaction).

(2) Conversion of Compound 9 to Compound 6

Compounds 2 and 9 are converted to Compound 6 by a coupling reaction of Compound 2 with Compound 9, which has a partial structure containing A, using a known organic chemistry reaction. The details of the reaction are similar to those of the method (1) described in Production Process 1 (a common coupling reaction).

(3) Conversion of Compound 6 to Compound 1a

The conversion of Compound 6 to Compound 1a is as illustrated in Production Process 1.

[Production Process 4]

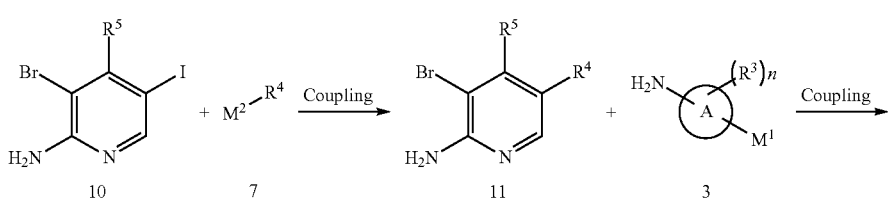

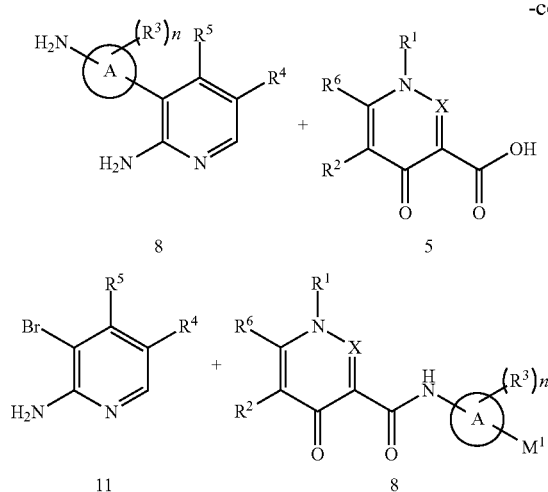
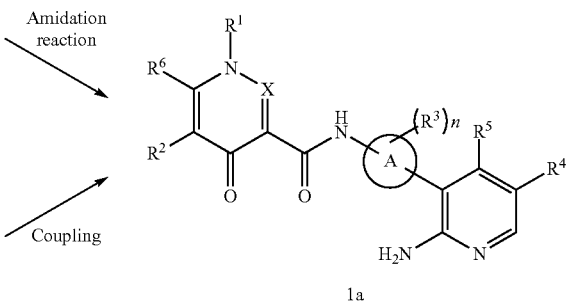

Compound 1a can also be produced using Compound 10.

The details of the reaction are similar to those of Production Processes 1 and 2, and Compounds 3 and 7 can be used in the reverse order in the steps of Production Process 4.

Compound 8 of Production Process 4 can also be produced according to the following reaction formula, for example.

[Production Process 5]

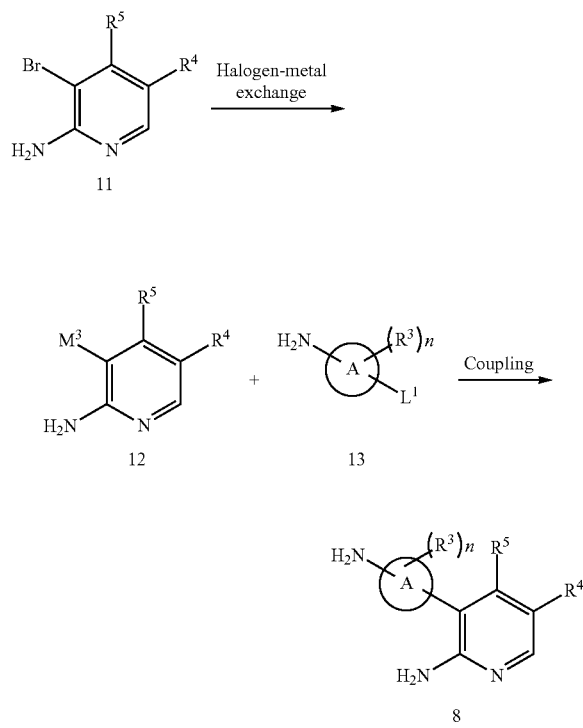

(1) Conversion of Compound 11 to Compound 12

Compound 11 is converted to Compound 12 by subjecting Compound 11 to halogen-metal exchange reaction using a known organic chemistry technique. The reaction is performed by adding to Compound 11 an organic or inorganic base (such as potassium acetate, sodium carbonate or diisopropylethylamine), a ligand (such as triphenylphosphine) and a known reaction-promoting additive (such as lithium chloride or copper iodide) as required in the presence of an appropriate diboronate ester, alkyltin compound or the like and an appropriate transition metal catalyst (such as a palladium compound), for example.

The above coupling reaction is performed using an appropriate solvent not adversely affecting the reaction (such as N,N-dimethylformamide, tetrahydrofuran, toluene, 1,4-dioxane or water) or a mixed solvent thereof. The reaction is performed at a temperature of preferably 0° C. to 300° C., and more preferably at room temperature to 200° C. The above reaction can also be performed by treatment in a sealed tube or under microwave irradiation. The diboronate ester or the like and the base may each be used in an amount of one to excess molar equivalents, and preferably 1 to 5 molar equivalents, in relation to Compound 11. The reaction time is preferably 1 minute to 60 hours, and more preferably minutes to 24 hours.

(2) Conversion of Compound 12 to Compound 8

Compound 12 is converted to Compound 8 by a coupling reaction of Compound 12 with Compound 13 using a known organic chemistry technique.

The reaction is performed by adding to Compound 12 an organic or inorganic base (such as sodium carbonate, potassium carbonate, tripotassium phosphate or diisopropylethylamine), a ligand (such as triphenylphosphine) and a known reaction promoting additive (such as lithium chloride or copper iodide) as required in the presence of Compound 13 and an appropriate transition metal catalyst (such as a palladium compound), for example.

The above coupling reaction is performed using an appropriate solvent not adversely affecting the reaction (such as N,N-dimethylformamide, tetrahydrofuran, toluene, 1,4-dioxane or water) or a mixed solvent thereof. The reaction is performed at a temperature of preferably 0° C. to 300° C., and more preferably at room temperature to 200° C. The optimum temperature is 80° C. to 100° C. The above reaction can also be performed by treatment in a sealed tube or under microwave irradiation. Compound 13 and the base may each be used in an amount of one to excess molar equivalents, and preferably 1 to 5 molar equivalents, in relation to Compound 12. The reaction time is preferably 1 minute to 60 hours, and more preferably 5 minutes to 24 hours.

Compound 1a can also be produced from Compound 14, which can be synthesized from Compounds 5 and 13, and the aforementioned Compound 12.

[Production Process 6]

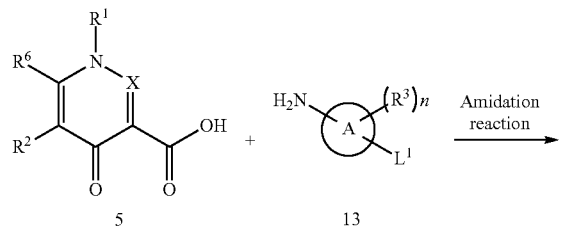

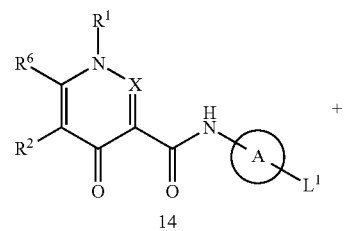

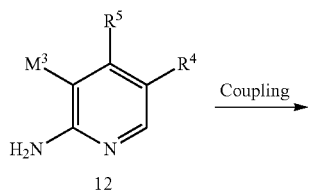

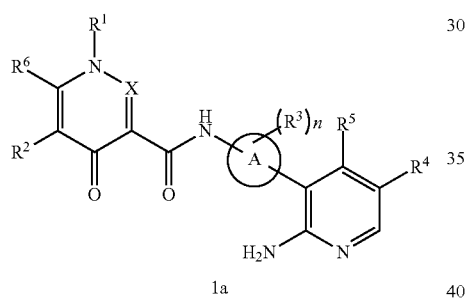

The details of the reaction are similar to those of Production Process 5.

Compound 1b which is a compound represented by formula (1), where W is N or CH, can be produced according to the following Production Process 7.

[Production Process 7]

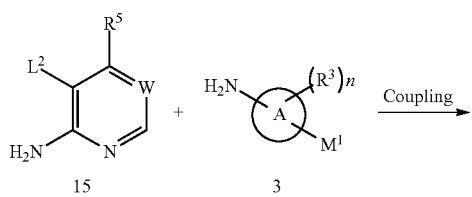

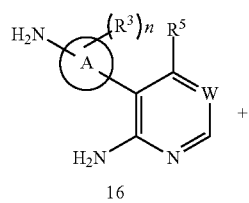

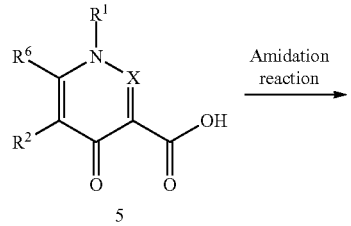

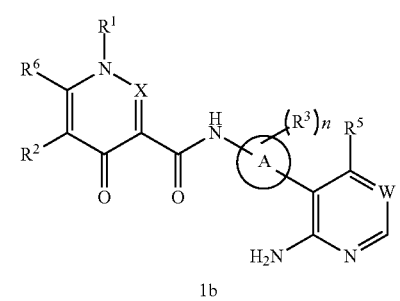

Compound 15 can be converted to Compound 16 by an operation similar to the common coupling reaction described in Production Process 1.

Compound 16 can be converted to Compound 1b by an operation similar to the common amidation reaction described in Production Process 1.

[Production Process 8]

Compound 1b can also be produced as in Production Process 8 where the reactions in Production Process 7 are performed in the reverse order.

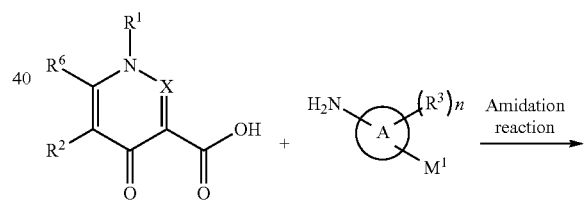

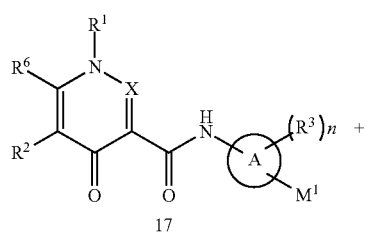

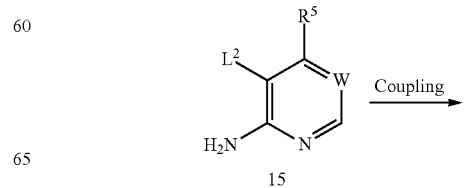

-continued

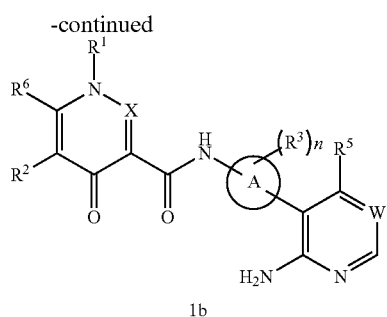

1b

The details of the reaction are similar to those of the method described in Production Process 7.

[Production Process 9]

Compound 5a illustrated below, which is a Compound 5, can be produced using Intermediate 18. Intermediate 18 is commercially available or can be synthesized by a known method or with reference to an example previously reported in J. Heterocyclic Chem. 1980, 17, 359, Chem. Pharm. Bull. 1995, 43, 450 or the like. Hereinafter, $L^3$ represents a halogen atom, a methanesulfonyloxy group, a trifluoromethanesulfonyloxy group, a p-toluenesulfonyloxy group or the like.

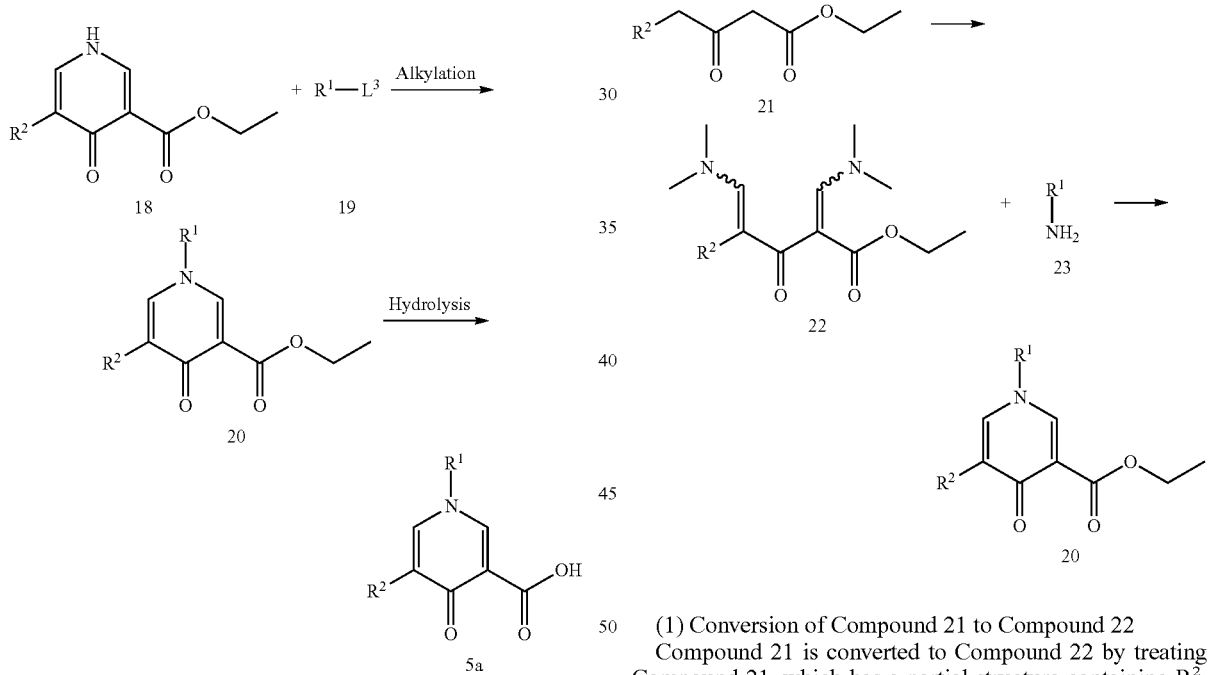

(1) Conversion of Compound 18 to Compound 20

Compound 18 may be converted to Compound 20 by subjecting Compound 18 to an alkylation reaction using a known organic chemistry technique. For example, the reaction is performed by treating Compound 18 with Compound 19, which has a partial structure containing $R^1$, (such as an alkyl halide compound, a methanesulfonyloxyalkyl compound, a trifluoromethanesulfonyloxyalkyl compound or a p-toluenesulfonyloxyalkyl compound) in an appropriate solvent not adversely affecting the reaction (such as N,N-dimethylformamide, dimethyl sulfoxide or acetonitrile) or a mixed solvent thereof. The reaction is performed in the presence of an organic or inorganic base (such as potassium carbonate, cesium carbonate, potassium tert-butoxide or triethylamine) at 0° C. to 300° C., and preferably at 0° C. to 100° C. Compound 19 and the base may each be used in an amount of one to excess molar equivalents, and preferably 1 to 5 molar equivalents, in relation to Compound 18. The reaction time is preferably 1 minute to 72 hours, and more preferably 5 minutes to 24 hours.

(2) Conversion of Compound 20 to Compound 5a

Compound 20 may be converted to Compound 5a by a common hydrolysis reaction. For example, the reaction is performed by treating Compound 20 with an appropriate acid (such as sulfuric acid or hydrochloric acid) or alkali (such as sodium hydroxide or potassium carbonate) in an appropriate solvent not adversely affecting the reaction (such as ethanol, propanol or water) or a mixed solvent thereof. The reaction is performed at a temperature of 0° C. to 200° C., and preferably at 0° C. to 100° C. Each of the appropriate acid or alkali is used in an amount of one to excess molar equivalents in relation to Compound 20. The reaction time is preferably 1 minute to 72 hours, and more preferably 5 minutes to 24 hours.

[Production Process 10]

Compound 20 in Production Process 9 can also be produced from an ester Compound 21 that can be synthesized with reference to J. Org. Chem. 1988, 53, 873 or the like.

(1) Conversion of Compound 21 to Compound 22

Compound 21 is converted to Compound 22 by treating Compound 21, which has a partial structure containing $R^2$, with N,N-dimethylformamide dimethylacetal without a solvent or in an appropriate solvent not adversely affecting the reaction (such as toluene, xylene, dichloromethane, ethanol, N,N-dimethylformamide or ethyl acetate) or a mixed solvent thereof. The reaction is performed at 0° C. to 300° C., and preferably at 0° C. to 130° C. N,N-Dimethylformamide dimethylacetal may be used in an amount of two to excess molar equivalents in relation to Compound 21. The reaction time is preferably 1 minute to 72 hours, and more preferably 5 minutes to 24 hours.

(2) Conversion of Compound 22 to Compound 20

Compound 22 is converted to Compound 20 by treating Compound 22 with Compound 23, which has a partial structure containing $R^2$, in an appropriate solvent not affecting the reaction (such as toluene, ethyl acetate, ethanol or 1,4-dioxane) or a mixed solvent thereof. The reaction is performed at 0° C. to 300° C., and preferably at 0° C. to 130° C. The reaction is performed by adding an organic or inorganic base (such as potassium carbonate, cesium carbonate, potassium tert-butoxide or triethylamine) or an acid (such as acetic acid, hydrogen chloride, hydrogen bromide or sulfuric acid) as required. Compound 23 and the base or acid may each be used in an amount of one to excess molar equivalents, and preferably 1 to 5 molar equivalents, in relation to Compound 22. The reaction time is preferably 1 minute to 72 hours, and more preferably 5 minutes to 24 hours.

In Production Process 10, an orthoformate (such as ethyl orthoformate) may also be used in place of N,N-dimethylformamide dimethylacetal.

In Production Process 10, it is also possible to use a salt of Compound 23, which has a partial structure containing $R^1$, with an acid.

[Production Process 11]

Compound 5a can also be produced using Compound 24, which is known from J. Med. Chem. 2008, 51, 5330.

mide, dimethyl sulfoxide, 1,4-dioxane or acetonitrile) or a mixed solvent thereof. The reaction is performed in the presence of an organic or inorganic base (such as potassium carbonate, cesium carbonate, potassium tert-butoxide or triethylamine) at 0° C. to 300° C., and preferably at 0° C. to 100° C. Compound 19 may be used in an amount of two to excess molar equivalents, and preferably 2 to 10 molar equivalents, in relation to Compound 24. The reaction time is preferably 1 minute to 72 hours, and more preferably 5 minutes to 24 hours.

(2) Compound 25 may be converted to Compound 27 by subjecting Compound 25 to an operation similar to the common coupling reaction described in Production Process 1.

(3) Compound 27 may be converted to Compound 5a by subjecting Compound 27 to an operation similar to the common hydrolysis reaction described in Production Process 9.

[Production Process 12]

Compound 27 in Production Process 11 can also be produced from a carboxylic acid Compound 28.

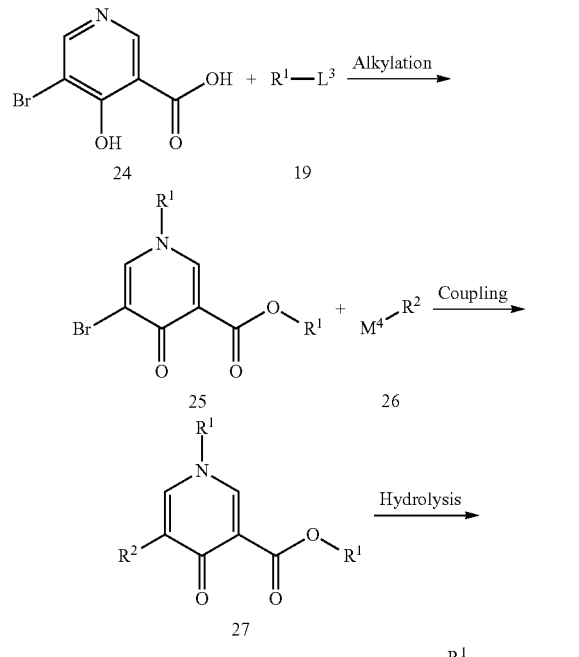

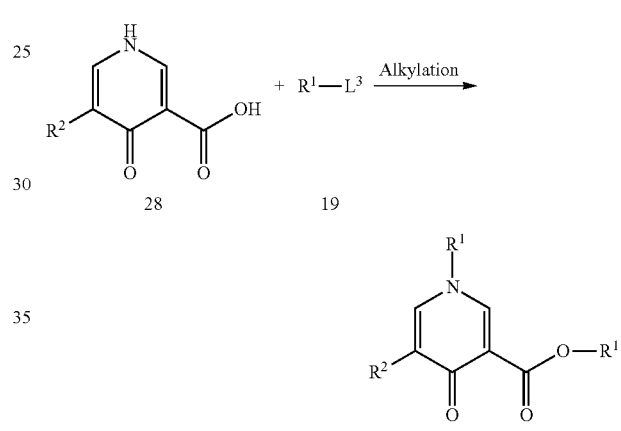

Compounds 28 and 19 may be converted to Compound 27 by subjecting Compound 28 to a reaction similar to the alkylation reaction described in Production Process 11-(1).

[Production Process 13]

Compound 5b shown below can be synthesized with reference to the method in Tetrahedron, 1995, 51, 12745.

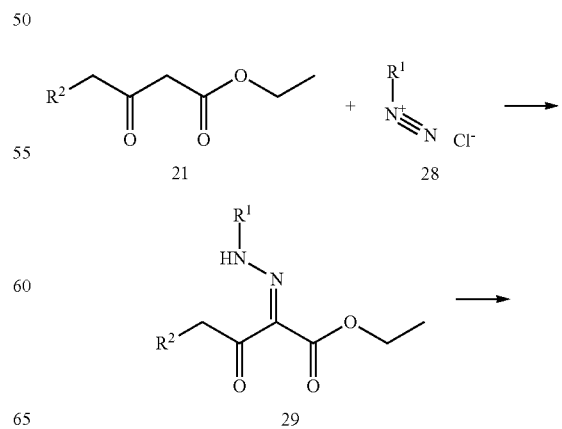

(1) Conversion of Compound 24 to Compound 25

Compound 24 may be converted to Compound 25 by subjecting Compound 24 to an alkylation reaction using a known organic chemistry technique. For example, the reaction is performed by treating Compound 24 with Compound 19, which has a partial structure containing $R^1$, (such as an alkyl halide compound, a methanesulfonyloxyalkyl compound, a trifluoromethanesulfonyloxyalkyl compound or a p-toluenesulfonyloxyalkyl compound) in an appropriate solvent not adversely affecting the reaction (such as N,N-dimethylforma- -continued

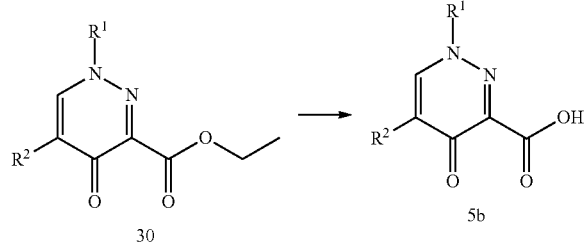

(1) Conversion of Compound 21 to Compound 29

Compound 21 is converted to Compound 29 by treating Compound 21 with a diazo Compound 28, which has a partial structure containing $R^1$, in an appropriate solvent not adversely affecting the reaction (such as acetone, methanol, ethanol or water) or a mixed solvent thereof. The reaction is performed in the presence of a base (such as potassium carbonate, sodium acetate or potassium acetate) at 0° C. to 300° C., and preferably at 0° C. to 100° C. Compound 28 may be used in an amount of one to excess molar equivalents, and preferably one molar equivalent, in relation to Compound 21. The reaction time is preferably 1 minute to 72 hours, and more preferably 5 minutes to 24 hours.

(2) Compound 29 may be converted to Compound 30 by subjecting Compound 29 to an operation similar to the method described in Production Process 10. N,N-Dimethylformamide dimethylacetal may be used in an amount of one to excess molar equivalents in relation to Compound 29.

(3) Compound 30 may be converted to Compound 5b by subjecting Compound 29 to an operation similar to the common hydrolysis reaction described in Production Process 9.

[Production Process 14]

As illustrated below, Compounds 5c and 5d shown below can be synthesized using Compound 27a, which has a partial structure containing a carboxylate, which is a Compound 27. Compound 27 can be synthesized according to Production Process 11. Hereinafter, $R^7$ and $R^8$ each represent a methyl group, an ethyl group, a tert-butyl group or the like.

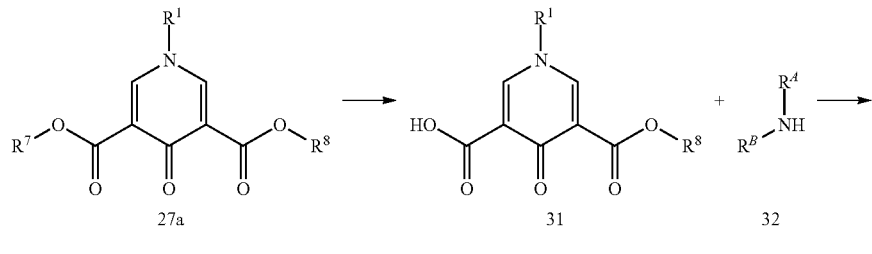

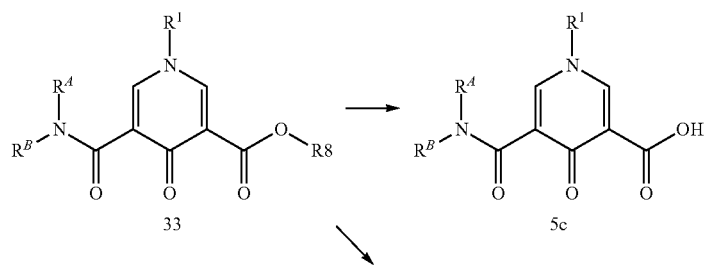

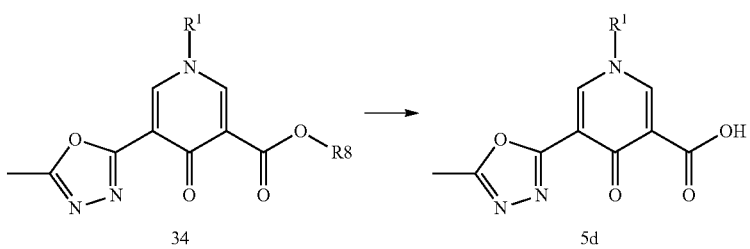

(1) Compound 27a may be converted to Compound 31 by subjecting Compound 27a to an operation similar to the hydrolysis reaction described in Production Process 9.

(2) Compound 31 may be converted to Compound 33 by subjecting Compound 31 to an operation similar to the common amidation reaction described in Production Process 1.

(3) Compound 33 can be converted to Compound 34 by subjecting Compound 33 to common reaction conditions for oxadiazole formation with reference to Tetrahedron Letters (2006), 47, 511, for example. The reaction is performed by treating Compound 33 with hexachloroethane and triphenylphosphine in an appropriate solvent not adversely affecting the reaction (such as dichloromethane, tetrahydrofuran or acetonitrile) or a mixed solvent thereof in the presence of a base (such as diisopropylethylamine or triethylamine). The reaction is performed at 0° C. to 300° C., and preferably at 0° C. to 100° C. The base, hexachloroethane and triphenylphosphine may each be used in an amount of one to excess molar equivalents, and preferably 1 to 5 molar equivalents, in relation to Compound 33. The reaction time is preferably 1 minute to 72 hours, and more preferably 5 minutes to 24 hours.

(4) Compound 33 may be converted to Compound 5c by subjecting Compound 33 to an operation similar to the hydrolysis reaction described in Production Process 9.

(5) Compound 34 can be converted to Compound 5d by alkali hydrolysis reaction. For example, the reaction is performed by treating Compound 34 with an appropriate alkali (such as sodium hydroxide or potassium carbonate) in an appropriate solvent not adversely affecting the reaction (such as ethanol, propanol, tetrahydrofuran or water) or a mixed solvent thereof. The reaction is performed at a temperature of 0° C. to 200° C., and preferably at room temperature to 150° C. The appropriate alkali is used in an amount of one to excess molar equivalents in relation to Compound 34. The reaction time is preferably 1 minute to 72 hours, and more preferably 5 minutes to 24 hours.

Production raw material 2, 10 or 15 is commercially available or can be synthesized according to a known method.

Production raw material 3 is commercially available or can be synthesized according to a known method such as described in the literature (such as Bioorg. Med. Chem. Lett., 2007, 17, 5406).

Production raw material 7 is commercially available or can be synthesized according to a known method or a method described in the Reference Examples.

Production raw material 18, 28, 21 or 27a is commercially available or can be synthesized according to a known method or a method described in Reference Examples.

Production raw material 19 is commercially available or can be synthesized according to a known method.

As described above, the Gas6/Axl signaling system has been reported to modulate various cellular responses such as cell survival, cell division, autophagy, cell migration, angiogenesis, platelet aggregation and NK cell differentiation (Rachel M A Linger et al., Expert Opin. Ther. Targets, 2010, 14, 1073). Therefore, Axl inhibitors are useful for treating diseases caused by Axl kinase hyperfunction, diseases associated with Axl kinase hyperfunction and/or diseases accompanied by Axl kinase hyperfunction.

Diseases caused by Axl kinase hyperfunction, diseases associated with Axl kinase hyperfunction and diseases accompanied by Axl kinase hyperfunction include diseases involving tissues in which Axl genes and/or proteins are overexpressed, and diseases involving tissues in which the phosphorylation activity of Axl is increased.

Examples of the above diseases include hyperproliferative diseases. Examples of hyperproliferative diseases include, but are not limited to, endometrial hyperplasia, thrombin-induced vascular smooth muscle cell (VSMC) growth, benign tumor, malignant tumor (cancer), acute and chronic glomerulonephritis, and diabetic nephropathy.

It has further been demonstrated that Axl has a role in immunity (Lu et al., Science, 2001, 293, 306), platelet function (Angelillo-Scherrer et al., Nat. Med., 2001, 7, 215), spermatogenesis (Lu et al., Nature, 1999, 398, 723), vascular calcification (Son et al., Eur. J. Pharmacol., 2007, 556, 1), (Nakano et al, J. Biol. Chem., 1995, 270, 5702), and various renal diseases such as chronic allograft rejection (Yanagita et al., J. Clin. Invest., 2002, 110, 239). Axl inhibitors are useful for treating many diseases such as vascular diseases (including, but not limited to, thrombosis, atherosclerosis and restenosis) and diseases with significant chaotic angiogenesis (including, but not limited to, diabetic retinopathy, retinopathy, psoriasis, rheumatoid arthritis, atheroma, Kaposi's sarcoma and hemangioma).

The compounds or salts thereof, or crystals thereof, according to the present invention inhibit Axl and are thus useful for treating the above-described diseases.

More preferably, the compounds or salts thereof, or crystals thereof, according to the present invention are useful for treating various cancers. Examples of cancers include, but are not limited to, breast cancer, colon cancer, prostate cancer, lung cancer, gastric cancer, ovarian cancer, cervical cancer, endometrial cancer, uterine body cancer, renal cancer, hepatocellular carcinoma, thyroid cancer, esophageal cancer, squamous cell carcinoma, leukemia, osteosarcoma, melanoma, glioblastoma, neuroblastoma, ovarian cancer, head and neck cancer, testicular tumor, colorectal cancer, blood cancer, retinoblastoma and pancreatic cancer.

Various reports on the relationship between cancer and Axl have been made in terms of inhibition of growth, inhibition of metastasis, migration and invasion, and overcoming drug resistance.

Axl dominant negative mutants have been reported to inhibit brain tumor growth (Vajkoczy et al., PNAS, 2006, 103, 5799). It has been reported that when Axl is expressed or Axl/Gas6 are coexpressed in tissues derived from glioblastoma patients, the tumors grow significantly more rapidly and the lifetime of the patients is shorter than in patients with low Axl expression or low Asl/Gas6 coexpression (Hutterer et al., Clin Cancer Res, 2008, 14, 130). Axl shRNA has been reported to inhibit proliferation of breast cancer cells (Yi-Xiang et al., Cancer Res, 2008, 68, 1905). As is clear from these reports, Axl inhibitors are useful for inhibiting cell proliferation in cancer.

On the other hand, Axl dominant negative mutants have been reported to inhibit cell migration and invasion (Zhang et al., Cancer Res, 2008 68, 1905, Vajkoczy et al., PNAS, 2006, 103, 5799 and Holland et al., Cancer Res, 2005, 65, 9294). Axl shRNA has been reported to inhibit metastasis in vivo (Li et al., Oncogene, 2009, 28, 3442). Anti-Axl antibodies and siRNA have been reported to inhibit tumor growth and metastasis in a mouse model (Li et al., Oncogene, 2009, 28, 3442 and Ye et al., Oncogene, 2010, 29, 5254). Axl has been reported to promote cell invasion (Tai et al., Oncogene, 2008, 27, 4044). R-428, an Axl inhibitor, has been reported to inhibit a diffusion model of metastatic breast cancer (Holland et al., Cancer Res, 2010, 70, 1544). Axl antibodies, Axl shRNA and NA80×1, an Axl inhibitor, have been reported to inhibit migration and invasion of breast cancer cells (Yi-Xiang et al., Cancer Res, 2008, 68 1905). Additionally, there have been reports on the involvement of Axl in metastasis and malignant progression of prostatic cancer, spleen cancer, metastatic ovarian cancer, thymic carcinoma and the like. As is clear from these reports, Axl inhibitors are useful for suppressing, treating and preventing cancer metastasis, cell migration and cell invasion, for example.

Also, Axl inhibitors have been reported to overcome imatinib resistance in gastric cancer (Mahadevan et al., Oncogene, 2007, 26, 3909). It has been demonstrated that Axl is induced in resistance to chemotherapeutic agents such as doxorubicin, VP16 and cisplatin in acute myeloid leukemia (Hong et al., Cancer Letters, 2008, 268, 314). It has been reported that Axl is activated in lapatinib resistance in HER-2 positive breast cancer cells (Liu et al., Cancer Res, 2009, 69, 6871). Axl has been reported to be involved in the PLX4032 (vemurafenib) resistance mechanism (Johannessen et al., Nature, 2010, 468, 968). Additionally, Axl has been reported to be involved in resistance to temozolomode, carboplatin and vincristine (AK Keeating et al., Mol Cancer Ther, 2010, 9(5), 1298). As is clear from these reports, Axl inhibitors are useful for overcoming drug resistance such as resistance to various anticancer agents.

Moreover, Axl has been reported to be involved in renal diseases such as fibril formation in the kidney and diabetic nephropathy (National Publication of International Patent Application No. 2005-517412), and Axl inhibitors are useful for treating the above renal diseases as well as fibrillization diseases such as idiopathic pulmonary fibrosis.

Axl inhibitory activity of compounds can be measured by methods including, but not limited to, the methods described in the Test Examples of the present application.

Another embodiment of the present invention is N-{4-[2-amino-5-(3,4-dimethoxyphenyl)pyridin-3-yl]phenyl}-5-(4-fluorophenyl)-4-oxo-1-(2,2,2-trifluoroethyl)-1,4-dihydropyridine-3-carboxamide (hereinafter sometimes described as "compound (1)" in the present specification) or a salt thereof, and preferably N-{4-[2-amino-5-(3,4-dimethoxyphenyl)pyridin-3-yl]phenyl}-5-(4-fluorophenyl)-4-oxo-1-(2,2,2-trifluoroethyl)-1,4-dihydropyridine-3-carboxamide hydrochloride.

Another embodiment of the present invention is crystals of N-{4-[2-amino-5-(3,4-dimethoxyphenyl)pyridin-3-yl]phenyl}-5-(4-fluorophenyl)-4-oxo-1-(2,2,2-trifluoroethyl)-1,4-dihydropyridine-3-carboxamide hydrochloride.

Here, "crystal" refers to a solid whose internal structure is formed by a three-dimensionally regular repetition of constituent atoms (or a group thereof), and is distinguished from an amorphous solid not having such a regular internal structure.

Further, salts of the compounds (1) include any of those in the Examples. The compounds (1) or salts thereof may exist as free forms or solvates. They may exist as solvates due to absorption of moisture in the air, for example. Solvates are not particularly limited if pharmaceutically acceptable, and specific examples include hydrates (such as monohydrates or dihydrates), ethanolates and 2-propanolates.

Crystals of the same compound having a plurality of different internal structures and physicochemical properties (crystal polymorphs) may be generated depending on the crystallization conditions. The crystals of the present invention may be any of these crystal polymorphs or may be a mixture of two or more crystal polymorphs.

The crystals of the present invention may form a hydrate when they absorb moisture or adsorb water when left to stand in the air or when they are heated to 25 to 150° C. under normal atmospheric conditions, for example. Further, the crystals of the present invention may also contain a solvent during crystallization in the attached residual solvent or solvate.

In the present specification, the crystals of the present invention may be represented based on powder X-ray diffraction data. Powder X-ray diffraction may be measured and analyzed by any technique usually used in the art such as a method described in the Examples. Generally, in hydrates and dehydrates, attachment and detachment of water of crystallization may change their lattice constants and thus diffraction angles (2θ) in powder X-ray diffraction. Also, the peak intensity may be changed by the difference in crystal growth surface or the like (crystal habit), for example. Accordingly, when the crystals of the present invention are represented based on powder X-ray diffraction data, crystals whose peak diffraction angles and powder X-ray diffraction patterns in powder X-ray diffraction are identical to those of the crystals of the present invention, as well as hydrates and dehydrates obtained from them, are encompassed within the scope of the present invention.

A preferred form of the crystals of the present invention is crystals having a powder X-ray diffraction pattern shown in FIG. 1 in a powder X-ray diffraction diagram obtained by irradiation with copper Kα radiation (wavelength λ=1.54 Å). The crystals are also crystals having characteristic peaks at diffraction angles 2θ of 7.44, 10.00, 13.48, 14.86, 16.10, 19.30, 20.30, 22.62, 23.02, 23.70, 24.54, 25.92 and 28.46 in a powder X-ray diffraction diagram obtained by irradiation with copper Kα radiation (wavelength λ=1.54 Å).

Figure 2:
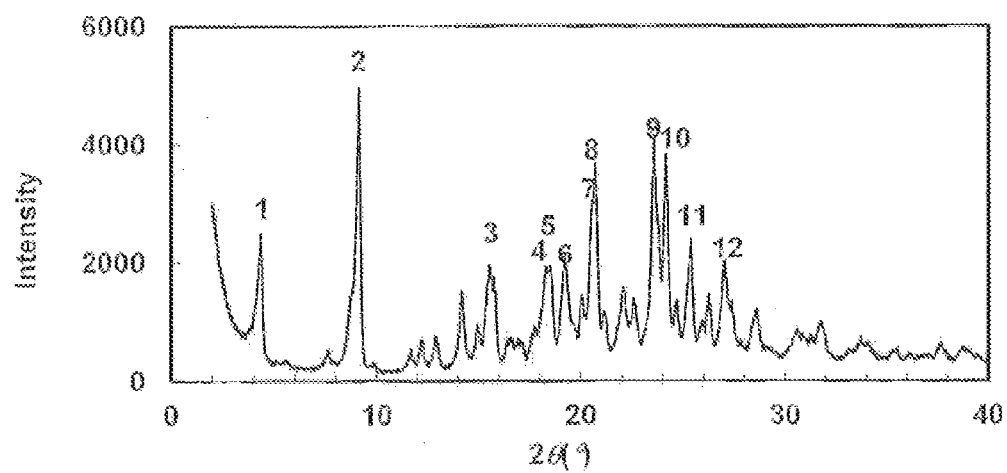
FIG. 2 is a powder X-ray diffraction diagram of the crystals obtained in Example 91, where the vertical axis represents diffraction intensity in counts per seconds (cps), and the horizontal axis represents values of diffraction angles 2θ.

Another preferred form of the crystals of the present invention is crystals having a powder X-ray diffraction pattern shown in FIG. 2 in a powder X-ray diffraction diagram obtained by irradiation with copper Kα radiation (wavelength λ=1.54 Å). The crystals are also crystals having characteristic peaks at diffraction angles 2θ of 4.32, 9.10, 15.52, 18.32, 18.54, 19.22, 20.54, 20.70, 23.54, 24.14, 25.34 and 27.02 in a powder X-ray diffraction diagram obtained by irradiation with copper Kα radiation (wavelength λ=1.54 Å).

Figure 3:
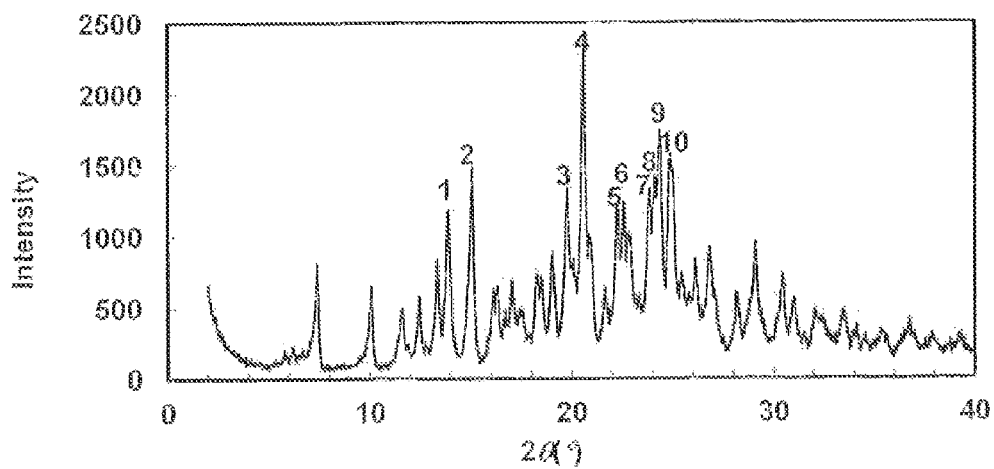
FIG. 3 is a powder X-ray diffraction diagram of the crystals obtained in Example 92, where the vertical axis represents diffraction intensity in counts per seconds (cps), and the horizontal axis represents values of diffraction angles 2θ.

Another preferred form of the crystals of the present invention is crystals having a powder X-ray diffraction pattern shown in FIG. 3 in a powder X-ray diffraction diagram obtained by irradiation with copper Kα radiation (wavelength λ=1.54 Å). The crystals are also crystals having characteristic peaks at diffraction angles 2θ of 13.86, 15.04, 19.76, 20.58, 22.26, 22.58, 23.82, 24.10, 24.36 and 24.88 in a powder X-ray diffraction diagram obtained by irradiation with copper Kα radiation (wavelength λ=1.54 Å).

Figure 4:
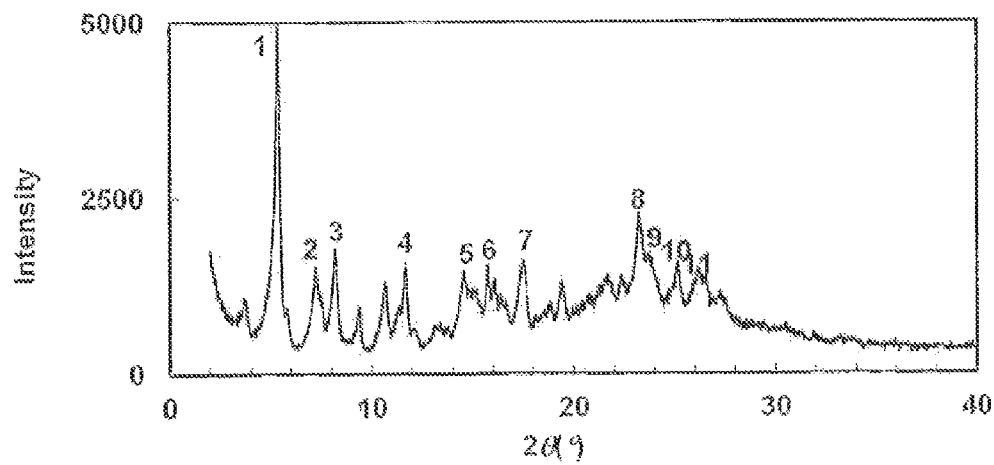
FIG. 4 is a powder X-ray diffraction diagram of the crystals obtained in Example 93, where the vertical axis represents diffraction intensity in counts per seconds (cps), and the horizontal axis represents values of diffraction angles 2θ.

Another preferred form of the crystals of the present invention is crystals having a powder X-ray diffraction pattern shown in FIG. 4 in a powder X-ray diffraction diagram obtained by irradiation with copper Kα radiation (wavelength λ=1.54 Å). The crystals are also crystals having characteristic peaks at diffraction angles 2θ of 5.34, 7.22, 8.20, 11.68, 14.54, 15.74, 17.54, 23.24, 23.72, 25.12 and 26.16 in a powder X-ray diffraction diagram obtained by irradiation with copper Kα radiation (wavelength λ=1.54 Å).

Figure 5:
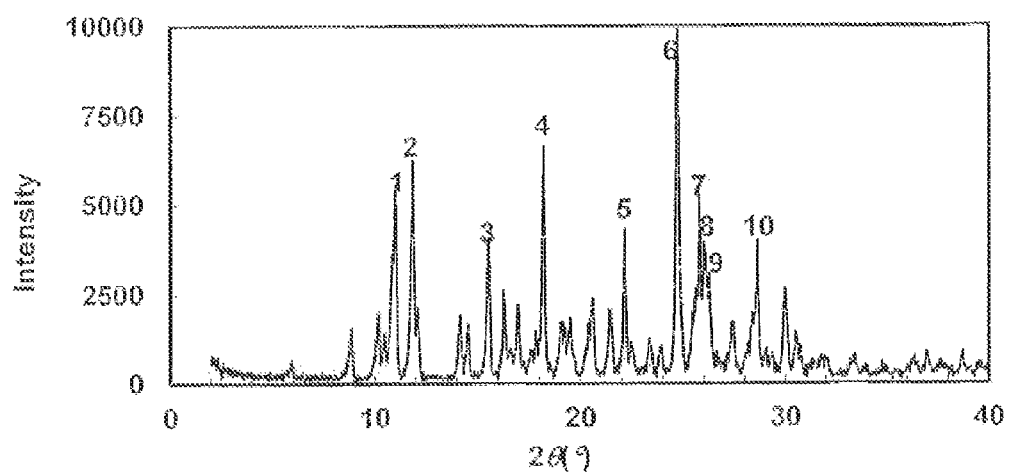
FIG. 5 is a powder X-ray diffraction diagram of the crystals obtained in Example 94, where the vertical axis represents diffraction intensity in counts per seconds (cps), and the horizontal axis represents values of diffraction angles 2θ.

Another preferred form of the crystals of the present invention is crystals having a powder X-ray diffraction pattern shown in FIG. 5 in a powder X-ray diffraction diagram obtained by irradiation with copper Kα radiation (wavelength λ=1.54 Å). The crystals are also crystals having characteristic peaks at diffraction angles 2θ of 11.02, 11.86, 15.56, 18.20, 22.12, 24.70, 25.80, 26.04, 26.26 and 28.62 in a powder X-ray diffraction diagram obtained by irradiation with copper Kα radiation (wavelength λ=1.54 Å).

Figure 6:
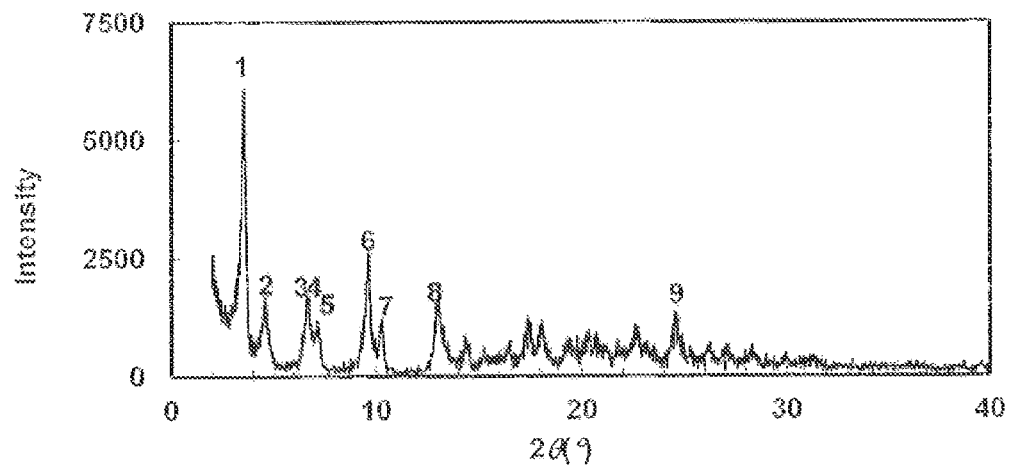
FIG. 6 is a powder X-ray diffraction diagram of the crystals obtained in Example 95, where the vertical axis represents diffraction intensity in counts per seconds (cps), and the horizontal axis represents values of diffraction angles 2θ.

Another preferred form of the crystals of the present invention is crystals having a powder X-ray diffraction pattern shown in FIG. 6 in a powder X-ray diffraction diagram obtained by irradiation with copper Kα radiation (wavelength λ=1.54 Å). The crystals are also crystals having characteristic peaks at diffraction angles 2θ of 3.58, 4.56, 6.60, 6.72, 7.20, 9.62, 10.28, 13.06 and 24.52 in a powder X-ray diffraction diagram obtained by irradiation with copper Kα radiation (wavelength λ=1.54 Å).

Figure 7:
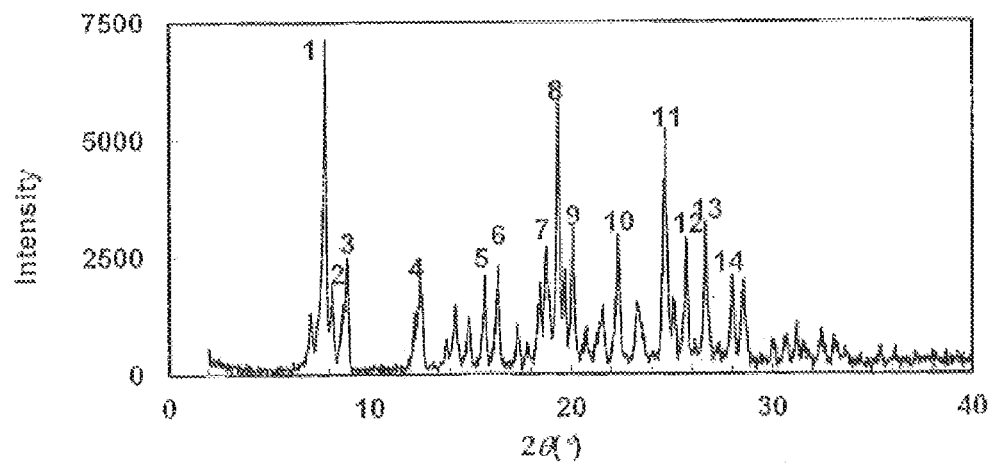
FIG. 7 is a powder X-ray diffraction diagram of the crystals obtained in Example 96, where the vertical axis represents diffraction intensity in counts per seconds (cps), and the horizontal axis represents values of diffraction angles 2θ.

Another preferred form of the crystals of the present invention is crystals having a powder X-ray diffraction pattern shown in FIG. 7 in a powder X-ray diffraction diagram obtained by irradiation with copper Kα radiation (wavelength λ=1.54 Å). The crystals are also crystals having characteristic peaks at diffraction angles 2θ of 7.78, 8.14, 8.88, 12.54, 15.68, 16.36, 18.76, 19.34, 20.08, 22.36, 24.66, 25.74, 26.70 and 28.02 in a powder X-ray diffraction diagram obtained by irradiation with copper Kα radiation (wavelength λ=1.54 Å).

Figure 8:
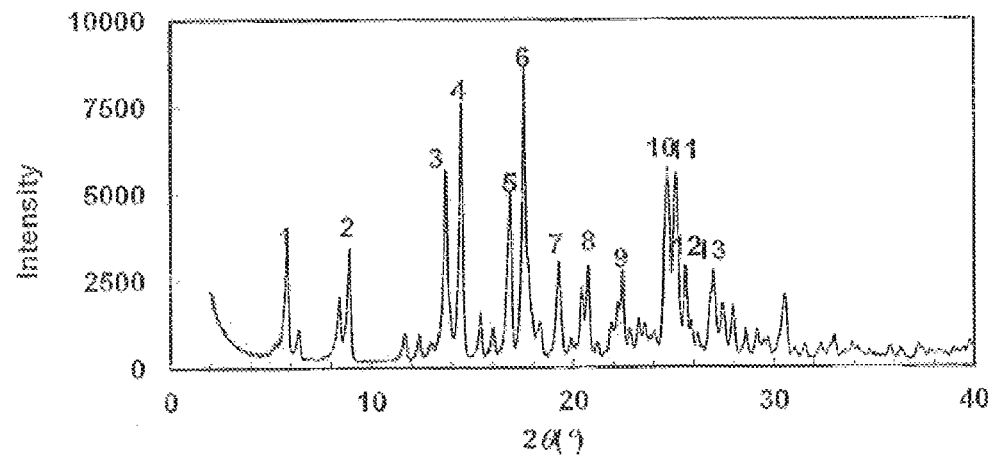
FIG. 8 is a powder X-ray diffraction diagram of the crystals obtained in Example 97, where the vertical axis represents diffraction intensity in counts per seconds (cps), and the horizontal axis represents values of diffraction angles 2θ.

Another preferred form of the crystals of the present invention is crystals having a powder X-ray diffraction pattern shown in FIG. 8 in a powder X-ray diffraction diagram obtained by irradiation with copper Kα radiation (wavelength λ=1.54 Å). The crystals are also crystals having characteristic peaks at diffraction angles 2θ of 5.78, 8.90, 13.66, 14.42, 16.84, 17.56, 19.26, 20.74, 22.42, 24.66, 25.12, 25.60 and 26.96 in a powder X-ray diffraction diagram obtained by irradiation with copper Kα radiation (wavelength λ=1.54 Å).

Figure 9:
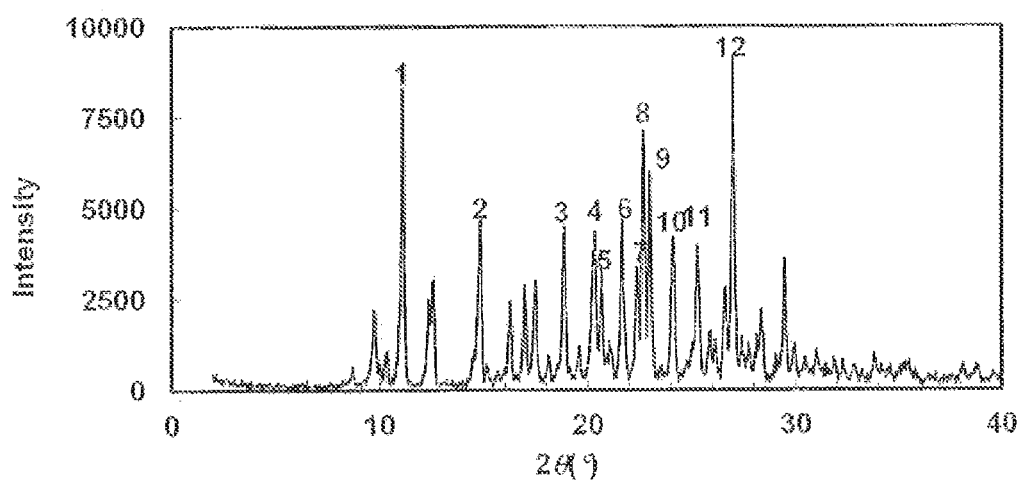
FIG. 9 is a powder X-ray diffraction diagram of the crystals obtained in Example 98, where the vertical axis represents diffraction intensity in counts per seconds (cps), and the horizontal axis represents values of diffraction angles 2θ.

Another preferred form of the crystals of the present invention is crystals having a powder X-ray diffraction pattern shown in FIG. 9 in a powder X-ray diffraction diagram obtained by irradiation with copper Kα radiation (wavelength λ=1.54 Å). The crystals are also crystals having characteristic peaks at diffraction angles 2θ of 11.12, 14.82, 18.86, 20.32, 20.66, 21.64, 22.36, 22.68, 23.00, 24.10, 25.26 and 27.00 in a powder X-ray diffraction diagram obtained by irradiation with copper Kα radiation (wavelength λ=1.54 Å).

Figure 10:
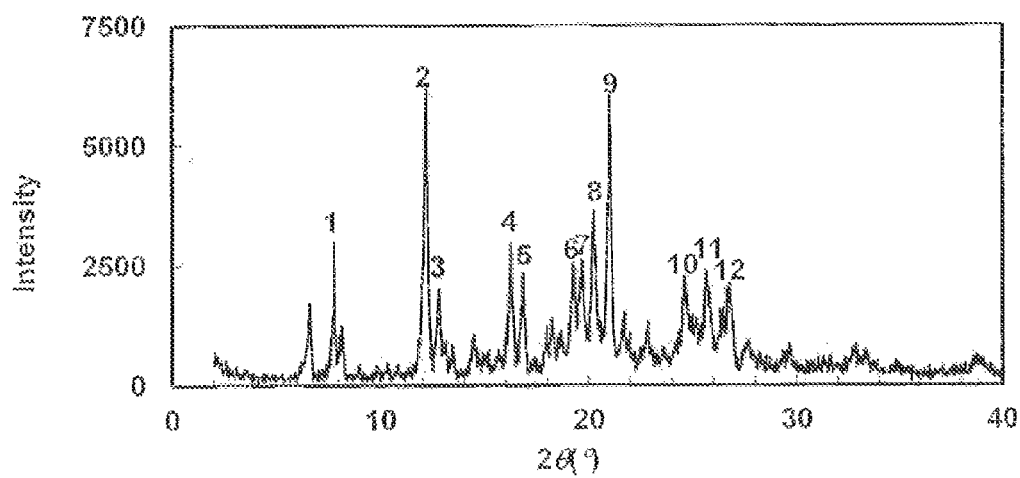
FIG. 10 is a powder X-ray diffraction diagram of the crystals obtained in Example 99, where the vertical axis represents diffraction intensity in counts per seconds (cps), and the horizontal axis represents values of diffraction angles 2θ.

Another preferred form of the crystals of the present invention is crystals having a powder X-ray diffraction pattern shown in FIG. 10 in a powder X-ray diffraction diagram obtained by irradiation with copper Kα radiation (wavelength λ=1.54 Å). The crystals are also crystals having characteristic peaks at diffraction angles 2θ of 7.80, 12.18, 12.78, 16.20, 16.82, 19.20, 19.66, 20.20, 21.20, 24.52, 25.68 and 26.78 in a powder X-ray diffraction diagram obtained by irradiation with copper Kα radiation (wavelength λ=1.54 Å).

Figure 11:
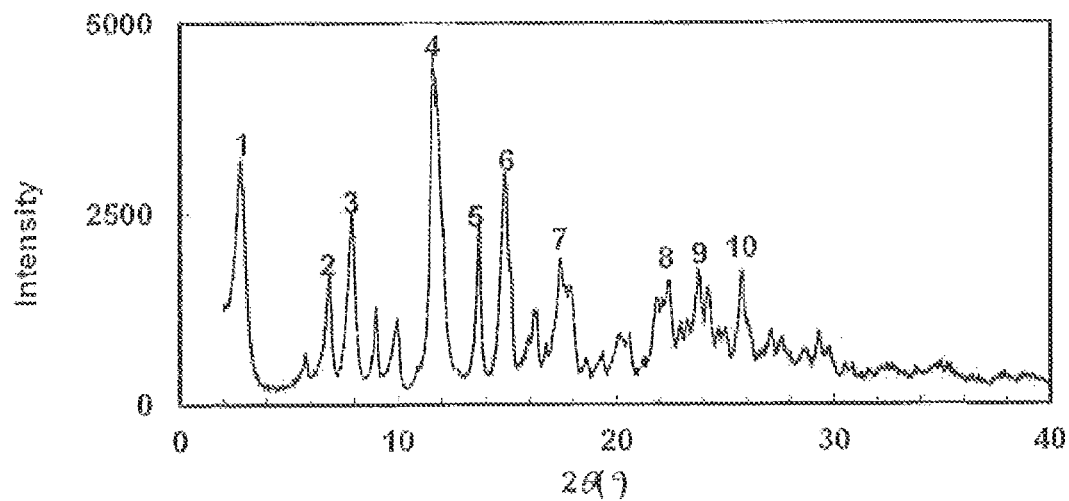
FIG. 11 is a powder X-ray diffraction diagram of the crystals obtained in Example 100, where the vertical axis represents diffraction intensity in counts per seconds (cps), and the horizontal axis represents values of diffraction angles 2θ.

Another preferred form of the crystals of the present invention is crystals having a powder X-ray diffraction pattern shown in FIG. 11 in a powder X-ray diffraction diagram obtained by irradiation with copper Kα radiation (wavelength λ=1.54 Å). The crystals are also crystals having characteristic peaks at diffraction angles 2θ of 2.80, 6.86, 7.88, 11.60, 13.68, 14.86, 17.40, 22.40, 23.78 and 25.74 in a powder X-ray diffraction diagram obtained by irradiation with copper Kα radiation (wavelength λ=1.54 Å).

Figure 12:
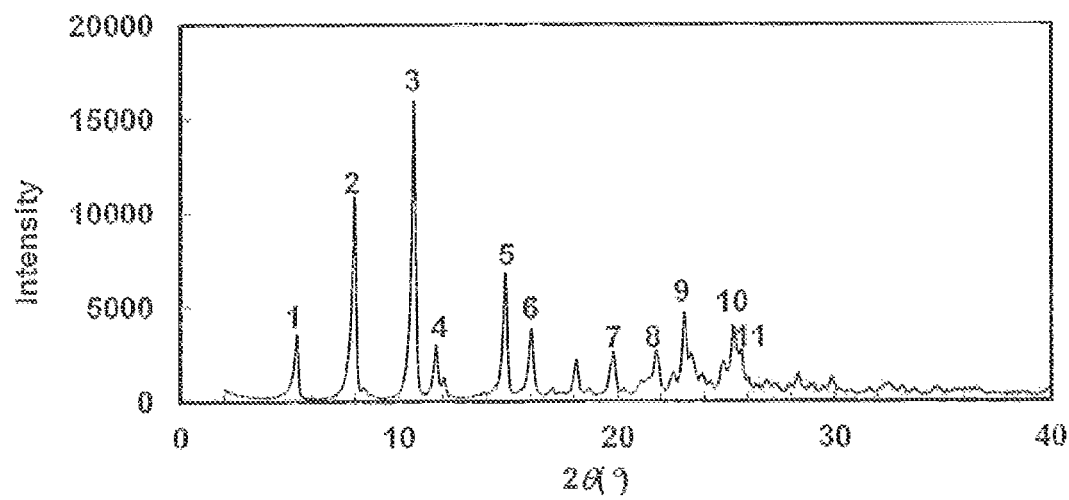
FIG. 12 is a powder X-ray diffraction diagram of the crystals obtained in Example 101, where the vertical axis represents diffraction intensity in counts per seconds (cps), and the horizontal axis represents values of diffraction angles 2θ.

Another preferred form of the crystals of the present invention is crystals having a powder X-ray diffraction pattern shown in FIG. 12 in a powder X-ray diffraction diagram obtained by irradiation with copper Kα radiation (wavelength λ=1.54 Å). The crystals are also crystals having characteristic peaks at diffraction angles 2θ of 5.32, 7.98, 10.68, 11.70, 14.84, 16.02, 19.78, 21.76, 23.08, 25.30 and 25.68 in a powder X-ray diffraction diagram obtained by irradiation with copper Kα radiation (wavelength λ=1.54 Å).

Figure 13:
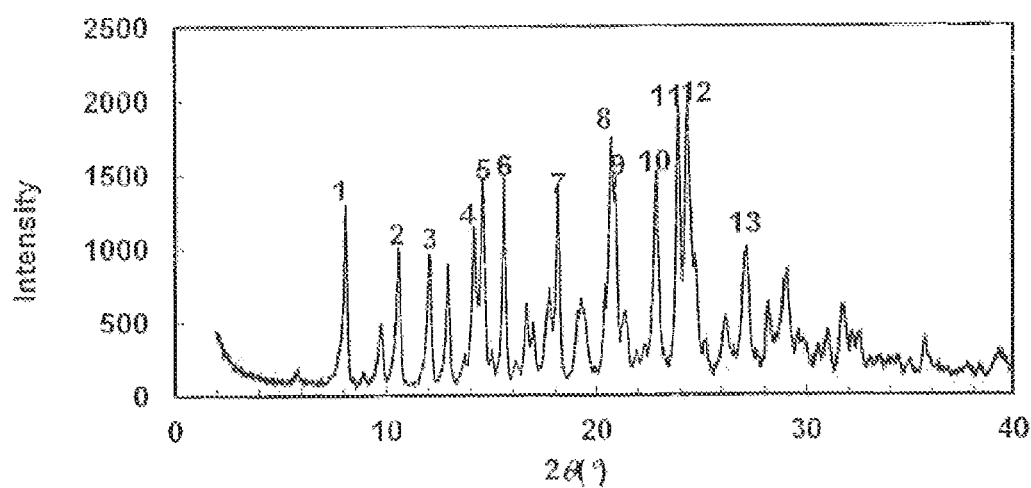
FIG. 13 is a powder X-ray diffraction diagram of the crystals obtained in Example 102, where the vertical axis represents diffraction intensity in counts per seconds (cps), and the horizontal axis represents values of diffraction angles 2θ.

Another preferred form of the crystals of the present invention is crystals having a powder X-ray diffraction pattern shown in FIG. 13 in a powder X-ray diffraction diagram obtained by irradiation with copper Kα radiation (wavelength λ=1.54 Å). The crystals are also crystals having characteristic peaks at diffraction angles 2θ of 8.10, 10.60, 12.06, 14.16, 14.58, 15.60, 18.16, 20.72, 20.94, 22.86, 23.90, 24.32 and 27.14 in a powder X-ray diffraction diagram obtained by irradiation with copper Kα radiation (wavelength λ=1.54 Å).

Figure 14:
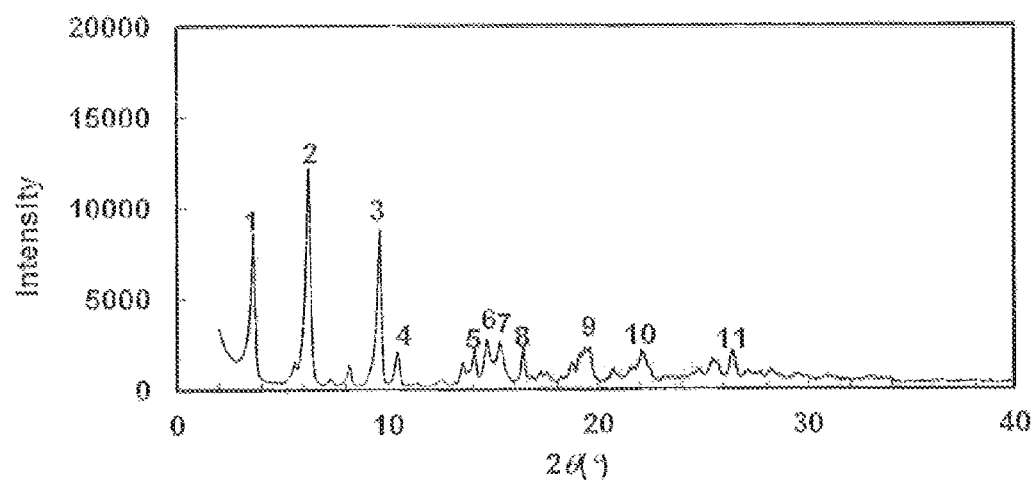
FIG. 14 is a powder X-ray diffraction diagram of the crystals obtained in Example 103, where the vertical axis represents diffraction intensity in counts per seconds (cps), and the horizontal axis represents values of diffraction angles 2θ.

Another preferred form of the crystals of the present invention is crystals having a powder X-ray diffraction pattern shown in FIG. 14 in a powder X-ray diffraction diagram obtained by irradiation with copper Kα radiation (wavelength λ=1.54 Å). The crystals are also crystals having characteristic peaks at diffraction angles 2θ of 3.60, 6.22, 9.56, 10.42, 14.04, 14.66, 15.30, 16.40, 19.52, 22.12 and 26.42 in a powder X-ray diffraction diagram obtained by irradiation with copper Kα radiation (wavelength λ=1.54 Å).

Figure 15:
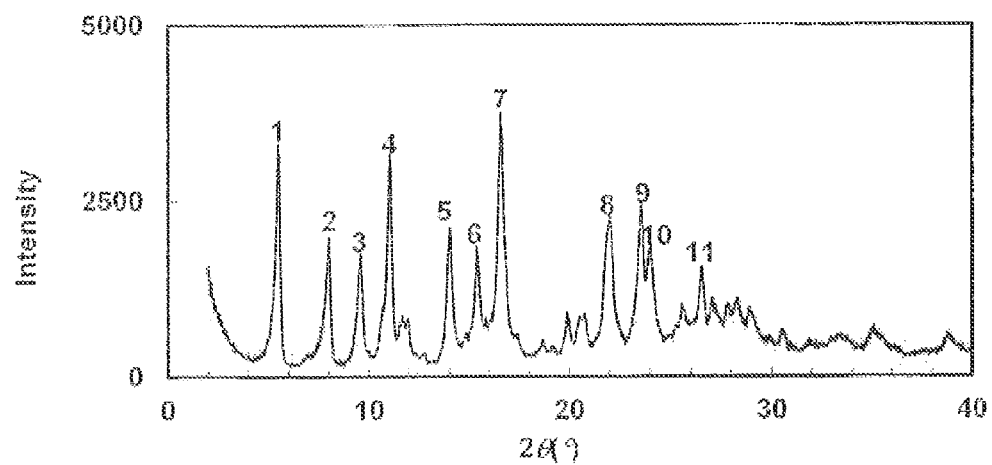
FIG. 15 is a powder X-ray diffraction diagram of the crystals obtained in Example 104, where the vertical axis represents diffraction intensity in counts per seconds (cps), and the horizontal axis represents values of diffraction angles 2θ.

Another preferred form of the crystals of the present invention is crystals having a powder X-ray diffraction pattern shown in FIG. 15 in a powder X-ray diffraction diagram obtained by irradiation with copper Kα radiation (wavelength λ=1.54 Å). The crystals are also crystals having characteristic peaks at diffraction angles 2θ of 5.46, 7.98, 9.54, 11.00, 14.00, 15.36, 16.56, 22.00, 23.54, 24.00 and 26.56 in a powder X-ray diffraction diagram obtained by irradiation with copper Kα radiation (wavelength λ=1.54 Å).

Figure 16:
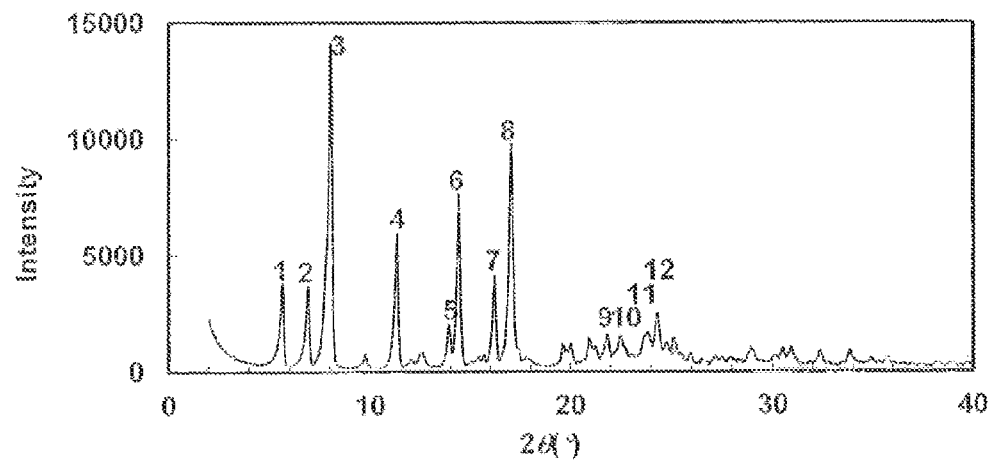
FIG. 16 is a powder X-ray diffraction diagram of the crystals obtained in Example 105, where the vertical axis represents diffraction intensity in counts per seconds (cps), and the horizontal axis represents values of diffraction angles 2θ.

Another preferred form of the crystals of the present invention is crystals having a powder X-ray diffraction pattern shown in FIG. 16 in a powder X-ray diffraction diagram obtained by irradiation with copper Kα radiation (wavelength λ=1.54 Å). The crystals are also crystals having characteristic peaks at diffraction angles 2θ of 5.64, 6.92, 8.06, 11.32, 14.40, 16.18, 17.04, 21.84, 22.50, 23.82 and 24.28 in a powder X-ray diffraction diagram obtained by irradiation with copper Kα radiation (wavelength λ=1.54 Å).

Another embodiment of the present invention relates to a medicine comprising the crystals of the present invention as an active ingredient.

A medicine comprising the crystals of the present invention as an active ingredient is preferably provided in the form of a pharmaceutical composition comprising the crystals of the present invention and one or more pharmaceutically acceptable carriers. The administration form of the medicine of the present invention is not particularly limited. The medicine can be orally or parenterally administered, but is preferably orally administered.

The pharmaceutical composition of the present invention at least partially comprises the compound (1) or a salt thereof, or crystals thereof. Crystal forms other than the crystals of the present invention may be present as the compound (1) in the pharmaceutical composition. The content of the crystals of the present invention contained in the pharmaceutical composition may be in the range of 0.01 wt % to 99.9 wt %, such as 0.01 wt % or more, 0.05 wt % or more, 0.1 wt % or more, 0.5 wt % or more, 1 wt % or more, 2 wt % or more, 3 wt % or more, 4 wt % or more, 5 wt % or more, 10 wt % or more, 20 wt % or more, 30 wt % or more, 40 wt % or more, 50 wt % or more, 60 wt % or more, 70 wt % or more, 80 wt % or more, 90 wt % or more, 95 wt % or more, 96 wt % or more, 97 wt % or more, 98 wt % or more, 99 wt % or more, 99.5 wt % or more, 99.6 wt % or more, 99.7 wt % or more, 99.8 wt % or more or 99.9 wt % or more, based on the total compound (1) in the pharmaceutical composition. Whether the crystals of the present invention are contained in the pharmaceutical composition or not can be confirmed by an instrumental analysis method described in the present specification (such as powder X-ray diffractometry, thermal analysis or infrared absorption spectrometry).

Cell proliferation inhibitory activity can be examined using any proliferation inhibition assay usually used by persons skilled in the art. Cell proliferation inhibitory activity can be examined by comparing the degree of proliferation of cells (such as tumor cells) in the presence or absence of the test compound. The degree of proliferation can be examined using a test system to measure living cells, for example. Examples of the method for measuring living cells include the [$^3$H]-thymidine uptake test, the BrdU method and the MTT assay.

In vivo antitumor activity can be examined using any antitumor assay usually used by persons skilled in the art. For example, in vivo antitumor activity according to the present invention can be confirmed by transplanting various tumor cells into mice or rats; administering the compound or salt thereof, or crystals thereof, according to the present invention orally or intravenously after engraftment of the transplanted cells has been confirmed; and comparing tumor growth in the drug non-administration group with tumor growth in the compound administration group several days to several weeks after the administration.

Additionally, metastasis suppressing activity, invasion inhibitory activity, migration inhibitory activity and drug resistance overcoming activity can be measured by test methods described in the documents listed above where the relationship between Axl and each of the activities has been reported.

The pharmaceutical compositions of the present invention comprise the compound or salt thereof, or crystals thereof, according to the present invention and a pharmaceutically acceptable carrier. The pharmaceutical compositions can be administered as various injections such as intravenous injections, intramuscular injections or subcutaneous injections or by various methods such as oral administration or transdermal administration. The pharmaceutically acceptable carrier refers to a pharmaceutically acceptable material (such as an excipient, a diluent, an additive or a solvent) involved in transport of the compound or salt thereof, or crystals thereof, according to the present invention or a composition comprising the compound or salt thereof, or crystals thereof, according to the present invention from an organ to another organ.

Formulations (such as oral formulations or injections) can be appropriately selected according to the administration method and prepared by methods usually used for preparing various formulations. Examples of oral formulations include tablets, powders, granules, capsules, pills, troches, solutions, syrups, elixirs, emulsions and oily or aqueous suspensions. They may be orally administered either in free forms or in salt forms. Aqueous formulations can be prepared by forming acid adducts with pharmaceutically acceptable acids or by forming salts of alkali metals such as sodium. In the case of injections, it is possible to use stabilizers, preservatives, solubilizing agents and the like in the formulations. Solutions that may contain these adjuvants may be stored in containers and then lyophilized, for example, to form solid formulations to be prepared before use. One dose may be stored in one container, or multiple doses may be stored in one container.

Examples of solid formulations include tablets, powders, granules, capsules, pills and troches. These solid formulations may contain pharmaceutically acceptable additives together with the compounds of the present invention. Examples of the additives include fillers, bulking agents, binders, disintegrants, dissolution promoters, wetting agents and lubricants, and they may be selected and mixed as necessary to prepare formulations.

Examples of liquid formulations include solutions, syrups, elixirs, emulsions and suspensions. These liquid formulations may contain pharmaceutically acceptable additives together with the compounds of the present invention. Examples of the additives include suspending agents and emulsifiers, and they may be selected and mixed as necessary to prepare formulations.

The compounds or salts thereof, or crystals thereof, according to the present invention can be used for treating cancer in mammals, in particular, humans. The dose and the dosage interval can be appropriately selected by the judgment of the physician according to the site of the disease and the height, weight, sex or medical history of the patient. When the compound of the present invention is administered to a human, the dose is in the range of about 0.01 mg/kg weight to about 500 mg/kg weight per day, and preferably about 0.1 mg/kg weight to about 100 mg/kg weight per day. In administration to a human, the dose is preferably administered in either a single dose or two to four separate doses per day, and the administration is preferably repeated at appropriate intervals. The daily dose may exceed the above dose according to the judgment of the physician if necessary.

The compounds or salts thereof, or crystals thereof, according to the present invention may be used in combination with other antitumor agents. Examples include antitumor antibiotics, antitumor plant ingredients, BRM (biological response modifiers), hormones, vitamins, antitumor antibodies, molecular target drugs and other antitumor agents.

More specifically, examples of alkylating agents include alkylating agents such as nitrogen mustard, nitrogen mustard N-oxide and chlorambucil; aziridine alkylating agents such as carboquone and thiotepa; epoxide alkylating agents such as dibromomannitol and dibromodulcitol; nitrosourea alkylating agents such as carmustine, lomustine, semustine, nimustine hydrochloride, streptozocin, chlorozotocin and ranimustine; busulfan, improsulfan tosilate and dacarbazine.

Examples of various antimetabolites include purine antimetabolites such as 6-mercaptopurine, 6-thioguanine and thioinosine; pyrimidine antimetabolites such as fluorouracil, tegafur, tegafur uracil, carmofur, doxifluridine, broxuridine, cytarabine and enocitabine; and antifolates such as methotrexate and trimetrexate.

Examples of antitumor antibiotics include anthracycline antibiotic antitumor agents such as mitomycin C, bleomycin, peplomycin, daunorubicin, aclarubicin, doxorubicin, pirarubicin, THP-adriamycin, 4'-epidoxorubicin and epirubicin; chromomycin A3 and actinomycin D.

Examples of antitumor plant ingredients include vinca alkaloids such as vindesine, vincristine and vinblastine; taxanes such as paclitaxel and docetaxel; and epipodophyllotoxins such as etoposide and teniposide.

Examples of BRM include tumor necrosis factors and indomethacin.

Examples of hormones include hydrocortisone, dexamethasone, methylprednisolone, prednisolone, prasterone, betamethasone, triamcinolone, oxymetholone, nandrolone, metenolone, fosfestrol, ethinyl estradiol, chlormadinone and medroxyprogesterone.

Examples of vitamins include vitamin C and vitamin A.

Antitumor antibodies and molecular target drugs include trastuzumab, rituximab, cetuximab, nimotuzumab, denosumab, bevacizumab, infliximab, imatinib mesylate, gefitinib, erlotinib, sunitinib, lapatinib, sorafenib, dasatinib, nilotinib and vemurafenib.

Examples of other antitumor agents include cisplatin, carboplatin, oxaliplatin, tamoxifen, camptothecin, ifosfamide, cyclophosphamide, melphalan, L-asparaginase, aceglatone, sizofiran, picibanil, procarbazine, pipobroman, neocarzinostatin, hydroxyurea, ubenimex and krestin.

The present invention also includes a method for preventing and/or treating cancer, comprising administering the compound or salt thereof, or crystals thereof, according to the present invention.

The present invention further includes use of the compounds or salts thereof, or crystals thereof, according to the present invention for manufacturing the above medicines.

The present invention will be specifically described with reference to the Examples illustrated below; however, the present invention is not limited to these Examples and they should not be construed as limiting in any sense. Reagents, solvents and starting materials not particularly described in the present specification are readily available from commercial sources or known from previous reports.

EXAMPLES

Abbreviations

DMF: N,N-Dimethylformamide
THF: Tetrahydrofuran
HATU: N,N,N',N'-Tetramethyl-O-(7-azabenzotriazol-1-yl)uronium hexafluorophosphate
HOAt: 1-Hydroxy-7-azabenzotriazole
DIPEA: N,N-Diisopropylethylamine
COMU: (1-Cyano-2-ethoxy-2-oxoethylideneaminooxy) dimethylamino-morpholino-carbenium hexafluorophosphate
TFA: Trifluoroacetic acid
EDC.HCl: 1-Ethyl-3-(3-dimethylaminopropyl)carbodiimide hydrochloride
HOBt: 1-Hydroxybenzotriazole
DMAP: 4-Dimethylaminopyridine
PLC: Preparative thin layer chromatography
HPLC: High performance liquid chromatography Example 1

N-{4-[2-Amino-5-(3,4-dimethoxyphenyl)pyridin-3-yl]phenyl}-5-(4-fluorophenyl)-4-oxo-1,4-dihydropyridine-3-carboxamide

[Step 1]
3-(4-Aminophenyl)-5-bromopyridin-2-amine

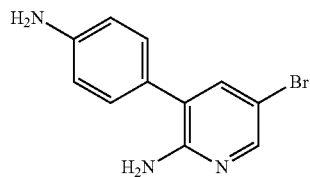 [SMILES: Nc1ccc(-c2cc(Br)cnc2N)cc1]

Tetrakis(triphenylphosphine)palladium (1.16 g), 4-(4,4,5,5-tetramethyl-1,3,2-dioxaborolan-2-yl)aniline (2.48 g) and potassium carbonate (4.15 g) were added to a solution of 5-bromo-3-iodopyridin-2-amine (2.99 g) in 1,4-dioxane (40 ml) and water (10 ml) at room temperature. The reaction mixture was stirred at 100° C. overnight. The reaction mixture was concentrated under reduced pressure, and the residue was then purified by silica gel chromatography [chloroform: methanol=9:1 (v/v)] to give 2.48 g of the title compound as a solid.

$^1$H-NMR (CDCl$_3$) δ: 3.80 (2H, br s), 4.58 (2H, br s), 6.76 (2H, dt, J=8.9, 2.3 Hz), 7.22 (2H, dt, J=8.9, 2.3 Hz), 7.43 (1H, d, J=2.3 Hz), 8.05 (1H, d, J=2.3 Hz).

MS (ESI) m/z: 264 (M+H)$^+$.

[Step 2] 3-(4-Aminophenyl)-5-(3,4-dimethoxyphenyl)pyridin-2-amine

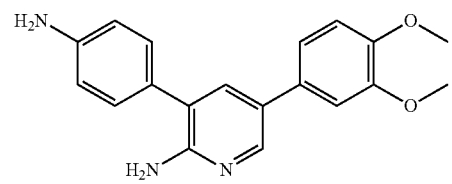 [SMILES: COc1ccc(-c2cnc(N)c(-c3ccc(N)cc3)c2)cc1OC]

Tetrakis(triphenylphosphine)palladium (1.09 g), 3,4-dimethoxyphenylboronic acid (1.92 g) and potassium carbonate (3.89 g) were added to a solution of the compound obtained in the above Step 1 (2.48 g) in 1,4-dioxane (40 ml) and water (10 ml) at room temperature. The reaction mixture was stirred at 95° C. overnight. The reaction mixture was concentrated under reduced pressure, and the residue was then purified by silica gel chromatography [chloroform: methanol=9:1 (v/v)] to give 2.48 g of the title compound as a solid.

$^1$H-NMR (CDCl$_3$) δ: 3.80 (2H, br s), 3.91 (3H, s), 3.93 (3H, s), 4.60 (2H, br s), 6.77-6.81 (2H, m), 6.93 (1H, d, J=8.3 Hz), 7.03 (1H, d, J=2.3 Hz), 7.08 (1H, dd, J=8.3, 2.3 Hz), 7.28-7.32 (2H, m), 7.53 (1H, d, J=2.3 Hz), 8.23 (1H, d, J=2.3 Hz).

MS (ESI) m/z: 322 (M+H)$^+$.

[Step 3] N-{4-[2-Amino-5-(3,4-dimethoxyphenyl)pyridin-3-yl]phenyl}-5-(4-fluorophenyl)-4-oxo-1,4-dihydropyridine-3-carboxamide

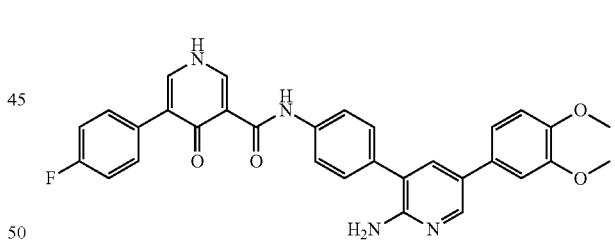

HOAt (14 mg), HATU (57 mg), DMAP (6 mg) and DIPEA (29 μl) were added to a solution of 5-(4-fluorophenyl)-4-oxo-1,4-dihydropyridine-3-carboxylic acid (23 mg) in DMF (1 ml) at room temperature. The reaction mixture was stirred at room temperature for three hours. The compound obtained in the above Step 2 (32 mg) was added to the reaction mixture at room temperature. The reaction mixture was stirred at room temperature overnight. Water was added to the reaction mixture, and the precipitated solid was collected by filtration, purified by PLC [organic layer of chloroform:methanol:water=7:3:1 (v/v)] and lyophilized with a dioxane-water mixed solvent to give the title compound (20 mg) as a solid.

$^1$H-NMR (CDCl$_3$-CD$_3$OD) δ: 3.98-3.88 (6H, m), 6.92-7.19 (5H, m), 7.44-7.70 (6H, m), 7.82-7.89 (2H, m), 8.15-8.21 (1H, m), 8.58-8.61 (1H, m).

MS (ESI) m/z: 537 (M+H)⁺.

Example 2

N-{4-[2-Amino-5-(3,4-dimethoxyphenyl)pyridin-3-yl]phenyl}-5-(4-fluorophenyl)-1-methyl-4-oxo-1,4-dihydropyridine-3-carboxamide

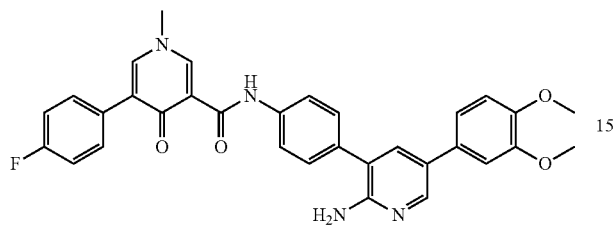

HOAt (23 mg), HATU (97 mg), DMAP (10 mg) and DIPEA (50 μl) were added to a solution of 5-(4-fluorophenyl)-1-methyl-4-oxo-1,4-dihydropyridine-3-carboxylic acid (46 mg) in DMF (1 ml) at room temperature. The reaction mixture was stirred at room temperature for three hours. The compound obtained in Step 2 of Example 1 (55 mg) was added to the reaction mixture at room temperature. The reaction mixture was stirred at room temperature overnight. Water was added to the reaction mixture, and the precipitated solid was collected by filtration. The resulting solid was purified by PLC [ethyl acetate:methanol=20:1 (v/v)] to give 19 mg of the title compound as a solid.

¹H-NMR (CDCl₃) δ: 3.90 (3H, s), 3.92 (3H, s), 3.94 (3H, s), 4.66 (2H, s), 6.94 (1H, d, J=8.3 Hz), 7.04 (1H, d, J=2.3 Hz), 7.09 (1H, dd, J=8.3, 2.3 Hz), 7.14-7.18 (2H, m), 7.46-7.51 (3H, m), 7.54-7.58 (3H, m), 7.86 (2H, d, J=8.7 Hz), 8.27 (1H, d, J=2.3 Hz), 8.61 (1H, d, J=2.3 Hz).

MS (ESI) m/z: 551 (M+H)⁺.

Example 3

N-{4-[2-Amino-5-(3,4-dimethoxyphenyl)pyridin-3-yl]phenyl}-1-ethyl-5-(4-fluorophenyl)-4-oxo-1,4-dihydropyridine-3-carboxamide

[Step 1] Ethyl 1-ethyl-5-(4-fluorophenyl)-4-oxo-1,4-dihydropyridine-3-carboxylate

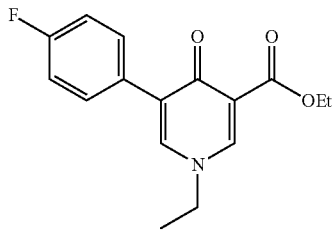 [SMILES: CCOC(=O)c1cn(CC)cc(-c2ccc(F)cc2)c1=O]

N,N-Dimethylformamide dimethylacetal (3.9 ml) was added to a solution of ethyl 4-(4-fluorophenyl)-3-oxobutanoate (1310 mg) in n-butyl acetate (15 ml) at room temperature, and the mixture was stirred at 90° C. for five hours. The solvent was distilled off under reduced pressure, and ethanol (20 ml) was added, followed by addition of ethylamine (2 M solution in THF, 4.4 ml). After stirring at 60° C. for two hours, ethylamine (2 M solution in THF, 3.0 ml) was added and the mixture was further stirred at 60° C. for two hours. The solvent was distilled off under reduced pressure, and the residue was purified by silica gel column chromatography [chloroform:methanol=300:1->70:1 (v/v)] to give 985 mg of the title compound as an oily substance.

¹H-NMR (CDCl₃) δ: 1.39 (3H, t, J=7.1 Hz), 1.53 (3H, t, J=7.3 Hz), 3.95 (2H, q, J=7.3 Hz), 4.38 (2H, q, J=7.1 Hz), 7.04-7.12 (2H, m), 7.37 (1H, d, J=2.8 Hz), 7.55-7.61 (2H, m), 8.18 (1H, d, J=2.8 Hz).

MS (ESI) m/z: 290 (M+H)⁺.

[Step 2] 1-Ethyl-5-(4-fluorophenyl)-4-oxo-1,4-dihydropyridine-3-carboxylic acid

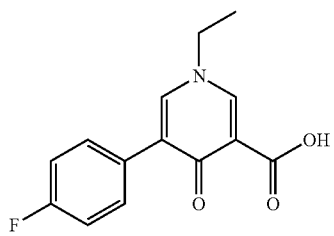 [SMILES: CCn1cc(C(=O)O)c(=O)c(-c2ccc(F)cc2)c1]

A 1 N aqueous sodium hydroxide solution (0.16 ml) was added to a solution of the compound obtained in the above Step 1 (24 mg) in methanol (1.0 ml) at room temperature, and the mixture was stirred for two hours. The solvent was distilled off under reduced pressure and a 1 N aqueous hydrochloric acid solution was added. The organic layer was extracted with chloroform and then dried over sodium sulfate. The solvent was distilled off under reduced pressure to give 22 mg of the title compound as a solid.

¹H-NMR (CDCl₃) δ: 1.60 (3H, t, J=7.6 Hz), 4.12 (2H, q, J=7.3 Hz), 7.12-7.20 (2H, m), 7.51-7.64 (3H, m), 8.55 (1H, d, J=2.3 Hz).

MS (ESI) m/z: 262 (M+H)⁺.

[Step 3] N-{4-[2-Amino-5-(3,4-dimethoxyphenyl)pyridin-3-yl]phenyl}-1-ethyl-5-(4-fluorophenyl)-4-oxo-1,4-dihydropyridine-3-carboxamide

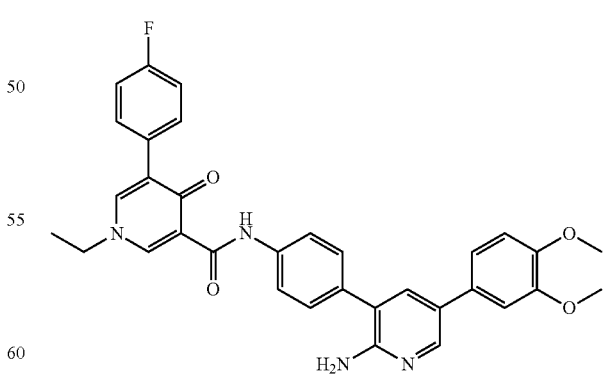

DIPEA (80 μl) was added to a solution of the compound obtained in the above Step 2 (60 mg) and COMU (128 mg) in DMF (2.0 ml) at room temperature, and the mixture was stirred for 30 minutes. The compound obtained in Step 2 of Example 1 (81 mg) was added at room temperature, and the mixture was stirred for 16 hours. A saturated aqueous sodium bicarbonate solution was then added, and the organic layer was extracted with ethyl acetate and dried over sodium sulfate. The solvent was distilled off under reduced pressure, and the residue was purified by silica gel column chromatography [ethyl acetate:dichloromethane:methanol=5:5:1 (v/v)]. The resulting solid was crystallized from ethyl acetate and diisopropyl ether to give 107 mg of the title compound as a solid.

$^1$H-NMR (CDCl$_3$) δ: 1.60 (3H, t, J=7.2 Hz), 3.92 (3H, s), 3.94 (3H, s), 4.09 (2H, q, J=7.2 Hz), 4.63 (2H, s), 6.90-7.21 (5H, m), 7.46-7.61 (6H, m), 7.84-7.90 (2H, m), 8.27 (1H, d, J=2.3 Hz), 8.66 (1H, d, J=2.3 Hz).

MS (ESI) m/z: 565 (M+H)$^+$.

Example 4

N-{4-[2-Amino-5-(3,4-dimethoxyphenyl)pyridin-3-yl]phenyl}-5-(4-fluorophenyl)-4-oxo-1-(propan-2-yl)-1,4-dihydropyridine-3-carboxamide

[Step 1] Ethyl 5-(4-fluorophenyl)-4-oxo-1-(propan-2-yl)-1,4-dihydropyridine-3-carboxylate

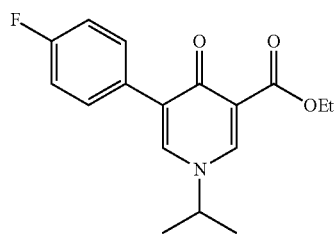 [SMILES: CCOC(=O)c1cn(C(C)C)cc(-c2ccc(F)cc2)c1=O]

N,N-Dimethylformamide dimethylacetal (3.6 ml) was added to a solution of ethyl 4-(4-fluorophenyl)-3-oxobutanoate (1200 mg) in n-propyl acetate (13 ml) at room temperature, and the mixture was stirred at 90° C. for four hours. The solvent was distilled off under reduced pressure, and ethanol (18 ml) was added, followed by addition of 2-propylamine (688 µl). After stirring at 60° C. for one hour, 2-propylamine (459 µl) was added and the mixture was further stirred at 60° C. for one hour. The solvent was distilled off under reduced pressure, and the residue was purified by silica gel column chromatography [chloroform:methanol=300:1->80:1 (v/v)] to give 620 mg of the title compound as an oily substance.

$^1$H-NMR (CDCl$_3$) δ: 1.39 (3H, t, J=7.1 Hz), 1.55 (6H, d, J=6.9 Hz), 4.13-4.25 (1H, m), 4.39 (2H, q, J=7.1 Hz), 7.04-7.12 (2H, m), 7.42 (1H, d, J=2.8 Hz), 7.54-7.61 (2H, m), 8.23 (1H, d, J=2.8 Hz).

MS (ESI) m/z: 304 (M+H)$^+$.

[Step 2] 5-(4-Fluorophenyl)-4-oxo-1-(propan-2-yl)-1,4-dihydropyridine-3-carboxylic acid

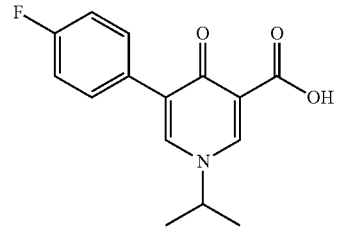 [SMILES: CC(C)n1cc(C(=O)O)c(=O)c(-c2ccc(F)cc2)c1]

A 1 N aqueous sodium hydroxide solution (4.0 ml) was added to a solution of the compound obtained in the above Step 1 (620 mg) in methanol (4.0 ml) at room temperature, and the mixture was stirred for one hour. The solvent was distilled off under reduced pressure and a 1 N aqueous hydrochloric acid solution was added. The precipitated solid was collected by filtration to give 327 mg of the title compound as a solid.

$^1$H-NMR (CDCl$_3$) δ: 1.62 (6H, d, J=6.9 Hz), 4.28-4.41 (1H, m), 7.12-7.20 (2H, m), 7.55-7.62 (2H, m), 7.67 (1H, d, J=2.3 Hz), 8.60 (1H, d, J=2.3 Hz).

MS (ESI) m/z: 276 (M+H)$^+$.

[Step 3] N-{4-[2-Amino-5-(3,4-dimethoxyphenyl)pyridin-3-yl]phenyl}-5-(4-fluorophenyl)-4-oxo-1-(propan-2-yl)-1,4-dihydropyridine-3-carboxamide

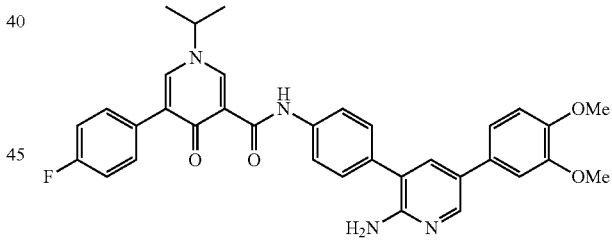

DIPEA (42 µl) was added to a solution of the compound obtained in the above Step 2 (45 mg) and COMU (91 mg) in DMF (1.0 ml) at room temperature, and the mixture was stirred for 40 minutes. The compound obtained in Step 2 of Example 1 (58 mg) was added at room temperature. The mixture was stirred for 16 hours, followed by the addition of water. The precipitated solid was collected by filtration and purified by silica gel column chromatography [chloroform:methanol=300:1->30:1 (v/v)] to give 56 mg of the title compound as a solid.

$^1$H-NMR (CDCl$_3$) δ: 1.62 (6H, d, J=6.4 Hz), 3.92 (3H, s), 3.94 (3H, s), 4.28-4.38 (1H, m), 4.72 (2H, s), 6.94 (1H, d, J=8.3 Hz), 7.01-7.11 (2H, m), 7.14-7.21 (2H, m), 7.46-7.61 (6H, m), 7.85-7.91 (2H, m), 8.26 (1H, d, J=2.3 Hz), 8.72 (1H, d, J=2.3 Hz).

MS (ESI) m/z: 579 (M+H)$^+$.

Example 5

N-{4-[2-Amino-5-(3,4-dimethoxyphenyl)pyridin-3-yl]phenyl}-5-(4-fluorophenyl)-1-(2-methoxyethyl)-4-oxo-1,4-dihydropyridine-3-carboxamide

[Step 1] 5-(4-Fluorophenyl)-1-(2-methoxyethyl)-4-oxo-1,4-dihydropyridine-3-carboxylic acid

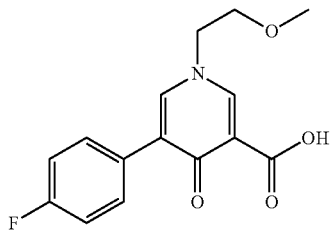

1-Bromo-2-methoxyethane (95 μl) was added to a suspension of ethyl 5-(4-fluorophenyl)-4-oxo-1,4-dihydropyridine-3-carboxylate (200 mg) and cesium carbonate (499 mg) in DMF (4 ml) at room temperature. The reaction mixture was stirred at room temperature for four hours. Then the reaction mixture was stirred at 50° C. overnight. Cesium carbonate (499 mg) and 1-bromo-2-methoxyethane (95 μl) were added to the reaction mixture at 50° C. The reaction mixture was stirred at 50° C. for nine hours. Then the reaction mixture was stirred at 80° C. for three days and returned to room temperature. A 1 N aqueous sodium hydroxide solution (4 ml) was added to the reaction mixture at room temperature. The reaction mixture was stirred at room temperature for five hours. A 1 N aqueous hydrochloric acid solution and water were added to the reaction mixture. The precipitated solid was collected by filtration, washed with water and then washed with a mixed solvent of hexane and diethyl ether [5:1 (v/v)] to give 113 mg of the title compound as a solid.

$^1$H-NMR (CDCl$_3$) δ: 3.39 (3H, s), 3.74 (2H, t, J=4.8 Hz), 4.17 (2H, t, J=4.8 Hz), 7.13-7.19 (2H, m), 7.56-7.61 (2H, m), 7.69 (1H, d, J=2.8 Hz), 8.54 (1H, d, J=2.3 Hz).

MS (ESI) m/z: 292 (M+H)$^+$.

[Step 2] N-{4-[2-Amino-5-(3,4-dimethoxyphenyl)pyridin-3-yl]phenyl}-5-(4-fluorophenyl)-1-(2-methoxyethyl)-4-oxo-1,4-dihydropyridine-3-carboxamide

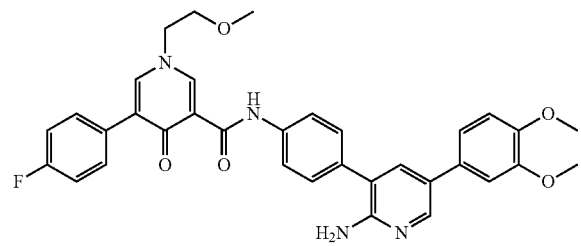 [SMILES: COCCn1cc(C(=O)Nc2ccc(-c3cc(-c4ccc(OC)c(OC)c4)cnc3N)cc2)c(=O)c(-c2ccc(F)cc2)c1]

HOAt (21 mg), HATU (89 mg), DMAP (10 mg) and DIPEA (46 μl) were added to a solution of the compound obtained in the above Step 1 (50 mg) in DMF (1 ml) at room temperature. The reaction mixture was stirred at room temperature for 3.5 hours. The compound obtained in Step 2 of Example 1 (50 mg) was added to the reaction mixture at room temperature. The reaction mixture was stirred at room temperature overnight. Water was added to the reaction mixture, and the precipitated solid was collected by filtration. The resulting solid was purified by PLC [ethyl acetate:methanol=8:1 (v/v)], and the eluate was concentrated under reduced pressure. The residue was purified by PLC [dichloromethane:methanol=15:1 (v/v)] to give 60 mg of the title compound as a solid.

$^1$H-NMR (CDCl$_3$) δ: 3.40 (3H, s), 3.76 (2H, t, J=4.8 Hz), 3.92 (3H, s), 3.94 (3H, s), 4.15 (2H, t, J=4.8 Hz), 4.65 (2H, s), 6.90-7.20 (5H, m), 7.48-7.60 (6H, m), 7.87 (2H, d, J=8.7 Hz), 8.27 (1H, d, J=2.3 Hz), 8.64 (1H, d, J=1.8 Hz).

MS (ESI) m/z: 595 (M+H)$^+$.

Example 6

N-{4-[2-Amino-5-(3,4-dimethoxyphenyl)pyridin-3-yl]phenyl}-5-(4-fluorophenyl)-4-oxo-1-[2-(tetrahydro-2H-pyran-2-yloxy)ethyl]-1,4-dihydropyridine-3-carboxamide (racemate)

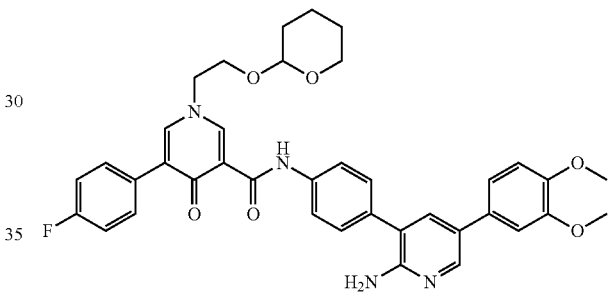

2-(2-Bromoethoxy)tetrahydro-2H-pyran (83 μl) was added to a suspension of the compound of Reference Example 9 and cesium carbonate (237 mg) in DMF (2 ml) at room temperature. The reaction mixture was stirred at 50° C. overnight. Then the reaction mixture was returned to room temperature, and a 1 N aqueous sodium hydroxide solution (2 ml) was added at room temperature. The reaction mixture was stirred at room temperature for one hour. A 1 N aqueous hydrochloric acid solution and water were added to the reaction mixture, followed by extraction with ethyl acetate. The organic layer was washed with water and brine, and then dried over sodium sulfate and filtered. The filtrate was then concentrated under reduced pressure to give 5-(4-fluorophenyl)-4-oxo-1-[2-(tetrahydro-2H-pyran-2-yloxy)ethyl]-1,4-dihydropyridine-3-carboxylic acid as an oily substance.

5-(4-Fluorophenyl)-4-oxo-1-[2-(tetrahydro-2H-pyran-2-yloxy)ethyl]-1,4-dihydropyridine-3-carboxylic acid was dissolved in DMF (2 ml), and HOAt (41 mg), HATU (170 mg), DMAP (18 mg) and DIPEA (88 μl) were added at room temperature. The reaction mixture was stirred at room temperature for three hours. The compound obtained in Step 2 of Example 1 (96 mg) was added to the reaction mixture at room temperature, followed by stirring overnight. Water was added to the reaction mixture, and the precipitated solid was collected by filtration to give 281 mg of the crude purified title compound as a solid. One hundred forty one mg of the solid was purified by PLC [dichloromethane:methanol=20:1 (v/v)], and the eluate was concentrated under reduced pressure. The residue was purified by PLC [ethyl acetate:methanol=15:1 (v/v)] to give 72 mg of the title compound.

¹H-NMR (CDCl₃) δ: 1.44-1.80 (6H, m), 3.47-3.51 (1H, m), 3.59-3.67 (1H, m), 3.75-3.81 (1H, m), 3.91 (3H, s), 3.94 (3H, s), 4.08-4.23 (3H, m), 4.59-4.69 (3H, m), 6.93 (1H, d, J=8.3 Hz), 7.02-7.11 (2H, m), 7.14-7.18 (2H, m), 7.46-7.51 (2H, m), 7.55-7.58 (3H, m), 7.66 (1H, d, J=2.3 Hz), 7.84-7.89 (2H, m), 8.26 (1H, d, J=2.8 Hz), 8.68 (1H, d, J=2.3 Hz).

MS (ESI) m/z: 665 (M+H)⁺.

Example 7

N-{4-[2-Amino-5-(3,4-dimethoxyphenyl)pyridin-3-yl]phenyl}-5-(4-fluorophenyl)-1-(2-hydroxyethyl)-4-oxo-1,4-dihydropyridine-3-carboxamide

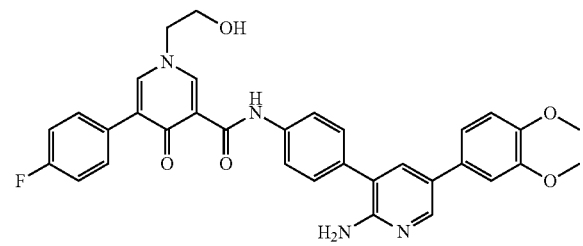 [SMILES: COc1ccc(-c2cnc(N)c(-c3ccc(NC(=O)c4cn(CCO)cc(-c5ccc(F)cc5)c4=O)cc3)c2)cc1OC]

The crude purified N-{4-[2-amino-5-(3,4-dimethoxyphenyl)pyridin-3-yl]phenyl}-5-(4-fluorophenyl)-4-oxo-1-[2-(tetrahydro-2H-pyran-2-yloxy)ethyl]-1,4-dihydropyridine-3-carboxamide obtained in Example 6 (141 mg) was dissolved in methanol (4 ml) and dichloromethane (2 ml). A 4 N solution of hydrochloric acid in dioxane (4 ml) was added to the reaction mixture at room temperature. The reaction mixture was stirred at room temperature for 2.5 hours. A saturated sodium bicarbonate solution was added to the reaction mixture, and the organic layer was extracted with ethyl acetate, washed with brine and dried over sodium sulfate. After filtration, the filtrate was concentrated under reduced pressure, the residue was purified by silica gel column chromatography [ethyl acetate:methanol=100:0->19:1->9:1 (v/v)], and the eluate was concentrated under reduced pressure. The residue was purified by PLC [dichloromethane:methanol=8:1 (v/v)] to give 9 mg of the title compound.

¹H-NMR (CDCl₃) δ: 3.91 (3H, s), 3.93 (3H, s), 4.05-4.14 (4H, m), 4.98 (2H, br s), 6.92 (1H, d, J=8.7 Hz), 6.98-7.14 (4H, m), 7.44-7.54 (4H, m), 7.59 (2H, t, J=2.5 Hz), 7.80 (2H, d, J=8.3 Hz), 8.14 (1H, d, J=2.3 Hz), 8.64 (1H, d, J=2.3 Hz).

MS (ESI) m/z: 581 (M+H)⁺.

Example 8

N-{4-[2-Amino-5-(3,4-dimethoxyphenyl)pyridin-3-yl]phenyl}-1-(2-fluoroethyl)-5-(4-fluorophenyl)-4-oxo-1,4-dihydropyridine-3-carboxamide

[Step 1] Ethyl 1-(2-fluoroethyl)-5-(4-fluorophenyl)-4-oxo-1,4-dihydropyridine-3-carboxylate

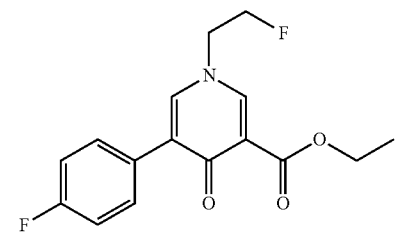 [SMILES: CCOC(=O)c1cn(CCF)cc(-c2ccc(F)cc2)c1=O]

2-Fluoroethyl 4-methylbenzenesulfonate (1.00 g) was added to a suspension of ethyl 5-(4-fluorophenyl)-4-oxo-1,4-dihydropyridine-3-carboxylate (1.00 g) and cesium carbonate (2.49 g) in DMF (9 ml) at room temperature. The reaction mixture was stirred at 80° C. for two hours. The reaction mixture was returned to room temperature and diluted by adding ethyl acetate. The organic layer was washed with water and brine and dried over sodium sulfate. After filtration, the filtrate was concentrated under reduced pressure, the residue was purified by silica gel column chromatography [ethyl acetate:hexane:methanol=1:1:0->7:3:0->1:0:0->19:0:1 (v/v)] to give 0.35 g of the title compound as an oily substance.

¹H-NMR (CDCl₃) δ: 1.32-1.40 (3H, m), 4.11-4.38 (4H, m), 4.63-4.84 (2H, m), 6.99-7.09 (2H, m), 7.41-7.58 (3H, m), 8.12-8.18 (1H, m).

MS (ESI) m/z: 308 (M+H)⁺.

[Step 2] 1-(2-Fluoroethyl)-5-(4-fluorophenyl)-4-oxo-1,4-dihydropyridine-3-carboxylic acid

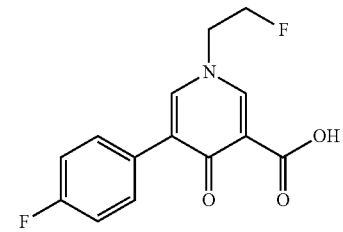 [SMILES: O=C(O)c1cn(CCF)cc(-c2ccc(F)cc2)c1=O]

Potassium carbonate (390 mg) and water (5 ml) were added to a solution of the compound obtained in the above Step 1 (347 mg) in methanol (10 ml) at room temperature. The reaction mixture was stirred at room temperature overnight. A 1 N aqueous hydrochloric acid solution and water were added to the reaction mixture, and the precipitated solid was collected by filtration and dried to give 210 mg of the title compound as a solid.

¹H-NMR (CD₃OD) δ: 4.47-4.59 (2H, m), 4.75-4.89 (2H, m), 7.16-7.22 (2H, m), 7.67-7.72 (2H, m), 8.20 (1H, d, J=2.3 Hz), 8.74 (1H, d, J=1.8 Hz)

MS (ESI) m/z: 280 (M+H)⁺..

[Step 3] N-{4-[2-Amino-5-(3,4-dimethoxyphenyl)pyridin-3-yl]phenyl}-1-(2-fluoroethyl)-5-(4-fluorophenyl)-4-oxo-1,4-dihydropyridine-3-carboxamide

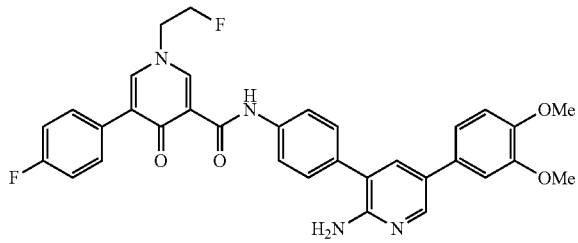 [SMILES: COc1ccc(-c2cnc(N)c(-c3ccc(NC(=O)c4cn(CCF)cc(-c5ccc(F)cc5)c4=O)cc3)c2)cc1OC]

DIPEA (47 μl) was added to a solution of the compound obtained in the above Step 2 (38 mg) and COMU (76 mg) in DMF (0.9 ml) at room temperature, and the mixture was stirred for 15 minutes. The compound obtained in Step 2 of Example 1 (48 mg) was added at room temperature. The mixture was stirred for five hours, followed by the addition of water. The organic layer was extracted with ethyl acetate, and then washed with water and brine and dried over sodium sulfate. The solvent was distilled off under reduced pressure, and the residue was purified by silica gel column chromatography [chloroform:methanol=300:1->30:1 (v/v)] to give 30 mg of the title compound as a solid.

$^1$H-NMR (CDCl$_3$) δ: 3.92 (3H, s), 3.94 (3H, s), 4.25-4.37 (2H, m), 4.66 (2H, s), 4.74-4.91 (2H, m), 6.94 (1H, d, J=8.3 Hz), 7.02-7.11 (2H, m), 7.14-7.20 (2H, m), 7.47-7.60 (6H, m), 7.84-7.89 (2H, m), 8.27 (1H, d, J=2.5 Hz), 8.65 (1H, d, J=2.5 Hz).

MS (ESI) m/z: 583 (M+H)$^+$.

Example 9

N-{4-[2-Amino-5-(3,4-dimethoxyphenyl)pyridin-3-yl]phenyl}-5-(4-fluorophenyl)-4-oxo-1-(2,2,2-trifluoroethyl)-1,4-dihydropyridine-3-carboxamide

[Step 1] Ethyl 5-(4-fluorophenyl)-4-oxo-1-(2,2,2-trifluoroethyl)-1,4-dihydropyridine-3-carboxylate

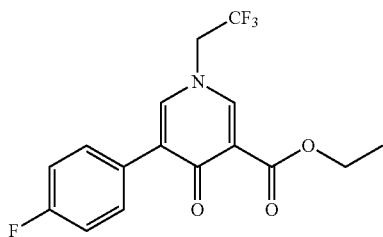 [SMILES: CCOC(=O)c1cn(CC(F)(F)F)cc(-c2ccc(F)cc2)c1=O]

A mixed solution of ethyl 4-(4-fluorophenyl)-3-oxobutanoate (0.95 g), N,N-dimethylformamide dimethylacetal (1.59 g) and toluene (7 ml) was stirred at 100° C. to 105° C. for 14 hours while methanol was distilled off. After cooling to room temperature, the residue was concentrated under reduced pressure. Further, 7 ml of toluene was added and the residue was concentrated to one-third of its volume under reduced pressure. Toluene (3.5 ml) was added to give a solution of ethyl 5-(dimethylamino)-2-[(dimethylamino)methylene]-4-(4-fluorophenyl)-3-oxopent-4-enoate. This solution was cooled to 0° C. to 5° C., trifluoroethyl amine (0.43 ml) and a 4.3 M solution of hydrogen chloride in ethyl acetate (1.57 ml) were added, and the mixture was stirred at 100° C. to 105° C. for three hours. After cooling to room temperature, the layers were separated by adding water, and the organic layer was concentrated to 3.5 ml. Toluene (1.4 ml) was added, followed by stirring at room temperature. The resulting solid was collected by filtration to give 1.07 g of the title compound as a solid.

$^1$H-NMR (CDCl$_3$) δ: 1.39 (3H, t, J=7.3 Hz), 4.33-4.42 (4H, m), 7.05-7.13 (2H, m), 7.32-7.37 (1H, m), 7.50-7.58 (2H, m), 8.13 (1H, d, J=2.7 Hz).

MS (ESI) m/z: 344 (M+H)$^+$

[Step 2] 5-(4-Fluorophenyl)-4-oxo-1-(2,2,2-trifluoroethyl)-1,4-dihydropyridine-3-carboxylic acid

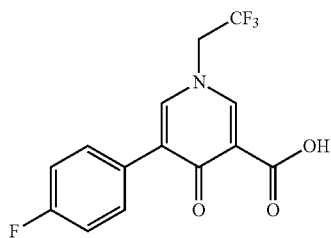 [SMILES: O=C(O)c1cn(CC(F)(F)F)cc(-c2ccc(F)cc2)c1=O]

A 1 N aqueous sodium hydroxide solution (0.8 ml) was added to a solution of the compound obtained in the above Step 1 (118 mg) in methanol (0.7 ml) at room temperature, and the mixture was stirred for two hours. The solvent was distilled off under reduced pressure and a 1 N aqueous hydrochloric acid solution was added. The precipitated solid was collected by filtration to give the title compound (87 mg).

$^1$H-NMR (CDCl$_3$) δ: 4.55 (2H, q, J=7.6 Hz), 7.14-7.22 (2H, m), 7.52-7.60 (3H, m), 8.55 (1H, d, J=2.3 Hz).

MS (ESI) m/z: 316 (M+H)$^+$.

[Step 3] N-{4-[2-Amino-5-(3,4-dimethoxyphenyl)pyridin-3-yl]phenyl}-5-(4-fluorophenyl)-4-oxo-1-(2,2,2-trifluoroethyl)-1,4-dihydropyridine-3-carboxamide

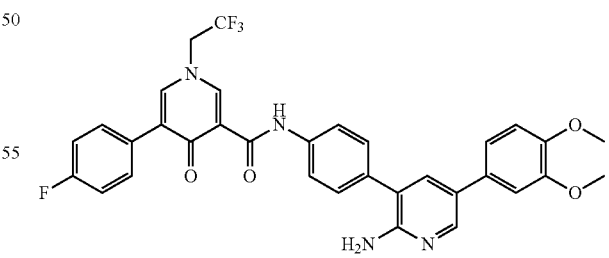

HOAt (25 mg), HATU (106 mg), DMAP (11 mg) and DIPEA (55 μl) were added to a solution of the compound obtained in the above Step 2 (60 mg) in DMF (1 ml) at room temperature. The reaction mixture was stirred at room temperature for 3.5 hours. The compound obtained in Step 2 of Example 1 (65 mg) was added to the reaction mixture at room temperature. The reaction mixture was stirred at room temperature overnight. Water was added to the reaction mixture, and the precipitated solid was collected by filtration. The resulting solid was purified by PLC [developed with ethyl acetate], and the eluate was concentrated under reduced pressure. The residue was purified by PLC [dichloromethane:methanol=20:1 (v/v)] to give 70 mg of the title compound as a solid.

$^1$H-NMR (CDCl$_3$) δ: 3.91 (3H, s), 3.94 (3H, s), 4.53 (2H, q, J=7.8 Hz), 4.65 (2H, s), 6.94 (1H, d, J=8.7 Hz), 7.04 (1H, d, J=2.3 Hz), 7.09 (1H, dd, J=8.3, 2.3 Hz), 7.16-7.20 (2H, m), 7.48-7.57 (6H, m), 7.85 (2H, dt, J=9.0, 2.3 Hz), 8.27 (1H, d, J=2.8 Hz), 8.66 (1H, d, J=2.3 Hz), 12.46 (1H, s).

MS (ESI) m/z: 619 (M+H)$^+$.

Example 10

N-{4-[2-Amino-5-(3,4-dimethoxyphenyl)pyridin-3-yl]phenyl}-1-benzyl-5-(4-fluorophenyl)-4-oxo-1,4-dihydropyridine-3-carboxamide

[Step 1] 1-Benzyl-5-(4-fluorophenyl)-4-oxo-1,4-dihydropyridine-3-carboxylic acid

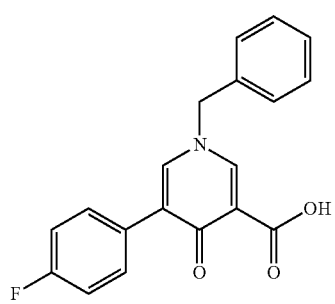 [SMILES: O=C(O)c1cn(Cc2ccccc2)cc(-c2ccc(F)cc2)c1=O]

Fifty-five percent sodium hydride (131 mg) dispersed in oil was added to a solution of 5-(4-fluorophenyl)-4-oxo-1,4-dihydropyridine-3-carboxylic acid (233 mg) in DMF (5 ml) under ice cooling, and the mixture was stirred at room temperature for one hour. Benzyl bromide (356 μl) was then added and the mixture was stirred for two days. A 1 N aqueous sodium hydroxide solution was then added, followed by stirring overnight. A 10% aqueous citric acid solution was added to the reaction solution, and the precipitate was collected by filtration to give the title compound (253 mg) as a solid.

$^1$H-NMR (CDCl$_3$) δ: 5.19 (2H, s), 7.09-7.15 (2H, m), 7.26-7.30 (2H, m), 7.43-7.47 (3H, m), 7.51-7.56 (2H, m), 7.63 (1H, d, J=2.3 Hz), 8.62 (1H, d, J=2.3 Hz).

MS (ESI) m/z: 324 (M+H)$^+$.

[Step 2] N-{4-[2-Amino-5-(3,4-dimethoxyphenyl)pyridin-3-yl]phenyl}-1-benzyl-5-(4-fluorophenyl)-4-oxo-1,4-dihydropyridine-3-carboxamide

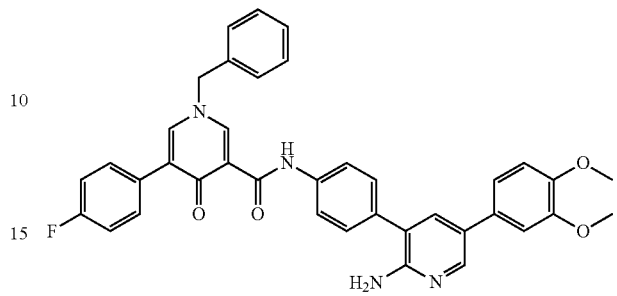

HOAt (14 mg), HATU (57 mg), DMAP (6 mg) and DIPEA (29 μl) were added to a solution of the compound obtained in the above Step 1 (35 mg) in DMF (1 ml) at room temperature. The reaction mixture was stirred at room temperature for three hours. The compound obtained in Step 2 of Example 1 (32 mg) was added to the reaction mixture at room temperature. The reaction mixture was stirred at room temperature overnight. Water was added to the reaction mixture, and the precipitated solid was collected by filtration, purified by PLC [chloroform:methanol=9:1 (v/v)] and lyophilized with a dioxane-water mixed solvent to give 37 mg of the title compound as a solid.

$^1$H-NMR (CDCl$_3$) δ: 3.91 (3H, s), 3.94 (3H, s), 4.73 (2H, br s), 5.17 (2H, s), 6.93 (1H, d, J=8.7 Hz), 7.03 (1H, d, J=2.3 Hz), 7.07-7.17 (3H, m), 7.28-7.32 (2H, m), 7.43-7.58 (9H, m), 7.86 (2H, d, J=8.7 Hz), 8.25 (1H, d, J=2.3 Hz), 8.74 (1H, d, J=2.3 Hz).

MS (ESI) m/z: 627 (M+H)$^+$.

Example 11

N-{4-[2-Amino-5-(3,4-dimethoxyphenyl)pyridin-3-yl]phenyl}-1-(4-fluorobenzyl)-5-(4-fluorophenyl)-4-oxo-1,4-dihydropyridine-3-carboxamide

[Step 1] 1-(4-Fluorobenzyl)-5-(4-fluorophenyl)-4-oxo-1,4-dihydropyridine-3-carboxylic acid

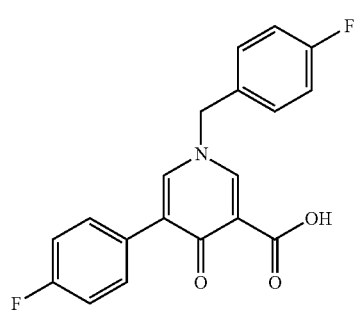 [SMILES: O=C(O)c1cn(Cc2ccc(F)cc2)cc(-c2ccc(F)cc2)c1=O]

1-(Bromomethyl)-4-fluorobenzene (122 μl) was added to a suspension of ethyl 5-(4-fluorophenyl)-4-oxo-1,4-dihydropyridine-3-carboxylate (200 mg) and cesium carbonate (499 mg) in DMF (4 ml) at room temperature. The reaction mixture was stirred at room temperature overnight. A 1 N aqueous sodium hydroxide solution (4 ml) was added to the reaction mixture at room temperature. The reaction mixture was stirred at room temperature for two hours. A 1 N aqueous hydrochloric acid solution and water were added to the reaction mixture, and the precipitated solid was collected by filtration, washed with water and then dried to give 250 mg of the title compound as a solid.

$^1$H-NMR (CDCl$_3$) δ: 5.15 (2H, s), 7.10-7.19 (4H, m), 7.26-7.30 (2H, m), 7.51-7.60 (3H, m), 8.60 (1H, d, J=1.8 Hz).

MS (ESI) m/z: 342 (M+H)$^+$.

[Step 2] N-{4-[2-Amino-5-(3,4-dimethoxyphenyl)pyridin-3-yl]phenyl}-1-(4-fluorobenzyl)-5-(4-fluorophenyl)-4-oxo-1,4-dihydropyridine-3-carboxamide

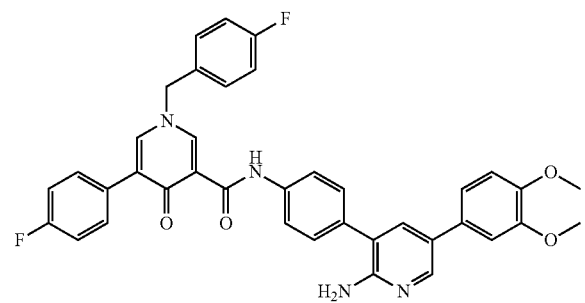 [SMILES: COc1ccc(-c2cnc(N)c(-c3ccc(NC(=O)c4cn(Cc5ccc(F)cc5)cc(-c5ccc(F)cc5)c4=O)cc3)c2)cc1OC]

HOAt (21 mg), HATU (89 mg), DMAP (10 mg) and DIPEA (46 μl) were added to a solution of the compound obtained in the above Step 1 (58 mg) in DMF (1 ml) at room temperature. The reaction mixture was stirred at room temperature for one hour. The compound obtained in Step 2 of Example 1 (50 mg) was added to the reaction mixture, followed by stirring at room temperature overnight. Water was added to the reaction mixture, and the precipitated solid was collected by filtration. The resulting solid was purified by PLC (developed with ethyl acetate), and the eluate was concentrated under reduced pressure. The residue was purified by PLC [dichloromethane:methanol=30:1 (v/v)] to give 61 mg of the title compound as a solid.

$^1$H-NMR (CDCl$_3$) δ: 3.91 (3H, s), 3.94 (3H, s), 4.66 (2H, s), 5.13 (2H, s), 6.93 (1H, d, J=7.8 Hz), 7.02-7.18 (6H, m), 7.25-7.32 (2H, m), 7.47-7.57 (6H, m), 7.85 (2H, d, J=8.3 Hz), 8.26 (1H, d, J=1.8 Hz), 8.71 (1H, d, J=1.8 Hz).

MS (ESI) m/z: 645 (M+H)$^+$.

Example 12

N-{4-[2-Amino-5-(3,4-dimethoxyphenyl)pyridin-3-yl]phenyl}-5-(4-fluorophenyl)-4-oxo-1-(pyridin-2-ylmethyl)-1,4-dihydropyridine-3-carboxamide

[Step 1] 5-(4-Fluorophenyl)-4-oxo-1-(pyridin-2-ylmethyl)-1,4-dihydropyridine-3-carboxylic acid

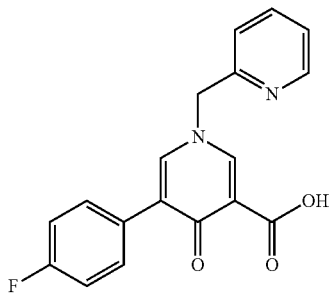 [SMILES: O=C(O)c1cn(Cc2ccccn2)cc(-c2ccc(F)cc2)c1=O]

2-(Bromomethyl)pyridine hydrobromide (126 mg) was added to a suspension of ethyl 5-(4-fluorophenyl)-4-oxo-1,4-dihydropyridine-3-carboxylate (100 mg) and cesium carbonate (437 mg) in DMF (2 ml) at room temperature. The reaction mixture was stirred at room temperature overnight. The reaction mixture was stirred at 80° C. for four hours and returned to room temperature. A 1 N aqueous sodium hydroxide solution (2 ml) was added to the reaction mixture at room temperature. The reaction mixture was stirred at room temperature for 1.5 hours. A 1 N aqueous hydrochloric acid solution and water were added to the reaction mixture, and the precipitated solid was collected by filtration, washed with water and then dried to give 94 mg of the title compound as a solid.

$^1$H-NMR (CDCl$_3$) δ: 5.23 (2H, s), 7.11-7.17 (2H, m), 7.30-7.38 (2H, m), 7.56-7.62 (2H, m), 7.76-7.87 (2H, m), 8.63 (2H, s).

[Step 2] N-{4-[2-Amino-5-(3,4-dimethoxyphenyl)pyridin-3-yl]phenyl}-5-(4-fluorophenyl)-4-oxo-1-(pyridin-2-ylmethyl)-1,4-dihydropyridine-3-carboxamide

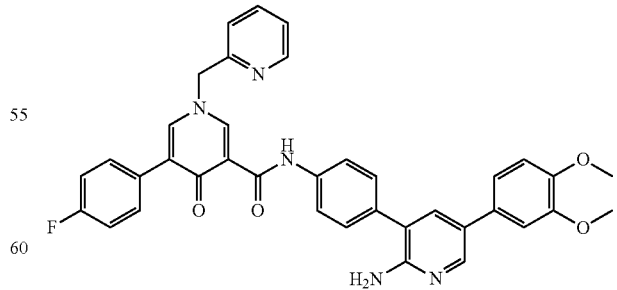

HOAt (18 mg), HATU (75 mg), DMAP (8 mg) and DIPEA (62 μl) were added to a solution of the compound obtained in the above Step 1 (47 mg) in DMF (1 ml) at room temperature. The reaction mixture was stirred at room temperature for one hour. The compound obtained in Step 2 of Example 1 (42 mg) was added to the reaction mixture at room temperature. The reaction mixture was stirred at room temperature overnight. HATU (75 mg) was added to the reaction mixture at room temperature. The reaction mixture was stirred at 50° C. for one hour and returned to room temperature. Water was added to the reaction mixture, and the precipitated solid was collected by filtration. The resulting solid was purified by PLC [ethyl acetate:methanol=8:1 (v/v)], and the eluate was concentrated under reduced pressure. The residue was purified by PLC [dichloromethane:methanol=15:1 (v/v)] to give 65 mg of the title compound as a solid.

$^1$H-NMR (CDCl$_3$) δ: 3.91 (3H, s), 3.94 (3H, s), 4.68 (2H, s), 5.24 (2H, s), 6.93 (1H, d, J=8.3 Hz), 7.03-7.17 (4H, m), 7.28-7.36 (2H, m), 7.48 (2H, d, J=8.7 Hz), 7.55-7.59 (3H, m), 7.72-7.80 (2H, m), 7.86 (2H, d, J=8.7 Hz), 8.26 (1H, d, J=2.3 Hz), 8.63-8.65 (1H, m), 8.75 (1H, d, J=2.3 Hz).

MS (ESI) m/z: 628 (M+H)$^+$.

Example 13

N-{4-[2-Amino-5-(3,4-dimethoxyphenyl)pyridin-3-yl]phenyl}-5-(4-fluorophenyl)-4-oxo-1-(pyridin-4-ylmethyl)-1,4-dihydropyridine-3-carboxamide

[Step 1] Ethyl 5-(4-fluorophenyl)-4-oxo-1-(pyridin-4-ylmethyl)-1,4-dihydropyridine-3-carboxylate

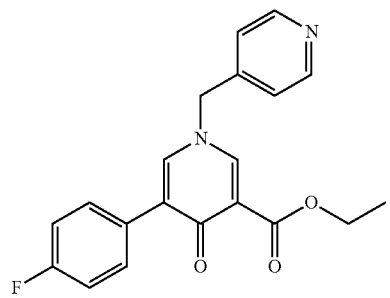 [SMILES: CCOC(=O)c1cn(Cc2ccncc2)cc(-c2ccc(F)cc2)c1=O]

4-(Bromomethyl)pyridine hydrobromide (290 mg) was added to a suspension of ethyl 5-(4-fluorophenyl)-4-oxo-1,4-dihydropyridine-3-carboxylate (200 mg) and cesium carbonate (998 mg) in DMF (5 ml) at room temperature. The reaction mixture was stirred at 100° C. overnight. The reaction mixture was returned to room temperature and diluted by adding ethyl acetate. The organic layer was washed with water and brine and dried over sodium sulfate. After filtration, the filtrate was concentrated under reduced pressure, the residue was purified by silica gel column chromatography [chloroform:methanol=10:0->19:1->9:1 (v/v)], and the eluate was concentrated under reduced pressure. The residue was purified by PLC [dichloromethane:methanol=10:1 (v/v)] to give 126 mg of the title compound as an oily substance.

$^1$H-NMR (CDCl$_3$) δ: 1.37 (3H, t, J=7.1 Hz), 4.36 (2H, q, J=7.2 Hz), 5.08 (2H, s), 7.02-7.14 (4H, m), 7.35 (1H, d, J=2.8 Hz), 7.50-7.56 (2H, m), 8.19 (1H, d, J=2.3 Hz), 8.67-8.69 (2H, m)

MS (ESI) m/z: 353 (M+H)$^+$.

[Step 2] N-{4-[2-Amino-5-(3,4-dimethoxyphenyl)pyridin-3-yl]phenyl}-5-(4-fluorophenyl)-4-oxo-1-(pyridin-4-ylmethyl)-1,4-dihydropyridine-3-carboxamide

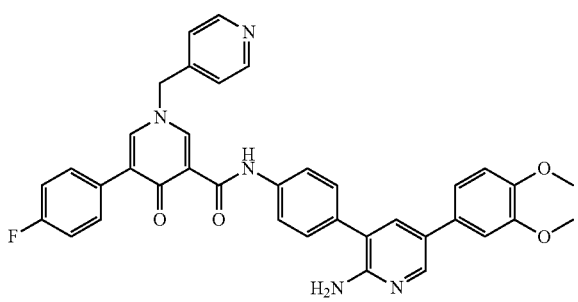 [SMILES: COc1ccc(-c2cnc(N)c(-c3ccc(NC(=O)c4cn(Cc5ccncc5)cc(-c5ccc(F)cc5)c4=O)cc3)c2)cc1OC]

Potassium hydroxide (136 mg) was added to a solution of the compound obtained in the above Step 1 (126 mg) in methanol (4 ml) at room temperature. The reaction mixture was stirred at room temperature for 37 hours. A 1 N aqueous hydrochloric acid solution (0.54 ml) was added to the reaction mixture. The reaction mixture was concentrated under reduced pressure and dried. The resulting solid was dissolved in DMF (2 ml), and HOAt (40 mg), HATU (169 mg), DMAP (18 mg) and DIPEA (88 μl) were added at room temperature. The reaction mixture was stirred at room temperature for four hours. The compound obtained in Step 2 of Example 1 (95 mg) was added to the reaction mixture at room temperature. The reaction mixture was stirred at room temperature overnight. HATU (169 mg) was added to the reaction mixture at room temperature. The reaction mixture was stirred at 50° C. for two hours and returned to room temperature. Water was added to the reaction mixture, and the precipitated solid was collected by filtration. The resulting solid was purified by PLC [ethyl acetate:methanol=8:1 (v/v)], and the eluate was concentrated under reduced pressure. The residue was purified by PLC [dichloromethane:methanol=15:1 (v/v)], and the eluate was concentrated under reduced pressure. The residue was purified by amino PLC [dichloromethane:methanol=15:1 (v/v)] to give 107 mg of the title compound as a solid.

$^1$H-NMR (CDCl$_3$) δ: 3.91 (3H, s), 3.94 (3H, s), 4.64 (2H, s), 5.19 (2H, s), 6.94 (1H, d, J=8.3 Hz), 7.03-7.17 (6H, m), 7.48-7.57 (6H, m), 7.86 (2H, d, J=8.3 Hz), 8.27 (1H, d, J=2.3 Hz), 8.69-8.72 (3H, m).

MS (ESI) m/z: 628 (M+H)$^+$.

Example 14

N-{4-[2-Amino-5-(3,4-dimethoxyphenyl)pyridin-3-yl]phenyl}-1-[(2S)-1,4-dioxan-2-ylmethyl]-5-(4-fluorophenyl)-4-oxo-1,4-dihydropyridine-3-carboxamide

[Step 1] 1-[(2S)-1,4-Dioxan-2-ylmethyl]-5-(4-fluorophenyl)-4-oxo-1,4-dihydropyridine-3-carboxylic acid

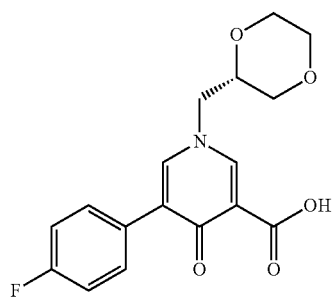 [SMILES: O=C(O)c1cn(C[C@H]2COCCO2)cc(-c2ccc(F)cc2)c1=O]

(2R)-1,4-Dioxan-2-ylmethyl methanesulfonate (95 mg) was added to a suspension of ethyl 5-(4-fluorophenyl)-4-oxo-1,4-dihydropyridine-3-carboxylate (100 mg) and cesium carbonate (264 mg) in DMF (2 ml) at room temperature. The reaction mixture was stirred at room temperature overnight. (2R)-1,4-Dioxan-2-ylmethyl methanesulfonate (32 mg) was added at room temperature. The reaction mixture was stirred at 80° C. overnight. (2R)-1,4-Dioxan-2-ylmethyl methanesulfonate (32 mg) was added at room temperature. The reaction mixture was stirred at 100° C. for three hours and then returned to room temperature. A 1 N aqueous sodium hydroxide solution (2 ml) was added to the reaction mixture at room temperature. The reaction mixture was stirred at room temperature for one hour. A 1 N aqueous hydrochloric acid solution and water were added to the reaction mixture, and the precipitated solid was collected by filtration, washed with water and then dried to give 101 mg of the title compound as a solid.

MS (ESI) m/z: 334 (M+H)$^+$.

[Step 2] N-{4-[2-Amino-5-(3,4-dimethoxyphenyl)pyridin-3-yl]phenyl}-1-[(2S)-1,4-dioxan-2-ylmethyl]-5-(4-fluorophenyl)-4-oxo-1,4-dihydropyridine-3-carboxamide

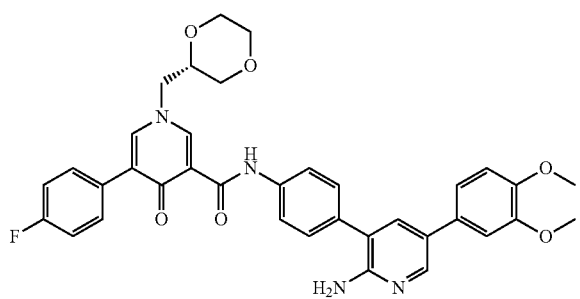 [SMILES: COc1ccc(-c2cnc(N)c(-c3ccc(NC(=O)c4cn(C[C@H]5COCCO5)cc(-c5ccc(F)cc5)c4=O)cc3)c2)cc1OC]

HOAt (21 mg), HATU (89 mg), DMAP (10 mg) and DIPEA (46 μl) were added to a solution of the compound obtained in the above Step 1 (57 mg) in DMF (1 ml) at room temperature. The reaction mixture was stirred at room temperature for three hours. The compound obtained in Step 2 of Example 1 (50 mg) was added to the reaction mixture at room temperature. The reaction mixture was stirred at room temperature overnight. Water was added to the reaction mixture, and the precipitated solid was collected by filtration. The resulting solid was purified by PLC [dichloromethane:methanol=20:1 (v/v)], and the eluate was concentrated under reduced pressure. The residue was purified by PLC [ethyl acetate:methanol=15:1 (v/v)] to give 75 mg of the title compound as a solid.

$^1$H-NMR (CDCl$_3$) δ: 3.33-3.38 (1H, m), 3.55-4.03 (8H, m), 3.91 (3H, s), 3.94 (3H, s), 4.68 (2H, s), 6.93 (1H, d, J=8.3 Hz), 7.04-7.19 (4H, m), 7.49 (2H, d, J=8.3 Hz), 7.55-7.60 (4H, m), 7.86 (2H, d, J=8.3 Hz), 8.26 (1H, d, J=2.3 Hz), 8.61 (1H, d, J=2.8 Hz).

MS (ESI) m/z: 637 (M+H)$^+$.

Example 15

N-{4-[2-Amino-5-(3,4-dimethoxyphenyl)pyridin-3-yl]phenyl}-5-(4-fluorophenyl)-1-[2-(methylamino)-2-oxoethyl]-4-oxo-1,4-dihydropyridine-3-carboxamide

[Step 1] [3-(Ethoxycarbonyl)-5-(4-fluorophenyl)-4-oxopyridin-1(4H)-yl]acetic acid

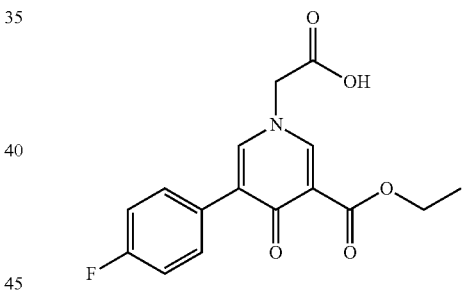

tert-Butyl bromoacetate (341 μl) was added to a suspension of ethyl 5-(4-fluorophenyl)-4-oxo-1,4-dihydropyridine-3-carboxylate (400 mg) and cesium carbonate (998 mg) in DMF (8 ml) at room temperature. The reaction mixture was stirred at room temperature overnight. The reaction mixture was diluted by adding ethyl acetate. The organic layer was washed with water and brine, dried over sodium sulfate and filtered, and the filtrate was then concentrated under reduced pressure. Dichloromethane (15 ml) and TFA (0.59 ml) were added to the residue at room temperature. The reaction mixture was stirred at room temperature for two hours. TFA (1.00 ml) was added to the reaction mixture at room temperature. The reaction mixture was stirred overnight. TFA (4.00 ml) was added to the reaction mixture at room temperature. The reaction mixture was stirred overnight. Water was added to the reaction mixture, and the organic layer was extracted with ethyl acetate, washed with brine and dried over sodium sulfate. After filtration, the filtrate was concentrated under reduced pressure, and the residue was purified by silica gel column chromatography [chloroform:methanol=19:1->17:3 (v/v)] to give 320 mg of the title compound as a solid.

$^1$H-NMR (CDCl$_3$) δ: 1.47 (3H, t, J=7.1 Hz), 4.57 (2H, q, J=7.2 Hz), 5.38 (2H, s), 7.16-7.22 (2H, m), 7.57-7.62 (2H, m), 8.50 (1H, s), 9.06 (1H, s).
MS (ESI) m/z: 320 (M+H)$^+$.

[Step 2] 5-(4-Fluorophenyl)-1-[2-(methylamino)-2-oxoethyl]-4-oxo-1,4-dihydropyridine-3-carboxylic acid

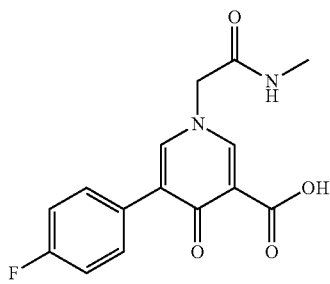

Methylamine (2 M solution in THF; 0.63 ml), EDC.HCl (96 mg), HOBt (35 mg) and DMF (3 ml) were added to the compound obtained in the above Step 1 (80 mg) at room temperature. The reaction mixture was stirred overnight. The reaction mixture was stirred at 50° C. for five hours. Water (1 ml) was added to the reaction mixture at 50° C. The reaction mixture was stirred at 50° C. for 1.5 hours and returned to room temperature. A 1 N aqueous sodium hydroxide solution (2 ml) was added to the reaction mixture at room temperature. The reaction mixture was stirred at room temperature for 0.5 hour. A 1 N aqueous hydrochloric acid solution and water were added to the reaction mixture, and the organic layer was extracted with dichloromethane and dried over sodium sulfate. After filtration, the filtrate was concentrated under reduced pressure, and the residue was washed with water to give 22 mg of the title compound as a solid.
$^1$H-NMR (CD$_3$OD) δ: 2.81 (3H, s), 4.94 (2H, s), 7.15-7.21 (2H, m), 7.65-7.72 (2H, m), 8.10 (1H, s), 8.65 (1H, s).
MS (ESI) m/z: 305 (M+H)$^+$.

[Step 3] N-{4-[2-Amino-5-(3,4-dimethoxyphenyl)pyridin-3-yl]phenyl}-5-(4-fluorophenyl)-1-[2-(methylamino)-2-oxoethyl]-4-oxo-1,4-dihydropyridine-3-carboxamide

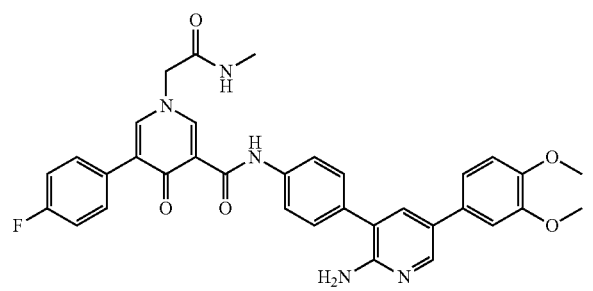 [SMILES: CNC(=O)Cn1cc(C(=O)Nc2ccc(-c3cc(-c4ccc(OC)c(OC)c4)cnc3N)cc2)c(=O)c(-c2ccc(F)cc2)c1]

HOAt (9 mg), HATU (37 mg), DMAP (4 mg) and DIPEA (20 μl) were added to a solution of the compound obtained in the above Step 2 (22 mg) in DMF (1 ml) at room temperature. The reaction mixture was stirred at room temperature for 3.5 hours. The compound obtained in Step 2 of Example 1 (21 mg) was added to the reaction mixture at room temperature. The reaction mixture was stirred at room temperature overnight. Water was added to the reaction mixture, and the precipitated solid was collected by filtration and washed with acetone to give 13 mg of the title compound as a solid.
$^1$H-NMR (DMSO-D$_6$) δ: 2.64-2.66 (3H, m), 3.74 (3H, s), 3.80 (3H, s), 4.91 (2H, s), 5.65 (2H, s), 6.96 (1H, d, J=8.7 Hz), 7.10-7.17 (2H, m), 7.27 (2H, t, J=8.9 Hz), 7.50 (2H, d, J=8.7 Hz), 7.58 (1H, d, J=2.8 Hz), 7.66-7.71 (2H, m), 7.80 (2H, d, J=8.7 Hz), 8.09 (1H, d, J=1.8 Hz), 8.22 (2H, d, J=2.3 Hz), 8.64 (1H, d, J=2.3 Hz).
MS (ESI) m/z: 608 (M+H)$^+$.

Example 16

N-{4-[2-Amino-5-(3,4-dimethoxyphenyl)pyridin-3-yl]phenyl}-1-[2-(dimethylamino)-2-oxoethyl]-5-(4-fluorophenyl)-4-oxo-1,4-dihydropyridine-3-carboxamide

[Step 1] 1-[2-(Dimethylamino)-2-oxoethyl]-5-(4-fluorophenyl)-4-oxo-1,4-dihydropyridine-3-carboxylic acid

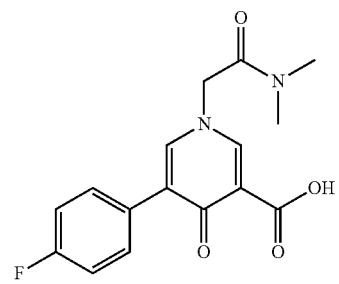 [SMILES: CN(C)C(=O)Cn1cc(C(=O)O)c(=O)c(-c2ccc(F)cc2)c1]

The compound obtained in Step 1 of Example 15 (100 mg) and dimethylamine (2 M solution in THF; 1.55 ml) yielded 33 mg of the title compound as a solid via a reaction similar to that in Step 2 of Example 15.
$^1$H-NMR (DMSO-D$_6$) δ: 2.89 (3H, s), 3.00 (3H, s), 5.27 (2H, s), 7.28-7.34 (2H, m), 7.68-7.73 (2H, m), 8.28 (1H, d, J=1.8 Hz), 8.68 (1H, d, J=2.3 Hz).
MS (ESI) m/z: 319 (M+H)$^+$.

[Step 2] N-{4-[2-Amino-5-(3,4-dimethoxyphenyl)pyridin-3-yl]phenyl}-1-[2-(dimethylamino)-2-oxoethyl]-5-(4-fluorophenyl)-4-oxo-1,4-dihydropyridine-3-carboxamide

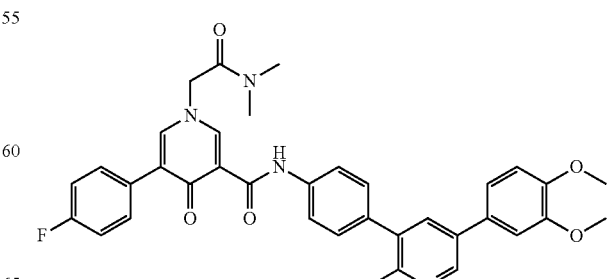

HOAt (13 mg), HATU (53 mg), DMAP (6 mg) and DIPEA (29 μl) were added to a solution of the compound obtained in the above Step 1 (33 mg) in DMF (1 ml) at room temperature. The reaction mixture was stirred at room temperature for three hours. The compound obtained in Step 2 of Example 1 (30 mg) was added to the reaction mixture at room temperature. The reaction mixture was stirred at room temperature overnight. Water was added to the reaction mixture, and the precipitated solid was collected by filtration. The resulting solid was purified by PLC [ethyl acetate:methanol=6:1 (v/v)], and the eluate was concentrated under reduced pressure. The residue was purified by PLC [dichloromethane:methanol=20:1 (v/v)] to give 10 mg of the title compound as a solid.

$^1$H-NMR (CDCl$_3$) δ: 3.06 (3H, s), 3.12 (3H, s), 3.92 (3H, s), 3.94 (3H, s), 4.67 (2H, s), 4.81 (2H, s), 6.94 (1H, d, J=8.3 Hz), 7.03-7.16 (4H, m), 7.45-7.50 (3H, m), 7.55-7.60 (3H, m), 7.86 (2H, d, J=8.3 Hz), 8.26 (1H, d, J=2.3 Hz), 8.51 (1H, d, J=2.8 Hz).

MS (ESI) m/z: 622 (M+H)$^+$.

Example 17

N-{4-[2-Amino-5-(3,4-dimethoxyphenyl)pyridin-3-yl]phenyl}-1-(2,2-difluoro-2-methoxyethyl)-5-(4-fluorophenyl)-4-oxo-1,4-dihydropyridine-3-carboxamide

[Step 1] 2,2,2-Trifluoroethyl 5-(4-fluorophenyl)-4-oxo-1-(2,2,2-trifluoroethyl)-1,4-dihydropyridine-3-carboxylate

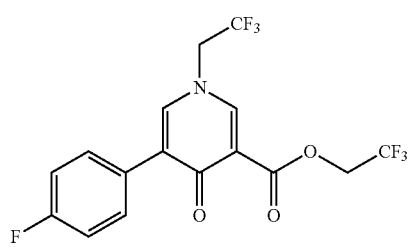 [SMILES: O=C(OCC(F)(F)F)c1cn(CC(F)(F)F)cc(-c2ccc(F)cc2)c1=O]

2,2,2-Trifluoroethyl trifluoromethanesulfonate (371 μl) was added to a suspension of 5-(4-fluorophenyl)-4-oxo-1,4-dihydropyridine-3-carboxylic acid (100 mg) and cesium carbonate (838 mg) in DMF (2 ml) at room temperature. The reaction mixture was stirred at room temperature for three hours and diluted by adding ethyl acetate. The organic layer was washed with water and brine and dried over sodium sulfate. After filtration, the filtrate was concentrated under reduced pressure, and the residue was purified by PLC [ethyl acetate:hexane=2:1 (v/v)] to give 123 mg of the title compound as a solid.

$^1$H-NMR (CDCl$_3$) δ: 4.37-4.46 (2H, m), 4.65-4.71 (2H, m), 7.05-7.12 (2H, m), 7.34-7.39 (1H, m), 7.49-7.56 (2H, m), 8.16 (1H, d, J=2.4 Hz).

MS (ESI) m/z: 398 (M+H)$^+$.

[Step 2] 1-(2,2-Difluoro-2-methoxyethyl)-5-(4-fluorophenyl)-4-oxo-1,4-dihydropyridine-3-carboxylic acid

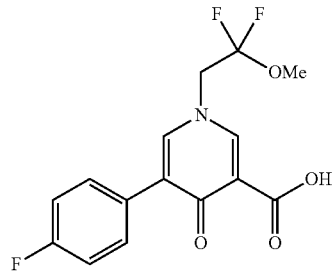 [SMILES: COC(F)(F)Cn1cc(C(=O)O)c(=O)c(-c2ccc(F)cc2)c1]

Methanol (2 ml) and a 1 N aqueous sodium hydroxide solution (2 ml) were added to a solution of the compound obtained in the above Step 1 (123 mg) in THF (2 ml) at room temperature. The reaction mixture was stirred at room temperature for three hours. The reaction mixture was stirred at 50° C. for one hour. The reaction mixture was stirred at 80° C. overnight. A 1 N aqueous sodium hydroxide solution (3 ml) was added to the reaction mixture, and the mixture was stirred at 80° C. overnight and returned to room temperature. A 1 N aqueous hydrochloric acid solution and water were added to the reaction mixture. The precipitated solid was collected by filtration, washed with water and then washed with a mixed solvent of hexane and diethyl ether [4:1 (v/v)] and dried to give 58 mg of the title compound as a solid.

[Step 3] N-{4-[2-Amino-5-(3,4-dimethoxyphenyl)pyridin-3-yl]phenyl}-1-(2,2-difluoro-2-methoxyethyl)-5-(4-fluorophenyl)-4-oxo-1,4-dihydropyridine-3-carboxamide

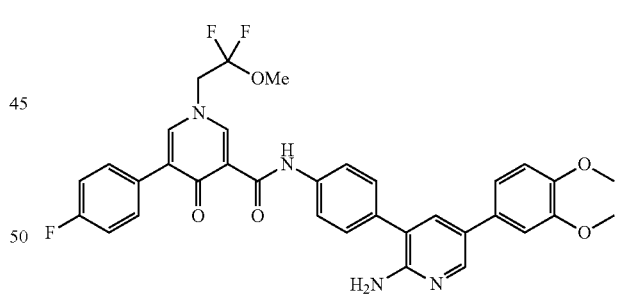

HOAt (25 mg), HATU (105 mg), DMAP (11 mg) and DIPEA (54 μl) were added to a solution of the compound obtained in the above Step 2 (58 mg) in DMF (1 ml) at room temperature. The reaction mixture was stirred at room temperature for three hours. The compound obtained in Step 2 of Example 1 (59 mg) was added to the reaction mixture at room temperature. The reaction mixture was stirred at room temperature overnight. Water was added to the reaction mixture, and the precipitated solid was collected by filtration. The resulting solid was purified by PLC (developed with ethyl acetate), and the eluate was concentrated under reduced pressure. The residue was purified by PLC [dichloromethane:methanol=20:1 (v/v)], and the eluate was concentrated under

Example 18

N-{4-[2-Amino-5-(3,4-dimethoxyphenyl)pyridin-3-yl]phenyl}-1-ethyl-4-oxo-5-phenyl-1,4-dihydropyridine-3-carboxamide

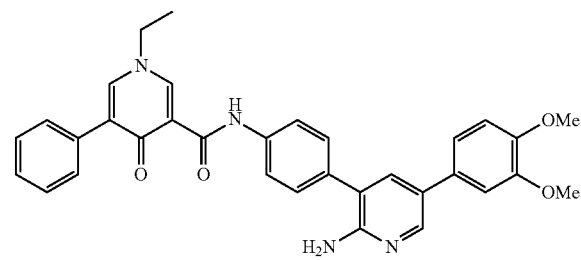 [SMILES: CCn1cc(C(=O)Nc2ccc(-c3cc(-c4ccc(OC)c(OC)c4)cnc3N)cc2)c(=O)c(-c2ccccc2)c1]

DIPEA (601 μl) was added to a solution of 1-ethyl-4-oxo-5-phenyl-1,4-dihydropyridine-3-carboxylic acid (420 mg) and COMU (961 mg) in DMF (5.0 ml) at room temperature, and the mixture was stirred for 20 minutes. The compound obtained in Step 2 of Example 1 (610 mg) was added at room temperature. The mixture was stirred for 15 hours, followed by the addition of water. The organic layer was extracted with ethyl acetate, and then washed with water and brine and dried over sodium sulfate. The solvent was distilled off under reduced pressure, and the residue was purified by silica gel column chromatography [chloroform:methanol=300:1->60:1 (v/v)] to give 700 mg of the title compound as a solid.

$^1$H-NMR (CDCl$_3$) δ: 1.58-1.64 (3H, m), 3.92 (3H, s), 3.95 (3H, s), 4.09 (2H, q, J=7.3 Hz), 4.70 (2H, s), 6.94 (1H, d, J=8.3 Hz), 7.02-7.12 (2H, m), 7.39-7.61 (9H, m), 7.85-7.91 (2H, m), 8.26 (1H, d, J=2.8 Hz), 8.66 (1H, d, J=2.8 Hz).

MS (ESI) m/z: 547 (M+H)$^+$.

reduced pressure. The residue was purified by PLC (NH) [dichloromethane:methanol=30:1 (v/v)] to give 16 mg of the title compound as a solid.

$^1$H-NMR (CDCl$_3$) δ: 3.66 (3H, s), 3.91 (3H, s), 3.94 (3H, s), 4.32 (2H, t, J=7.3 Hz), 4.69 (2H, s), 6.91-6.95 (1H, m), 7.03-7.05 (1H, m), 7.06-7.10 (1H, m), 7.14-7.20 (2H, m), 7.47-7.58 (6H, m), 7.84-7.88 (2H, m), 8.26 (1H, d, J=2.3 Hz), 8.62 (1H, d, J=2.3 Hz).

MS (ESI) m/z: 631 (M+H)$^+$.

Example 19

N-{4-[2-Amino-5-(3,4-dimethoxyphenyl)pyridin-3-yl]phenyl}-1-(2-fluoroethyl)-4-oxo-5-phenyl-1,4-dihydropyridine-3-carboxamide

[Step 1] Ethyl 1-(2-fluoroethyl)-4-oxo-5-phenyl-1,4-dihydropyridine-3-carboxylate

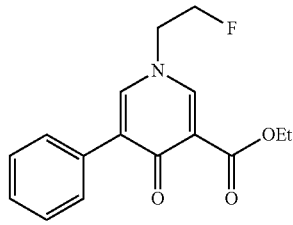 [SMILES: CCOC(=O)c1cn(CCF)cc(-c2ccccc2)c1=O]

Ethyl 4-oxo-5-phenyl-1,4-dihydropyridine-3-carboxylate (190 mg) was suspended in DMF (2.5 ml). Cesium carbonate (509 mg) and 2-fluoroethyl 4-methylbenzenesulfonate (256 mg) were sequentially added and the mixture was stirred at 50° C. for three hours. A 1 N aqueous hydrochloric acid solution was added under ice cooling, and the organic layer was extracted with ethyl acetate, washed with water and brine and then dried over sodium sulfate. The solvent was distilled off under reduced pressure, and the residue was purified by silica gel column chromatography [chloroform:methanol=300:1->40:1 (v/v)] to give 181 mg of the title compound as an oily substance.

$^1$H-NMR (CDCl$_3$) δ: 1.39 (3H, t, J=7.2 Hz), 4.09-4.22 (2H, m), 4.38 (2H, q, J=7.2 Hz), 4.68-4.73 (1H, m), 4.79-4.85 (1H, m), 7.31-7.43 (4H, m), 7.56-7.61 (2H, m), 8.16 (1H, d, J=2.8 Hz).

MS (ESI) m/z: 290 (M+H)$^+$.

[Step 2] 1-(2-Fluoroethyl)-4-oxo-5-phenyl-1,4-dihydropyridine-3-carboxylic acid

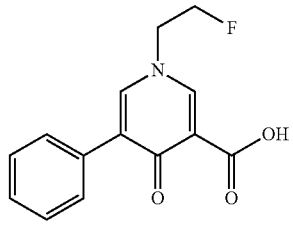 [SMILES: O=C(O)c1cn(CCF)cc(-c2ccccc2)c1=O]

A 1 N aqueous sodium hydroxide solution (1.2 ml) was added to a solution of the compound obtained in the above Step 1 (181 mg) in methanol (1.5 ml) at room temperature, and the mixture was stirred for two hours. The solvent was distilled off under reduced pressure and a 1 N aqueous hydrochloric acid solution was added. The precipitated solid was collected by filtration to give 98 mg of the title compound.

$^1$H-NMR (CDCl$_3$) δ: 4.26-4.39 (2H, m), 4.74-4.91 (2H, m), 7.40-7.51 (3H, m), 7.56-7.62 (2H, m), 7.68 (1H, d, J=2.0 Hz), 8.56 (1H, d, J=2.0 Hz)

MS (ESI) m/z: 262 (M+H)$^+$..

[Step 3] N-{4-[2-Amino-5-(3,4-dimethoxyphenyl)
pyridin-3-yl]phenyl}-1-(2-fluoroethyl)-4-oxo-5-phe-
nyl-1,4-dihydropyridine-3-carboxamide

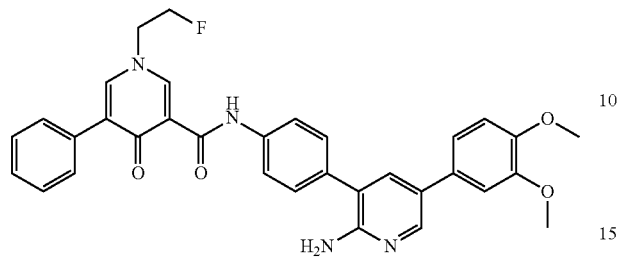

DIPEA (133 µl) was added to a solution of the compound obtained in the above Step 2 (100 mg) and COMU (213 mg) in DMF (5.0 ml) at room temperature, and the mixture was stirred for one hour. The compound obtained in Step 2 of Example 1 (135 mg) was added at room temperature. The mixture was stirred for five hours, followed by the addition of water. The organic layer was extracted with ethyl acetate, and then washed with water and brine and dried over sodium sulfate. The solvent was distilled off under reduced pressure, and the residue was purified by silica gel column chromatography [chloroform:methanol=19:1 (v/v)] to give 192 mg of the title compound as a solid.

$^1$H-NMR (CDCl$_3$) δ: 3.92 (3H, s), 3.94 (3H, s), 4.27 (1H, t, J=4.6 Hz), 4.33 (1H, t, J=4.4 Hz), 4.64 (2H, s), 4.77 (1H, t, J=4.6 Hz), 4.88 (1H, t, J=4.4 Hz), 6.94 (1H, d, J=8.3 Hz), 7.04 (1H, d, J=2.3 Hz), 7.09 (1H, dd, J=8.3, 1.8 Hz), 7.40-7.51 (5H, m), 7.56-7.60 (4H, m), 7.87 (2H, d, J=8.7 Hz), 8.27 (1H, d, J=2.3 Hz), 8.65 (1H, d, J=2.8 Hz).

MS (ESI) m/z: 565 (M+H)$^+$.

Example 20

N-{4-[2-Amino-5-(3,4-dimethoxyphenyl)pyridin-3-
yl]phenyl}-4-oxo-5-phenyl-1-(2,2,2-trifluoroethyl)-
1,4-dihydropyridine-3-carboxamide

[Step 1] Ethyl 4-oxo-5-phenyl-1-(2,2,2-trifluoroet-
hyl)-1,4-dihydropyridine-3-carboxylate

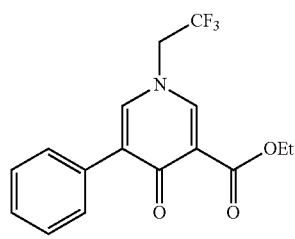 [SMILES: CCOC(=O)c1cn(CC(F)(F)F)cc(-c2ccccc2)c1=O]

Ethyl 4-oxo-5-phenyl-1,4-dihydropyridine-3-carboxylate (100 mg) was suspended in DMF (1.5 ml). Cesium carbonate (268 mg) and 2,2,2-trifluoroethyl trifluoromethanesulfonate (83 µl) were sequentially added and the mixture was stirred at room temperature for three hours. A 1 N aqueous hydrochloric acid solution was added under ice cooling, followed by extraction with ethyl acetate. The organic layer was washed with water and brine and then dried over sodium sulfate. The solvent was distilled off under reduced pressure, and the residue was purified by silica gel column chromatography [chloroform:methanol=300:1->40:1 (v/v)] to give 159 mg of the title compound as an oily substance.

$^1$H-NMR (CDCl$_3$) δ: 1.39 (3H, t, J=7.1 Hz), 4.33-4.42 (4H, m), 7.33-7.44 (4H, m), 7.51-7.58 (2H, m), 8.13 (1H, d, J=2.8 Hz).

MS (ESI) m/z: 326 (M+H)$^+$.

[Step 2] 4-Oxo-5-phenyl-1-(2,2,2-trifluoroethyl)-1,4-
dihydropyridine-3-carboxylic acid

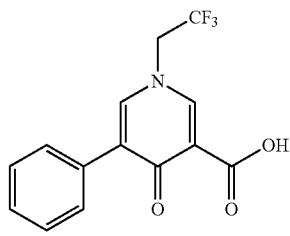 [SMILES: O=C(O)c1cn(CC(F)(F)F)cc(-c2ccccc2)c1=O]

A 1 N aqueous sodium hydroxide solution (0.73 ml) was added to a solution of the compound obtained in the above Step 1 (158 mg) in methanol (2.0 ml) at room temperature, and the mixture was stirred for two hours. The solvent was distilled off under reduced pressure and a 1 N aqueous hydrochloric acid solution was added. The precipitated solid was collected by filtration to give 90 mg of the title compound.

$^1$H-NMR (CDCl$_3$) δ: 4.54 (2H, q, J=7.6 Hz), 7.42-7.64 (6H, m), 8.54 (1H, d, J=2.8 Hz).

MS (ESI) m/z: 296 (M−H)$^-$.

[Step 3] N-{4-[2-Amino-5-(3,4-dimethoxyphenyl)
pyridin-3-yl]phenyl}-4-oxo-5-phenyl-1-(2,2,2-trif-
luoroethyl)-1,4-dihydropyridine-3-carboxamide

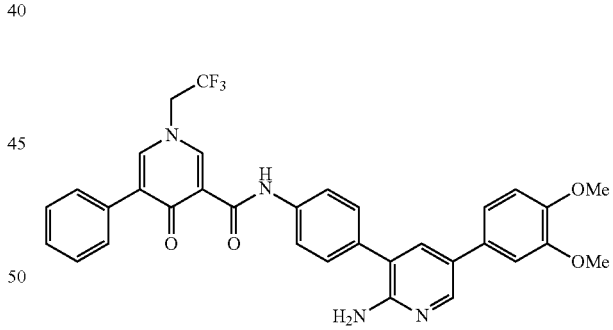

DIPEA (289 µl) was added to a solution of the compound obtained in the above Step 2 (247 mg) and COMU (462 mg) in DMF (2.5 ml) at room temperature, and the mixture was stirred for 10 minutes. The compound obtained in Step 2 of Example 1 (267 mg) was added at room temperature. The mixture was stirred for 17 hours, followed by the addition of water. The organic layer was extracted with ethyl acetate, and then washed with water and brine and dried over sodium sulfate. The solvent was distilled off under reduced pressure, and the residue was purified by silica gel column chromatography [chloroform:methanol=300:1->40:1 (v/v)] to give 320 mg of the title compound as a solid.

$^1$H-NMR (CDCl$_3$) δ: 3.92 (3H, s), 3.94 (3H, s), 4.51 (2H, q, J=7.8 Hz), 4.65 (2H, s), 6.94 (1H, d, J=8.3 Hz), 7.02-7.11

(2H, m), 7.42-7.59 (9H, m), 7.83-7.89 (2H, m), 8.27 (1H, d, J=2.8 Hz), 8.64 (1H, d, J=2.8 Hz).

MS (ESI) m/z: 601 (M+H)+.

Example 21

N-{4-[2-Amino-5-(3,4-dimethoxyphenyl)pyridin-3-yl]phenyl}-5-(2-fluorophenyl)-4-oxo-1-(2,2,2-trifluoroethyl)-1,4-dihydropyridine-3-carboxamide

[Step 1] Ethyl 5-(2-fluorophenyl)-4-oxo-1-(2,2,2-trifluoroethyl)-1,4-dihydropyridine-3-carboxylate

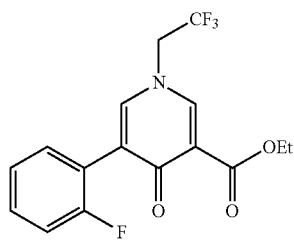 [SMILES: CCOC(=O)c1cn(CC(F)(F)F)cc(-c2ccccc2F)c1=O]

The compound obtained in Reference Example 1 (110 mg) was suspended in DMF (1.5 ml). Cesium carbonate (274 mg) and 2,2,2-trifluoroethyl trifluoromethanesulfonate (85 μl) were sequentially added and the mixture was stirred at room temperature for four hours. A 1 N aqueous hydrochloric acid solution was added under ice cooling, followed by extraction with ethyl acetate. The organic layer was washed with water and brine and then dried over sodium sulfate. The solvent was distilled off under reduced pressure, and the residue was purified by silica gel column chromatography [chloroform:methanol=300:1->60:1 (v/v)] to give 134 mg of the title compound as an oily substance.

1H-NMR (CDCl3) δ: 1.38 (3H, t, J=7.1 Hz), 4.33-4.41 (4H, m), 7.09-7.22 (2H, m), 7.30-7.38 (1H, m), 7.45 (1H, br s), 7.55-7.61 (1H, m), 8.15 (1H, d, J=2.8 Hz).

MS (ESI) m/z: 344 (M+H)+.

[Step 2] 5-(2-Fluorophenyl)-4-oxo-1-(2,2,2-trifluoroethyl)-1,4-dihydropyridine-3-carboxylic acid

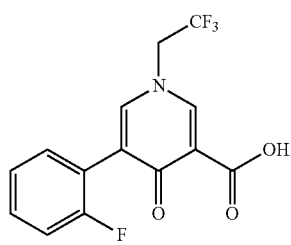 [SMILES: O=C(O)c1cn(CC(F)(F)F)cc(-c2ccccc2F)c1=O]

A 1 N aqueous sodium hydroxide solution (0.78 ml) was added to a solution of the compound obtained in the above Step 1 (134 mg) in methanol (1.2 ml) at room temperature, and the mixture was stirred for two hours. The solvent was distilled off under reduced pressure and a 1 N aqueous hydrochloric acid solution was added. The precipitated solid was collected by filtration to give 103 mg of the title compound.

1H-NMR (CDCl3) δ: 4.54 (2H, q, J=7.8 Hz), 7.17-7.30 (2H, m), 7.40-7.48 (1H, m), 7.55-7.61 (1H, m), 7.70 (1H, br s), 8.57 (1H, d, J=2.3 Hz).

MS (ESI) m/z: 316 (M+H)+.

[Step 3] N-{4-[2-Amino-5-(3,4-dimethoxyphenyl)pyridin-3-yl]phenyl}-5-(2-fluorophenyl)-4-oxo-1-(2,2,2-trifluoroethyl)-1,4-dihydropyridine-3-carboxamide

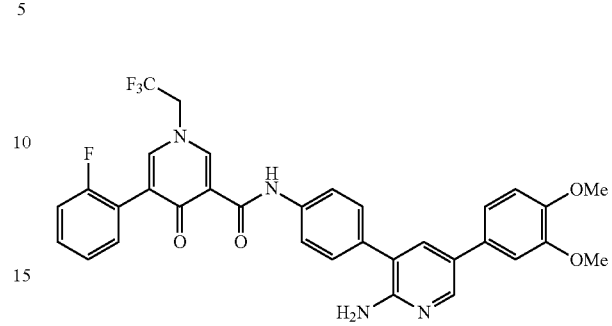

DIPEA (35 μl) was added to a solution of the compound obtained in the above Step 2 (32 mg) and COMU (57 mg) in DMF (1.0 ml) at room temperature, and the mixture was stirred for 20 minutes. The compound obtained in Step 2 of Example 1 (36 mg) was added at room temperature. The mixture was stirred for seven hours, followed by addition of a 1 N aqueous hydrochloric acid solution. After extraction with ethyl acetate, the organic layer was washed with water and brine and then dried over sodium sulfate. The solvent was distilled off under reduced pressure, and the residue was purified by silica gel column chromatography [chloroform:methanol=300:1->30:1 (v/v)] to give 49 mg of the title compound as a solid.

1H-NMR (CDCl3) δ: 3.92 (3H, s), 3.94 (3H, s), 4.51 (2H, q, J=7.8 Hz), 4.62 (2H, s), 6.94 (1H, d, J=8.3 Hz), 7.02-7.11 (2H, m), 7.18-7.31 (2H, m), 7.40-7.62 (6H, m), 7.82-7.87 (2H, m), 8.27 (1H, d, J=2.3 Hz), 8.66 (1H, d, J=2.3 Hz), 12.40 (1H, s).

MS (ESI) m/z: 619 (M+H)+.

Example 22

N-{4-[2-Amino-5-(3,4-dimethoxyphenyl)pyridin-3-yl]phenyl}-5-(3-fluorophenyl)-4-oxo-1-(2,2,2-trifluoroethyl)-1,4-dihydropyridine-3-carboxamide

[Step 1] 5-(3-Fluorophenyl)-4-oxo-1-(2,2,2-trifluoroethyl)-1,4-dihydropyridine-3-carboxylic acid

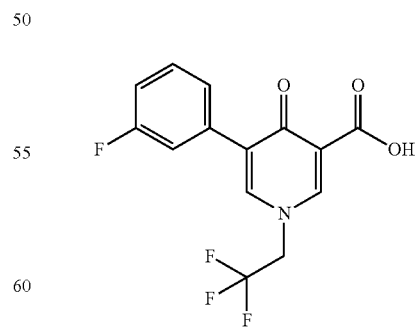

The compound obtained in Reference Example 2 (75 mg) was suspended in DMF. Cesium carbonate (140 mg) and 2,2,2-trifluoroethyl trifluoromethanesulfonate (54 μl) were sequentially added and the mixture was stirred at room temperature for four hours. The reaction solution was filtered. After washing with a small amount of DMF, a 1 N aqueous sodium hydroxide solution (0.57 ml) was added to the filtrate at room temperature, and the mixture was stirred for three hours. The solvent was distilled off under reduced pressure and a 1 N aqueous hydrochloric acid solution was added. The precipitated solid was collected by filtration to give 77 mg of the title compound.

$^1$H-NMR (CDCl$_3$) δ: 4.56 (2H, q, J=7.8 Hz), 7.12-7.19 (1H, m), 7.30-7.38 (2H, m), 7.41-7.49 (1H, m), 7.61-7.65 (1H, m), 8.54-8.59 (1H, m).

MS (ESI) m/z: 316 (M+H)$^+$.

[Step 2] N-{4-[2-Amino-5-(3,4-dimethoxyphenyl) pyridin-3-yl]phenyl}-5-(3-fluorophenyl)-4-oxo-1-(2, 2,2-trifluoroethyl)-1,4-dihydropyridine-3-carboxamide

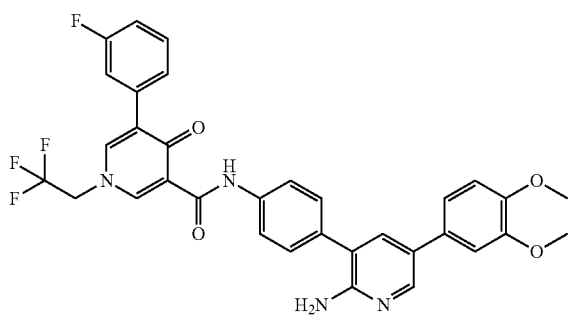 [SMILES: COc1ccc(-c2cnc(N)c(-c3ccc(NC(=O)c4cn(CC(F)(F)F)cc(-c5cccc(F)c5)c4=O)cc3)c2)cc1OC]

DIPEA (64 μl) was added to a solution of the carboxylic acid obtained in the above Step 1 (77 mg) and COMU (136 mg) in DMF (1.0 ml) at room temperature, and the mixture was stirred for 30 minutes. The compound obtained in Step 2 of Example 1 (73 mg) was added at room temperature. The mixture was stirred for 15 hours, followed by the addition of water. The precipitated solid was collected by filtration, and the resulting solid was purified by silica gel column chromatography [ethyl acetate:dichloromethane:methanol=10:10:1 (v/v)] and then crystallized from dichloromethane and diisopropyl ether to give 92 mg of the title compound as a solid.

$^1$H-NMR (CDCl$_3$) δ: 3.92 (3H, s), 3.94 (3H, s), 4.48-4.56 (2H, m), 4.62 (2H, s), 6.90-7.19 (4H, m), 7.21-7.36 (2H, m), 7.42-7.61 (5H, m), 7.82-7.89 (2H, m), 8.25-8.30 (1H, m), 8.62-8.66 (1H, m), 12.43 (1H, s).

MS (ESI) m/z: 619 (M+H)$^+$.

Example 23

N-{4-[2-Amino-5-(3,4-dimethoxyphenyl)pyridin-3-yl]phenyl}-6'-fluoro-4-oxo-1-(2,2,2-trifluoroethyl)-1, 4-dihydro-3,3'-bipyridine-5-carboxamide

[Step 1] 5-Bromo-4-hydroxypyridine-3-carboxylic acid

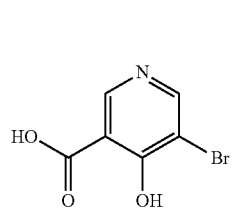

A solution of methyllithium in ether (1 M, 4.8 ml) was added to a solution of 3,5-dibromopyridin-4-ol (1200 mg) in THF (10 ml) at −78° C., and the mixture was stirred for 30 minutes. A solution of n-butyllithium in hexane (1.65 M, 6.0 ml) was added at −78° C., and the mixture was stirred for one hour. Dry ice was added at −78° C. and the mixture was stirred at 0° C. for 20 minutes, followed by addition of a 4 N aqueous hydrochloric acid solution. The precipitated solid was collected by filtration and washed with water to give a mixture of the title compound and 3,5-dibromopyridin-4-ol.

[Step 2] 2,2,2-Trifluoroethyl 5-bromo-4-oxo-1-(2,2, 2-trifluoroethyl)-1,4-dihydropyridine-3-carboxylate

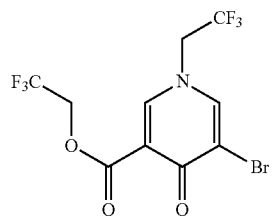 [SMILES: O=C(OCC(F)(F)F)c1cn(CC(F)(F)F)cc(Br)c1=O]

DMF (5 ml), cesium carbonate (2140 mg) and 2,2,2-trifluoroethyl trifluoromethanesulfonate (945 μl) were sequentially added to the compound obtained in the above Step 1, and the mixture was stirred at room temperature for two hours. A 1 N aqueous hydrochloric acid solution was added, followed by extraction with ethyl acetate. The organic layer was washed with a saturated aqueous sodium bicarbonate solution and brine and then dried over sodium sulfate. The solvent was distilled off under reduced pressure, and the residue was purified by silica gel column chromatography

[chloroform:methanol=300:1->30:1 (v/v)] to give the title compound as a mixture with an inseparable by-product.

[Step 3] 6'-Fluoro-4-oxo-1-(2,2,2-trifluoroethyl)-1,4-dihydro-3,3'-bipyridine-5-carboxylic acid

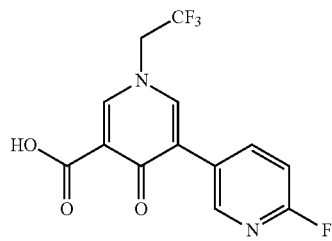 [SMILES: O=C(O)c1cn(CC(F)(F)F)cc(-c2ccc(F)nc2)c1=O]

The compound obtained in the above Step 2 was suspended in a mixed solvent of 1,4-dioxane/water (7.0/0.7 ml). (6-Fluoropyridin-3-yl)boronic acid (420 mg), potassium carbonate (659 mg) and tetrakis(triphenylphosphine)palladium (138 mg) were sequentially added, and the mixture was stirred at 100° C. for seven hours. The mixture was left to cool, followed by addition of a 1 N aqueous hydrochloric acid solution. The organic layer was extracted with chloroform and dried over sodium sulfate. The solvent was distilled off under reduced pressure, and the residue was purified by silica gel column chromatography [chloroform:methanol=300:1->20:1 (v/v)] to give the title compound as a mixture with an inseparable by-product.

[Step 4] N-{4-[2-Amino-5-(3,4-dimethoxyphenyl)pyridin-3-yl]phenyl}-6'-fluoro-4-oxo-1-(2,2,2-trifluoroethyl)-1,4-dihydro-3,3'-bipyridine-5-carboxamide

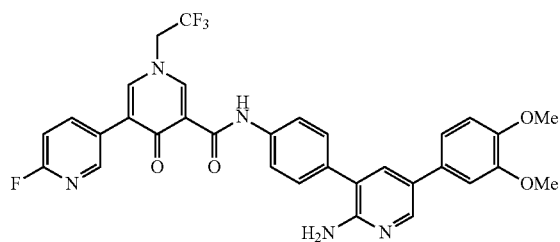 [SMILES: COc1ccc(-c2cnc(N)c(-c3ccc(NC(=O)c4cn(CC(F)(F)F)cc(-c5ccc(F)nc5)c4=O)cc3)c2)cc1OC]

DIPEA (31 µl) was added to a solution of the compound obtained in the above Step 3 and COMU (49 mg) in DMF (1.0 ml) at room temperature, and the mixture was stirred for 20 minutes. The compound obtained in Step 2 of Example 1 (31 mg) was added at room temperature. The mixture was stirred for seven hours, followed by the addition of water. After extraction with ethyl acetate, the organic layer was washed with water and brine and then dried over sodium sulfate. The solvent was distilled off under reduced pressure, and the residue was purified by PLC [chloroform:methanol=15:1 (v/v)] to give 21 mg of the title compound as a solid.

$^1$H-NMR (CDCl$_3$) δ: 3.92 (3H, s), 3.94 (3H, s), 4.55 (2H, q, J=7.8 Hz), 4.64 (2H, s), 6.94 (1H, d, J=8.3 Hz), 7.02-7.12 (3H, m), 7.49-7.60 (4H, m), 7.82-7.88 (2H, m), 8.16-8.22 (1H, m), 8.26-8.33 (2H, m), 8.68 (1H, d, J=2.3 Hz), 12.29 (1H, s).

MS (ESI) m/z: 620 (M+H)$^+$.

Example 24

N-{4-[2-Amino-5-(3,4-dimethoxyphenyl)pyridin-3-yl]phenyl}-5-(4-methylphenyl)-4-oxo-1-(2,2,2-trifluoroethyl)-1,4-dihydropyridine-3-carboxamide

[Step 1] 5-(4-Methylphenyl)-4-oxo-1-(2,2,2-trifluoroethyl)-1,4-dihydropyridine-3-carboxylic acid

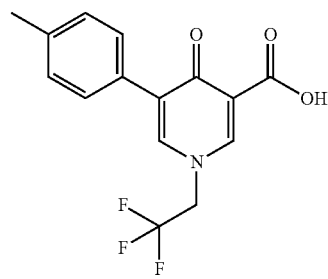 [SMILES: Cc1ccc(-c2cn(CC(F)(F)F)cc(C(=O)O)c2=O)cc1]

The compound obtained in Reference Example 3 (75 mg) and 2,2,2-trifluoroethyl trifluoromethanesulfonate (55 µl) yielded 71 mg of the title compound via a reaction similar to that in Step 1 of Example 22.

$^1$H-NMR (CDCl$_3$) δ: 2.41 (3H, s), 4.52 (2H, q, J=7.6 Hz), 7.23-7.32 (2H, m), 7.43-7.49 (2H, m), 7.57-7.61 (1H, m), 8.50-8.54 (1H, m).

MS (ESI) m/z: 312 (M+H)$^+$.

[Step 2] N-{4-[2-Amino-5-(3,4-dimethoxyphenyl)pyridin-3-yl]phenyl}-5-(4-methylphenyl)-4-oxo-1-(2,2,2-trifluoroethyl)-1,4-dihydropyridine-3-carboxamide

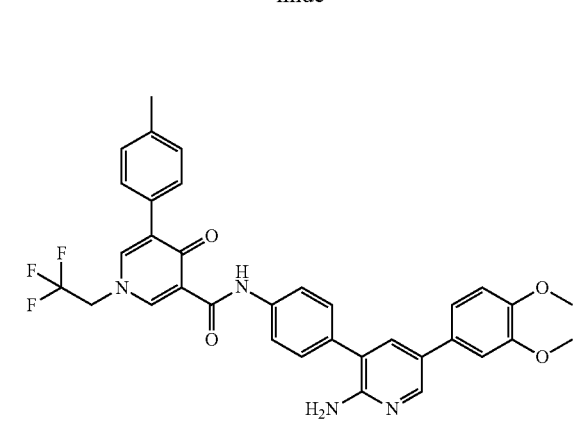

The carboxylic acid obtained in the above Step 1 (71 mg) and the compound obtained in Step 2 of Example 1 (67 mg) yielded 60 mg of the title compound as a solid via a reaction similar to that in Step 3 of Example 3.

$^1$H-NMR (CDCl$_3$) δ: 2.42 (3H, s), 3.92 (3H, s), 3.94 (3H, s), 4.45-4.54 (2H, m), 4.63 (2H, s), 6.90-7.14 (3H, m), 7.20-7.33 (2H, m), 7.42-7.59 (6H, m), 7.83-7.89 (2H, m), 8.25-8.30 (1H, m), 8.60-8.64 (1H, m), 12.55 (1H, s).

MS (ESI) m/z: 615 (M+H)$^+$.

Example 25

N-{4-[2-Amino-5-(3,4-dimethoxyphenyl)pyridin-3-yl]phenyl}-5-(4-chlorophenyl)-4-oxo-1-(2,2,2-trifluoroethyl)-1,4-dihydropyridine-3-carboxamide

[Step 1] 5-(4-Chlorophenyl)-4-oxo-1-(2,2,2-trifluoroethyl)-1,4-dihydropyridine-3-carboxylic acid

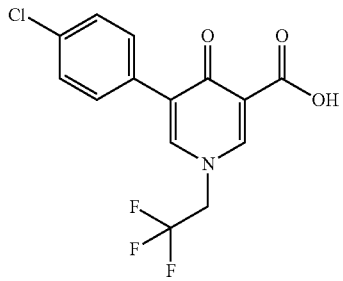 [SMILES: O=C(O)c1cn(CC(F)(F)F)cc(-c2ccc(Cl)cc2)c1=O]

The compound obtained in Reference Example 4 (75 mg) and 2,2,2-trifluoroethyl trifluoromethanesulfonate (51 µl) yielded 76 mg of the title compound via a reaction similar to that in Step 1 of Example 22.

$^1$H-NMR (CDCl$_3$) δ: 4.51-4.60 (2H, m), 7.42-7.56 (4H, m), 7.59-7.63 (1H, m), 8.54-8.57 (1H, m).

MS (ESI) m/z: 332 (M+H)$^+$.

[Step 2] N-{4-[2-Amino-5-(3,4-dimethoxyphenyl)pyridin-3-yl]phenyl}-5-(4-chlorophenyl)-4-oxo-1-(2,2,2-trifluoroethyl)-1,4-dihydropyridine-3-carboxamide

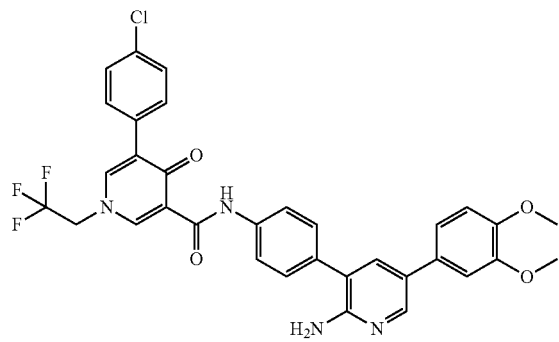 [SMILES: COc1ccc(-c2cnc(N)c(-c3ccc(NC(=O)c4cn(CC(F)(F)F)cc(-c5ccc(Cl)cc5)c4=O)cc3)c2)cc1OC]

The compound obtained in the above Step 1 (76 mg) and the compound obtained in Step 2 of Example 1 (68 mg) yielded 107 mg of the title compound as a solid via a reaction similar to that in Step 3 of Example 3.

$^1$H-NMR (CDCl$_3$) δ: 3.92 (3H, s), 3.94 (3H, s), 4.47-4.56 (2H, m), 4.63 (2H, s), 6.91-7.12 (3H, m), 7.44-7.59 (8H, m), 7.82-7.88 (2H, m), 8.26-8.29 (1H, m), 8.62-8.66 (1H, m), 12.43 (1H, s).

MS (ESI) m/z: 635 (M+H)$^+$.

Example 26

N-{4-[2-Amino-5-(3,4-dimethoxyphenyl)pyridin-3-yl]phenyl}-1-(4-fluorobenzyl)-4-oxo-5-(pyrrolidin-1-ylcarbonyl)-1,4-dihydropyridine-3-carboxamide

[Step 1] Dimethyl 1-(4-fluorobenzyl)-4-oxo-1,4-dihydropyridine-3,5-dicarboxylate

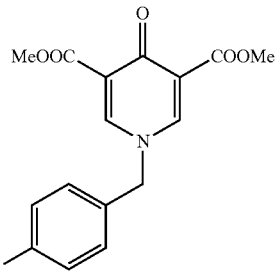

N,N-Dimethylformamide dimethylacetal (25.6 ml) was added to a solution of dimethyl 1,3-acetone-dicarboxylate (7.22 ml) in n-butyl acetate (150 ml), and the mixture was stirred at 100° C. for 1.5 hours. The reaction mixture was concentrated under reduced pressure, and methanol (100 ml) and 4-fluorobenzylamine (8.6 ml) were added to the residue. The mixture was heated under reflux overnight. The reaction mixture was concentrated under reduced pressure, and the residue was then purified by silica gel chromatography [chloroform:methanol=9:1 (v/v)] to give the title compound (6.24 g) as a solid.

$^1$H-NMR (CDCl$_3$) δ: 3.87 (6H, s), 5.00 (2H, s), 7.11-7.16 (2H, m), 7.22-7.26 (2H, m), 8.10 (2H, s).

MS (ESI) m/z: 320 (M+H)$^+$.

[Step 2] 1-(4-Fluorobenzyl)-5-(methoxycarbonyl)-4-oxo-1,4-dihydropyridine-3-carboxylic acid

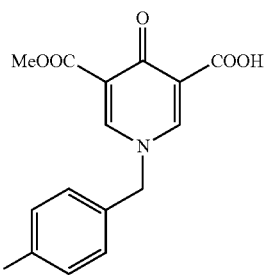

1 N sodium hydroxide (19.5 ml) was added to a solution of the compound obtained in the above Step 1 (6.24 g) in methanol (50 ml), and the mixture was stirred at room temperature overnight. Subsequently, the mixture was stirred at 50° C. for one day, and 1 N sodium hydroxide (19.5 ml) was further added, followed by stirring for two days. The reaction mixture was returned to room temperature and the precipitate was then collected by filtration. Methanol (200 ml) and acidic resin IR-120B (20 g) were added to the resulting solid, and the mixture was heated under reflux for one day. The resin was separated by filtration, and the filtrate was concentrated under reduced pressure. The precipitate was then collected by filtration from a mixed solvent of acetic acid and ethyl ether to give the title compound (1.48 g) as a solid.

¹H-NMR (DMSO-D₆) δ: 3.81 (3H, s), 5.46 (2H, s), 7.25-7.30 (2H, m) 7.53-7.59 (2H, m), 8.84 (1H, d, J=2.3 Hz), 8.93 (1H, d, J=1.8 Hz).

[Step 3] Methyl 1-(4-fluorobenzyl)-4-oxo-5-(pyrrolidin-1-ylcarbonyl)-1,4-dihydropyridine-3-carboxylate

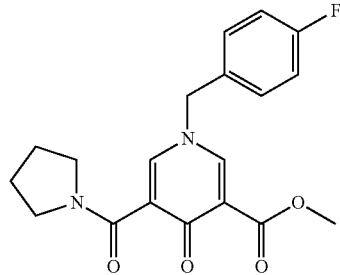 [SMILES: COC(=O)c1cn(Cc2ccc(F)cc2)cc(C(=O)N2CCCC2)c1=O]

EDC.HCl (106 mg) and pyrrolidine (71 μl) were added to a solution of the compound obtained in the above Step 2 (130 mg) and HOBt (29 mg) in DMF (1.6 ml) at room temperature, followed by stirring for 90 minutes. The mixture was further stirred at 60° C. for three hours, and water was then added at room temperature, followed by extraction with ethyl acetate. The organic layer was washed with brine and then dried over sodium sulfate. The solvent was distilled off under reduced pressure, and the residue was purified by silica gel column chromatography [chloroform:methanol=300:1->30:1 (v/v)] to give 45 mg of the title compound as an oily substance.

¹H-NMR (CDCl₃) δ: 1.81-1.96 (4H, m), 3.45 (2H, t, J=6.4 Hz), 3.57 (2H, t, J=6.7 Hz), 3.88 (3H, s), 4.96 (2H, s), 7.10-7.17 (2H, m), 7.22-7.28 (2H, m), 7.63 (1H, d, J=2.5 Hz), 8.19 (1H, d, J=2.5 Hz).

MS (ESI) m/z: 359 (M+H)⁺.

[Step 4] 1-(4-Fluorobenzyl)-4-oxo-5-(pyrrolidin-1-ylcarbonyl)-1,4-dihydropyridine-3-carboxylic acid

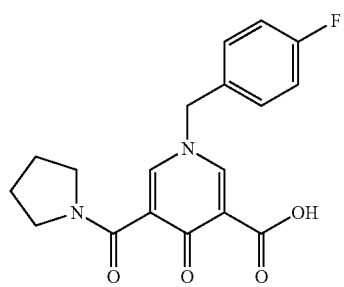 [SMILES: O=C(O)c1cn(Cc2ccc(F)cc2)cc(C(=O)N2CCCC2)c1=O]

A 1 N aqueous sodium hydroxide solution (0.26 ml) was added to a solution of the compound obtained in the above Step 3 (45 mg) in methanol (1.0 ml) at room temperature, and the mixture was stirred for 90 minutes. The solvent was distilled off under reduced pressure and a 1 N aqueous hydrochloric acid solution was added. The precipitated solid was collected by filtration to give 33 mg of the title compound.

¹H-NMR (CDCl₃) δ: 1.86-2.01 (4H, m), 3.43 (2H, t, J=6.7 Hz), 3.61 (2H, t, J=6.9 Hz), 5.10 (2H, s), 7.12-7.19 (2H, m), 7.26-7.30 (2H, m), 7.87 (1H, d, J=2.5 Hz), 8.54 (1H, d, J=2.5 Hz).

MS (ESI) m/z: 345 (M+H)⁺.

[Step 5] N-{4-[2-Amino-5-(3,4-dimethoxyphenyl)pyridin-3-yl]phenyl}-1-(4-fluorobenzyl)-4-oxo-5-(pyrrolidin-1-ylcarbonyl)-1,4-dihydropyridine-3-carboxamide

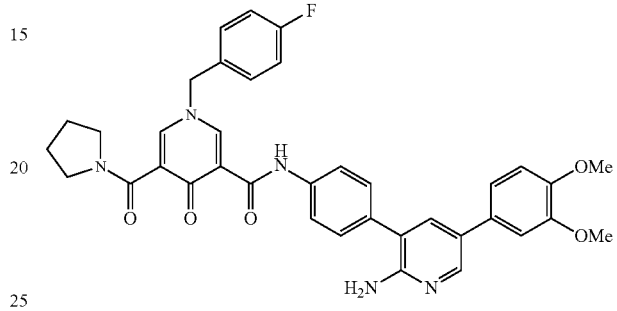

The compound obtained in the above Step 4 (29 mg) and the compound obtained in Step 2 of Example 1 (30 mg) yielded 46 mg of the title compound as a solid via a reaction similar to that in Step 3 of Example 3.

¹H-NMR (CDCl₃) δ: 1.88-2.03 (4H, m), 3.46 (2H, t, J=6.4 Hz), 3.64 (2H, t, J=6.7 Hz), 3.92 (3H, s), 3.94 (3H, s), 4.63 (2H, s), 5.09 (2H, s), 6.94 (1H, d, J=8.3 Hz), 7.02-7.18 (4H, m), 7.27-7.32 (2H, m), 7.47-7.51 (2H, m), 7.55-7.58 (1H, m), 7.75 (1H, d, J=2.8 Hz), 7.82-7.87 (2H, m), 8.27 (1H, d, J=2.3 Hz), 8.65 (1H, d, J=2.8 Hz), 12.46 (1H, s).

MS (ESI) m/z: 648 (M+H)⁺.

Example 27

N-{4-[2-Amino-5-(3,4-dimethoxyphenyl)pyridin-3-yl]phenyl}-5-{[(2R,6S)-2,6-dimethylmorpholin-4-yl]carbonyl}-1-(4-fluorobenzyl)-4-oxo-1,4-dihydropyridine-3-carboxamide

[Step 1] Methyl 5-{[(2R,6S)-2,6-dimethylmorpholin-4-yl]carbonyl}-1-(4-fluorobenzyl)-4-oxo-1,4-dihydropyridine-3-carboxylate

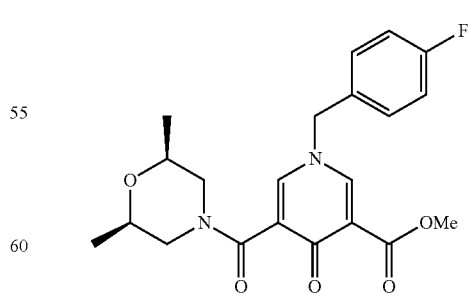

DIPEA (228 μl) was added to a solution of the compound obtained in Step 2 of Example 26 (200 mg) and COMU (365 mg) in DMF (2.5 ml) at room temperature, and the mixture was stirred for 15 minutes. cis-2,6-Dimethylmorpholine (162

μl) was added and the mixture was stirred for four hours. A 1 N hydrochloric acid solution was added at room temperature, and the organic layer was extracted with ethyl acetate, washed with brine and then dried over sodium sulfate. The solvent was distilled off under reduced pressure, and the residue was purified by silica gel column chromatography [chloroform:methanol=300:1->30:1 (v/v)] to give 30 mg of the title compound as an oily substance.

$^1$H-NMR (CDCl$_3$) δ: 1.11 (3H, d, J=6.4 Hz), 1.22 (3H, d, J=6.4 Hz), 2.46-2.55 (1H, m), 2.83-2.94 (1H, m), 3.21-3.28 (1H, m), 3.59-3.79 (2H, m), 3.88 (3H, s), 4.43-4.51 (1H, m), 4.99 (2H, s), 7.11-7.17 (2H, m), 7.22-7.31 (2H, m), 7.62 (1H, d, J=2.8 Hz), 8.21 (1H, d, J=2.8 Hz).

MS (ESI) m/z: 403 (M+H)$^+$.

[Step 2] 5-{[(2R,6S)-2,6-Dimethylmorpholin-4-yl]carbonyl}-1-(4-fluorobenzyl)-4-oxo-1,4-dihydropyridine-3-carboxylic acid

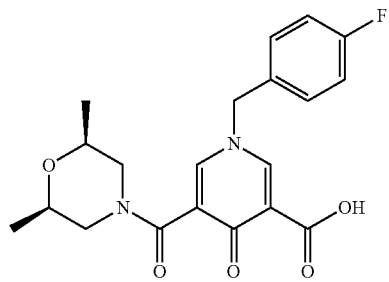 [SMILES: C[C@@H]1CN(C(=O)c2cn(Cc3ccc(F)cc3)cc(C(=O)O)c2=O)C[C@H](C)O1]

A 1 N aqueous sodium hydroxide solution (0.14 ml) was added to a solution of the compound obtained in the above Step 1 (30 mg) in methanol (1.0 ml) at room temperature, and the mixture was stirred for two hours. The solvent was distilled off under reduced pressure and a 1 N aqueous hydrochloric acid solution was added. The organic layer was extracted with chloroform and then dried over sodium sulfate. The solvent was distilled off under reduced pressure to give 28 mg of the title compound as an oily substance.

$^1$H-NMR (CDCl$_3$) δ: 1.14 (3H, d, J=6.4 Hz), 1.24 (3H, d, J=6.0 Hz), 2.49-2.58 (1H, m), 2.82-2.92 (1H, m), 3.15-3.23 (1H, m), 3.61-3.78 (2H, m), 4.44-4.52 (1H, m), 5.11 (2H, s), 7.13-7.20 (2H, m), 7.27-7.32 (2H, m), 7.86 (1H, d, J=2.3 Hz), 8.56 (1H, d, J=2.3 Hz).

MS (ESI) m/z: 389 (M+H)$^+$.

[Step 3] N-{4-[2-Amino-5-(3,4-dimethoxyphenyl)pyridin-3-yl]phenyl}-5-{[(2R,6S)-2,6-dimethylmorpholin-4-yl]carbonyl}-1-(4-fluorobenzyl)-4-oxo-1,4-dihydropyridine-3-carboxamide

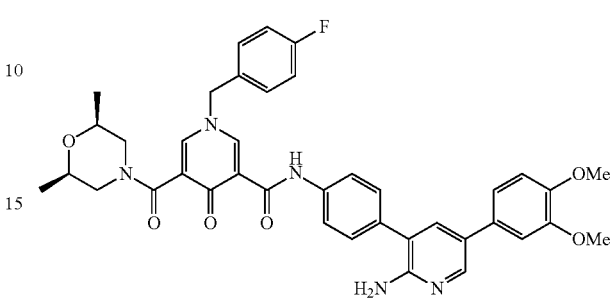

The compound obtained in the above Step 2 (28 mg) and the compound obtained in Step 2 of Example 1 (25 mg) yielded 24 mg of the title compound as a solia via a reaction similar to that in Step 3 of Example 3.

$^1$H-NMR (CDCl$_3$) δ: 1.15 (3H, d, J=6.4 Hz), 1.25 (3H, d, J=6.0 Hz), 2.52-2.61 (1H, m), 2.86-2.97 (1H, m), 3.24-3.31 (1H, m), 3.64-3.76 (2H, m), 3.92 (3H, s), 3.94 (3H, s), 4.50-4.56 (1H, m), 4.63 (2H, s), 5.10 (2H, s), 6.94 (1H, d, J=8.3 Hz), 7.02-7.11 (2H, m), 7.12-7.19 (2H, m), 7.27-7.33 (2H, m), 7.48-7.53 (2H, m), 7.57 (1H, d, J=2.3 Hz), 7.72 (1H, d, J=2.8 Hz), 7.82-7.87 (2H, m), 8.27 (1H, d, J=2.3 Hz), 8.66 (1H, d, J=2.8 Hz), 12.37 (1H, s).

MS (ESI) m/z: 692 (M+H)$^+$.

Example 28

N-{4-[2-Amino-5-(3,4-dimethoxyphenyl)pyridin-3-yl]phenyl}-1-(4-fluorobenzyl)-5-(5-methyl-1,3,4-oxadiazol-2-yl)-4-oxo-1,4-dihydropyridine-3-carboxamide

[Step 1] Methyl 5-[(2-acetylhydrazinyl)carbonyl]-1-(4-fluorobenzyl)-4-oxo-1,4-dihydropyridine-3-carboxylate

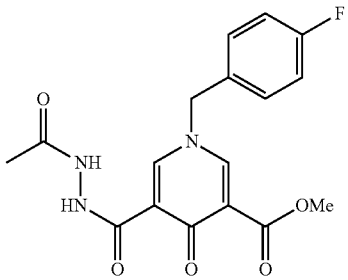 [SMILES: COC(=O)c1cn(Cc2ccc(F)cc2)cc(C(=O)NNC(C)=O)c1=O]

The compound obtained in Step 2 of Example 26 (250 mg) and acetohydrazide (76 mg) yielded 159 mg of the title compound via a reaction similar to that in Step 1 of Example 27.

¹H-NMR (CDCl₃) δ: 2.09 (3H, s), 3.91 (3H, s), 5.08 (2H, s), 7.11-7.18 (2H, m), 7.23-7.28 (2H, m), 7.95-8.00 (1H, m), 8.22 (1H, d, J=2.5 Hz), 8.47 (1H, d, J=2.5 Hz), 12.21 (1H, d, J=5.5 Hz).

[Step 2] Methyl 1-(4-fluorobenzyl)-5-(5-methyl-1,3,4-oxadiazol-2-yl)-4-oxo-1,4-dihydropyridine-3-carboxylate

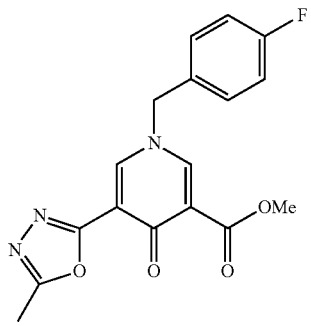 [SMILES: COC(=O)c1cn(Cc2ccc(F)cc2)cc(-c2nnc(C)o2)c1=O]

Hexachloroethane (260 mg), the compound obtained in the above Step 1 (159 mg) and triethylamine (368 μl) were sequentially added to a solution of triphenylphosphine (346 mg) in dichloromethane (3.0 ml) under ice cooling. The mixture was gradually warmed to room temperature and then stirred for 18 hours. Water was added, followed by extraction with ethyl acetate. The organic layer was washed with brine and then dried over sodium sulfate. The solvent was distilled off under reduced pressure, and the residue was purified by silica gel column chromatography [chloroform:methanol=300:1->30:1 (v/v)] to give 105 mg of the title compound as an oily substance.

¹H-NMR (CDCl₃) δ: 2.60 (3H, s), 3.91 (3H, s), 5.04 (2H, s), 7.10-7.18 (2H, m), 7.24-7.30 (2H, m), 8.21-8.25 (2H, m).
MS (ESI) m/z: 344 (M+H)⁺.

[Step 3] 1-(4-Fluorobenzyl)-5-(5-methyl-1,3,4-oxadiazol-2-yl)-4-oxo-1,4-dihydropyridine-3-carboxylic acid

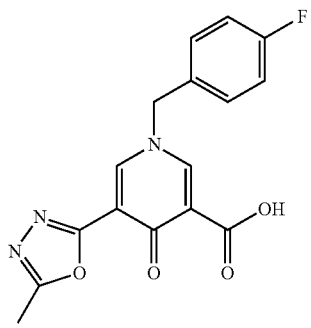

A 1 N aqueous sodium hydroxide solution (0.66 ml) was added to a mixed solution of the compound obtained in the above Step 2 (113 mg) in methanol (1.5 ml)/tetrahydrofuran (0.2 ml) at room temperature, and the mixture was stirred for two hours. The solvent was distilled off under reduced pressure and a 1 N aqueous hydrochloric acid solution was added. The precipitated solid was collected by filtration to give 74 mg of the title compound.

¹H-NMR (CDCl₃) δ: 2.66 (3H, s), 5.19 (2H, s), 7.14-7.21 (2H, m), 7.28-7.35 (2H, m), 8.49 (1H, d, J=2.3 Hz), 8.63 (1H, d, J=2.3 Hz).
MS (ESI) m/z: 330 (M+H)⁺.

[Step 4] N-{4-[2-Amino-5-(3,4-dimethoxyphenyl)pyridin-3-yl]phenyl}-1-(4-fluorobenzyl)-5-(5-methyl-1,3,4-oxadiazol-2-yl)-4-oxo-1,4-dihydropyridine-3-carboxamide

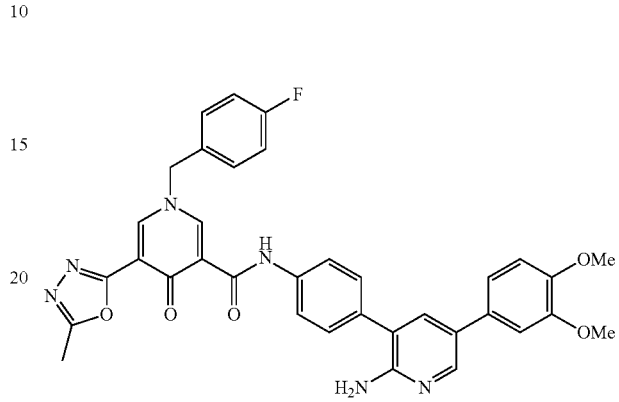

The compound obtained in the above Step 3 (28 mg) and the compound obtained in Step 2 of Example 1 (30 mg) yielded 42 mg of the title compound as a solid via a reaction similar to that in Step 3 of Example 3.

¹H-NMR (CDCl₃) δ: 2.68 (3H, s), 3.92 (3H, s), 3.94 (3H, s), 4.63 (2H, s), 5.18 (2H, s), 6.94 (1H, d, J=8.3 Hz), 7.02-7.20 (4H, m), 7.30-7.35 (2H, m), 7.48-7.59 (3H, m), 7.83-7.88 (2H, m), 8.28 (1H, d, J=2.8 Hz), 8.38 (1H, d, J=2.3 Hz), 8.74 (1H, d, J=2.8 Hz), 12.32 (1H, s).
MS (ESI) m/z: 633 (M+H)⁺.

Example 29

N-{4-[2-Amino-5-(3,4-dimethoxyphenyl)pyridin-3-yl]-3-fluorophenyl}-5-(4-fluorophenyl)-4-oxo-1-(2,2,2-trifluoroethyl)-1,4-dihydropyridine-3-carboxamide

[Step 1]
3-(4-Amino-2-fluorophenyl)-5-bromopyridin-2-amine

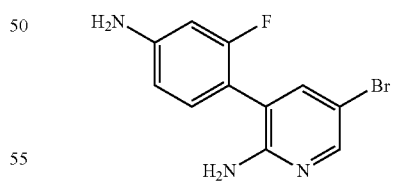

5-Bromo-3-iodopyridin-2-amine (300 mg), 3-fluoro-4-(4,4,5,5-tetramethyl-1,3,2-dioxaborolan-2-yl)aniline (238 mg), tetrakis(triphenylphosphine)palladium (58 mg) and potassium carbonate (416 mg) were suspended in dioxane (5 ml) and water (0.5 ml), and the suspension was heated under reflux at 80° C. for two days. After leaving to cool, a saturated aqueous sodium bicarbonate solution was added, and the organic layer was extracted with ethyl acetate and dried over sodium sulfate. The solvent was distilled off under reduced pressure, and the residue was purified by silica gel column chromatography [hexane:ethyl acetate=1:2 (v/v)] to give 248 mg of the title compound as a solid.

$^1$H-NMR (CDCl$_3$) δ: 3.92 (2H, s), 4.50 (2H, s), 6.44-6.56 (2H, m), 7.06-7.13 (1H, m), 7.43-7.48 (1H, m), 8.08-8.12 (1H, m).

MS (ESI) m/z: 282, 284 (M+H)$^+$.

[Step 2] 3-(4-Amino-2-fluorophenyl)-5-(3,4-dimethoxyphenyl)pyridin-2-amine

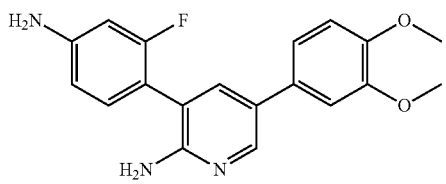 [SMILES: COc1ccc(-c2cnc(N)c(-c3ccc(N)cc3F)c2)cc1OC]

The compound obtained in the above Step 1 (2.00 g), 3,4-dimethoxyphenylboronic acid (1.42 g), [1,1'-bis(diphenylphosphino)ferrocene]palladium(II) dichloride-dichloromethane adduct (0.29 g) and potassium carbonate (2.94 g) were suspended in dioxane (20 ml) and water (4.0 ml), and the suspension was refluxed at 100° C. for four hours. After leaving to cool, a saturated aqueous sodium bicarbonate solution was added, and the organic layer was extracted with ethyl acetate and dried over sodium sulfate. The solvent was distilled off under reduced pressure, and the residue was purified by silica gel column chromatography [ethyl acetate:dichloromethane:methanol=10:10:1 (v/v)]. The resulting solid was recrystallized from dichloromethane and diisopropyl ether to give 1.93 g of the title compound as a solid.

$^1$H-NMR (CDCl$_3$) δ: 3.91 (3H, s), 3.94 (3H, s), 4.51 (2H, s), 6.49-6.58 (2H, m), 6.91-7.21 (4H, m), 7.55 (1H, d, J=2.4 Hz), 8.28 (1H, d, J=2.4 Hz).

MS (ESI) m/z: 340 (M+H)$^+$.

[Step 3] N-{4-[2-Amino-5-(3,4-dimethoxyphenyl)pyridin-3-yl]-3-fluorophenyl}-5-(4-fluorophenyl)-4-oxo-1-(2,2,2-trifluoroethyl)-1,4-dihydropyridine-3-carboxamide

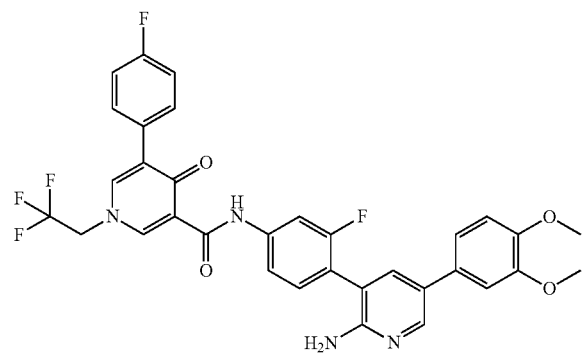 [SMILES: COc1ccc(-c2cnc(N)c(-c3ccc(NC(=O)c4cn(CC(F)(F)F)cc(-c5ccc(F)cc5)c4=O)cc3F)c2)cc1OC]

DIPEA (83 μl) was added to a solution of the compound obtained in Step 2 of Example 9 (75 mg) and COMU (132 mg) in DMF (1.0 ml) at room temperature, and the mixture was stirred for one hour. The compound obtained in the above Step 2 (70 mg) was added at room temperature. The mixture was stirred for 23 hours, followed by the addition of water. The precipitated solid was collected by filtration, and the resulting solid was purified by silica gel column chromatography [ethyl acetate] and then subjected to lyophilization using dioxane to give 119 mg of the title compound as a solid.

$^1$H-NMR (CDCl$_3$) δ: 3.91 (3H, s), 3.94 (3H, s), 4.48-4.61 (4H, m), 6.90-7.22 (5H, m), 7.34-7.61 (6H, m), 7.86-7.93 (1H, m), 8.30-8.33 (1H, m), 8.62-8.66 (1H, m).

MS (ESI) m/z: 637 (M+H)$^+$.

Example 30

N-{4-[2-Amino-5-(3,4-dimethoxyphenyl)pyridin-3-yl]-3-methylphenyl}-5-(4-fluorophenyl)-4-oxo-1-(2,2,2-trifluoroethyl)-1,4-dihydropyridine-3-carboxamide

[Step 1] 3-Bromo-5-(3,4-dimethoxyphenyl)pyridin-2-amine

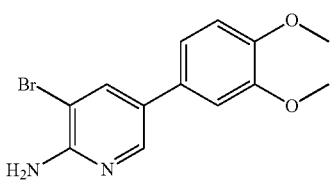 [SMILES: COc1ccc(-c2cnc(N)c(Br)c2)cc1OC]

3-Bromo-5-iodopyridin-2-amine (7.50 g), 3,4-dimethoxyphenylboronic acid (4.79 g), tetrakis(triphenylphosphine)palladium (1.45 g) and potassium carbonate (10.4 g) were suspended in dioxane (100 ml) and water (10 ml), and the suspension was heated at 80° C. for 9.5 hours. After leaving to cool, a saturated aqueous ammonium chloride solution was added, and the organic layer was extracted with ethyl acetate and dried over sodium sulfate. The solvent was distilled off under reduced pressure, and the residue was purified by silica gel column chromatography [ethyl acetate] to give 7.36 g of the title compound as a solid.

MS (ESI) m/z: 309, 311 (M+H)$^+$.

[Step 2] 3-(4-Amino-2-methylphenyl)-5-(3,4-dimethoxyphenyl)pyridin-2-amine

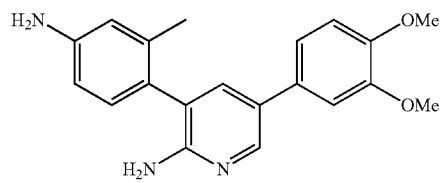 [SMILES: COc1ccc(-c2cnc(N)c(-c3ccc(N)cc3C)c2)cc1OC]

Water (0.1 ml), potassium carbonate (55 mg) and [1,1'-bis(diphenylphosphino)ferrocene]palladium(II) dichloride-dichloromethane adduct (5.4 mg) were added to a solution of the compound obtained in the above Step 1 (41 mg) and 3-methyl-4-(4,4,5,5-tetramethyl-1,3,2-dioxaborolan-2-yl)aniline (34 mg) in 1,4-dioxane (1.0 ml), and the mixture was stirred at 100° C. for 26 hours. After leaving to cool, the reaction solution was diluted with ethyl acetate. The organic layer was washed with water and brine and dried over sodium sulfate. The solvent was distilled off under reduced pressure, and the residue was purified by silica gel column chromatography [chloroform:methanol=300:1->40:1 (v/v)] to give 29 mg of the title compound as a solid.

$^1$H-NMR (CDCl$_3$) δ: 2.14 (3H, s), 3.72 (2H, s), 3.91 (3H, s), 3.93 (3H, s), 4.41 (2H, s), 6.55-6.68 (2H, m), 6.90-6.95 (1H, m), 6.99-7.10 (3H, m), 7.45-7.50 (1H, m), 8.27 (1H, d, J=2.3 Hz).

MS (ESI) m/z: 336 (M+H)$^+$.

[Step 3] N-{4-[2-Amino-5-(3,4-dimethoxyphenyl)pyridin-3-yl]-3-methylphenyl}-5-(4-fluorophenyl)-4-oxo-1-(2,2,2-trifluoroethyl)-1,4-dihydropyridine-3-carboxamide

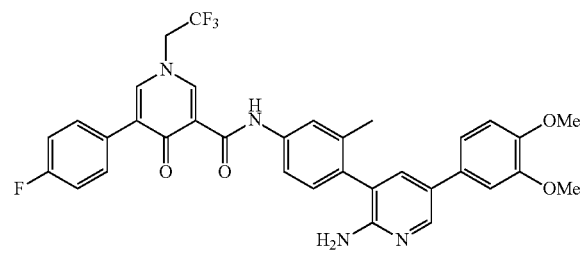 [SMILES: COc1ccc(-c2cnc(N)c(-c3ccc(NC(=O)c4cn(CC(F)(F)F)cc(-c5ccc(F)cc5)c4=O)cc3C)c2)cc1OC]

DIPEA (16 µl) was added to a solution of the compound obtained in Step 2 of Example 9 (20 mg) and COMU (35 mg) in DMF (0.8 ml) at room temperature, and the mixture was stirred for 15 minutes. 3-(4-Amino-2-methylphenyl)-5-(3,4-dimethoxyphenyl)pyridin-2-amine obtained in the above Step 2 (27 mg) was added at room temperature. After stirring for three hours, water was added. The precipitated solid was collected by filtration and purified by silica gel column chromatography [chloroform:methanol=300:1->50:1 (v/v)] to give 16 mg of the title compound as a solid.

$^1$H-NMR (CDCl$_3$) δ: 2.23 (3H, s), 3.91 (3H, s), 3.94 (3H, s), 4.43 (2H, s), 4.51 (2H, q, J=7.8 Hz), 6.93 (1H, d, J=8.6 Hz), 7.01-7.11 (2H, m), 7.15-7.25 (3H, m), 7.49-7.58 (4H, m), 7.68-7.73 (2H, m), 8.30 (1H, d, J=2.3 Hz), 8.64 (1H, d, J=2.3 Hz), 12.40 (1H, s).

MS (ESI) m/z: 633 (M+H)$^+$.

Example 31

N-[4-(2-Amino-5-phenylpyridin-3-yl)phenyl]-5-(4-fluorophenyl)-4-oxo-1-(2,2,2-trifluoroethyl)-1,4-dihydropyridine-3-carboxamide

[Step 1] N-[4-(2-Amino-5-bromopyridin-3-yl)phenyl]-5-(4-fluorophenyl)-4-oxo-1-(2,2,2-trifluoroethyl)-1,4-dihydropyridine-3-carboxamide

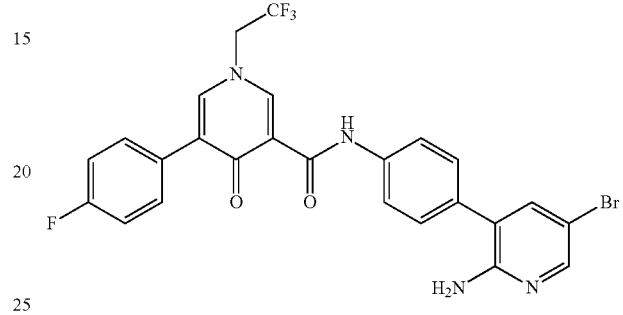

DIPEA (414 µl) was added to a solution of the compound obtained in Step 2 of Example 9 (500 mg) and COMU (883 mg) in DMF (8.0 ml) at room temperature, and the mixture was stirred for 25 minutes. The compound obtained in Step 1 of Example 1 (440 mg) was added at room temperature. The mixture was stirred for 19 hours, followed by the addition of water. The precipitated solid was collected by filtration, suspended in chloroform/diisopropyl ether and then collected by filtration to give 800 mg of the title compound.

$^1$H-NMR (CDCl$_3$) δ: 4.52 (2H, q, J=7.8 Hz), 4.62 (2H, s), 7.14-7.22 (2H, m), 7.39-7.58 (6H, m), 7.80-7.86 (2H, m), 8.09 (1H, d, J=2.8 Hz), 8.63 (1H, d, J=2.8 Hz), 12.47 (1H, s).

[Step 2] N-[4-(2-Amino-5-phenylpyridin-3-yl)phenyl]-5-(4-fluorophenyl)-4-oxo-1-(2,2,2-trifluoroethyl)-1,4-dihydropyridine-3-carboxamide

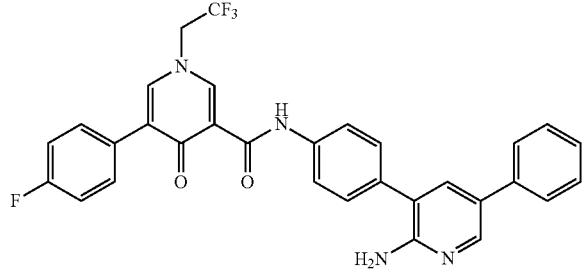 [SMILES: Nc1ncc(-c2ccccc2)cc1-c1ccc(NC(=O)c2cn(CC(F)(F)F)cc(-c3ccc(F)cc3)c2=O)cc1]

Water (0.1 ml), potassium carbonate (70 mg) and tetrakis(triphenylphosphine)palladium (19 mg) were added to a solution of the compound obtained in the above Step 1 (95 mg) and phenylboronic acid (25 mg) in 1,2-dimethoxyethane (1.5 ml), and the mixture was stirred at 80° C. for 21 hours. After leaving to cool, the reaction solution was diluted with ethyl acetate. The organic layer was washed with water and brine and dried over sodium sulfate. The solvent was distilled off under reduced pressure, and the residue was purified by silica gel column chromatography [chloroform:methanol=300:1->40:1 (v/v)] to give 39 mg of the title compound as a solid.

¹H-NMR (CDCl₃) δ: 4.52 (2H, q, J=7.8 Hz), 4.68 (2H, s), 7.14-7.21 (2H, m), 7.29-7.35 (1H, m), 7.39-7.64 (10H, m), 7.82-7.88 (2H, m), 8.31 (1H, d, J=2.3 Hz), 8.64 (1H, d, J=2.3 Hz).

MS (ESI) m/z: 559 (M+H)⁺.

Example 32

N-{4-[2-Amino-5-(4-methoxyphenyl)pyridin-3-yl]phenyl}-5-(4-fluorophenyl)-4-oxo-1-(2,2,2-trifluoroethyl)-1,4-dihydropyridine-3-carboxamide

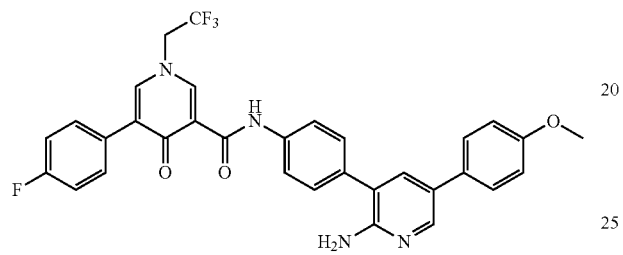

The compound obtained in Step 1 of Example 31 (95 mg) and 4-methoxyphenylboronic acid (31 mg) yielded 50 mg of the title compound as a solid via a reaction similar to that in Step 2 of Example 31.

¹H-NMR (DMSO-D₆) δ: 3.78 (3H, s), 5.28 (2H, q, J=8.6 Hz), 5.68 (2H, s), 6.95-7.01 (2H, m), 7.28-7.36 (2H, m), 7.51-7.60 (5H, m), 7.65-7.72 (2H, m), 7.78-7.85 (2H, m), 8.22 (1H, d, J=2.3 Hz), 8.28 (1H, d, J=1.8 Hz), 8.88 (1H, d, J=2.3 Hz).

MS (ESI) m/z: 589 (M+H)⁺.

Example 33

N-{4-[2-Amino-5-(3-methoxyphenyl)pyridin-3-yl]phenyl}-5-(4-fluorophenyl)-4-oxo-1-(2,2,2-trifluoroethyl)-1,4-dihydropyridine-3-carboxamide

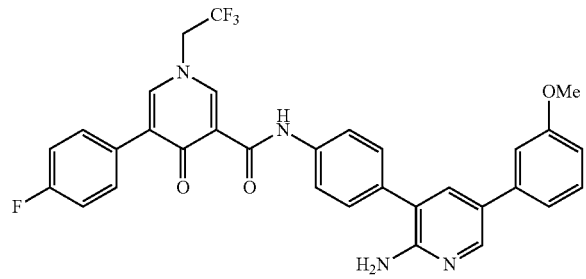 [SMILES: COc1cccc(-c2cnc(N)c(-c3ccc(NC(=O)c4cn(CC(F)(F)F)cc(-c5ccc(F)cc5)c4=O)cc3)c2)c1]

Water (0.1 ml), potassium carbonate (70 mg) and tetrakis(triphenylphosphine)palladium (19 mg) were added to a solution of the compound obtained in Step 1 of Example 31 (95 mg) and 3-methoxyphenylboronic acid (31 mg) in 1,4-dioxane (1.5 ml), and the mixture was stirred at 90° C. for 17 hours. After leaving to cool, the reaction solution was diluted with ethyl acetate. The organic layer was washed with water and brine and dried over sodium sulfate. The solvent was distilled off under reduced pressure, and the residue was purified by silica gel column chromatography [ethyl acetate:methanol=300:1->100:1 (v/v)] to give 10 mg of the title compound as a solid.

¹H-NMR (CDCl₃) δ: 3.86 (3H, s), 4.52 (2H, q, J=8.0 Hz), 4.67 (2H, s), 6.84-6.90 (1H, m), 7.05-7.09 (1H, m), 7.11-7.22 (3H, m), 7.31-7.38 (1H, m), 7.47-7.63 (6H, m), 7.82-7.88 (2H, m), 8.31 (1H, d, J=2.8 Hz), 8.64 (1H, d, J=2.8 Hz), 12.46 (1H, s).

MS (ESI) m/z: 589 (M+H)⁺.

Example 34

N-{4-[2-Amino-5-(2-methoxyphenyl)pyridin-3-yl]phenyl}-5-(4-fluorophenyl)-4-oxo-1-(2,2,2-trifluoroethyl)-1,4-dihydropyridine-3-carboxamide

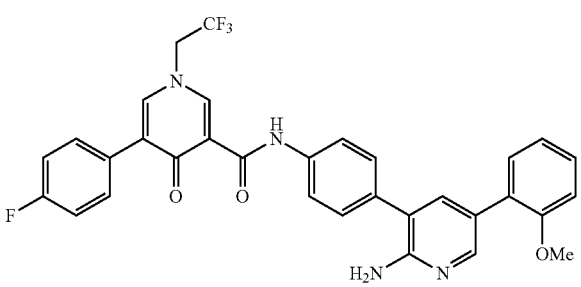 [SMILES: COc1ccccc1-c1cnc(N)c(-c2ccc(NC(=O)c3cn(CC(F)(F)F)cc(-c4ccc(F)cc4)c3=O)cc2)c1]

Water (0.1 ml), potassium carbonate (70 mg) and [1,1'-bis(diphenylphosphino)ferrocene]palladium(II) dichloride-dichloromethane adduct (6.9 mg) were added to a solution of the compound obtained in Step 1 of Example 31 (95 mg) and 2-methoxyphenylboronic acid (31 mg) in 1,2-dimethoxyethane (1.5 ml), and the mixture was stirred at 80° C. for 20 hours. After leaving to cool, the reaction solution was diluted with ethyl acetate. The organic layer was washed with water and brine and dried over sodium sulfate. The solvent was distilled off under reduced pressure, and the residue was purified by silica gel column chromatography [hexane:ethyl acetate=3:1->1:3 (v/v)] to give 34 mg of the title compound as a solid.

¹H-NMR (CDCl₃) δ: 3.83 (3H, s), 4.45-4.55 (2H, m), 4.63 (2H, s), 6.94-7.07 (2H, m), 7.15-7.34 (4H, m), 7.49-7.62 (6H, m), 7.83 (2H, d, J=8.6 Hz), 8.25 (1H, d, J=2.3 Hz), 8.64 (1H, s), 12.43 (1H, s).

MS (ESI) m/z: 589 (M+H)⁺.

Example 35

N-{4-[2-Amino-5-(4-methylphenyl)pyridin-3-yl]phenyl}-5-(4-fluorophenyl)-4-oxo-1-(2,2,2-trifluoroethyl)-1,4-dihydropyridine-3-carboxamide

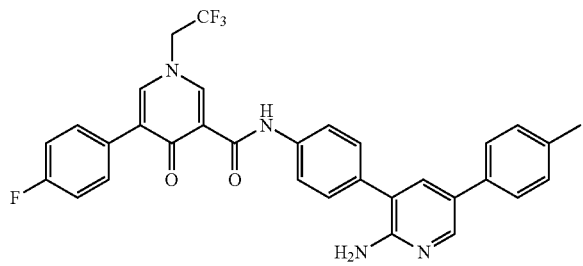 [SMILES: Cc1ccc(-c2cnc(N)c(-c3ccc(NC(=O)c4cn(CC(F)(F)F)cc(-c5ccc(F)cc5)c4=O)cc3)c2)cc1]

The compound obtained in Step 1 of Example 31 (95 mg) and 4-methylphenylboronic acid (27 mg) yielded 20 mg of the title compound as a solid via a reaction similar to that in Example 34.

$^1$H-NMR (CDCl$_3$) δ: 2.38 (3H, s), 4.51 (2H, q, J=7.8 Hz), 4.63 (2H, s), 7.15-7.25 (4H, m), 7.42-7.62 (8H, m), 7.82-7.87 (2H, m), 8.30 (1H, d, J=2.3 Hz), 8.64 (1H, d, J=2.3 Hz), 12.45 (1H, s).
MS (ESI) m/z: 573 (M+H)$^+$.

Example 36

N-{4-[2-Amino-5-(3-chlorophenyl)pyridin-3-yl]phenyl}-5-(4-fluorophenyl)-4-oxo-1-(2,2,2-trifluoroethyl)-1,4-dihydropyridine-3-carboxamide

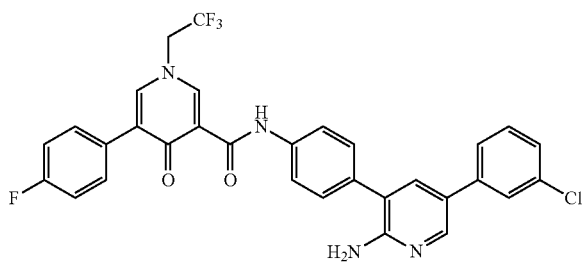 [SMILES: Nc1ncc(-c2cccc(Cl)c2)cc1-c1ccc(NC(=O)c2cn(CC(F)(F)F)cc(-c3ccc(F)cc3)c2=O)cc1]

The compound obtained in Step 1 of Example 31 (95 mg) and 3-chlorophenylboronic acid (32 mg) yielded 44 mg of the title compound as a solid via a reaction similar to that in Example 34.

$^1$H-NMR (CDCl$_3$) δ: 4.52 (2H, q, J=7.6 Hz), 4.75 (2H, s), 7.15-7.22 (2H, m), 7.27-7.44 (3H, m), 7.46-7.61 (7H, m), 7.83-7.89 (2H, m), 8.28 (1H, d, J=2.3 Hz), 8.65 (1H, d, J=2.3 Hz), 12.46 (1H, s).
MS (ESI) m/z: 593 (M+H)$^+$.

Example 37

N-{4-[2-Amino-5-(4-hydroxy-3-methoxyphenyl)pyridin-3-yl]phenyl}-5-(4-fluorophenyl)-4-oxo-1-(2,2,2-trifluoroethyl)-1,4-dihydropyridine-3-carboxamide

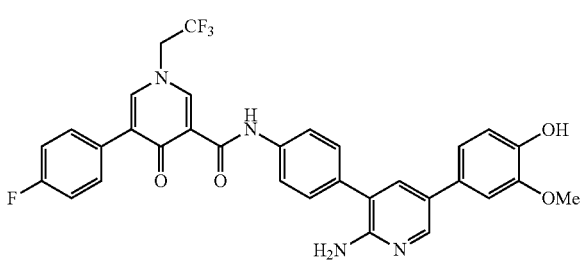 [SMILES: COc1cc(-c2cnc(N)c(-c3ccc(NC(=O)c4cn(CC(F)(F)F)cc(-c5ccc(F)cc5)c4=O)cc3)c2)ccc1O]

Water (0.1 ml), potassium carbonate (70 mg) and [1,1'-bis(diphenylphosphino)ferrocene]palladium(II) dichloride-dichloromethane adduct (6.9 mg) were added to a solution of the compound obtained in Step 1 of Example 31 (95 mg) and 2-methoxy-4-(4,4,5,5-tetramethyl-1,3,2-dioxaborolan-2-yl)phenol (51 mg) in 1,4-dioxane (1.5 ml), and the mixture was stirred at 100° C. for four hours. After leaving to cool, the reaction solution was diluted with ethyl acetate. The organic layer was washed with water and brine and dried over sodium sulfate. The solvent was distilled off under reduced pressure, and the residue was purified by silica gel column chromatography [chloroform:methanol=300:1->30:1 (v/v)] to give 43 mg of the title compound as a solid.

$^1$H-NMR (CDCl$_3$) δ: 3.95 (3H, s), 4.52 (2H, q, J=7.8 Hz), 4.65 (2H, s), 5.64 (1H, s), 6.95-7.07 (3H, m), 7.15-7.22 (2H, m), 7.47-7.58 (6H, m), 7.83-7.88 (2H, m), 8.25 (1H, d, J=2.3 Hz), 8.64 (1H, d, J=2.3 Hz), 12.46 (1H, s).
MS (ESI) m/z: 605 (M+H)$^+$.

Example 38

N-(4-{2-Amino-5-[3-methoxy-4-(2-methoxyethoxy)phenyl]pyridin-3-yl}phenyl)-5-(4-fluorophenyl)-4-oxo-1-(2,2,2-trifluoroethyl)-1,4-dihydropyridine-3-carboxamide

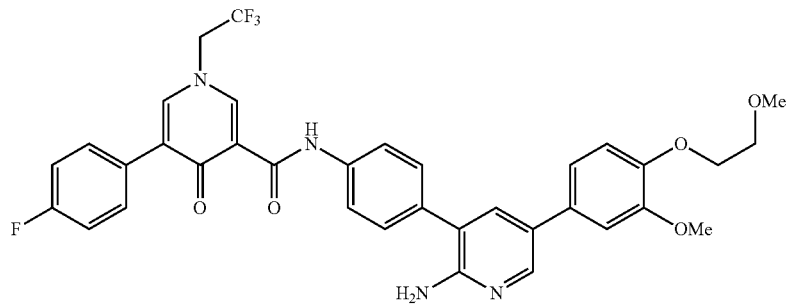 [SMILES: COCCOc1ccc(-c2cnc(N)c(-c3ccc(NC(=O)c4cn(CC(F)(F)F)cc(-c5ccc(F)cc5)c4=O)cc3)c2)cc1OC]

The compound obtained in Step 1 of Example 31 (95 mg) and 2-[3-methoxy-4-(2-methoxyethoxy)phenyl]-4,4,5,5-tetramethyl-1,3,2-dioxaborolane (62 mg) yielded 34 mg of the title compound as a solid via a reaction similar to that in Example 34.

¹H-NMR (CDCl₃) δ: 3.46 (3H, s), 3.78-3.83 (2H, m), 3.92 (3H, s), 4.18-4.23 (2H, m), 4.52 (2H, q, J=7.8 Hz), 4.63 (2H, s), 6.96-7.09 (3H, m), 7.15-7.22 (2H, m), 7.47-7.59 (6H, m), 7.83-7.88 (2H, m), 8.27 (1H, d, J=2.3 Hz), 8.64 (1H, d, J=2.3 Hz), 12.46 (1H, s).

MS (ESI) m/z: 663 (M+H)⁺.

Example 39

N-[4-(2-Amino-5-{3-methoxy-4-[2-(pyrrolidin-1-yl)ethoxy]phenyl}pyridin-3-yl)phenyl]-5-(4-fluorophenyl)-4-oxo-1-(2,2,2-trifluoroethyl)-1,4-dihydropyridine-3-carboxamide

[Step 1] 3-Bromo-5-[3-methoxy-4-(2-pyrrolidin-1-ylethoxy)phenyl]pyridin-2-amine

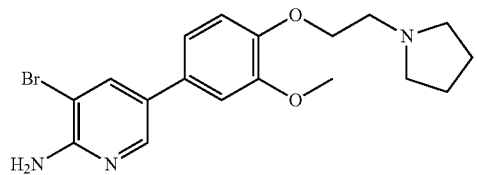 [SMILES: COc1cc(-c2cnc(N)c(Br)c2)ccc1OCCN1CCCC1]

1-{2-[2-Methoxy-4-(4,4,5,5-tetramethyl-1,3,2-dioxaborolan-2-yl)phenoxy]ethyl}pyrrolidine (5.81 g), tetrakis(triphenylphosphine)palladium (0.97 g) and potassium carbonate (6.94 g) were added to a solution of 3-bromo-5-iodopyridin-2-amine (5.00 g) in dioxane (40 ml) and water (4 ml) at room temperature. The reaction mixture was stirred at 80° C. overnight. The reaction mixture was returned to room temperature and a saturated aqueous sodium bicarbonate solution was added, followed by extraction with ethyl acetate. The organic layer was dried over magnesium sulfate. After filtration, the filtrate was concentrated under reduced pressure, and the residue was purified by silica gel column chromatography [chloroform:methanol=50:1->20:1->10:1 (v/v)] to give 4.03 g of the title compound as an oily substance.

¹H-NMR (CDCl₃) δ: 1.24 (4H, s), 2.63-2.68 (4H, m), 2.98 (2H, t, J=6.4 Hz), 3.92 (3H, s), 4.19 (2H, t, J=6.4 Hz), 4.91 (2H, s), 6.93-7.02 (3H, m), 7.85 (1H, d, J=1.8 Hz), 8.22 (1H, d, J=2.3 Hz).

MS (ESI) m/z: 392, 394 (M+H)⁺.

[Step 2] N-[4-(2-Amino-5-{3-methoxy-4-[2-(pyrrolidin-1-yl)ethoxy]phenyl}pyridin-3-yl)phenyl]-5-(4-fluorophenyl)-4-oxo-1-(2,2,2-trifluoroethyl)-1,4-dihydropyridine-3-carboxamide

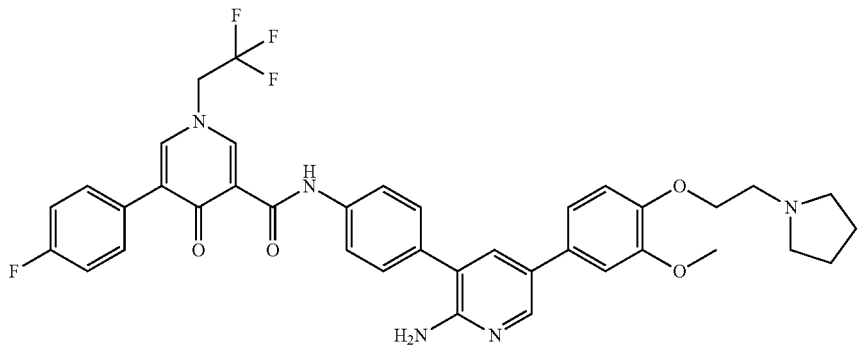 [SMILES: COc1cc(-c2cnc(N)c(-c3ccc(NC(=O)c4cn(CC(F)(F)F)cc(-c5ccc(F)cc5)c4=O)cc3)c2)ccc1OCCN1CCCC1]

COMU (391 mg) and DIPEA (159 μl) were added to a solution of the compound obtained in Step 2 of Example 9 (216 mg) in DMF (2 ml) at room temperature. The reaction mixture was stirred at room temperature for 15 minutes. 4-(4,4,5,5-Tetramethyl-1,3,2-dioxaborolan-2-yl)aniline (100 mg) was added to the reaction mixture at room temperature. The reaction mixture was stirred at 50° C. overnight. Then the reaction mixture was stirred at 80° C. for two days. Water was added to the reaction mixture, followed by extraction with ethyl acetate. The organic layer was dried over sodium sulfate and filtered, and the filtrate was then concentrated under reduced pressure. The residue was purified by silica gel column chromatography [hexane:ethyl acetate=1:1->1:3->0:100 (v/v)], and the eluate was concentrated under reduced pressure. The compound obtained in the above Step 1 (76 mg), tetrakis(triphenylphosphine)palladium (22 mg) and potassium carbonate (40 mg) were added to a solution of part of the resulting oily substance (50 mg) in dioxane (3 ml) and water (0.3 ml) at room temperature. The reaction mixture was stirred at 100° C. for two days and returned to room temperature. The reaction mixture was concentrated under reduced pressure, the residue was purified by silica gel column chromatography (NH) [ethyl acetate:methanol=100:0->9:1 (v/v)], and the eluate was concentrated under reduced pressure. The residue was purified by PLC (NH) [dichloromethane:methanol=15:1 (v/v)], and the eluate was concentrated under reduced pressure. The residue was purified by PLC (NH) [dichloromethane:methanol=40:1 (v/v)] to give 1.8 mg of the title compound as an oily substance.

¹H-NMR (CDCl₃) δ: 1.80-1.88 (4H, m), 2.62-2.72 (4H, m), 2.99 (2H, t, J=6.2 Hz), 3.92 (3H, s), 4.20 (2H, t, J=6.2 Hz), 4.52 (2H, q, J=7.6 Hz), 4.66 (2H, s), 6.97-7.20 (5H, m), 7.47-7.59 (6H, m), 7.85 (2H, d, J=7.3 Hz), 8.27 (1H, s), 8.64 (1H, s), 12.46 (1H, s).

MS (ESI) m/z: 702 (M+H)⁺.

Example 40

N-(4-{2-Amino-5-[3-methoxy-4-(2-pyrrolidin-1-ylethoxy)phenyl]pyridin-3-yl}phenyl)-1-(2-fluoroethyl)-4-oxo-5-phenyl-1,4-dihydropyridine-3-carboxamide

[Step 1] 3-(4-Aminophenyl)-5-[3-methoxy-4-(2-pyrrolidin-1-ylethoxy)phenyl]pyridin-2-amine

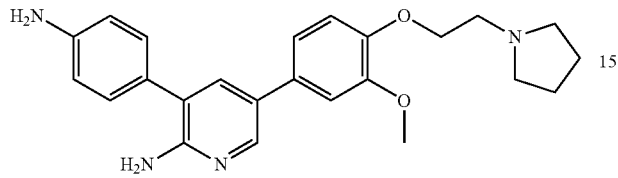

4-(4,4,5,5-Tetramethyl-1,3,2-dioxaborolan-2-yl)aniline (285 mg), tetrakis(triphenylphosphine)palladium (110 mg) and potassium carbonate (396 mg) were added to a solution of the compound obtained in Step 1 of Example 39 (375 mg) in dioxane (10 ml) and water (1 ml) at room temperature. The reaction mixture was stirred at 100° C. for five hours. The reaction mixture was returned to room temperature, followed by extraction with chloroform. The organic layer was dried over magnesium sulfate. After filtration, the filtrate was concentrated under reduced pressure, and the residue was purified by column chromatography [chloroform:methanol=19:1 (v/v)] to give 407 mg of the title compound as an oily substance.

MS (ESI) m/z: 405 (M+H)$^+$.

[Step 2] N-(4-[2-Amino-5-[3-methoxy-4-(2-pyrrolidin-1-ylethoxy)phenyl]pyridin-3-yl]phenyl)-1-(2-fluoroethyl)-4-oxo-5-phenyl-1,4-dihydropyridine-3-carboxamide

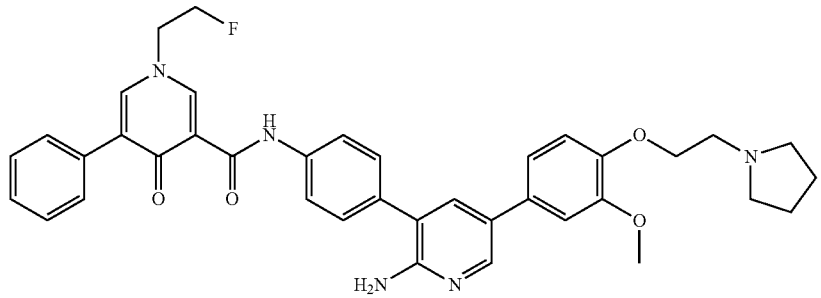 [SMILES: COc1cc(-c2cnc(N)c(-c3ccc(NC(=O)c4cn(CCF)cc(-c5ccccc5)c4=O)cc3)c2)ccc1OCCN1CCCC1]

DIPEA (67 µl) was added to a solution of the compound obtained in Step 2 of Example 19 (50 mg) and COMU (106 mg) in DMF (5.0 ml) at room temperature, and the mixture was stirred for one hour. The compound obtained in the above Step 1 (85 mg) was added at room temperature. The mixture was stirred for five hours, followed by the addition of water. The organic layer was extracted with ethyl acetate, and then washed with water and brine and dried over sodium sulfate. The solvent was distilled off under reduced pressure, and the residue was purified by reverse phase HPLC [acetonitrile:water:formic acid] to give 51 mg of the title compound as a solid.

$^1$H-NMR (CDCl$_3$) δ: 1.79-1.85 (4H, m), 2.62-2.69 (4H, m), 2.97 (2H, t, J=6.4 Hz), 3.92 (3H, s), 4.19 (2H, t, J=6.4 Hz), 4.27 (1H, t, J=4.6 Hz), 4.33 (1H, t, J=4.6 Hz), 4.64 (2H, s), 4.76 (1H, t, J=4.6 Hz), 4.88 (1H, t, J=4.6 Hz), 6.95 (1H, d, J=8.3 Hz), 7.03 (1H, d, J=2.3 Hz), 7.07 (1H, dd, J=8.3, 1.8 Hz), 7.39-7.51 (5H, m), 7.55-7.60 (4H, m), 7.87 (2H, dt, J=8.3, 2.3 Hz), 8.26 (1H, d, J=2.3 Hz), 8.65 (1H, d, J=2.8 Hz).

MS (ESI) m/z: 648 (M+H)$^+$.

Example 41

N-[4-(2-Amino-5-{4-[(2R)-1,4-dioxan-2-ylmethoxy]-3-methoxyphenyl}pyridin-3-yl)phenyl]-1-benzyl-5-(4-fluorophenyl)-4-oxo-1,4-dihydropyridine-3-carboxamide

[Step 1] 1-Benzyl-5-(4-fluorophenyl)-4-oxo-N-[4-(4,4,5,5-tetramethyl-1,3,2-dioxaborolan-2-yl)phenyl]-1,4-dihydropyridine-3-carboxamide

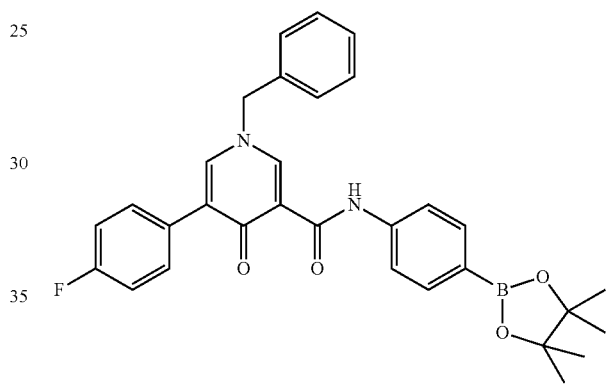

EDC.HCl (152 mg), HOBt (73 mg) and 4-(4,4,5,5-tetramethyl-1,3,2-dioxaborolan-2-yl)aniline (128 mg) were added to a solution of 1-benzyl-5-(4-fluorophenyl)-4-oxo-1,4-dihydropyridine-3-carboxylic acid (171 mg) in DMF (3 ml) at room temperature. The reaction mixture was stirred at 50° C. overnight. EDC.HCl (76 mg) and 4-(4,4,5,5-tetramethyl-1,3,2-dioxaborolan-2-yl)aniline (64 mg) were added to the reaction mixture at 50° C. The reaction mixture was stirred at 50° C. overnight. The reaction mixture was stirred at 80° C. overnight. The reaction mixture was returned to room temperature and diluted by adding water. The precipitated solid was collected by filtration. The resulting solid was purified by silica gel column chromatography [hexane:ethyl acetate=5:1->4:1->3:1->1:1 (v/v)] to give 112 mg of the title compound as a solid.

MS (ESI) m/z: 525 (M+H)⁺.

[Step 2] 3-Bromo-5-{4-[(2R)-1,4-dioxan-2-yl-methoxy]-3-methoxyphenyl}pyridin-2-amine

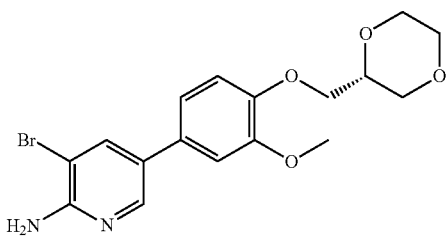 [SMILES: COc1cc(-c2cnc(N)c(Br)c2)ccc1OC[C@H]1COCCO1]

The compound obtained in Reference Example 7 (2.64 g), 3-bromo-5-iodopyridin-2-amine (2.25 g), tetrakis(triphenylphosphine)palladium (430 mg) and potassium carbonate (3.12 g) were suspended in dioxane (30 ml) and water (6 ml), and the suspension was stirred at 80° C. overnight. After leaving to cool, the reaction solution was diluted with chloroform, followed by washing with water. The organic layer was dried over sodium sulfate, and the solvent was distilled off under reduced pressure. The residue was then purified by silica gel column chromatography [ethyl acetate:hexane=1:1->chloroform:methanol=19:1 (v/v)] to give 2.05 g of the title compound as a solid.

MS (ESI) m/z: 395, 397 (M+H)⁺.

[Step 3] N-[4-(2-Amino-5-{4-[(2R)-1,4-dioxan-2-ylmethoxy]-3-methoxyphenyl}pyridin-3-yl)phenyl]-1-benzyl-5-(4-fluorophenyl)-4-oxo-1,4-dihydropyridine-3-carboxamide

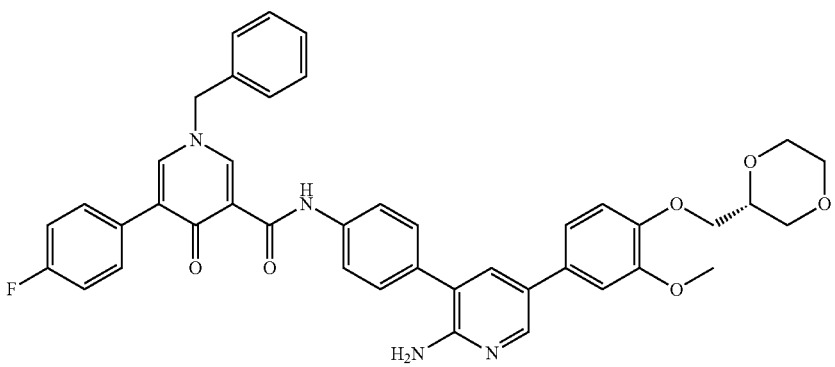 [SMILES: COc1cc(-c2cnc(N)c(-c3ccc(NC(=O)c4cn(Cc5ccccc5)cc(-c5ccc(F)cc5)c4=O)cc3)c2)ccc1OC[C@H]1COCCO1]

The compound obtained in the above Step 2 (93 mg), tetrakis(triphenylphosphine)palladium (49 mg) and potassium carbonate (88 mg) were added to a solution of the compound obtained in the above Step 1 (112 mg) in dioxane (3 ml) and water (0.3 ml) at room temperature. The reaction mixture was stirred at 100° C. overnight. The reaction mixture was returned to room temperature and diluted by adding ethyl acetate. The organic layer was washed with water and brine, dried over sodium sulfate and filtered, and the filtrate was then concentrated under reduced pressure. The residue was purified by PLC (developed with ethyl acetate), and the eluate was concentrated under reduced pressure. The residue was purified by PLC [dichloromethane:methanol=15:1 (v/v)] to give 57 mg of the title compound as a solid.

¹H-NMR (CDCl₃) δ: 3.52-3.83 (5H, m), 3.89 (3H, s), 3.93-4.09 (4H, m), 4.72 (2H, s), 5.15 (2H, s), 6.95 (1H, d, J=8.3 Hz), 7.01-7.06 (2H, m), 7.09-7.15 (2H, m), 7.25-7.30 (2H, m), 7.40-7.56 (9H, m), 7.82-7.87 (2H, m), 8.25 (1H, d, J=2.3 Hz), 8.73 (1H, d, J=2.3 Hz).

MS (ESI) m/z: 713 (M+H)⁺.

Example 42

N-[4-(2-Amino-5-{4-[(2R)-1,4-dioxan-2-ylmethoxy]-3-methoxyphenyl}pyridin-3-yl)phenyl]-5-(4-fluorophenyl)-4-oxo-1-(2,2,2-trifluoroethyl)-1,4-dihydropyridine-3-carboxamide

[Step 1] 3-(4-Aminophenyl)-5-{4-[(2R)-1,4-dioxan-2-ylmethoxy]-3-methoxyphenyl}pyridin-2-amine

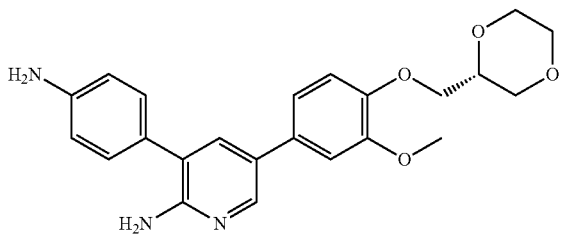 [SMILES: COc1cc(-c2cnc(N)c(-c3ccc(N)cc3)c2)ccc1OC[C@H]1COCCO1]

The compound obtained in Step 2 of Example 41 (2.05 g), 4-(4,4,5,5-tetramethyl-1,3,2-dioxaborolan-2-yl)aniline (1.14 g), tetrakis(triphenylphosphine)palladium (0.3 g), and potassium carbonate (2.15 g) were suspended in dioxane (30 ml) and water (6 ml), and the suspension was stirred at 100° C. for two hours. After leaving to cool, the reaction solution was diluted with chloroform, followed by washing with water. The organic layer was dried over anhydrous sodium sulfate. The solvent was distilled off under reduced pressure, and the residue was purified by silica gel column chromatography [ethyl acetate:hexane=1:1->chloroform:ethanol=19:1 (v/v)] to give 1.27 g of the title compound as a solid.

MS (ESI) m/z: 408 (M+H)⁺.

[Step 2] N-[4-(2-Amino-5-{4-[(2R)-1,4-dioxan-2-ylmethoxy]-3-methoxyphenyl}pyridin-3-yl)phenyl]-5-(4-fluorophenyl)-4-oxo-1-(2,2,2-trifluoroethyl)-1,4-dihydropyridine-3-carboxamide

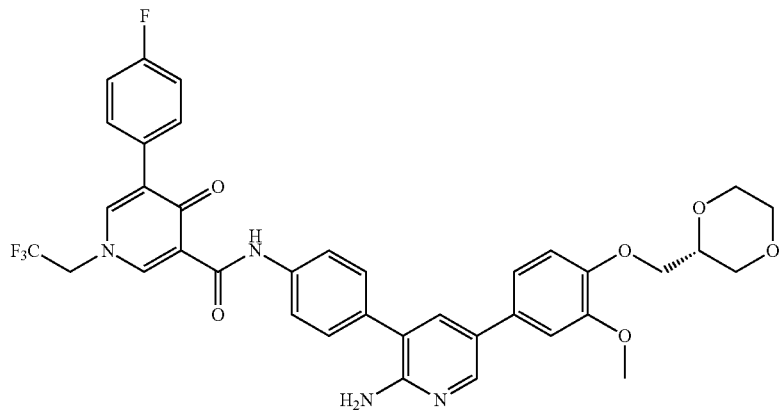 [SMILES: COc1cc(-c2cnc(N)c(-c3ccc(NC(=O)c4cn(CC(F)(F)F)cc(-c5ccc(F)cc5)c4=O)cc3)c2)ccc1OC[C@H]1COCCO1]

COMU (82 mg) and DIPEA (51 µl) were added to a solution of the compound obtained in Step 2 of Example 9 (51 mg) in DMF (1 ml), and the mixture was stirred at room temperature for five minutes. The compound obtained in the above Step 1 (60 mg) was added at room temperature, and the mixture was stirred at room temperature for five hours. Water was added to the reaction solution, followed by extraction with ethyl acetate. The organic layer was dehydrated with sodium sulfate, and the solvent was distilled off under reduced pressure. The resulting residue was suspended in ethyl acetate and diisopropyl ether. The solid obtained by filtration was subjected to silica gel column chromatography [ethyl acetate:methanol=99:1->9:1 (v/v)] and then purified by reverse phase HPLC [acetonitrile:water:formic acid] to give 14 mg of the title compound as a solid.

$^1$H-NMR (CDCl$_3$) δ: 3.50-3.55 (1H, m), 3.61-3.69 (1H, m), 3.70-3.76 (1H, m), 3.78-3.85 (2H, m), 3.88 (3H, s), 3.92-3.99 (2H, m), 4.00-4.08 (2H, m), 4.50 (2H, q, J=7.8 Hz), 4.60-4.66 (2H, m), 6.94 (1H, d, J=8.2 Hz), 6.99-7.05 (2H, m), 7.13-7.19 (2H, m), 7.45-7.50 (3H, m), 7.50-7.55 (3H, m), 7.83 (2H, d, J=8.7 Hz), 8.24 (1H, d, J=1.8 Hz), 8.62 (1H, d, J=2.3 Hz), 12.43 (1H, s).

MS (ESI) m/z: 705 (M+H)$^+$.

Example 43

N-[4-(2-Amino-5-{4-[(2R)-1,4-dioxan-2-ylmethoxy]-3-methoxyphenyl}pyridin-3-yl)phenyl]-1-(2-fluoroethyl)-5-(4-fluorophenyl)-4-oxo-1,4-dihydropyridine-3-carboxamide

[Step 1] N-[4-(2-Amino-5-bromopyridin-3-yl)phenyl]-1-(2-fluoroethyl)-5-(4-fluorophenyl)-4-oxo-1,4-dihydropyridine-3-carboxamide

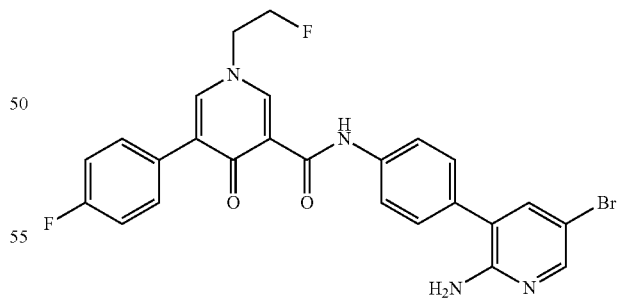

DIPEA (114 µl) was added to a solution of the compound obtained in Step 2 of Example 8 (91 mg) and COMU (181 mg) in DMF (2.0 ml) at room temperature, and the mixture was stirred for 20 minutes. The compound obtained in Step 1 of Example 1 (95 mg) was added at room temperature. The mixture was stirred for six hours, followed by the addition of water. After extraction with ethyl acetate, the organic layer was washed with brine and then dried over sodium sulfate.

The solvent was distilled off under reduced pressure, and the residue was purified by silica gel column chromatography [chloroform:methanol=300:1->30:1 (v/v)] to give 139 mg of the title compound as a solid.

¹H-NMR (CDCl₃) δ: 4.24-4.36 (2H, m), 4.63 (2H, s), 4.73-4.91 (2H, m), 7.13-7.21 (2H, m), 7.39-7.44 (2H, m), 7.48 (1H, d, J=2.3 Hz), 7.53-7.60 (3H, m), 7.82-7.88 (2H, m), 8.08 (1H, d, J=2.3 Hz), 8.64 (1H, d, J=2.3 Hz).

MS (ESI) m/z: 525 (M+H)⁺.

[Step 2] N-[4-(2-Amino-5-{4-[(2R)-1,4-dioxan-2-ylmethoxy]-3-methoxyphenyl}pyridin-3-yl)phenyl]-1-(2-fluoroethyl)-5-(4-fluorophenyl)-4-oxo-1,4-dihydropyridine-3-carboxamide

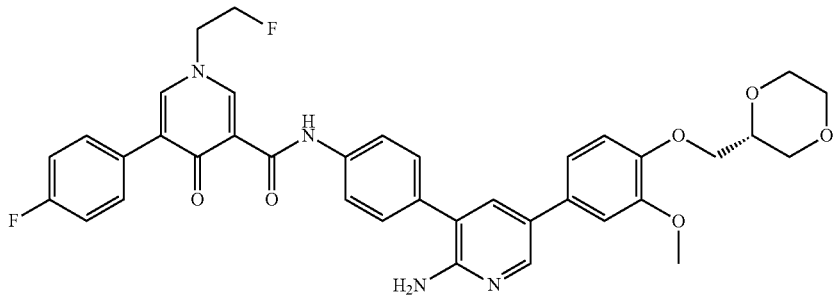 [SMILES: COc1cc(-c2cnc(N)c(-c3ccc(NC(=O)c4cn(CCF)cc(-c5ccc(F)cc5)c4=O)cc3)c2)ccc1OC[C@H]1COCCO1]

Water (0.1 ml), potassium carbonate (61 mg) and tetrakis (triphenylphosphine)palladium (17 mg) were added to a solution of the compound obtained in the above Step 1 (77 mg) and the compound obtained in Reference Example 7 (56 mg) in 1,4-dioxane (1.4 ml), and the mixture was stirred at 100° C. for six hours. After leaving to cool, the reaction solution was diluted with chloroform. The organic layer was washed with water and then dried over sodium sulfate. The solvent was distilled off under reduced pressure, and the residue was purified by reverse phase HPLC [acetonitrile:water:formic acid] to give 35 mg of the title compound as a solid.

¹H-NMR (CDCl₃) δ: 3.51-3.88 (5H, m), 3.90 (3H, s), 3.94-4.16 (4H, m), 4.24-4.37 (2H, m), 4.64 (2H, s), 4.74-4.91 (2H, m), 6.94-7.08 (3H, m), 7.14-7.20 (2H, m), 7.46-7.60 (6H, m), 7.83-7.90 (2H, m), 8.26 (1H, d, J=2.5 Hz), 8.65 (1H, d, J=2.5 Hz).

MS (ESI) m/z: 669 (M+H)⁺.

Example 44

N-[4-(2-Amino-5-{4-[(2R)-1,4-dioxan-2-ylmethoxy]-3-methoxyphenyl}pyridin-3-yl)phenyl]-1-(2-fluoroethyl)-4-oxo-5-phenyl-1,4-dihydropyridine-3-carboxamide

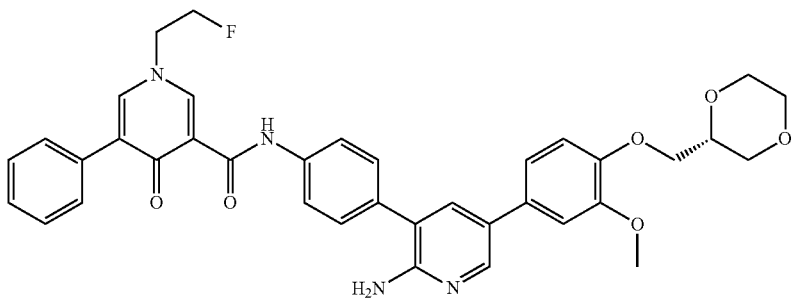 [SMILES: COc1cc(-c2cnc(N)c(-c3ccc(NC(=O)c4cn(CCF)cc(-c5ccccc5)c4=O)cc3)c2)ccc1OC[C@H]1COCCO1]

DIPEA (60 μl) was added to a solution of the compound obtained in Step 2 of Example 19 (50 mg) and COMU (96 mg) in DMF (3.0 ml) at room temperature, and the mixture was stirred for one hour. The compound obtained in Step 1 of Example 42 (70 mg) was added at room temperature. The mixture was stirred for five hours, followed by the addition of water. The organic layer was extracted with ethyl acetate, and then washed with water and brine and dried over sodium sulfate. The solvent was distilled off under reduced pressure, and the residue was purified by silica gel column chromatography [chloroform:methanol=19:1->9:1 (v/v)] to give 87 mg of the title compound as a solid.

$^1$H-NMR (CDCl$_3$) δ: 3.51-3.88 (5H, m), 3.90 (3H, s), 3.94-4.11 (4H, m), 4.27 (1H, t, J=4.6 Hz), 4.33 (1H, t, J=4.4 Hz), 4.65 (2H, s), 4.77 (1H, t, J=4.4 Hz), 4.88 (1H, t, J=4.4 Hz), 6.96 (1H, d, J=8.3 Hz), 7.02-7.07 (2H, m), 7.39-7.51 (5H, m), 7.56-7.60 (4H, m), 7.87 (2H, d, J=8.7 Hz), 8.26 (1H, d, J=2.3 Hz), 8.65 (1H, d, J=2.8 Hz).

MS (ESI) m/z: 651 (M+H)$^+$.

Example 45

N-[4-(2-Amino-5-{4-[(2R)-1,4-dioxan-2-ylmethoxy]-3-methoxyphenyl}pyridin-3-yl)phenyl]-1-ethyl-4-oxo-5-phenyl-1,4-dihydropyridine-3-carboxamide

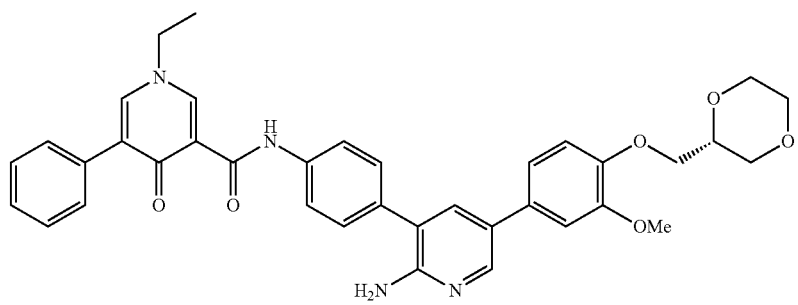 [SMILES: CCn1cc(C(=O)Nc2ccc(-c3cc(-c4ccc(OC[C@H]5COCCO5)c(OC)c4)cnc3N)cc2)c(=O)c(-c2ccccc2)c1]

DIPEA (240 μl) was added to a solution of 1-ethyl-4-oxo-5-phenyl-1,4-dihydropyridine-3-carboxylic acid (168 mg) and COMU (384 mg) in DMF (2.3 ml) at room temperature, and the mixture was stirred for 20 minutes. The compound obtained in Step 1 of Example 42 (295 mg) was added at room temperature. The mixture was stirred for 15 hours, followed by the addition of water. The organic layer was extracted with ethyl acetate, and then washed with water and brine and dried over sodium sulfate. The solvent was distilled off under reduced pressure, and the residue was purified by silica gel column chromatography [chloroform:methanol=300:1->30:1 (v/v)] to give 235 mg of the title compound as a solid.

$^1$H-NMR (CDCl$_3$) δ: 1.57-1.63 (3H, m), 3.50-3.59 (1H, m), 3.63-3.89 (4H, m), 3.91 (3H, s), 3.94-4.14 (6H, m), 4.80 (2H, s), 6.94-7.08 (3H, m), 7.39-7.51 (5H, m), 7.54-7.61 (4H, m), 7.86-7.91 (2H, m), 8.24 (1H, d, J=2.5 Hz), 8.66 (1H, d, J=2.5 Hz).

MS (ESI) m/z: 633 (M+H)$^+$.

Example 46

N-[4-(2-Amino-5-{4-[(2R)-1,4-dioxan-2-yl-methoxy]-3-methoxyphenyl}pyridin-3-yl)phenyl]-1-ethyl-5-(4-fluorophenyl)-4-oxo-1,4-dihydropyridine-3-carboxamide

[Step 1] N-[4-(2-Amino-5-bromopyridin-3-yl)phenyl]-1-ethyl-5-(4-fluorophenyl)-4-oxo-1,4-dihydropyridine-3-carboxamide

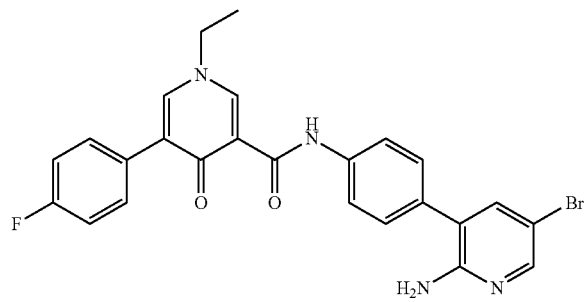 [SMILES: CCn1cc(C(=O)Nc2ccc(-c3cc(Br)cnc3N)cc2)c(=O)c(-c2ccc(F)cc2)c1]

DIPEA (120 µl) was added to a solution of the compound obtained in Step of Example 3 (80 mg) and COMU (192 mg) in DMF (1.5 ml) at room temperature, and the mixture was stirred for 10 minutes. The compound obtained in Step 1 of Example 1 (100 mg) was added at room temperature. The mixture was stirred for four hours, followed by the addition of water. The precipitated solid was collected by filtration to give 174 mg of the title compound.

$^1$H-NMR (CDCl$_3$) δ: 1.60 (3H, t, J=7.3 Hz), 4.09 (2H, q, J=7.3 Hz), 4.71 (2H, s), 7.13-7.21 (2H, m), 7.38-7.44 (2H, m), 7.47-7.61 (4H, m), 7.83-7.88 (2H, m), 8.08 (1H, d, J=2.3 Hz), 8.65 (1H, d, J=2.3 Hz).

[Step 2] N-[4-(2-Amino-5-{4-[(2R)-1,4-dioxan-2-ylmethoxy]-3-methoxyphenyl}pyridin-3-yl)phenyl]-1-ethyl-5-(4-fluorophenyl)-4-oxo-1,4-dihydropyridine-3-carboxamide

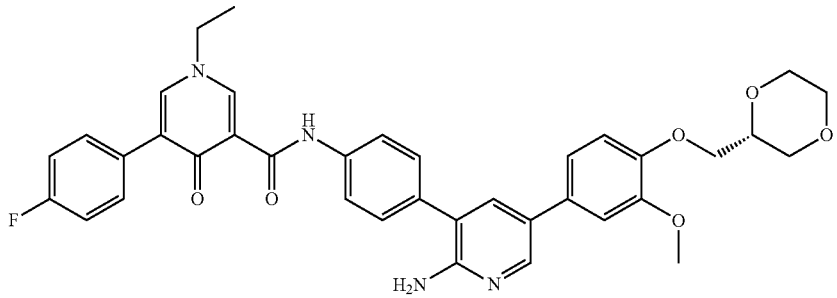 [SMILES: CCn1cc(C(=O)Nc2ccc(-c3cc(-c4ccc(OC[C@H]5COCCO5)c(OC)c4)cnc3N)cc2)c(=O)c(-c2ccc(F)cc2)c1]

Water (0.1 ml), potassium carbonate (65 mg) and tetrakis(triphenylphosphine)palladium (18 mg) were added to a solution of the compound obtained in the above Step 1 (80 mg) and the compound obtained in Reference Example 7 (61 mg) in 1,4-dioxane (1.5 ml), and the mixture was stirred at 100° C. for seven hours. After leaving to cool, the reaction solution was diluted with ethyl acetate. The organic layer was washed with water and brine and then dried over sodium sulfate. The solvent was distilled off under reduced pressure, and the residue was purified by silica gel column chromatography [ethyl acetate:methanol=300:1->50:1 (v/v)] to give 21 mg of the title compound as a solid.

$^1$H-NMR (CDCl$_3$) δ: 1.60 (3H, t, J=7.3 Hz), 3.51-3.60 (1H, m), 3.63-3.87 (4H, m), 3.91 (3H, s), 3.94-4.14 (6H, m), 4.64 (2H, s), 6.92-7.08 (3H, m), 7.13-7.20 (2H, m), 7.46-7.60 (6H, m), 7.84-7.90 (2H, m), 8.26 (1H, d, J=2.3 Hz), 8.66 (1H, d, J=2.3 Hz).

MS (ESI) m/z: 651 (M+H)$^+$.

Example 47

N-{4-[2-Amino-5-(1-methyl-1H-pyrazol-4-yl)pyridin-3-yl]phenyl}-1-ethyl-5-(4-fluorophenyl)-4-oxo-1,4-dihydropyridine-3-carboxamide

[Step 1] 3-(4-Aminophenyl)-5-(1-methyl-1H-pyrazol-4-yl)pyridin-2-amine

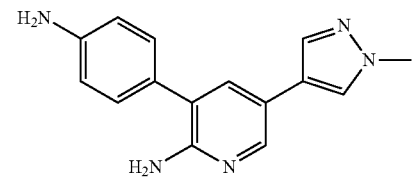 [SMILES: Cn1cc(-c2cnc(N)c(-c3ccc(N)cc3)c2)cn1]

Water (5 ml), potassium carbonate (1742 mg) and tetrakis(triphenylphosphine)palladium (242 mg) were added to a solution of the compound obtained in Step 1 of Example 1 (1110 mg) and 1-methyl-4-(4,4,5,5-tetramethyl-1,3,2-dioxaborolan-2-yl)-1H-pyrazole (874 mg) in 1,4-dioxane (50 ml), and the mixture was stirred at 100° C. for five hours. After leaving to cool, the reaction solution was diluted with chloroform. The organic layer was washed with water and brine and dried over sodium sulfate. The solvent was distilled off under reduced pressure, and the residue was purified by silica gel column chromatography [chloroform:methanol=96:4 (v/v)] to give 638 mg of the title compound as a solid.

MS (ESI) m/z: 266 (M+H)$^+$.

[Step 2] N-{4-[2-Amino-5-(1-methyl-1H-pyrazol-4-yl)pyridin-3-yl]phenyl}-1-ethyl-5-(4-fluorophenyl)-4-oxo-1,4-dihydropyridine-3-carboxamide

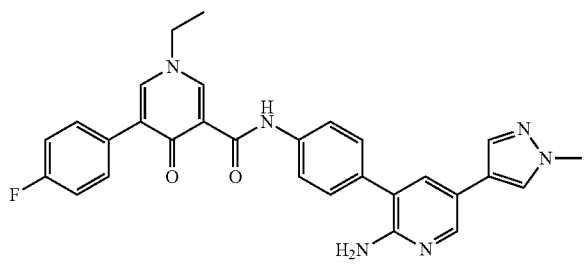 [SMILES: CCn1cc(C(=O)Nc2ccc(-c3cc(-c4cnn(C)c4)cnc3N)cc2)c(=O)c(-c2ccc(F)cc2)c1]

DIPEA (29 µl) was added to a solution of the compound obtained in Step 2 of Example 3 (22 mg) and COMU (47 mg) in DMF (1.0 ml) at room temperature, and the mixture was stirred for 20 minutes. The compound obtained in the above Step 1 (25 mg) was added at room temperature. The mixture was stirred for 7 hours, followed by the addition of water. The organic layer was extracted with ethyl acetate, and then washed with water and brine and dried over sodium sulfate. The solvent was distilled off under reduced pressure, and the residue was purified by PLC (NH) [chloroform:methanol=30:1 (v/v)] to give 22 mg of the title compound as a solid.

$^1$H-NMR (CDCl$_3$) δ: 1.57-1.62 (3H, m), 3.94 (3H, s), 4.09 (2H, q, J=7.5 Hz), 4.58 (2H, s), 7.14-7.20 (2H, m), 7.44-7.49 (3H, m), 7.52-7.60 (4H, m), 7.69 (1H, s), 7.84-7.89 (2H, m), 8.19 (1H, d, J=2.5 Hz), 8.66 (1H, d, J=2.5 Hz).

MS (ESI) m/z: 509 (M+H)$^+$.

Example 48

N-{4-[2-Amino-5-(1-methyl-1H-pyrazol-4-yl)pyridin-3-yl]phenyl}-1-(2-fluoroethyl)-5-(4-fluorophenyl)-4-oxo-1,4-dihydropyridine-3-carboxamide

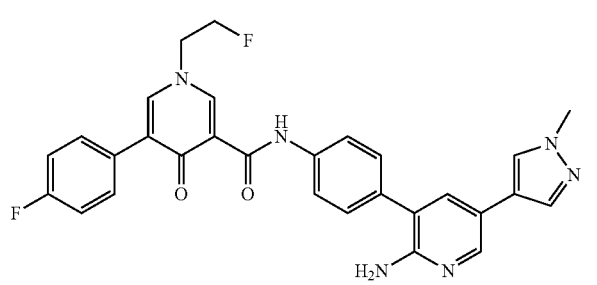 [SMILES: Cn1cc(-c2cnc(N)c(-c3ccc(NC(=O)c4cn(CCF)cc(-c5ccc(F)cc5)c4=O)cc3)c2)cn1]

The compound obtained in Step 2 of Example 8 (96 mg) and the compound obtained in Step 1 of Example 47 (70 mg) yielded 61 mg of the title compound as a solid via a reaction similar to that in Step 2 of Example 47.

$^1$H-NMR (CDCl$_3$) δ: 3.94 (3H, s), 4.25-4.36 (2H, m), 4.58 (2H, s), 4.74-4.91 (2H, m), 7.15-7.19 (2H, m), 7.44-7.49 (3H, m), 7.54-7.59 (4H, m), 7.69 (1H, s), 7.83-7.88 (2H, m), 8.20 (1H, d, J=2.3 Hz), 8.65 (1H, d, J=2.3 Hz).

MS (ESI) m/z: 527 (M+H)$^+$.

Example 49

N-{4-[2-Amino-5-(1-methyl-1H-pyrazol-4-yl)pyridin-3-yl]phenyl}-1-(2,2-difluoroethyl)-5-(4-fluorophenyl)-4-oxo-1,4-dihydropyridine-3-carboxamide

[Step 1] Ethyl 1-(2,2-difluoroethyl)-5-(4-fluorophenyl)-4-oxo-1,4-dihydropyridine-3-carboxylate

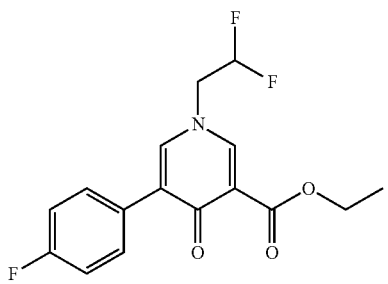 [SMILES: CCOC(=O)c1cn(CC(F)F)cc(-c2ccc(F)cc2)c1=O]

Ethyl 5-(4-fluorophenyl)-4-oxo-1,4-dihydropyridine-3-carboxylate (1.50 g) and 2,2-difluoroethyl trifluoromethanesulfonate (2.20 g) yielded 0.31 g of the title compound as an oily substance via a reaction similar to that in Step 1 of Example 8.

$^1$H-NMR (CDCl$_3$) δ: 1.38 (3H, t, J=7.1 Hz), 4.15-4.26 (2H, m), 4.37 (2H, q, J=7.1 Hz), 5.95-6.28 (1H, m), 7.04-7.11 (2H, m), 7.36 (1H, d, J=2.3 Hz), 7.51-7.57 (2H, m), 8.13 (1H, d, J=2.3 Hz).

MS (ESI) m/z: 326 (M+H)$^+$.

[Step 2] 1-(2,2-Difluoroethyl)-5-(4-fluorophenyl)-4-oxo-1,4-dihydropyridine-3-carboxylic acid

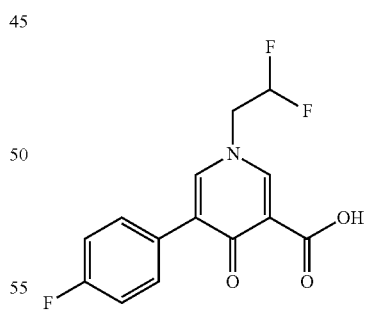

Potassium carbonate (0.33 g) and water (2 ml) were added to a solution of the compound obtained in the above Step 1 (0.31 g) in methanol (4 ml) at room temperature. The reaction mixture was stirred at room temperature overnight. A 1 N aqueous hydrochloric acid solution and water were added to the reaction mixture. The precipitated solid was collected by filtration, washed with water and then dried to give 0.19 g of the title compound as a solid.

MS (ESI) m/z: 298 (M+H)$^+$.

[Step 3] N-{4-[2-Amino-5-(1-methyl-1H-pyrazol-4-yl)pyridin-3-yl]phenyl}-1-(2,2-difluoroethyl)-5-(4-fluorophenyl)-4-oxo-1,4-dihydropyridine-3-carboxamide

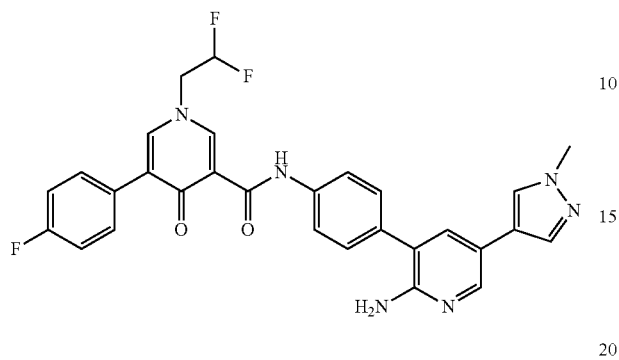

The compound obtained in the above Step 2 (86 mg) and the compound obtained in Step 1 of Example 47 (70 mg) yielded 53 mg of the title compound as a solid via a reaction similar to that in Step 3 of Example 1.

$^1$H-NMR (CDCl$_3$) δ: 3.92 (3H, s), 4.26-4.38 (2H, m), 4.61 (2H, s), 5.97-6.32 (1H, m), 7.13-7.17 (2H, m), 7.43-7.55 (7H, m), 7.67 (1H, s), 7.82 (2H, d, J=8.3 Hz), 8.17 (1H, d, J=1.8 Hz), 8.60 (1H, d, J=2.8 Hz).

MS (ESI) m/z: 545 (M+H)$^+$.

Example 50

N-{4-[2-Amino-5-(1-methyl-1H-pyrazol-4-yl)pyridin-3-yl]phenyl}-5-(4-fluorophenyl)-4-oxo-1-(2,2,2-trifluoroethyl)-1,4-dihydropyridine-3-carboxamide

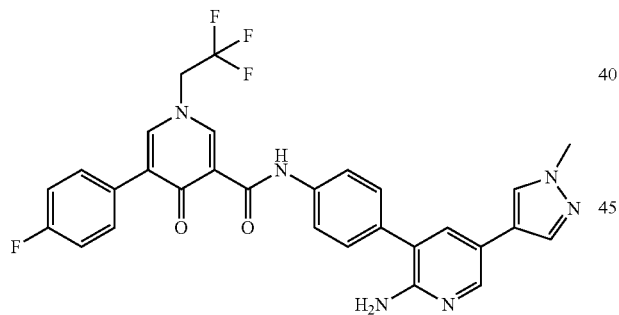

HOBt (51 mg), HATU (215 mg), DMAP (23 mg) and DIPEA (131 μl) were added to a solution of the Compound obtained in Step 2 of Example 9 (131 mg) in DMF (2 ml) at room temperature. The reaction mixture was stirred at room temperature for 1.5 hours. The compound obtained in Step 1 of Example 47 (100 mg) was added to the reaction mixture at room temperature. The reaction mixture was stirred at 50° C. for 1.5 hours and returned to room temperature. Water was added to the reaction mixture, and the precipitated solid was collected by filtration. The resulting solid was purified by PLC [dichloromethane:methanol=15:1 (v/v)] to give 64 mg of the title compound as a solid.

$^1$H-NMR (CDCl$_3$) δ: 3.94 (3H, s), 4.51 (2H, q, J=7.8 Hz), 4.60 (2H, s), 7.15-7.23 (2H, m), 7.46-7.57 (7H, m), 7.69 (1H, s), 7.84 (2H, d, J=8.3 Hz), 8.19 (1H, d, J=2.3 Hz), 8.64 (1H, d, J=2.3 Hz), 12.45 (1H, s).

MS (ESI) m/z: 563 (M+H)$^+$.

Example 51

N-{4-[2-Amino-5-(1-methyl-1H-pyrazol-4-yl)pyridin-3-yl]phenyl}-1-benzyl-5-(4-fluorophenyl)-4-oxo-1,4-dihydropyridine-3-carboxamide

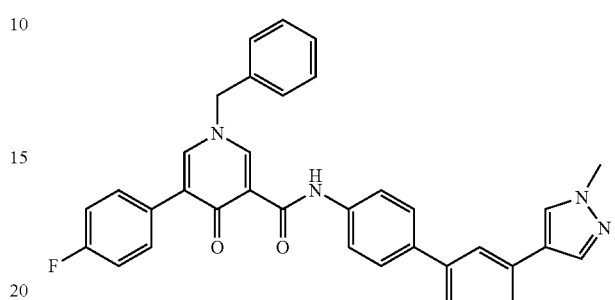

The compound obtained in Step 1 of Example 10 (67 mg) and the compound obtained in Step 1 of Example 47 (50 mg) yielded 39 mg of the title compound as a solid via a reaction similar to that in Step 3 of Example 1.

$^1$H-NMR (CDCl$_3$) δ: 3.93 (3H, s), 4.61 (2H, s), 5.16 (2H, s), 7.09-7.16 (2H, m), 7.25-7.30 (2H, m), 7.40-7.48 (6H, m), 7.48-7.55 (4H, m), 7.68 (1H, s), 7.84 (2H, d, J=8.3 Hz), 8.19 (1H, d, J=2.3 Hz), 8.73 (1H, d, J=2.3 Hz).

MS (ESI) m/z: 571 (M+H)$^+$.

Example 52

N-{4-[2-Amino-5-(1-methyl-1H-pyrazol-4-yl)pyridin-3-yl]phenyl}-1-ethyl-4-oxo-5-phenyl-1,4-dihydropyridine-3-carboxamide

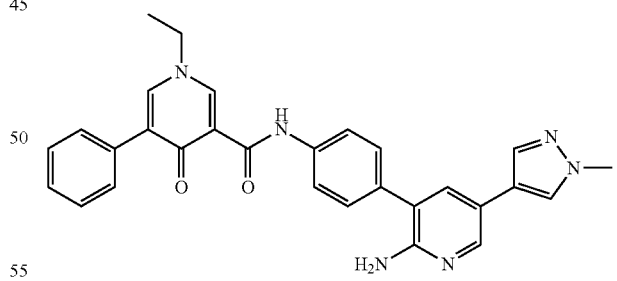

1-Ethyl-4-oxo-5-phenyl-1,4-dihydropyridine-3-carboxylic acid (20 mg) and the compound obtained in Step 1 of Example 47 (25 mg) yielded 22 mg of the title compound as a solid via a reaction similar to that in Step 2 of Example 47.

$^1$H-NMR (CDCl$_3$) δ: 1.58-1.62 (3H, m), 3.94 (3H, s), 4.03-4.14 (2H, m), 4.58 (2H, s), 7.38-7.60 (10H, m), 7.69 (1H, s), 7.83-7.90 (2H, m), 8.20 (1H, d, J=2.29 Hz), 8.66 (1H, d, J=2.75 Hz).

MS (ESI) m/z: 491 (M+H)$^+$.

Example 53

N-{4-[2-Amino-5-(1-methyl-1H-pyrazol-4-yl)pyridin-3-yl]phenyl}-1-(2-fluoroethyl)-4-oxo-5-phenyl-1,4-dihydropyridine-3-carboxamide

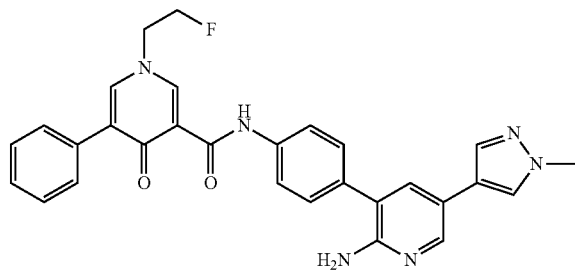 [SMILES: Cn1cc(-c2cnc(N)c(-c3ccc(NC(=O)c4cn(CCF)cc(-c5ccccc5)c4=O)cc3)c2)cn1]

The compound obtained in Step 2 of Example 19 (38 mg) and the compound obtained in Step 1 of Example 47 (42 mg) yielded 42 mg of the title compound as a solid via a reaction similar to that in Step 2 of Example 47.

¹H-NMR (CDCl₃) δ: 3.94 (3H, s), 4.24-4.37 (2H, m), 4.58 (2H, s), 4.74-4.91 (2H, m), 7.41-7.60 (10H, m), 7.69 (1H, s), 7.83-7.89 (2H, m), 8.20 (1H, d, J=2.5 Hz), 8.65 (1H, d, J=2.5 Hz).

MS (ESI) m/z: 509 (M+H)⁺.

Example 54

N-{4-[2-Amino-5-(1-methyl-1H-pyrazol-4-yl)pyridin-3-yl]phenyl}-4-oxo-5-phenyl-1-(2,2,2-trifluoroethyl)-1,4-dihydropyridine-3-carboxamide

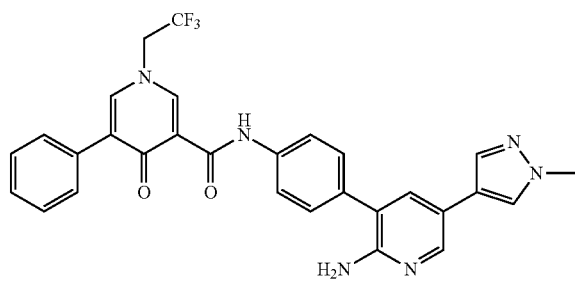 [SMILES: Cn1cc(-c2cnc(N)c(-c3ccc(NC(=O)c4cn(CC(F)(F)F)cc(-c5ccccc5)c4=O)cc3)c2)cn1]

The compound obtained in Step 2 of Example 20 (41 mg) and the compound obtained in Step 1 of Example 47 (40 mg) yielded 47 mg of the title compound as a solid via a reaction similar to that in Step 2 of Example 47.

¹H-NMR (CDCl₃) δ: 3.94 (3H, s), 4.45-4.64 (4H, m), 7.42-7.58 (10H, m), 7.69 (1H, s), 7.82-7.88 (2H, m), 8.20 (1H, d, J=2.3 Hz), 8.64 (1H, d, J=2.3 Hz).

MS (ESI) m/z: 545 (M+H)⁺.

Example 55

N-{4-[2-Amino-5-(1-methyl-1H-pyrazol-4-yl)pyridin-3-yl]-3-fluorophenyl}-1-(2-fluoroethyl)-4-oxo-5-phenyl-1,4-dihydropyridine-3-carboxamide

[Step 1] 3-(4-Amino-2-fluorophenyl)-5-(1-methyl-1H-pyrazol-4-yl)pyridin-2-amine

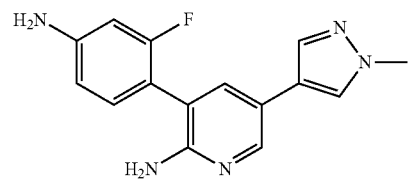 [SMILES: Cn1cc(-c2cnc(N)c(-c3ccc(N)cc3F)c2)cn1]

The compound obtained in Step 1 of Example 29 (2 g), 1-methyl-4-(4,4,5,5-tetramethyl-1,3,2-dioxaborolan-2-yl)-1H-pyrazole (1.62 g), tetrakis(triphenylphosphine)palladium (0.41 g) and potassium carbonate (2.94 g) were suspended in dioxane (10 ml) and water (1 ml), and the suspension was heated under reflux at 100° C. for 61 hours. After leaving to cool, a saturated aqueous sodium bicarbonate solution was added, and the organic layer was extracted with ethyl acetate and dried over sodium sulfate. The solvent was distilled off under reduced pressure, and the residue was purified by silica gel column chromatography [ethyl acetate:methanol=10:1 (v/v)] to give 1.88 g of the title compound as a solid.

MS (ESI) m/z: 284 (M+H)⁺.

[Step 2] N-{4-[2-Amino-5-(1-methyl-1H-pyrazol-4-yl)pyridin-3-yl]-3-fluorophenyl}-1-(2-fluoroethyl)-4-oxo-5-phenyl-1,4-dihydropyridine-3-carboxamide The compound obtained in Step 2 of Example 19 (50 mg) and the compound obtained in the above Step 1 (60 mg) yielded 51 mg of the title compound as a solid via a reaction similar to that in Step 2 of Example 47.

¹H-NMR (CDCl₃) δ: 3.94 (3H, s), 4.28 (1H, t, J=4.4 Hz), 4.34 (1H, t, J=4.6 Hz), 4.53 (2H, s), 4.77 (1H, t, J=4.6 Hz), 4.88 (1H, t, J=4.6 Hz), 7.34 (1H, t, J=8.3 Hz), 7.37-7.54 (5H, m), 7.54-7.60 (4H, m), 7.68 (1H, d, J=0.9 Hz), 7.91 (1H, dd, J=12.2, 2.1 Hz), 8.23 (1H, d, J=2.3 Hz), 8.64 (1H, d, J=2.3 Hz).

MS (ESI) m/z: 527 (M+H)⁺.

Example 56

N-{4-[2-Amino-5-(1-methyl-1H-pyrazol-4-yl)pyridin-3-yl]phenyl}-1-(4-fluorobenzyl)-4-oxo-1,4-dihydropyridine-3-carboxamide

[Step 1] 1-(4-Fluorobenzyl)-4-oxo-1,4-dihydropyridine-3-carboxylic acid

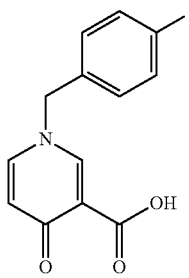

Ethyl 4-oxo-1,4-dihydropyridine-3-carboxylate (0.75 g) and 1-(bromomethyl)-4-fluorobenzene (1.38 ml) yielded 0.91 g of the title compound as a solid via a reaction similar to that in Step 1 of Example 11.

$^1$H-NMR (CDCl$_3$) δ: 5.11 (2H, s), 6.72-6.77 (1H, m), 7.11-7.18 (2H, m), 7.24-7.27 (2H, m), 7.49-7.55 (1H, m), 8.56-8.60 (1H, m).

MS (ESI) m/z: 248 (M+H)$^+$.

[Step 2] N-{4-[2-Amino-5-(1-methyl-1H-pyrazol-4-yl)pyridin-3-yl]phenyl}-1-(4-fluorobenzyl)-4-oxo-1,4-dihydropyridine-3-carboxamide

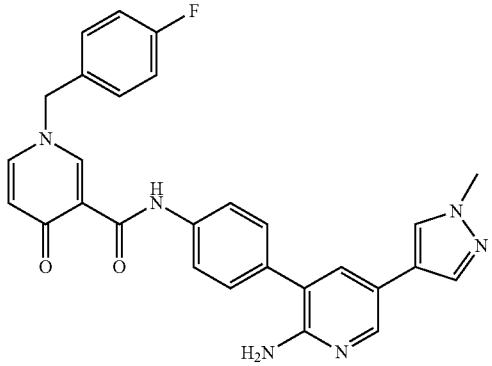 [SMILES: Cn1cc(-c2cnc(N)c(-c3ccc(NC(=O)c4cn(Cc5ccc(F)cc5)ccc4=O)cc3)c2)cn1]

The compound obtained in the above Step 1 (72 mg) and the compound obtained in Step 1 of Example 47 (70 mg) yielded 33 mg of the title compound as a solid via a reaction similar to that in Step 2 of Example 47.

$^1$H-NMR (CDCl$_3$) δ: 3.94 (3H, s), 4.59 (2H, s), 5.08 (2H, s), 6.66 (1H, d, J=7.8 Hz), 7.10-7.17 (2H, m), 7.23-7.28 (2H, m), 7.41 (1H, dd, J=7.6, 2.5 Hz), 7.45-7.49 (3H, m), 7.55 (1H, s), 7.69 (1H, s), 7.82-7.86 (2H, m), 8.20 (1H, s), 8.66 (1H, d, J=2.3 Hz).

MS (ESI) m/z: 495 (M+H)$^+$.

Example 57

N-{4-[2-Amino-5-(1-methyl-1H-pyrazol-4-yl)pyridin-3-yl]phenyl}-1-(4-fluorobenzyl)-6-methyl-4-oxo-1,4-dihydropyridine-3-carboxamide

[Step 1] 1-(4-Fluorobenzyl)-6-methyl-4-oxo-1,4-dihydropyridine-3-carboxylic acid

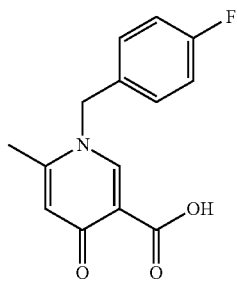 [SMILES: Cc1cc(=O)c(C(=O)O)cn1Cc1ccc(F)cc1]

Ethyl 6-methyl-4-oxo-1,4-dihydropyridine-3-carboxylate (0.75 g) and 1-(bromomethyl)-4-fluorobenzene (1.27 ml) yielded 0.86 g of the title compound as a solid via a reaction similar to that in Step 1 of Example 11.

$^1$H-NMR (CDCl$_3$) δ: 2.36 (3H, s), 5.20 (2H, s), 6.62 (1H, s), 7.05-7.14 (4H, m), 8.55 (1H, s).

MS (ESI) m/z: 262 (M+H)$^+$.

[Step 2] N-{4-[2-Amino-5-(1-methyl-1H-pyrazol-4-yl)pyridin-3-yl]phenyl}-1-(4-fluorobenzyl)-6-methyl-4-oxo-1,4-dihydropyridine-3-carboxamide

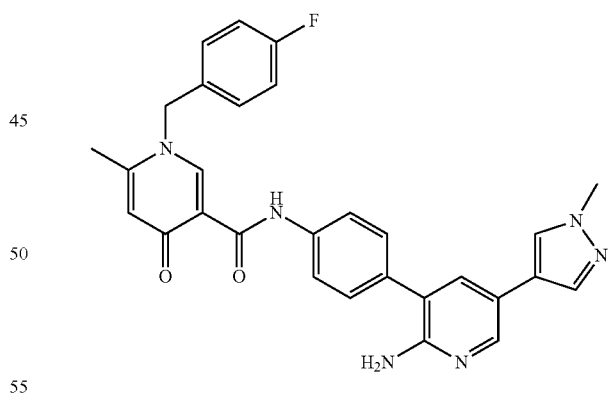

The compound obtained in the above Step 1 (76 mg) and the compound obtained in Step 1 of Example 47 (70 mg) yielded 58 mg of the title compound as a solid via a reaction similar to that in Step 2 of Example 47.

$^1$H-NMR (CDCl$_3$) δ: 2.31 (3H, s), 3.94 (3H, s), 4.61 (2H, s), 5.17 (2H, s), 6.54 (1H, d, J=0.9 Hz), 7.06-7.14 (4H, m), 7.45-7.49 (3H, m), 7.56 (1H, s), 7.69 (1H, d, J=0.9 Hz), 7.82-7.87 (2H, m), 8.20 (1H, d, J=2.3 Hz), 8.63 (1H, s).

MS (ESI) m/z: 509 (M+H)$^+$.

Example 58

N-{4-[2-Amino-5-(1-methyl-1H-pyrazol-4-yl)pyridin-3-yl]phenyl}-1-(4-fluorobenzyl)-5-methyl-4-oxo-1,4-dihydropyridine-3-carboxamide

[Step 1] 1-(4-Fluorobenzyl)-5-methyl-4-oxo-1,4-dihydropyridine-3-carboxylic acid

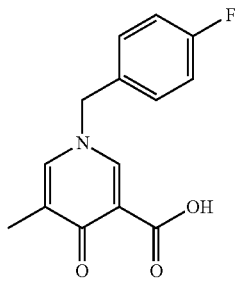 [SMILES: Cc1cn(Cc2ccc(F)cc2)cc(C(=O)O)c1=O]

The compound obtained in Reference Example 5 (0.40 g) and 1-(bromomethyl)-4-fluorobenzene (0.35 ml) yielded 0.35 g of the title compound as a solid via a reaction similar to that in Step 1 of Example 11.

$^1$H-NMR (DMSO-D$_6$) δ: 2.11 (3H, d, J=0.9 Hz), 5.30 (2H, s), 7.14-7.18 (2H, m), 7.41-7.45 (2H, m), 8.01-8.02 (1H, m), 8.73 (1H, d, J=1.8 Hz).

MS (ESI) m/z: 262 (M+H)$^+$.

[Step 2] N-{4-[2-Amino-5-(1-methyl-1H-pyrazol-4-yl)pyridin-3-yl]phenyl}-1-(4-fluorobenzyl)-5-methyl-4-oxo-1,4-dihydropyridine-3-carboxamide

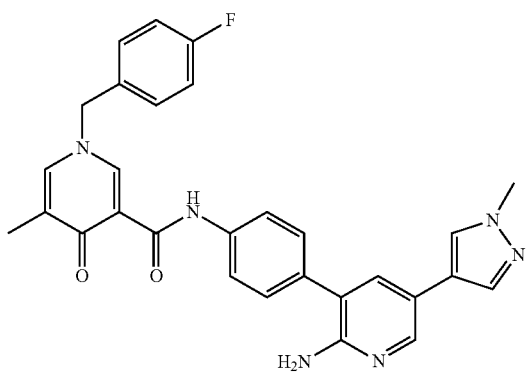 [SMILES: Cc1cn(Cc2ccc(F)cc2)cc(C(=O)Nc2ccc(-c3cc(-c4cnn(C)c4)cnc3N)cc2)c1=O]

The compound obtained in the above Step 1 (70 mg) and the compound obtained in Step 1 of Example 47 (75 mg) yielded 28 mg of the title compound as a solid via a reaction similar to that in Step 2 of Example 47.

$^1$H-NMR (CDCl$_3$) δ: 2.13 (3H, s), 3.94 (3H, s), 4.58 (2H, s), 5.06 (2H, s), 7.14 (2H, d, J=8.3 Hz), 7.23-7.26 (2H, m), 7.34-7.37 (1H, m), 7.44-7.49 (3H, m), 7.55 (1H, s), 7.69 (1H, s), 7.86 (2H, d, J=7.8 Hz), 8.20 (1H, d, J=2.3 Hz), 8.64 (1H, d, J=2.3 Hz).

MS (ESI) m/z: 509 (M+H)$^+$.

Example 59

N-{4-[2-Amino-5-(1-methyl-1H-pyrazol-4-yl)pyridin-3-yl]phenyl}-1-(4-fluorobenzyl)-5-methoxy-4-oxo-1,4-dihydropyridine-3-carboxamide

[Step 1] 1-(4-Fluorobenzyl)-5-methoxy-4-oxo-1,4-dihydropyridine-3-carboxylic acid

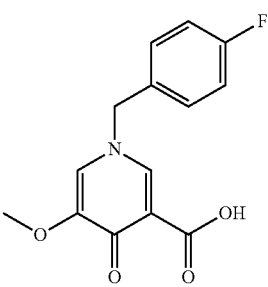 [SMILES: COc1cn(Cc2ccc(F)cc2)cc(C(=O)O)c1=O]

1-(Bromomethyl)-4-fluorobenzene (74 μl) was added to a suspension of the compound obtained in Reference Example 6 (92 mg) and potassium carbonate (129 mg) in DMF (2 ml) at room temperature. The reaction mixture was stirred at room temperature for two hours. Then a 1 N aqueous sodium hydroxide solution (1 ml) was added to the reaction mixture at room temperature, and the reaction mixture was stirred at room temperature for 2.5 hours. Next, methanol (2 ml) was added to the reaction mixture at room temperature, and the reaction mixture was stirred at room temperature for two hours. Then a 1 N aqueous sodium hydroxide solution (1.0 ml) and methanol (10 ml) were added to the reaction mixture at room temperature, and the reaction mixture was stirred at 50° C. overnight. Next, a 1 N aqueous hydrochloric acid solution and water were added to the reaction mixture, and the precipitated solid was collected by filtration, washed with water and then dried to give 109 mg of the title compound as a solid.

$^1$H-NMR (CDCl$_3$) δ: 3.82 (3H, s), 5.12 (2H, s), 7.03 (1H, d, J=2.3 Hz), 7.13-7.18 (2H, m), 7.23-7.26 (2H, m), 8.48 (1H, d, J=2.3 Hz).

MS (ESI) m/z: 278 (M+H)$^+$.

[Step 2] N-{4-[2-Amino-5-(1-methyl-1H-pyrazol-4-yl)pyridin-3-yl]phenyl}-1-(4-fluorobenzyl)-5-methoxy-4-oxo-1,4-dihydropyridine-3-carboxamide

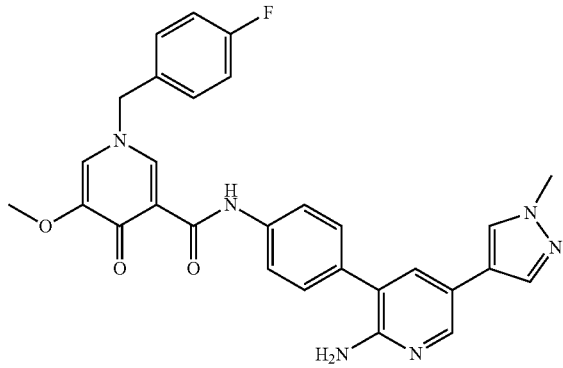 [SMILES: COc1cn(Cc2ccc(F)cc2)cc(C(=O)Nc2ccc(-c3cc(-c4cnn(C)c4)cnc3N)cc2)c1=O]

The compound obtained in the above Step 1 (50 mg) and the compound obtained in Step 1 of Example 47 (57 mg) yielded 50 mg of the title compound as a solid via a reaction similar to that in Step 2 of Example 47.

$^1$H-NMR (CDCl$_3$) δ: 3.81 (3H, s), 3.94 (3H, s), 4.58 (2H, s), 5.11 (2H, s), 6.95 (1H, d, J=2.3 Hz), 7.12-7.17 (2H, m), 7.23-7.28 (2H, m), 7.45-7.49 (3H, m), 7.55 (1H, s), 7.69 (1H, s), 7.84 (2H, d, J=8.7 Hz), 8.20 (1H, d, J=2.3 Hz), 8.59 (1H, d, J=2.3 Hz).

MS (ESI) m/z: 525 (M+H)$^+$.

Example 60

N'-{4-[2-Amino-5-(1-methyl-1H-pyrazol-4-yl)pyridin-3-yl]phenyl}-1-(4-fluorobenzyl)-N,N-dimethyl-4-oxo-1,4-dihydropyridine-3,5-dicarboxamide

[Step 1] Methyl 5-(dimethylcarbamoyl)-1-(4-fluorobenzyl)-4-oxo-1,4-dihydropyridine-3-carboxylate

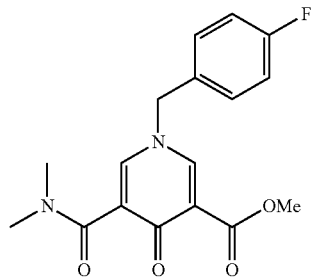 [SMILES: COC(=O)c1cn(Cc2ccc(F)cc2)cc(C(=O)N(C)C)c1=O]

The compound obtained in Step 2 of Example 26 (200 mg) and dimethylamine (2 M solution in THF, 0.66 ml) yielded 38 mg of the title compound as an oily substance via a reaction similar to that in Step 1 of Example 27.

$^1$H-NMR (CDCl$_3$) δ: 2.96 (3H, s), 3.05 (3H, s), 3.89 (3H, s), 4.96 (2H, s), 7.10-7.17 (2H, m), 7.22-7.29 (2H, m), 7.58 (1H, d, J=2.8 Hz), 8.21 (1H, d, J=2.8 Hz).

MS (ESI) m/z: 333 (M+H)$^+$.

[Step 2] 5-(Dimethylcarbamoyl)-1-(4-fluorobenzyl)-4-oxo-1,4-dihydropyridine-3-carboxylic acid

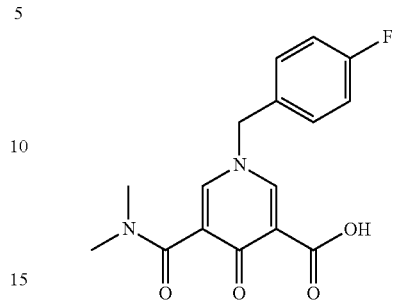

The compound obtained in the above Step 1 (38 mg) yielded 18 mg of the title compound via a reaction similar to that in Step 4 of Example 26.

$^1$H-NMR (CDCl$_3$) δ: 2.96 (3H, s), 3.10 (3H, s), 5.10 (2H, s), 7.12-7.19 (2H, m), 7.25-7.31 (2H, m), 7.82 (1H, d, J=2.3 Hz), 8.55 (1H, d, J=2.3 Hz).

MS (ESI) m/z: 319 (M+H)$^+$.

[Step 3] N'-{4-[2-Amino-5-(1-methyl-1H-pyrazol-4-yl)pyridin-3-yl]phenyl}-1-(4-fluorobenzyl)-N,N-dimethyl-4-oxo-1,4-dihydropyridine-3,5-dicarboxamide

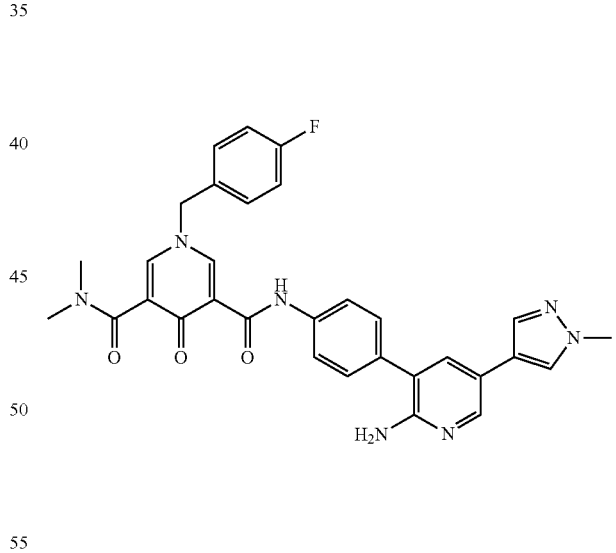

The compound obtained in the above Step 2 (18 mg) and the compound obtained in Step 1 of Example 47 (16 mg) yielded 23 mg of the title compound as a solid via a reaction similar to that in Step 2 of Example 47.

$^1$H-NMR (CDCl$_3$) δ: 3.00 (3H, s), 3.12 (3H, s), 3.94 (3H, s), 4.57 (2H, s), 5.10 (2H, s), 7.11-7.18 (2H, m), 7.27-7.33 (2H, m), 7.43-7.50 (3H, m), 7.55 (1H, s), 7.68-7.72 (2H, m), 7.80-7.86 (2H, m), 8.20 (1H, d, J=2.3 Hz), 8.66 (1H, d, J=2.8 Hz), 12.42 (1H, s).

MS (ESI) m/z: 566 (M+H)$^+$.

Example 61

N-{4-[2-Amino-5-(1-methyl-1H-pyrazol-4-yl)pyridin-3-yl]phenyl}-5-(4-fluorophenyl)-1-(4-methoxyphenyl)-4-oxo-1,4-dihydropyridazine-3-carboxamide

[Step 1] Ethyl 5-(4-fluorophenyl)-1-(4-methoxyphenyl)-4-oxo-1,4-dihydropyridazine-3-carboxylate

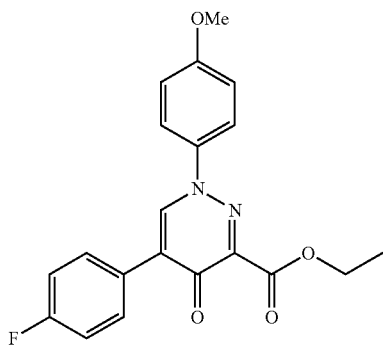 [SMILES: CCOC(=O)c1nn(-c2ccc(OC)cc2)cc(-c2ccc(F)cc2)c1=O]

A 0.67 N aqueous hydrochloric acid solution (3 ml) was added to 4-methoxyaniline (165 mg), and a solution of sodium nitrite (138 mg) in water (1 ml) was added at 0° C. The reaction mixture was stirred at 0° C. for five minutes. A suspension of sodium acetate (329 mg) and ethyl 4-(4-fluorophenyl)-3-oxobutanoate (300 mg) in ethanol (3 ml) was added to the reaction mixture at 0° C. The reaction mixture was stirred at room temperature overnight. The reaction mixture was diluted with water, followed by extraction with ethyl acetate. The organic layer was washed with brine and dried over sodium sulfate. After filtration, the filtrate was concentrated under reduced pressure. N,N-Dimethylformamide dimethylacetal (3 ml) was added to the resulting oily substance at room temperature. The reaction mixture was stirred at 110° C. for 1.5 hours and returned to room temperature. The reaction mixture was diluted with water, followed by extraction with ethyl acetate. The organic layer was washed with water and brine and dried over sodium sulfate. After filtration, the filtrate was concentrated under reduced pressure, and the residue was purified by silica gel column chromatography [ethyl acetate:hexane] to give 345 mg of the title compound as an oily substance.

$^1$H-NMR (CDCl$_3$) δ: 1.42 (3H, t, J=7.1 Hz), 3.87 (3H, s), 4.48 (2H, q, J=7.1 Hz), 7.01-7.04 (2H, m), 7.11-7.17 (2H, m), 7.51-7.55 (2H, m), 7.75-7.80 (2H, m), 8.30 (1H, s).

MS (ESI) m/z: 369 (M+H)$^+$.

[Step 2] N-{4-[2-Amino-5-(1-methyl-1H-pyrazol-4-yl)pyridin-3-yl]phenyl}-5-(4-fluorophenyl)-1-(4-methoxyphenyl)-4-oxo-1,4-dihydropyridazine-3-carboxamide

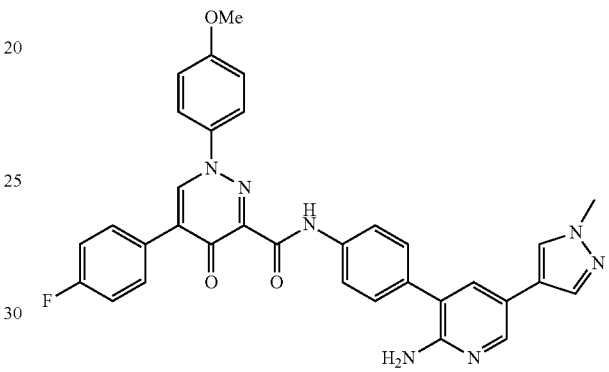

Cerium(IV) ammonium nitrate (1540 mg) and water (5 ml) were added to a solution of the compound obtained in the above Step 1 (345 mg) in acetonitrile (5 ml) at 0° C. The reaction mixture was stirred at 0° C. for 30 minutes, and an aqueous sodium thiosulfate solution was added to the reaction mixture. The reaction mixture was concentrated under reduced pressure. The residue was washed with water, washed with a mixed solvent of ethyl acetate and hexane [1:1 (v/v)] and then dried. Part of the resulting solid (70 mg) and the compound obtained in Step 1 of Example 47 (60 mg) yielded 19 mg of the title compound as a solid via a reaction similar to that in Step 2 of Example 47.

$^1$H-NMR (CDCl$_3$) δ: 3.89 (3H, s), 3.94 (3H, s), 4.65 (2H, s), 7.03-7.08 (2H, m), 7.19-7.25 (2H, m), 7.46-7.57 (4H, m), 7.64-7.78 (5H, m), 7.91-7.96 (2H, m), 8.20 (1H, d, J=2.3 Hz), 8.47 (1H, s).

MS (ESI) m/z: 588 (M+H)$^+$.

Example 62

N-{4-[2-Amino-5-(1-piperidin-4-yl-1H-pyrazol-4-yl)pyridin-3-yl]phenyl}-1-(2-fluoroethyl)-5-(4-fluorophenyl)-4-oxo-1,4-dihydropyridine-3-carboxamide

[Step 1] tert-Butyl 4-(4-[6-amino-5-[4-({[1-(2-fluoroethyl)-5-(4-fluorophenyl)-4-oxo-1,4-dihydropyridin-3-yl]carbonyl}amino)phenyl]pyridin-3-yl]-1H-pyrazol-1-yl)piperidin-1-carboxylate

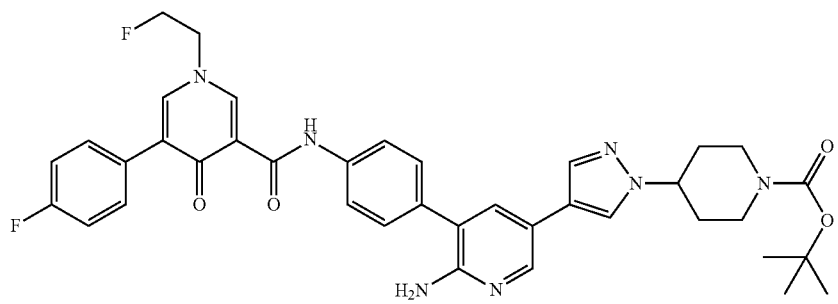 [SMILES: CC(C)(C)OC(=O)N1CCC(n2cc(-c3cnc(N)c(-c4ccc(NC(=O)c5cn(CCF)cc(-c6ccc(F)cc6)c5=O)cc4)c3)cn2)CC1]

Water (0.5 ml), cesium carbonate (60 mg) and tetrakis(triphenylphosphine)palladium (16 mg) were added to a solution of the compound obtained in Step 1 of Example 43 (75 mg) and tert-butyl 4-[4-(4,4,5,5-tetramethyl-1,3,2-dioxaborolan-2-yl)-1H-pyrazol-1-yl]piperidine-1-carboxylate (59 mg) in dimethoxyethane (4 ml). The mixture was stirred under microwave irradiation at 100° C. for 10 minutes. After leaving to cool, the reaction product was purified by silica gel column chromatography [chloroform:methanol=99:1->9:1 (v/v)]. Further, the resulting crude purified product was crystallized from ethyl acetate to give 120 mg of the title compound as a solid.

MS (ESI) m/z: 696 (M+H)$^+$.

[Step 2] N-{4-[2-Amino-5-(1-piperidin-4-yl-1H-pyrazol-4-yl)pyridin-3-yl]phenyl}-1-(2-fluoroethyl)-5-(4-fluorophenyl)-4-oxo-1,4-dihydropyridine-3-carboxamide TFA (1 ml) was added dropwise to a solution of the compound obtained in the above Step 1 (120 mg) in dichloromethane (1 ml) under ice cooling, and the mixture was stirred at room temperature. The solvent was distilled off under reduced pressure, and the resulting residue was purified by silica gel column chromatography (NH) [chloroform:methanol=99:1->19:1 (v/v)] to give 60 mg of the title compound as a solid.

$^1$H-NMR (DMSO-D$_6$) δ: 1.74-1.82 (2H, m), 1.95-1.98 (2H, m), 2.56-2.64 (2H, m), 3.02-3.05 (2H, m), 4.12-4.17 (1H, m), 4.52-4.59 (2H, m), 4.80-4.91 (2H, m), 5.54 (2H, s), 7.28-7.32 (2H, m), 7.49 (2H, d, J=8.6 Hz), 7.57 (1H, d, J=2.3 Hz), 7.72-7.75 (2H, m), 7.80-7.82 (3H, m), 8.15 (1H, s), 8.22 (2H, dd, J=8.0, 2.3 Hz), 8.77 (1H, d, J=2.3 Hz).

MS (ESI) m/z: 596 (M+H)$^+$.

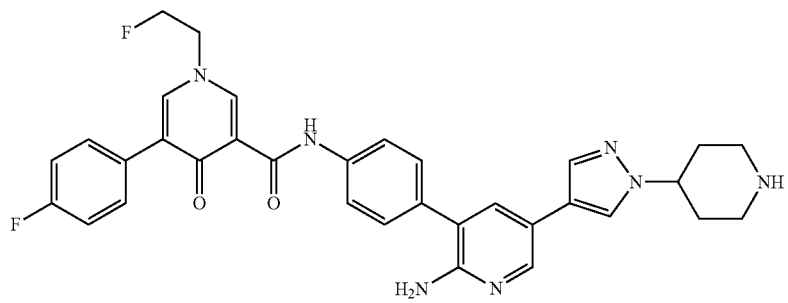 [SMILES: Nc1ncc(-c2cnn(C3CCNCC3)c2)cc1-c1ccc(NC(=O)c2cn(CCF)cc(-c3ccc(F)cc3)c2=O)cc1]

Example 63

N-(4-{2-Amino-5-[1-(2-hydroxypropyl)-1H-pyrazol-4-yl]pyridin-3-yl}phenyl)-1-(2-fluoroethyl)-5-(4-fluorophenyl)-4-oxo-1,4-dihydropyridine-3-carboxamide (racemate)

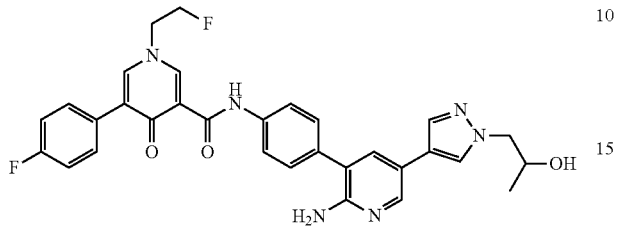

The compound obtained in Step 1 of Example 43 (80 mg) and 1-[4-(4,4,5,5-tetramethyl-1,3,2-dioxaborolan-2-yl)-1H-pyrazol-1-yl]propan-2-ol (50 mg) yielded 43 mg of the title compound as a solid via a reaction similar to that in Step 1 of Example 62.
$^1$H-NMR (CDCl$_3$) δ: 1.25 (3H, d, J=6.4 Hz), 3.39 (1H, s), 3.98-4.06 (1H, m), 4.16-4.37 (4H, m), 4.59 (2H, s), 4.74-4.91 (2H, m), 7.14-7.20 (2H, m), 7.44-7.49 (3H, m), 7.54-7.63 (4H, m), 7.74 (1H, s), 7.83-7.89 (2H, m), 8.20 (1H, d, J=2.3 Hz), 8.65 (1H, d, J=2.3 Hz).
MS (ESI) m/z: 571 (M+H)$^+$.

Example 64

N-[4-(2-Amino-5-{1-[(2S)-1,4-dioxan-2-ylmethyl]-1H-pyrazol-4-yl}pyridin-3-yl)phenyl]-1-ethyl-5-(4-fluorophenyl)-4-oxo-1,4-dihydropyridine-3-carboxamide

[Step 1] 3-(4-Aminophenyl)-5-{1-[(2S)-1,4-dioxan-2-ylmethyl]-1H-pyrazol-4-yl}pyridin-2-amine

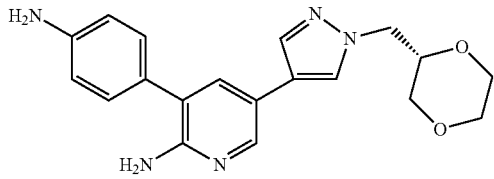 [SMILES: Nc1ccc(-c2cc(-c3cnn(C[C@H]4COCCO4)c3)cnc2N)cc1]

4-(4,4,5,5-Tetramethyl-1,3,2-dioxaborolan-2-yl)-1H-pyrazole (10.0 g) was added to a suspension of cesium carbonate (75.6 g) in 1,4-dioxane (200 ml), followed by stirring. (2R)-1,4-Dioxan-2-ylmethyl methanesulfonate (12.1 g) and tetra-n-butylammonium iodide (0.95 g) were then added, and the mixture was stirred at 100° C. for six hours. After cooling the reaction solution to room temperature, 3-(4-aminophenyl)-5-bromopyridin-2-amine (10.9 g) and [1,1'-bis(diphenylphosphino)ferrocene]palladium(II) dichloride-dichloromethane adduct (2.1 g) were added, and the mixture was stirred at 100° C. for one hour. The reaction solution was returned to room temperature, ethyl acetate was added, and the insoluble matter was then removed by filtration. The resulting organic layer was sequentially washed with water and brine and then dried over anhydrous sodium sulfate. The solvent was distilled off under reduced pressure, and the residue was purified by silica gel column chromatography [chloroform:methanol=99:1->19:1 (v/v)] to give 10.3 g of the title compound as a solid.
$^1$H-NMR (CDCl$_3$) δ: 3.28-3.33 (1H, m), 3.55-3.83 (7H, m), 3.95-4.01 (1H, m), 4.16 (1H, s), 4.17 (1H, s), 4.56 (2H, br s), 6.77-6.79 (2H, m), 7.26-7.29 (2H, m), 7.43 (1H, d, J=2.3 Hz), 7.63 (1H, s), 7.70-7.70 (1H, m), 8.17 (1H, d, J=2.3 Hz).
MS (ESI) m/z: 352 (M+H)$^+$.

[Step 2] N-[4-(2-Amino-5-{1-[(2S)-1,4-dioxan-2-ylmethyl]-1H-pyrazol-4-yl}pyridin-3-yl)phenyl]-1-ethyl-5-(4-fluorophenyl)-4-oxo-1,4-dihydropyridine-3-carboxamide

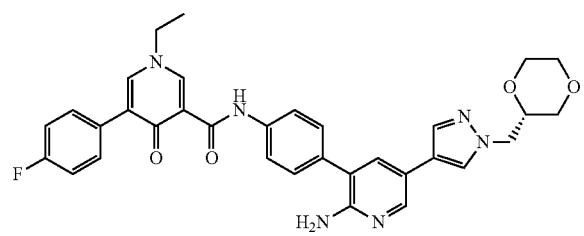 [SMILES: CCn1cc(C(=O)Nc2ccc(-c3cc(-c4cnn(C[C@H]5COCCO5)c4)cnc3N)cc2)c(=O)c(-c2ccc(F)cc2)c1]

The compound obtained in Step 2 of Example 3 (35 mg) and the compound obtained in the above Step 1 (52 mg) yielded 58 mg of the title compound as a solid via a reaction similar to that in Step 2 of Example 47.
$^1$H-NMR (CDCl$_3$) δ: 1.60 (3H, t, J=7.3 Hz), 3.31 (1H, dd, J=11.5, 10.1 Hz), 3.54-3.63 (1H, m), 3.67-3.85 (4H, m), 3.94-4.02 (1H, m), 4.05-4.20 (4H, m), 4.58 (2H, s), 7.14-7.20 (2H, m), 7.44-7.49 (3H, m), 7.51-7.60 (3H, m), 7.64 (1H, s), 7.71 (1H, s), 7.84-7.90 (2H, m), 8.21 (1H, d, J=2.5 Hz), 8.66 (1H, d, J=2.5 Hz).
MS (ESI) m/z: 595 (M+H)$^+$.

Example 65

N-[4-(2-Amino-5-{1-[(2S)-1,4-dioxan-2-ylmethyl]-1H-pyrazol-4-yl}pyridin-3-yl)phenyl]-1-(2-fluoroethyl)-5-(4-fluorophenyl)-4-oxo-1,4-dihydropyridine-3-carboxamide

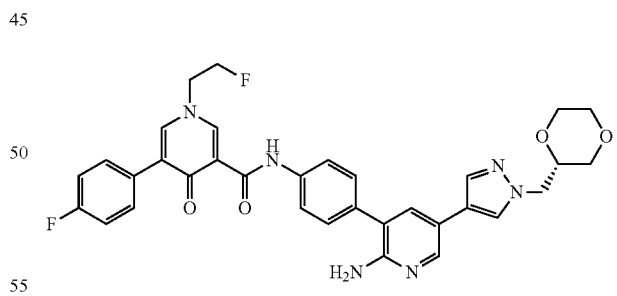

The compound obtained in Step 2 of Example 8 (40 mg) and the compound obtained in Step 1 of Example 64 (55 mg) yielded 88 mg of the title compound as a solid via a reaction similar to that in Step 2 of Example 47.
$^1$H-NMR (CDCl$_3$) δ: 3.27-3.36 (1H, m), 3.54-3.63 (1H, m), 3.67-3.85 (4H, m), 3.95-4.03 (1H, m), 4.15-4.19 (2H, m), 4.25-4.37 (2H, m), 4.58 (2H, br s), 4.74-4.91 (2H, m), 7.14-7.20 (2H, m), 7.44-7.49 (3H, m), 7.54-7.60 (3H, m), 7.65 (1H, s), 7.71 (1H, s), 7.84-7.88 (2H, m), 8.22 (1H, d, J=2.5 Hz), 8.65 (1H, d, J=2.5 Hz).
MS (ESI) m/z: 613 (M+H)$^+$.

Example 66

N-[4-(2-Amino-5-{1-[(2S)-1,4-dioxan-2-ylmethyl]-1H-pyrazol-4-yl}pyridin-3-yl)phenyl]-5-(4-fluorophenyl)-1-(2-methoxyethyl)-4-oxo-1,4-dihydropyridine-3-carboxamide

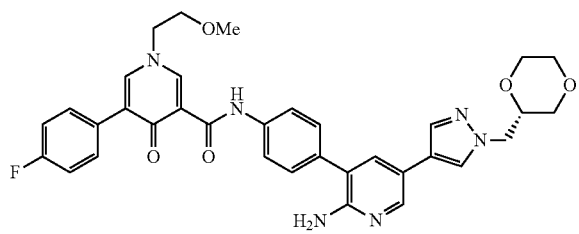

The compound obtained in Step 1 of Example 5 (33 mg) and the compound obtained in Step 1 of Example 64 (44 mg) yielded 44 mg of the title compound as a solid via a reaction similar to that in Step 2 of Example 47.

$^1$H-NMR (CDCl$_3$) δ: 3.27-3.35 (1H, m), 3.40 (3H, s), 3.53-3.62 (1H, m), 3.67-3.85 (6H, m), 3.94-4.03 (1H, m), 4.08-4.15 (4H, m), 4.57 (2H, s), 7.13-7.20 (2H, m), 7.44-7.49 (3H, m), 7.54-7.61 (3H, m), 7.64 (1H, d, J=0.92 Hz), 7.71 (1H, d, J=0.92 Hz), 7.84-7.89 (2H, m), 8.20-8.23 (1H, m), 8.64 (1H, d, J=2.8 Hz).

MS (ESI) m/z: 625 (M+H)$^+$.

Example 67

N-[4-(2-Amino-5-{1-[(2S)-1,4-dioxan-2-ylmethyl]-1H-pyrazol-4-yl}pyridin-3-yl)phenyl]-1-(2-ethoxyethyl)-5-(4-fluorophenyl)-4-oxo-1,4-dihydropyridine-3-carboxamide

[Step 1] Ethyl 1-(2-ethoxyethyl)-5-(4-fluorophenyl)-4-oxo-1,4-dihydropyridine-3-carboxylate

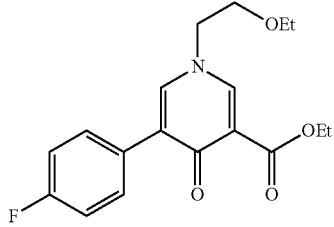 [SMILES: CCOCCn1cc(C(=O)OCC)c(=O)c(-c2ccc(F)cc2)c1]

Ethyl 5-(4-fluorophenyl)-4-oxo-1,4-dihydropyridine-3-carboxylate (270 mg) and 2-bromoethyl ethyl ether (196 μl) yielded 251 mg of the title compound as a solid via a reaction similar to that in Step 1 of Example 19.

$^1$H-NMR (CDCl$_3$) δ: 1.19 (3H, t, J=6.9 Hz), 1.38 (3H, t, J=7.1 Hz), 3.51 (2H, q, J=6.9 Hz), 3.73 (2H, t, J=4.9 Hz), 4.01 (2H, t, J=4.9 Hz), 4.37 (2H, q, J=7.1 Hz), 7.03-7.11 (2H, m), 7.46 (1H, d, J=2.5 Hz), 7.54-7.62 (2H, m), 8.19 (1H, d, J=2.5 Hz).

MS (ESI) m/z: 334 (M+H)$^+$.

[Step 2] 1-(2-Ethoxyethyl)-5-(4-fluorophenyl)-4-oxo-1,4-dihydropyridine-3-carboxylic acid

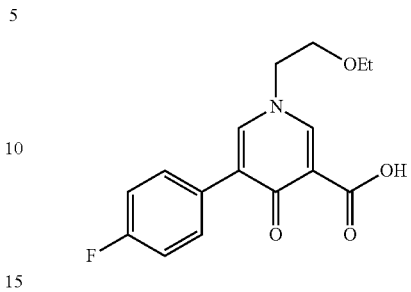

The compound obtained in the above Step 1 (250 mg) yielded 109 mg of the title compound as a solid via a reaction similar to that in Step 2 of Example 19.

$^1$H-NMR (CDCl$_3$) δ: 1.19 (3H, t, J=7.1 Hz), 3.53 (2H, q, J=7.1 Hz), 3.78 (2H, t, J=4.8 Hz), 4.16 (2H, t, J=4.8 Hz), 7.12-7.19 (2H, m), 7.55-7.63 (2H, m), 7.73 (1H, d, J=2.3 Hz), 8.54 (1H, d, J=2.3 Hz).

MS (ESI) m/z: 306 (M+H)$^+$.

[Step 3] N-[4-(2-Amino-5-{1-[(2S)-1,4-dioxan-2-ylmethyl]-1H-pyrazol-4-yl}pyridin-3-yl)phenyl]-1-(2-ethoxyethyl)-5-(4-fluorophenyl)-4-oxo-1,4-dihydropyridine-3-carboxamide

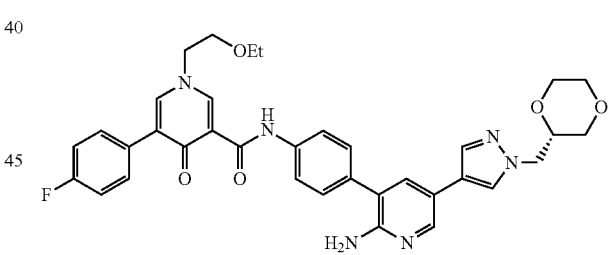

The compound obtained in the above Step 2 (37 mg) and the compound obtained in Step 1 of Example 64 (47 mg) yielded 59 mg of the title compound as a solid via a reaction similar to that in Step 2 of Example 47.

$^1$H-NMR (CDCl$_3$) δ: 1.20 (3H, t, J=6.9 Hz), 3.31 (1H, dd, J=11.92, 10.1 Hz), 3.50-3.62 (3H, m), 3.67-3.85 (6H, m), 3.94-4.03 (1H, m), 4.10-4.19 (4H, m), 4.59 (2H, s), 7.13-7.20 (2H, m), 7.43-7.50 (3H, m), 7.54-7.61 (2H, m), 7.62-7.66 (2H, m), 7.71 (1H, d, J=0.92 Hz), 7.83-7.90 (2H, m), 8.21 (1H, d, J=2.5 Hz), 8.65 (1H, d, J=2.5 Hz).

MS (ESI) m/z: 639 (M+H)$^+$.

Example 68

N-[4-(2-Amino-5-{1-[(2S)-1,4-dioxan-2-ylmethyl]-1H-pyrazol-4-yl}pyridin-3-yl)phenyl]-5-(4-fluorophenyl)-1-(2-hydroxy-2-methylpropyl)-4-oxo-1,4-dihydropyridine-3-carboxamide

[Step 1] Ethyl 5-(4-fluorophenyl)-1-(2-hydroxy-2-methylpropyl)-4-oxo-1,4-dihydropyridine-3-carboxylate

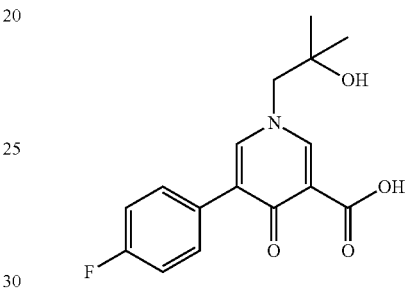

Ethyl 5-(4-fluorophenyl)-4-oxo-1,4-dihydropyridine-3-carboxylate (400 mg) was suspended in DMF (5.0 ml). Cesium carbonate (1200 mg), 1-chloro-2-methyl-2-propanol (345 μl) and tetra-n-butylammonium iodide (56 mg) were added sequentially, and the mixture was stirred at 70° C. for 10 hours. A 1 N aqueous hydrochloric acid solution was added at room temperature. The insoluble matter was removed by filtration through celite, followed by extraction with ethyl acetate. The organic layer was washed with water and brine and then dried over sodium sulfate. The solvent was distilled off under reduced pressure, and the residue was purified by silica gel column chromatography [chloroform:methanol=300:1->60:1 (v/v)] to give 57 mg of the title compound as a solid.

$^1$H-NMR (CDCl$_3$) δ: 1.32 (6H, s), 1.37 (3H, t, J=7.1 Hz), 3.43 (1H, s), 3.79 (2H, s), 4.36 (2H, q, J=7.1 Hz), 7.00-7.09 (2H, m), 7.45-7.49 (1H, m), 7.51-7.60 (2H, m), 8.16 (1H, d, J=2.3 Hz).

MS (ESI) m/z: 334 (M+H)$^+$.

[Step 2] 5-(4-Fluorophenyl)-1-(2-hydroxy-2-methylpropyl)-4-oxo-1,4-dihydropyridine-3-carboxylic acid The compound obtained in the above Step 1 (77 mg) yielded 42 mg of the title compound via a reaction similar to that in Step 2 of Example 19.

$^1$H-NMR (CDCl$_3$) δ: 1.35 (6H, s), 3.96 (2H, s), 7.10-7.18 (2H, m), 7.56-7.64 (2H, m), 7.77 (1H, d, J=2.3 Hz), 8.54 (1H, d, J=2.3 Hz).

MS (ESI) m/z: 306 (M+H)$^+$.

[Step 3] N-[4-(2-Amino-5-{1-[(2S)-1,4-dioxan-2-ylmethyl]-1H-pyrazol-4-yl}pyridin-3-yl)phenyl]-5-(4-fluorophenyl)-1-(2-hydroxy-2-methylpropyl)-4-oxo-1,4-dihydropyridine-3-carboxamide

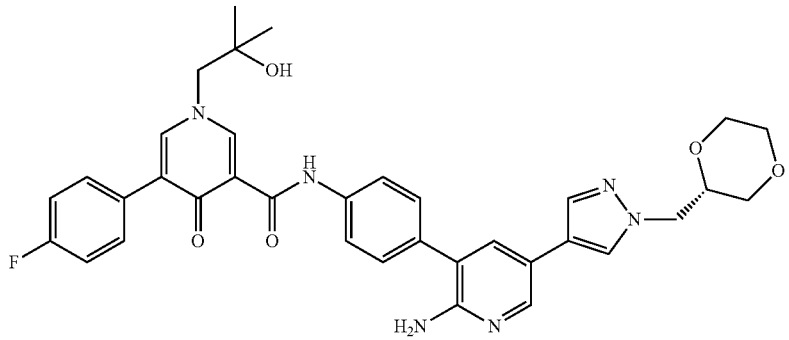 [SMILES: CC(C)(O)Cn1cc(C(=O)Nc2ccc(-c3cc(-c4cnn(C[C@H]5COCCO5)c4)cnc3N)cc2)c(=O)c(-c2ccc(F)cc2)c1]

The compound obtained in the above Step 2 (37 mg) and the compound obtained in Step 1 of Example 64 (47 mg) yielded 52 mg of the title compound as a solid via a reaction similar to that in Step 2 of Example 47.

¹H-NMR (CDCl₃) δ: 1.37 (6H, s), 3.27-3.35 (1H, m), 3.54-3.62 (1H, m), 3.67-3.85 (4H, m), 3.92-4.03 (3H, m), 4.15-4.20 (2H, m), 4.58 (2H, s), 7.11-7.19 (2H, m), 7.43-7.49 (3H, m), 7.54-7.61 (2H, m), 7.64 (1H, s), 7.68 (1H, d, J=2.3 Hz), 7.71 (1H, s), 7.83-7.89 (2H, m), 8.21 (1H, d, J=2.3 Hz), 8.61 (1H, d, J=2.3 Hz).

MS (ESI) m/z: 639 (M+H)⁺.

Example 69

N-[4-(2-Amino-5-{1-[(2S)-1,4-dioxan-2-ylmethyl]-1H-pyrazol-4-yl}pyridin-3-yl)phenyl]-1-[2-(diethylamino)ethyl]-5-(4-fluorophenyl)-4-oxo-1,4-dihydropyridine-3-carboxamide

[Step 1] Ethyl 1-[2-(diethylamino)ethyl]-5-(4-fluorophenyl)-4-oxo-1,4-dihydropyridine-3-carboxylate

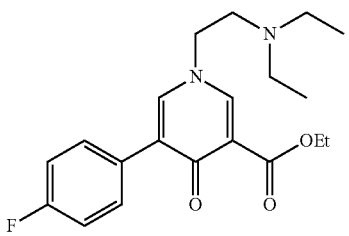 [SMILES: CCN(CC)CCn1cc(C(=O)O)c(=O)c(-c2ccc(F)cc2)c1]

Ethyl 5-(4-fluorophenyl)-4-oxo-1,4-dihydropyridine-3-carboxylate (270 mg) was suspended in DMF (3.0 ml). Cesium carbonate (1180 mg) and 2-bromo-N,N-diethylethylamine hydrobromide (405 mg) were added sequentially, and the mixture was stirred at 50° C. for six hours. A 1 N aqueous hydrochloric acid solution was added under ice cooling, and the insoluble matter was then removed by filtration through celite. After extraction with ethyl acetate, the organic layer was washed with water and brine and then dried over sodium sulfate. The solvent was distilled off under reduced pressure, and the residue was purified by silica gel column chromatography [chloroform:methanol=300:1->60:1 (v/v)] to give 89 mg of the title compound as an oily substance.

¹H-NMR (CDCl₃) δ: 0.96 (6H, t, J=7.1 Hz), 1.39 (3H, t, J=7.2 Hz), 2.49-2.57 (4H, m), 2.77 (2H, t, J=5.7 Hz), 3.85 (2H, t, J=5.7 Hz), 4.38 (2H, q, J=7.2 Hz), 7.03-7.11 (2H, m), 7.42 (1H, d, J=2.3 Hz), 7.54-7.61 (2H, m), 8.20 (1H, d, J=2.3 Hz).

MS (ESI) m/z: 361 (M+H)⁺.

[Step 2] 1-[2-(Diethylamino)ethyl]-5-(4-fluorophenyl)-4-oxo-1,4-dihydropyridine-3-carboxylic acid

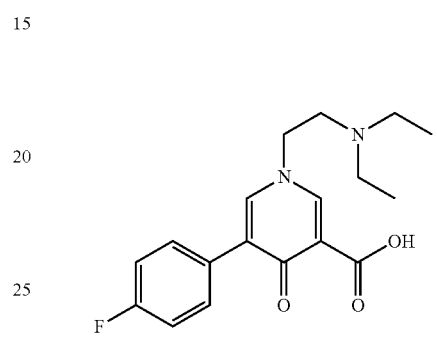

A 1 N aqueous sodium hydroxide solution (0.50 ml) was added to a solution of the compound obtained in the above Step 1 (89 mg) in methanol (0.8 ml) at room temperature, and the mixture was stirred for three hours. The solvent was distilled off under reduced pressure and a 1 N aqueous hydrochloric acid solution was added, followed by extraction with chloroform. The organic layer was dried over sodium sulfate, and the solvent was distilled off under reduced pressure to give 53 mg of the title compound.

¹H-NMR (CDCl₃) δ: 0.89-1.11 (6H, m), 2.48-2.75 (4H, m), 2.80-3.03 (2H, m), 3.91-4.28 (2H, m), 7.11-7.19 (2H, m), 7.56-7.64 (2H, m), 7.78 (1H, br s), 8.59 (1H, br s).

MS (ESI) m/z: 333 (M+H)⁺.

[Step 3] N-[4-(2-Amino-5-{1-[(2S)-1,4-dioxan-2-ylmethyl]-1H-pyrazol-4-yl}pyridin-3-yl)phenyl]-1-[2-(diethylamino)ethyl]-5-(4-fluorophenyl)-4-oxo-1,4-dihydropyridine-3-carboxamide

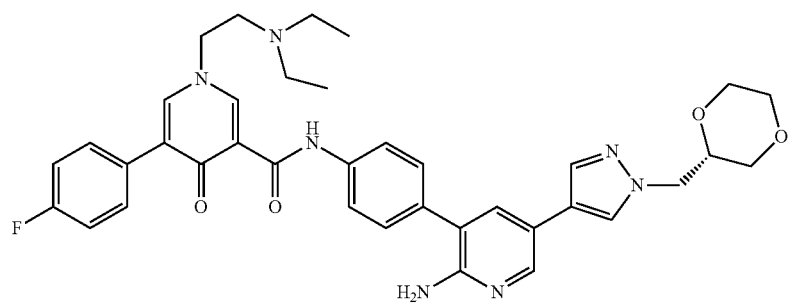 [SMILES: CCN(CC)CCn1cc(C(=O)Nc2ccc(-c3cc(-c4cnn(C[C@H]5COCCO5)c4)cnc3N)cc2)c(=O)c(-c2ccc(F)cc2)c1]

The compound obtained in the above Step 2 (39 mg) and the compound obtained in Step 1 of Example 64 (45 mg) yielded 46 mg of the title compound as a solid via a reaction similar to that in Step 2 of Example 47.

¹H-NMR (CDCl₃) δ: 0.97 (6H, t, J=7.1 Hz), 2.56 (4H, q, J=7.1 Hz), 2.80-2.86 (2H, m), 3.31 (1H, dd, J=11.7, 9.9 Hz), 3.53-3.63 (1H, m), 3.67-3.85 (4H, m), 3.94-4.02 (3H, m), 4.15-4.19 (2H, m), 4.58 (2H, s), 7.13-7.20 (2H, m), 7.43-7.50 (3H, m), 7.53-7.61 (3H, m), 7.65 (1H, s), 7.71 (1H, s), 7.84-7.90 (2H, m), 8.21 (1H, d, J=2.3 Hz), 8.63 (1H, d, J=2.3 Hz).
MS (ESI) m/z: 666 (M+H)⁺.

Example 70

N'-[4-(2-Amino-5-{1-[(2S)-1,4-dioxan-2-ylmethyl]-1H-pyrazol-4-yl}pyridin-3-yl)phenyl]-N,N-diethyl-1-(4-fluorobenzyl)-4-oxo-1,4-dihydropyridine-3,5-dicarboxamide

[Step 1] tert-Butyl ethyl 1-(4-fluorobenzyl)-4-oxo-1,4-dihydropyridine-3,5-dicarboxylate

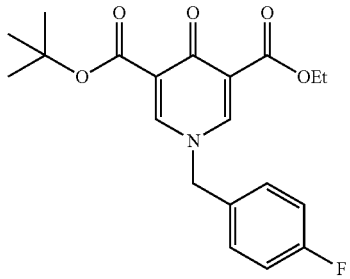 [SMILES: CCOC(=O)c1cn(Cc2ccc(F)cc2)cc(C(=O)OC(C)(C)C)c1=O]

N,N-Dimethylformamide dimethylacetal (11.0 ml) was added to a solution of tert-butyl ethyl 3-oxopentanedicarboxylate (4.76 g) in n-butyl acetate (60 ml), and the mixture was stirred at 100° C. for 90 minutes. The solvent was distilled off under reduced pressure, and the residue was then dissolved in ethanol (40 ml). 4-Fluorobenzylamine (2.59 ml) was added and the mixture was stirred at 70° C. for five hours. The solvent was distilled off under reduced pressure, and the residue was purified by silica gel column chromatography [chloroform:methanol=300:1->50:1 (v/v)] to give 5.8 g of the title compound as an oily substance.

¹H-NMR (CDCl₃) δ: 1.35 (3H, t, J=7.1 Hz), 1.55 (9H, s), 4.35 (2H, q, J=7.1 Hz), 4.95 (2H, s), 7.09-7.17 (2H, m), 7.19-7.25 (2H, m), 7.94 (1H, d, J=2.8 Hz), 8.04 (1H, d, J=2.8 Hz).

[Step 2] 5-(Ethoxycarbonyl)-1-(4-fluorobenzyl)-4-oxo-1,4-dihydropyridine-3-carboxylic acid

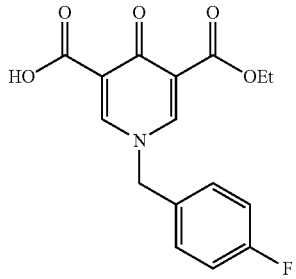 [SMILES: CCOC(=O)c1cn(Cc2ccc(F)cc2)cc(C(=O)O)c1=O]

TFA (40 ml) was added to a solution of the compound obtained in the above Step 1 (5.81 g) in dichloromethane (40 ml) under ice cooling. The mixture was gradually warmed to room temperature and stirred for two hours. The solvent was distilled off under reduced pressure, and diethyl ether was added to the residue. The precipitated solid was collected by filtration to give 3.7 g of the title compound.

¹H-NMR (CDCl₃) δ: 1.40 (3H, t, J=7.1 Hz), 4.41 (2H, q, J=7.1 Hz), 5.13 (2H, s), 7.13-7.20 (2H, m), 7.25-7.30 (2H, m), 8.33 (1H, d, J=2.5 Hz), 8.55 (1H, d, J=2.5 Hz).
MS (ESI) m/z: 320 (M+H)⁺.

[Step 3] Ethyl 5-(diethylcarbamoyl)-1-(4-fluorobenzyl)-4-oxo-1,4-dihydropyridine-3-carboxylate

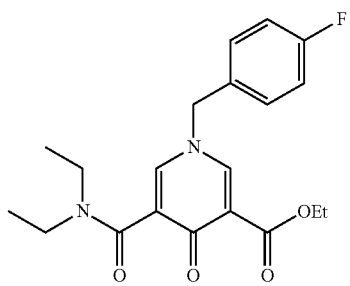 [SMILES: CCN(CC)C(=O)c1cn(Cc2ccc(F)cc2)cc(C(=O)O)c1=O]

Diethylamine (130 μl) and 1H-benzotriazol-1-yloxytripyrrolidinophosphonium hexafluorophosphate (528 mg) were added to a solution of the compound obtained in Step 2 (270 mg) in dichloromethane (3.0 ml) at room temperature, and the mixture was stirred for five hours. The solvent was distilled off under reduced pressure, and the residue was purified by silica gel column chromatography [chloroform:methanol=300:1->30:1 (v/v)] to give 160 mg of the title compound as an oily substance.

¹H-NMR (CDCl₃) δ: 1.02 (3H, J=7.1 Hz), 1.20 (3H, t, J=7.1 Hz), 1.36 (3H, t, J=7.1 Hz), 3.19-3.26 (2H, m), 3.47 (2H, q, J=7.1 Hz), 4.35 (2H, q, J=7.1 Hz), 4.97 (2H, s), 7.08-7.16 (2H, m), 7.21-7.25 (2H, m), 7.45 (1H, d, J=2.8 Hz), 8.17 (1H, d, J=2.8 Hz).
MS (ESI) m/z: 375 (M+H)⁺.

[Step 4] 5-(Diethylcarbamoyl)-1-(4-fluorobenzyl)-4-oxo-1,4-dihydropyridine-3-carboxylic acid

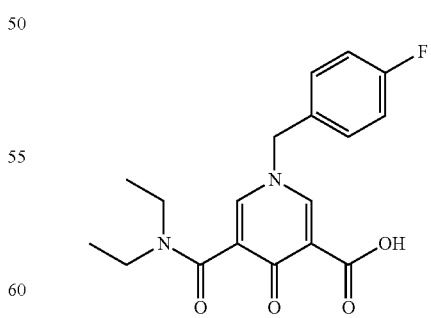

The compound obtained in the above Step 3 (160 mg) yielded 110 mg of the title compound via a reaction similar to that in Step 2 of Example 19.

¹H-NMR (CDCl₃) δ: 1.10 (3H, t, J=7.2 Hz), 1.24 (3H, t, J=7.2 Hz), 3.22 (2H, q, J=7.2 Hz), 3.53 (2H, q, J=7.2 Hz), 5.09 (2H, s), 7.11-7.19 (2H, m), 7.22-7.29 (2H, m), 7.70 (1H, d, J=2.3 Hz), 8.54 (1H, d, J=2.3 Hz).

MS (ESI) m/z: 347 (M+H)+.

[Step 5] N'-[4-(2-Amino-5-{1-[(2S)-1,4-dioxan-2-ylmethyl]-1H-pyrazol-4-yl}pyridin-3-yl)phenyl]-N,N-diethyl-1-(4-fluorobenzyl)-4-oxo-1,4-dihydropyridine-3,5-dicarboxamide

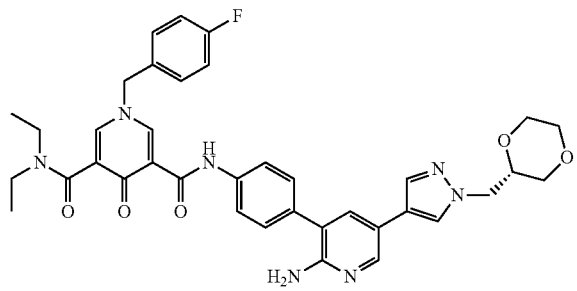 [SMILES: CCN(CC)C(=O)c1cn(Cc2ccc(F)cc2)cc(C(=O)Nc2ccc(-c3cc(-c4cnn(C[C@H]5COCCO5)c4)cnc3N)cc2)c1=O]

The compound obtained in the above Step 4 (40 mg) and the compound obtained in Step 1 of Example 64 (45 mg) yielded 30 mg of the title compound as a solid via a reaction similar to that in Step 2 of Example 47.

¹H-NMR (CDCl₃) δ: 1.09 (3H, t, J=7.1 Hz), 1.24-1.30 (3H, m), 3.23-3.35 (3H, m), 3.50-3.62 (3H, m), 3.67-3.86 (4H, m), 3.94-4.02 (1H, m), 4.15-4.19 (2H, m), 4.58 (2H, s), 5.09 (2H, s), 7.11-7.18 (2H, m), 7.27-7.32 (2H, m), 7.44-7.49 (3H, m), 7.57 (1H, d, J=2.8 Hz), 7.65 (1H, s), 7.71 (1H, s), 7.81-7.86 (2H, m), 8.21 (1H, d, J=2.3 Hz), 8.66 (1H, d, J=2.3 Hz), 12.39 (1H, s).

MS (ESI) m/z: 680 (M+H)+.

Example 71

N-[4-(2-Amino-5-{1-[(2S)-1,4-dioxan-2-ylmethyl]-1H-pyrazol-4-yl}pyridin-3-yl)phenyl]-1-(4-fluorobenzyl)-4-oxo-5-(pyrrolidin-1-ylcarbonyl)-1,4-dihydropyridine-3-carboxamide

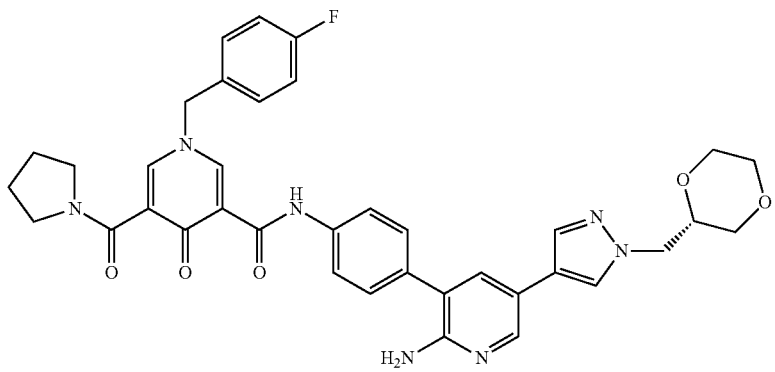 [SMILES: Nc1ncc(-c2cnn(C[C@H]3COCCO3)c2)cc1-c1ccc(NC(=O)c2cn(Cc3ccc(F)cc3)cc(C(=O)N3CCCC3)c2=O)cc1]

The compound obtained in Step 4 of Example 26 (38 mg) and the compound obtained in Step 1 of Example 64 (42 mg) yielded 25 mg of the title compound as a solid via a reaction similar to that in Step 2 of Example 47.

¹H-NMR (CDCl₃) δ: 1.87-2.03 (4H, m), 3.27-3.35 (1H, m), 3.27-3.35 (2H, m), 3.54-3.85 (7H, m), 3.94-4.02 (1H, m), 4.16-4.19 (2H, m), 4.58 (2H, s), 5.09 (2H, s), 7.11-7.18 (2H, m), 7.27-7.32 (2H, m), 7.44-7.49 (3H, m), 7.65 (1H, d, J=0.9 Hz), 7.70-7.76 (2H, m), 7.81-7.86 (2H, m), 8.21 (1H, d, J=2.5 Hz), 8.65 (1H, d, J=2.5 Hz), 12.46 (1H, s).

MS (ESI) m/z: 678 (M+H)+.

Example 72

N-[4-(2-Amino-5-{1-[(2S)-1,4-dioxan-2-ylmethyl]-1H-pyrazol-4-yl}pyridin-3-yl)phenyl]-1-(4-fluorobenzyl)-5-[(3-methoxyazetidin-1-yl)carbonyl]-4-oxo-1,4-dihydropyridine-3-carboxamide

[Step 1] Methyl 1-(4-fluorobenzyl)-5-[(3-methoxyazetidin-1-yl)carbonyl]-4-oxo-1,4-dihydropyridine-3-carboxylate

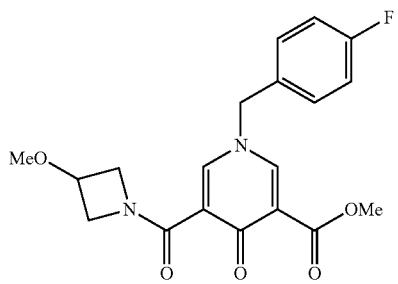 [SMILES: COC(=O)c1cn(Cc2ccc(F)cc2)cc(C(=O)N2CC(OC)C2)c1=O]

3-Methoxyazetidine hydrochloride (67 mg), 1H-benzotriazol-1-yloxytripyrrolidinophosphonium hexafluorophosphate (206 mg) and triethylamine (100 μl) were added to a solution of the compound obtained in Step 2 of Example 26 (110 mg) in dichloromethane/DMF (2.0/0.5 ml) at room temperature, and the mixture was stirred for seven hours. After adding a small amount of water, the mixture was diluted with ethyl acetate, followed by drying over sodium sulfate. The solvent was distilled off under reduced pressure, and the residue was purified by silica gel column chromatography [chloroform:methanol=300:1->20:1 (v/v)] to give 63 mg of the title compound as an oily substance.

¹H-NMR (CDCl₃) δ: 3.27 (3H, s), 3.88 (3H, s), 3.96-4.07 (2H, m), 4.17-4.32 (2H, m), 4.48-4.55 (1H, m), 4.97 (2H, s), 7.10-7.16 (2H, m), 7.22-7.26 (2H, m), 7.88 (1H, d, J=2.5 Hz), 8.16 (1H, d, J=2.5 Hz).

MS (ESI) m/z: 375 (M+H)+.

[Step 2] 1-(4-Fluorobenzyl)-5-[(3-methoxyazetidin-1-yl)carbonyl]-4-oxo-1,4-dihydropyridine-3-carboxylic acid The compound obtained in the above Step 2 (40 mg) and the compound obtained in Step 1 of Example 64 (43 mg) yielded 42 mg of the title compound as a solid via a reaction similar to that in Step 2 of Example 47.

$^1$H-NMR (CDCl$_3$) δ: 3.28-3.34 (4H, m), 3.54-3.84 (5H, m), 3.95-4.09 (3H, m), 4.16-4.20 (2H, m), 4.23-4.63 (5H, m), 5.10 (2H, s), 7.11-7.19 (2H, m), 7.27-7.33 (2H, m), 7.46-7.50 (3H, m), 7.65 (1H, s), 7.72 (1H, s), 7.81-7.86 (2H, m), 7.97 (1H, d, J=2.3 Hz), 8.22 (1H, d, J=2.3 Hz), 8.65 (1H, d, J=2.3 Hz), 12.46 (1H, s).

MS (ESI) m/z: 694 (M+H)$^+$.

Example 73

N-[4-(2-Amino-5-{1-[(2S)-1,4-dioxan-2-ylmethyl]-1H-pyrazol-4-yl}pyridin-3-yl)phenyl]-5-[(3,3-difluoropyrrolidin-1-yl)carbonyl]-1-(4-fluorobenzyl)-4-oxo-1,4-dihydropyridine-3-carboxamide

[Step 1] Ethyl 5-[(3,3-difluoropyrrolidin-1-yl)carbonyl]-1-(4-fluorobenzyl)-4-oxo-1,4-dihydropyridine-3-carboxylate

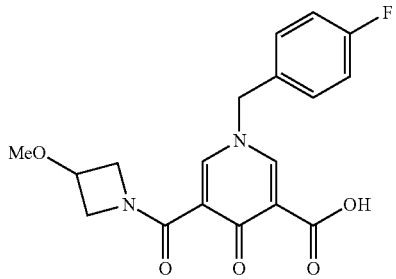 [SMILES: COC1CN(C(=O)c2cn(Cc3ccc(F)cc3)cc(C(=O)O)c2=O)C1]

The compound obtained in the above Step 1 (63 mg) yielded 44 mg of the title compound via a reaction similar to that in Step 2 of Example 19.

$^1$H-NMR (CDCl$_3$) δ: 3.30 (3H, s), 4.00-4.06 (2H, m), 4.20-4.35 (2H, m), 4.43-4.49 (1H, m), 5.10 (2H, s), 7.13-7.18 (2H, m), 7.27-7.32 (2H, m), 8.10 (1H, d, J=2.3 Hz), 8.54 (1H, d, J=2.3 Hz).

MS (ESI) m/z: 361 (M+H)$^+$.

[Step 3] N-[4-(2-Amino-5-{1-[(2S)-1,4-dioxan-2-ylmethyl]-1H-pyrazol-4-yl}pyridin-3-yl)phenyl]-1-(4-fluorobenzyl)-5-[(3-methoxyazetidin-1-yl)carbonyl]-4-oxo-1,4-dihydropyridine-3-carboxamide

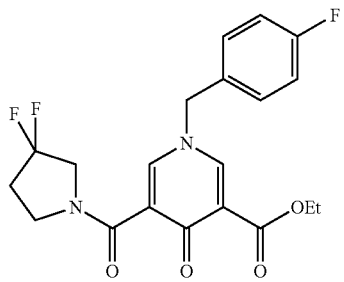

The compound obtained in Step 2 of Example 70 (220 mg) and 3,3-difluoropyrrolidine hydrochloride (148 mg) yielded 148 mg of the title compound as an isomeric mixture via a reaction similar to that in Step 1 of Example 72.

MS (ESI) m/z: 409 (M+H)$^+$.

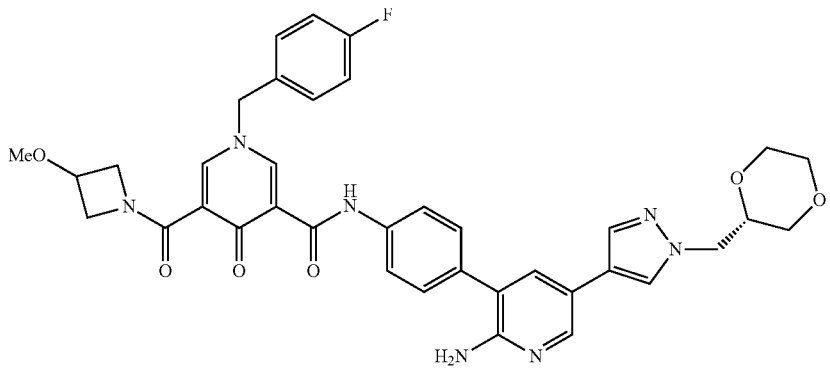 [SMILES: COC1CN(C(=O)c2cn(Cc3ccc(F)cc3)cc(C(=O)Nc3ccc(-c4cc(-c5cnn(C[C@H]6COCCO6)c5)cnc4N)cc3)c2=O)C1]

[Step 2] 5-[(3,3-Difluoropyrrolidin-1-yl)carbonyl]-1-(4-fluorobenzyl)-4-oxo-1,4-dihydropyridine-3-carboxylic acid

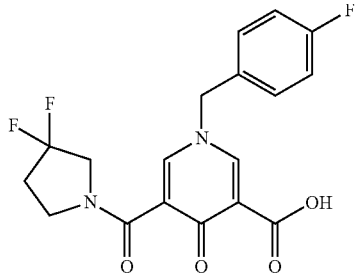 [SMILES: O=C(O)c1cn(Cc2ccc(F)cc2)cc(C(=O)N2CCC(F)(F)C2)c1=O]

The compound obtained in the above Step 1 (148 mg) yielded 118 mg of the title compound as an isomeric mixture via reaction similar to that in Step 2 of Example 19.

MS (ESI) m/z: 381 (M+H)$^+$.

[Step 3] N-[4-(2-Amino-5-{1-[(2S)-1,4-dioxan-2-ylmethyl]-1H-pyrazol-4-yl}pyridin-3-yl)phenyl]-5-[(3,3-difluoropyrrolidin-1-yl)carbonyl]-1-(4-fluorobenzyl)-4-oxo-1,4-dihydropyridine-3-carboxamide

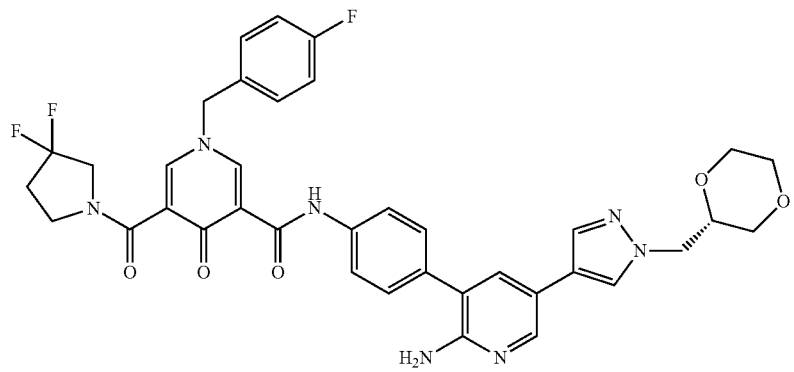 [SMILES: Nc1ncc(-c2cnn(C[C@H]3COCCO3)c2)cc1-c1ccc(NC(=O)c2cn(Cc3ccc(F)cc3)cc(C(=O)N3CCC(F)(F)C3)c2=O)cc1]

The compound obtained in the above Step 2 (40 mg) and the compound obtained in Step 1 of Example 64 (41 mg) yielded 52 mg of the title compound as a solid via a reaction similar to that in Step 2 of Example 47.

$^1$H-NMR (DMSO-D$_6$) δ: 3.21-3.93 (13H, m), 4.10-4.15 (2H, m), 5.39 (2H, s), 5.56 (2H, s), 7.25-7.33 (2H, m), 7.47-7.58 (5H, m), 7.75-7.85 (3H, m), 8.07 (1H, s), 8.20 (1H, d, J=2.3 Hz), 8.35 (1H, d, J=2.3 Hz), 8.85-8.91 (1H, m).

MS (ESI) m/z: 714 (M+H)$^+$.

Example 74

N-[4-(2-Amino-5-{1-[(2S)-1,4-dioxan-2-ylmethyl]-1H-pyrazol-4-yl}pyridin-3-yl)phenyl]-1-(4-fluorobenzyl)-5-(5-methyl-1,3,4-oxadiazol-2-yl)-4-oxo-1,4-dihydropyridine-3-carboxamide

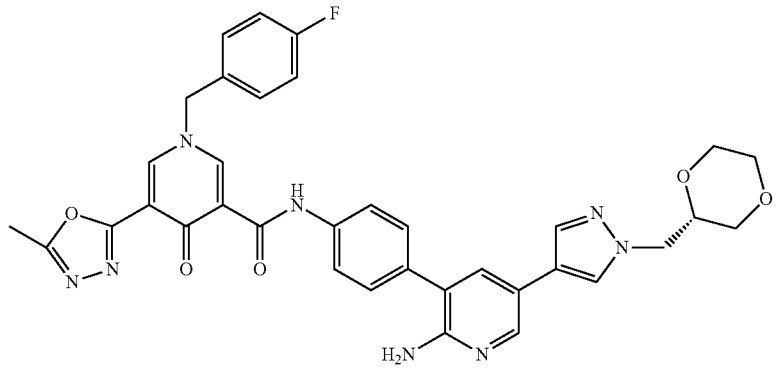 [SMILES: Cc1nnc(-c2cn(Cc3ccc(F)cc3)cc(C(=O)Nc3ccc(-c4cc(-c5cnn(C[C@H]6COCCO6)c5)cnc4N)cc3)c2=O)o1]

The compound obtained in Step 3 of Example 28 (39 mg) and the compound obtained in Step 1 of Example 64 (46 mg) yielded 53 mg of the title compound as a solid via a reaction similar to that in Step 2 of Example 47.

$^1$H-NMR (CDCl$_3$) δ: 2.68 (3H, s), 3.31 (1H, dd, J=11.5, 10.1 Hz), 3.54-3.63 (1H, m), 3.67-3.85 (4H, m), 3.94-4.03 (1H, m), 4.15-4.20 (2H, m), 4.58 (2H, s), 5.18 (2H, s), 7.13-7.20 (2H, m), 7.29-7.36 (2H, m), 7.46-7.51 (3H, m), 7.65 (1H, s), 7.71 (1H, s), 7.82-7.88 (2H, m), 8.22 (1H, d, J=2.3 Hz), 8.38 (1H, d, J=2.8 Hz), 8.74 (1H, d, J=2.8 Hz), 12.32 (1H, s). MS (ESI) m/z: 663 (M+H)$^+$.

Example 75

N-[4-(2-Amino-5-{1-[(2S)-1,4-dioxan-2-ylmethyl]-1H-pyrazol-4-yl}pyridin-3-yl)-3-fluorophenyl]-1-(2-fluoroethyl)-4-oxo-5-phenyl-1,4-dihydropyridine-3-carboxamide

[Step 1] 3-(4-Amino-2-fluorophenyl)-5-{1-[(2S)-1,4-dioxan-2-ylmethyl]-1H-pyrazol-4-yl}pyridin-2-amine

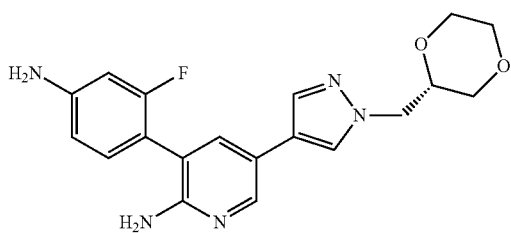 [SMILES: Nc1ccc(-c2cc(-c3cnn(C[C@H]4COCCO4)c3)cnc2N)c(F)c1]

Water (1.5 ml), cesium carbonate (1730 mg) and tetrakis(triphenylphosphine)palladium (204 mg) were added to a solution of the compound obtained in Step 1 of Example 29 (500 mg) and the compound obtained in Reference Example 8 (782 mg) in 1,4-dioxane (15 ml). The mixture was stirred under microwave irradiation at 100° C. for one hour. After leaving to cool, the reaction solution was diluted with chloroform. The organic layer was washed with water and brine and dried over sodium sulfate. The solvent was distilled off under reduced pressure, and the residue was purified by silica gel column chromatography [chloroform:methanol=19:1 (v/v)] to give 450 mg of the title compound as a solid. MS (ESI) m/z: 370 (M+H)$^+$.

[Step 2] N-[4-(2-Amino-5-{1-[(2S)-1,4-dioxan-2-ylmethyl]-1H-pyrazol-4-yl]pyridin-3-yl)-3-fluorophenyl}-1-(2-fluoroethyl)-4-oxo-5-phenyl-1,4-dihydropyridine-3-carboxamide

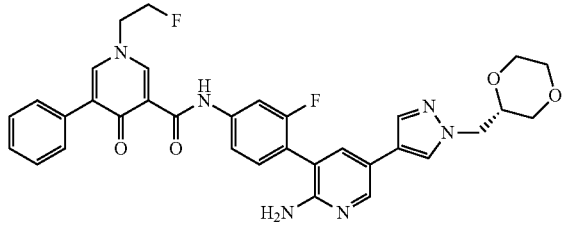 [SMILES: Nc1ncc(-c2cnn(C[C@H]3COCCO3)c2)cc1-c1ccc(NC(=O)c2cn(CCF)cc(-c3ccccc3)c2=O)cc1F]

The compound obtained in Step 2 of Example 19 (34 mg) and the compound obtained in the above Step 1 (53 mg) yielded 57 mg of the title compound as a solid via a reaction similar to that in Step 2 of Example 47.

$^1$H-NMR (CDCl$_3$) δ: 3.26-3.35 (1H, m), 3.53-3.63 (1H, m), 3.67-3.85 (4H, m), 3.94-4.02 (1H, m), 4.15-4.19 (2H, m), 4.25-4.37 (2H, m), 4.49 (2H, s), 4.74-4.91 (2H, m), 7.31-7.37 (1H, m), 7.40-7.52 (5H, m), 7.55-7.61 (3H, m), 7.64 (1H, s), 7.71 (1H, s), 7.88-7.95 (1H, m), 8.26 (1H, d, J=2.5 Hz), 8.64 (1H, d, J=2.5 Hz).

MS (ESI) m/z: 613 (M+H)$^+$.

Example 76

N-[4-(2-Amino-5-{1-[(2S)-1,4-dioxan-2-ylmethyl]-1H-pyrazol-4-yl}pyridin-3-yl)-3-fluorophenyl]-1-(4-fluorobenzyl)-4-oxo-5-(pyrrolidin-1-ylcarbonyl)-1,4-dihydropyridine-3-carboxamide

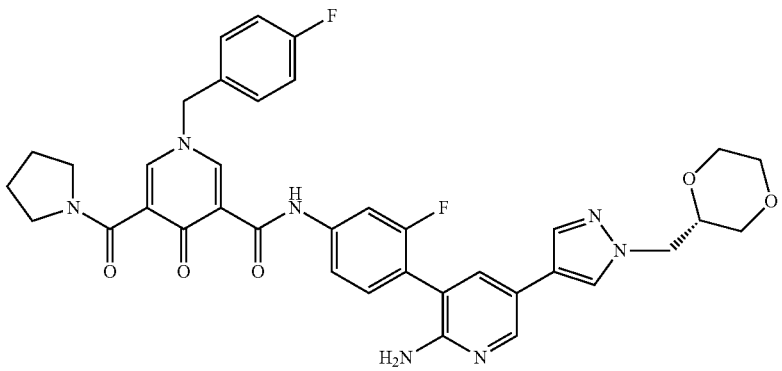 [SMILES: Nc1ncc(-c2cnn(C[C@H]3COCCO3)c2)cc1-c1ccc(NC(=O)c2cn(Cc3ccc(F)cc3)cc(C(=O)N3CCCC3)c2=O)cc1F]

The compound obtained in Step 4 of Example 26 (38 mg) and the compound obtained in Step 1 of Example 75 (45 mg) yielded 28 mg of the title compound as a solid via a reaction similar to that in Step 2 of Example 47.

$^1$H-NMR (CDCl$_3$) δ: 1.87-2.03 (4H, m), 3.31 (1H, dd, J=11.7, 9.9 Hz), 3.42-3.49 (2H, m), 3.53-3.85 (7H, m), 3.94-4.02 (1H, m), 4.15-4.19 (2H, m), 4.49 (2H, s), 5.10 (2H, s), 7.11-7.19 (2H, m), 7.27-7.38 (3H, m), 7.41-7.46 (1H, m), 7.49 (1H, d, J=2.3 Hz), 7.64 (1H, s), 7.71 (1H, s), 7.75 (1H, d, J=2.3 Hz), 7.84-7.91 (1H, m), 8.26 (1H, d, J=2.5 Hz), 8.64 (1H, d, J=2.5 Hz).

MS (ESI) m/z: 696 (M+H)$^+$.

Example 77

N-[4-(6-Amino-2'-methyl-3,4'-bipyridin-5-yl)phenyl]-5-(4-fluorophenyl)-4-oxo-1-(2,2,2-trifluoroethyl)-1,4-dihydropyridine-3-carboxamide

[Step 1] 5-(4-Aminophenyl)-2'-methyl-3,4'-bipyridin-6-amine

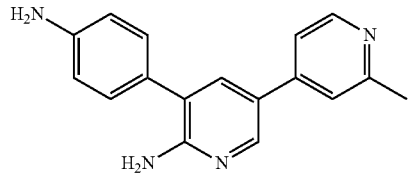 [SMILES: Cc1cc(-c2cnc(N)c(-c3ccc(N)cc3)c2)ccn1]

The compound obtained in Step 1 of Example 1 (2.0 g) and 2-methyl-4-(4,4,5,5-tetramethyl-1,3,2-dioxaborolan-2-yl)pyridine (1.66 g) yielded 871 mg of the title compound as a solid via a reaction similar to that in Step 1 of Example 47.

MS (ESI) m/z: 277 (M+H)$^+$.

[Step 2] N-[4-(6-Amino-2'-methyl-3,4'-bipyridin-5-yl)phenyl]-5-(4-fluorophenyl)-4-oxo-1-(2,2,2-trifluoroethyl)-1,4-dihydropyridine-3-carboxamide

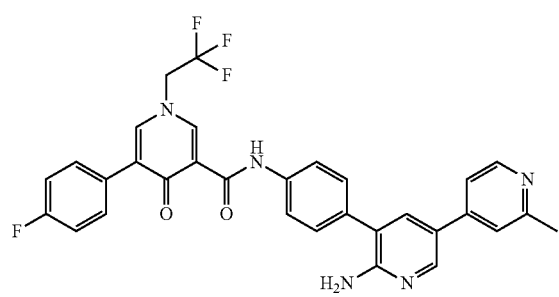 [SMILES: Cc1cc(-c2cnc(N)c(-c3ccc(NC(=O)c4cn(CC(F)(F)F)cc(-c5ccc(F)cc5)c4=O)cc3)c2)ccn1]

The compound obtained in Step 2 of Example 9 (63 mg) and the compound obtained in the above Step 1 (50 mg) yielded 6.5 mg of the title compound as a solid via a reaction similar to that in Step 3 of Example 1.

$^1$H-NMR (CDCl$_3$) δ: 2.58 (3H, s), 4.50 (2H, q, J=7.9 Hz), 4.77 (2H, s), 7.14-7.20 (2H, m), 7.31 (1H, s), 7.45-7.55 (6H, m), 7.63 (1H, d, J=2.3 Hz), 7.85 (2H, d, J=8.7 Hz), 8.36 (1H, d, J=2.3 Hz), 8.48 (1H, d, J=5.0 Hz), 8.62 (1H, d, J=2.8 Hz), 12.46 (1H, s).

MS (ESI) m/z: 574 (M+H)$^+$.

Example 78

N-[4-(6-Amino-2'-methyl-3,4'-bipyridin-5-yl)phenyl]-1-(2-fluoroethyl)-5-(4-fluorophenyl)-4-oxo-1,4-dihydropyridine-3-carboxamide

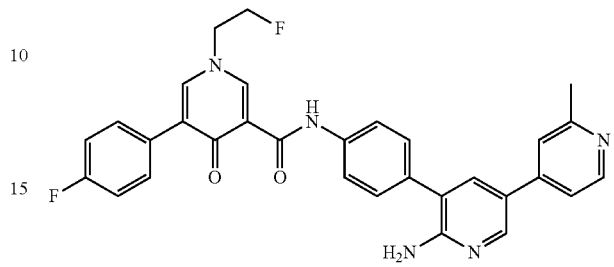

Water (0.1 ml), potassium carbonate (48 mg) and tetrakis(triphenylphosphine)palladium (13 mg) were added to a solution of the compound obtained in Step 1 of Example 43 (61 mg) and 2-methyl-4-(4,4,5,5-tetramethyl-1,3,2-dioxaborolan-2-yl)pyridine (28 mg) in 1,4-dioxane (1.2 ml), and the mixture was stirred at 100° C. for six hours. After leaving to cool, the reaction solution was diluted with chloroform. The organic layer was washed with water and then dried over sodium sulfate. The solvent was distilled off under reduced pressure, and the residue was purified by silica gel column chromatography [chloroform:methanol=300:1->10:1 (v/v)] to give 24 mg of the title compound as a solid.

$^1$H-NMR (CDCl$_3$) δ: 2.61 (3H, s), 4.24-4.37 (2H, m), 4.74-4.92 (4H, m), 7.13-7.21 (2H, m), 7.27-7.36 (3H, m), 7.45-7.67 (5H, m), 7.84-7.91 (2H, m), 8.38 (1H, d, J=2.3 Hz), 8.51 (1H, d, J=5.0 Hz), 8.65 (1H, d, J=2.3 Hz).

MS (ESI) m/z: 538 (M+H)$^+$.

Example 79

N-[4-(6-Amino-1'-methyl-1',2',3',6'-tetrahydro-3,4'-bipyridin-5-yl)phenyl]-5-(4-fluorophenyl)-4-oxo-1-(2,2,2-trifluoroethyl)-1,4-dihydropyridine-3-carboxamide

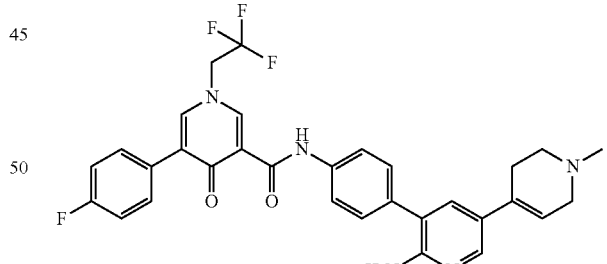

The compound obtained in Step 1 of Example 31 (100 mg) and 1-methyl-4-(4,4,5,5-tetramethyl-1,3,2-dioxaborolan-2-yl)-1,2,3,6-tetrahydropyridine (48 mg) yielded 40 mg of the title compound as a solid via a reaction similar to that in Step 1 of Example 62.

$^1$H-NMR (DMSO-D$_6$) δ: 2.26 (3H, s), 2.44-2.46 (2H, m), 2.52-2.54 (2H, m), 2.96-2.98 (2H, m), 5.25-5.30 (2H, m), 5.63 (2H, br s), 6.03 (1H, br s), 7.30-7.34 (2H, m), 7.39 (1H, d, J=2.3 Hz), 7.47 (2H, d, J=8.6 Hz), 7.66-7.69 (2H, m), 7.80 (2H, d, J=8.6 Hz), 8.03 (1H, d, J=2.3 Hz), 8.28 (1H, d, J=2.3 Hz), 8.87 (1H, d, J=2.3 Hz).

MS (ESI) m/z: 578 (M+H)$^+$.

Example 80

N-[4-(1'-Acetyl-6-amino-1',2',3',6'-tetrahydro-3,4'-bipyridin-5-yl)phenyl]-5-(4-fluorophenyl)-4-oxo-1-(2,2,2-trifluoroethyl)-1,4-dihydropyridine-3-carboxamide

[Step 1] tert-Butyl 6-amino-5-[4-({[5-(4-fluorophenyl)-4-oxo-1-(2,2,2-trifluoroethyl)-1,4-dihydropyridin-3-yl]carbonyl}amino)phenyl]-3',6'-dihydro-3,4'-bipyridine-1'(2'H)-carboxylate

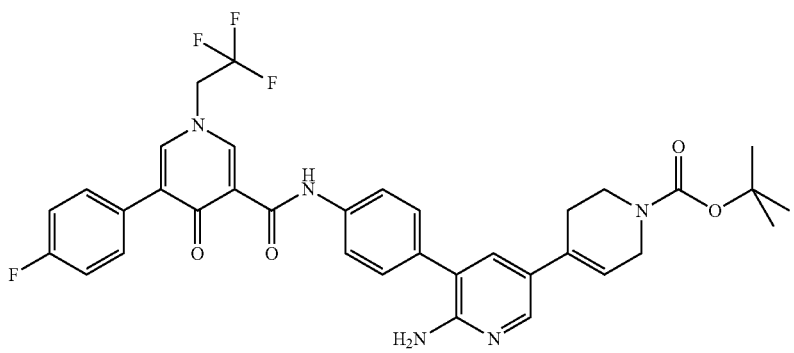 [SMILES: CC(C)(C)OC(=O)N1CC=C(c2cnc(N)c(-c3ccc(NC(=O)c4cn(CC(F)(F)F)cc(-c5ccc(F)cc5)c4=O)cc3)c2)CC1]

The compound obtained in Step 1 of Example 31 (500 mg) and tert-butyl 4-(4,4,5,5-tetramethyl-1,3,2-dioxaborolan-2-yl)-3,6-dihydropyridine-1(2H)-carboxylate (302 mg) yielded 300 mg of the title compound as a solid via a reaction similar to that in Step 1 of Example 62.

MS (ESI) m/z: 664 (M+H)$^+$.

[Step 2] N-[4-(6-Amino-1',2',3',6'-tetrahydro-3,4'-bipyridin-5-yl)phenyl]-5-(4-fluorophenyl)-4-oxo-1-(2,2,2-trifluoroethyl)-1,4-dihydropyridine-3-carboxamide

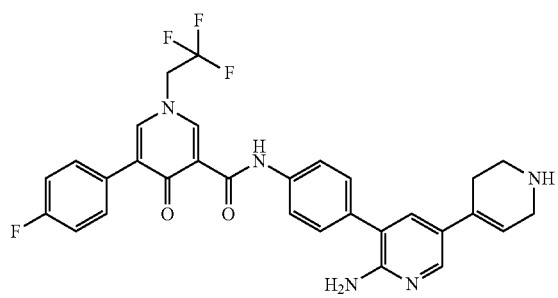 [SMILES: Nc1ncc(C2=CCNCC2)cc1-c1ccc(NC(=O)c2cn(CC(F)(F)F)cc(-c3ccc(F)cc3)c2=O)cc1]

A 4 N solution of hydrochloric acid in dioxane (1.1 ml) was added dropwise to a solution of the compound obtained in the above Step 1 (300 mg) in dichloromethane (5 ml) under ice cooling. The mixture was then stirred at room temperature for five days. The solvent was distilled off under reduced pressure to give 300 mg of a hydrochloride of the title compound as a solid.

MS (ESI) m/z: 564 (M+H)$^+$.

[Step 3] N-[4-(1'-Acetyl-6-amino-1',2',3',6'-tetrahydro-3,4'-bipyridin-5-yl)phenyl]-5-(4-fluorophenyl)-4-oxo-1-(2,2,2-trifluoroethyl)-1,4-dihydropyridine-3-carboxamide Triethylamine (32 μl) and acetic anhydride (12 μl) were added dropwise to a solution of the compound obtained in the above Step 2 (75 mg) in DMF (3 ml) under ice cooling, and the mixture was stirred at room temperature. The solvent was distilled off under reduced pressure, and the resulting residue was purified by reverse phase HPLC [acetonitrile:water:formic acid] and then purified by silica gel column chromatography (NH) [chloroform:methanol=99:1->9:1 (v/v)]. Further, the resulting crude purified product was crystallized from ethyl acetate to give 35 mg of the title compound as a solid.

$^1$H-NMR (DMSO-D$_6$) δ: 2.02-2.06 (3H, m), 3.33-3.37 (2H, m), 3.59-3.65 (2H, m), 4.04-4.11 (2H, m), 5.25-5.30 (2H, m), 5.68 (2H, s), 6.06 (1H, s), 7.30-7.34 (2H, m), 7.42 (1H, dd, J=8.0, 2.3 Hz), 7.48 (2H, d, J=8.6 Hz), 7.66-7.69 (2H, m), 7.80 (2H, d, J=8.6 Hz), 8.05 (1H, dd, J=8.0, 2.3 Hz), 8.28 (1H, d, J=2.3 Hz), 8.87 (1H, d, J=2.3 Hz).

MS (ESI) m/z: 606 (M+H)$^+$.

Example 81

N-{4-[5-(8-Acetyl-8-azabicyclo[3.2.1]oct-2-en-3-yl)-2-aminopyridin-3-yl]phenyl}-1-(2-fluoroethyl)-5-(4-fluorophenyl)-4-oxo-1,4-dihydropyridine-3-carboxamide

[Step 1] tert-Butyl 3-{6-amino-5-[4-({[1-(2-fluoroethyl)-5-(4-fluorophenyl)-4-oxo-1,4-dihydropyridin-3-yl]carbonyl}amino)phenyl]pyridin-3-yl}-8-azabicyclo[3.2.1]oct-2-ene-8-carboxylate

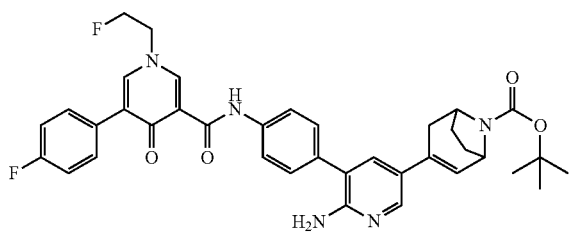 [SMILES: CC(C)(C)OC(=O)N1C2C=C(c3cnc(N)c(-c4ccc(NC(=O)c5cn(CCF)cc(-c6ccc(F)cc6)c5=O)cc4)c3)CC1CC2]

The compound obtained in Step 1 of Example 43 (150 mg) and tert-butyl 3-(4,4,5,5-tetramethyl-1,3,2-dioxaborolan-2-yl)-8-azabicyclo[3.2.1]oct-2-ene-8-carboxylate (105 mg) yielded 152 mg of the title compound as a solid via a reaction similar to that in Step 1 of Example 62.

MS (ESI) m/z: 654 (M+H)+.

[Step 2] N-{4-[2-Amino-5-(8-azabicyclo[3.2.1]oct-2-en-3-yl)pyridin-3-yl]phenyl}-1-(2-fluoroethyl)-5-(4-fluorophenyl)-4-oxo-1,4-dihydropyridine-3-carboxamide

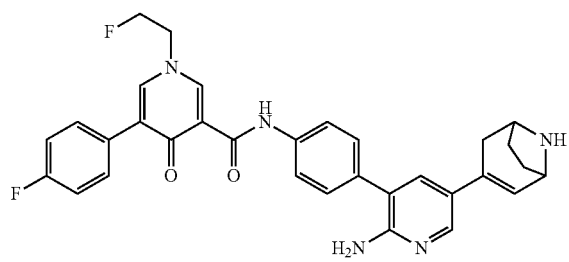 [SMILES: Nc1ncc(C2=CC3CCC(C2)N3)cc1-c1ccc(NC(=O)c2cn(CCF)cc(-c3ccc(F)cc3)c2=O)cc1]

The compound obtained in the above Step 1 (152 mg) yielded 77 mg of the title compound as a solid via a reaction similar to that in Step 2 of Example 62.

MS (ESI) m/z: 554 (M+H)+.

[Step 3] N-{4-[5-(8-Acetyl-8-azabicyclo[3.2.1]oct-2-en-3-yl)-2-aminopyridin-3-yl]phenyl}-1-(2-fluoroethyl)-5-(4-fluorophenyl)-4-oxo-1,4-dihydropyridine-3-carboxamide

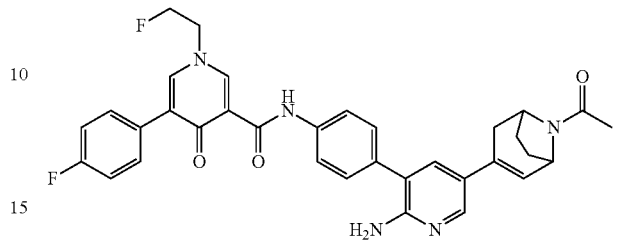

The compound obtained in the above Step 2 (77 mg) yielded 65 mg of the title compound as a solid via a reaction similar to that in Step 3 of Example 80.

$^1$H-NMR (DMSO-D$_6$) δ: 1.62-1.88 (2H, m), 1.99-2.00 (3H, m), 2.19-2.40 (2H, m), 2.84-2.95 (1H, m), 3.30-3.32 (1H, m), 4.42-4.73 (4H, m), 4.78-4.93 (2H, m), 5.68-5.69 (2H, m), 6.38-6.43 (1H, m), 7.28-7.33 (2H, m), 7.37-7.38 (1H, m), 7.45 (2H, d, J=8.6 Hz), 7.72-7.76 (2H, m), 7.80 (2H, d, J=8.6 Hz), 8.00 (1H, t, J=2.3 Hz), 8.23 (1H, d, J=2.3 Hz), 8.77 (1H, d, J=2.3 Hz).

MS (ESI) m/z: 596 (M+H)+.

Example 82

N-[4-(2-Amino-4-methoxypyridin-3-yl)phenyl]-5-(4-fluorophenyl)-4-oxo-1-(2,2,2-trifluoroethyl)-1,4-dihydropyridine-3-carboxamide

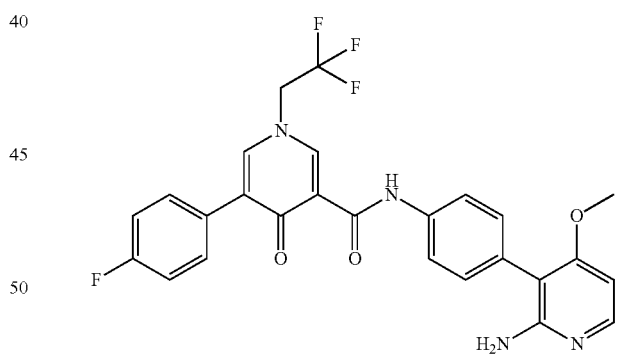

COMU (391 mg) and DIPEA (159 μl) were added to a solution of the compound obtained in Step 2 of Example 9 (216 mg) in DMF (2 ml) at room temperature. The reaction mixture was stirred at room temperature for 15 minutes. 4-(4,4,5,5-Tetramethyl-1,3,2-dioxaborolan-2-yl)aniline (100 mg) was added to the reaction mixture at room temperature. The reaction mixture was stirred at 50° C. overnight, and then at 80° C. for two days. Water was added to the reaction mixture, followed by extraction with ethyl acetate. The organic layer was dried over sodium sulfate and filtered, and the filtrate was then concentrated under reduced pressure. The residue was purified by silica gel column chromatography [hexane:ethyl acetate=1:1->1:3->0:100 (v/v)], and the eluate was concentrated under reduced pressure. 3-Iodo-4-methoxypyridine-2-amine (47 mg), tetrakis(triphenylphosphine)palladium (14 mg) and potassium carbonate (52 mg) were added to a solution of part of the resulting oily substance (65 mg) in dioxane (3 ml) and water (0.3 ml) at room temperature. The reaction mixture was stirred at 100° C. overnight, returned to room temperature and diluted by adding ethyl acetate. After purification by silica gel column chromatography (NH) (developed with ethyl acetate), the eluate was concentrated under reduced pressure. The residue was purified by reverse phase HPLC [acetonitrile:water:formic acid] to give 5.6 mg of the title compound as a solid.

$^1$H-NMR (CDCl$_3$) δ: 3.76 (3H, s), 4.50 (2H, q, J=7.9 Hz), 4.69 (2H, s), 6.40 (1H, d, J=6.0 Hz), 7.10-7.34 (4H, m), 7.49-7.56 (3H, m), 7.82-7.84 (2H, m), 7.96 (1H, d, J=6.0 Hz), 8.63 (1H, d, J=2.3 Hz), 12.40 (1H, s).

MS (ESI) m/z: 513 (M+H)$^+$.

Example 83

N-[4-(2-Amino-4-methoxypyridin-3-yl)phenyl]-1-(2-fluoroethyl)-5-(4-fluorophenyl)-4-oxo-1,4-dihydropyridine-3-carboxamide

[Step 1]
3-(4-Aminophenyl)-4-methoxypyridin-2-amine

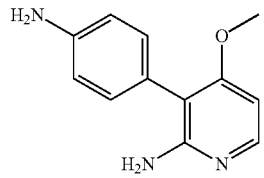 [SMILES: COc1ccnc(N)c1-c1ccc(N)cc1]

3-Iodo-4-methoxypyridin-2-amine (350 mg), 4-(4,4,5,5-tetramethyl-1,3,2-dioxaborolan-2-yl)aniline (322 mg), [1,1'-bis(diphenylphosphino)ferrocene]palladium(II) dichloride-dichloromethane adduct (81 mg) and cesium fluoride (580 mg) were suspended in methanol (5.0 ml), and the suspension was heated under reflux at 80° C. for 19 hours. After leaving to cool, a saturated aqueous ammonium chloride solution was added, and the organic layer was extracted with ethyl acetate and dried over sodium sulfate. The solvent was distilled off under reduced pressure, and the residue was purified by silica gel column chromatography [ethyl acetate:dichloromethane:methanol=5:5:1 (v/v)] to give 245 mg of the title compound as a solid.

MS (ESI) m/z: 216 (M+H)$^+$.

[Step 2] N-[4-(2-Amino-4-methoxypyridin-3-yl)phenyl]-1-(2-fluoroethyl)-5-(4-fluorophenyl)-4-oxo-1,4-dihydropyridine-3-carboxamide

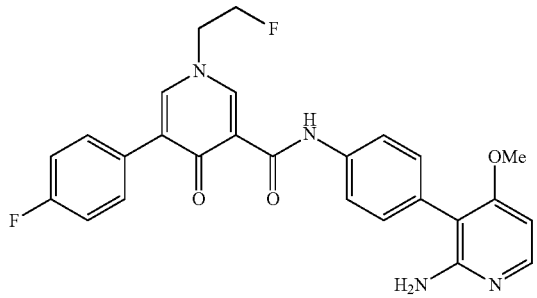 [SMILES: COc1ccnc(N)c1-c1ccc(NC(=O)c2cn(CCF)cc(-c3ccc(F)cc3)c2=O)cc1]

The compound obtained in Step 2 of Example 8 (40 mg) and the compound obtained in the above Step 1 (34 mg) yielded 69 mg of the title compound as a solid via a reaction similar to that in Step 2 of Example 47.

$^1$H-NMR (CDCl$_3$) δ: 3.75 (3H, s), 4.24-4.38 (4H, m), 4.73-4.91 (2H, m), 6.39 (1H, d, J=6.0 Hz), 7.14-7.20 (2H, m), 7.29-7.35 (2H, m), 7.53-7.60 (3H, m), 7.81-7.87 (2H, m), 7.99 (1H, d, J=6.0 Hz), 8.64 (1H, d, J=2.8 Hz).

MS (ESI) m/z: 477 (M+H)$^+$.

Example 84

N-[4-(2-Amino-4-methoxypyridin-3-yl)phenyl]-1-(4-fluorobenzyl)-4-oxo-5-(pyrrolidin-1-ylcarbonyl)-1,4-dihydropyridine-3-carboxamide

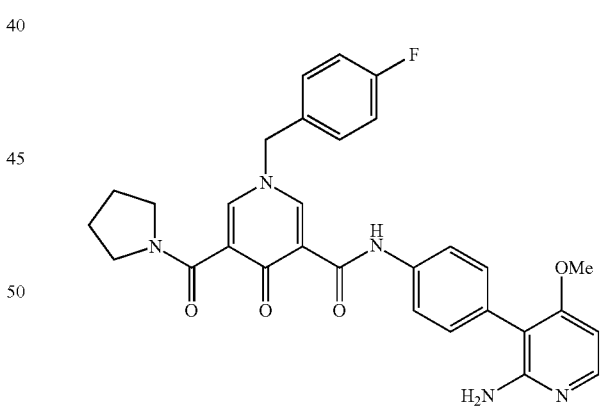

The compound obtained in Step 4 of Example 26 (38 mg) and the compound obtained in Step 1 of Example 83 (26 mg) yielded 36 mg of the title compound as a solid via a reaction similar to that in Step 2 of Example 47.

$^1$H-NMR (CDCl$_3$) δ: 1.87-2.03 (4H, m), 3.41-3.67 (4H, m), 3.75 (3H, s), 4.33 (2H, s), 5.08 (2H, s), 6.39 (1H, d, J=6.0 Hz), 7.11-7.18 (2H, m), 7.27-7.35 (4H, m), 7.74 (1H, d, J=2.8 Hz), 7.79-7.84 (2H, m), 8.00 (1H, d, J=6.0 Hz), 8.65 (1H, d, J=2.8 Hz), 12.40 (1H, s).

MS (ESI) m/z: 542 (M+H)$^+$.

Example 85

N-[4-(2-Amino-4-methoxypyridin-3-yl)-3-fluorophenyl]-5-(4-fluorophenyl)-4-oxo-1-(2,2,2-trifluoroethyl)-1,4-dihydropyridine-3-carboxamide

[Step 1] 3-(4-Amino-2-fluorophenyl)-4-methoxypyridin-2-amine

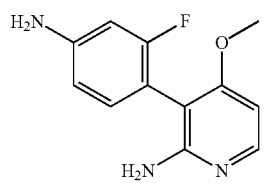

3-Iodo-4-methoxypyridin-2-ylamine (250 mg) and 4-amino-2-fluorophenylboronic acid pinacol ester (261 mg) yielded 146 mg of the title compound as a solid via a reaction similar to that in Step 1 of Example 83.

MS (ESI) m/z: 234 (M+H)+.

[Step 2] N-[4-(2-Amino-4-methoxypyridin-3-yl)-3-fluorophenyl]-5-(4-fluorophenyl)-4-oxo-1-(2,2,2-trifluoroethyl)-1,4-dihydropyridine-3-carboxamide

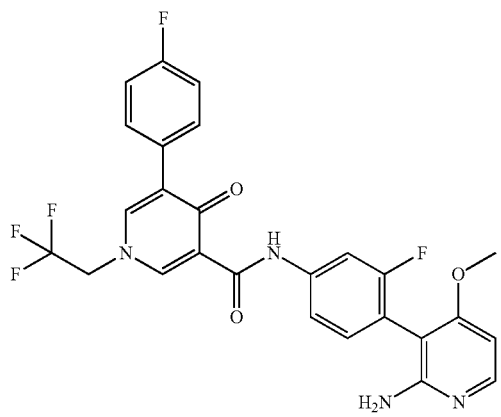 [SMILES: COc1ccnc(N)c1-c1ccc(NC(=O)c2cn(CC(F)(F)F)cc(-c3ccc(F)cc3)c2=O)cc1F]

The compound obtained in Step 2 of Example 9 (75 mg) and the compound obtained in the above Step 1 (55 mg) yielded 66 mg of the title compound as a solid via a reaction similar to that in Step 3 of Example 1.

1H-NMR (CDCl3) δ: 3.77 (3H, s), 4.31 (2H, s), 4.51 (2H, q, J=7.9 Hz), 6.37-6.41 (1H, m), 7.15-7.35 (3H, m), 7.39-7.46 (1H, m), 7.49-7.59 (3H, m), 7.82-7.88 (1H, m), 8.02-8.05 (1H, m), 8.60-8.64 (1H, m), 12.5 (1H, s).

MS (ESI) m/z: 531 (M+H)+.

Example 86

N-[4-(4-Amino-6-methoxypyrimidin-5-yl)phenyl]-5-(4-fluorophenyl)-4-oxo-1-(2,2,2-trifluoroethyl)-1,4-dihydropyridine-3-carboxamide

[Step 1]
5-(4-Aminophenyl)-6-methoxypyrimidin-4-amine

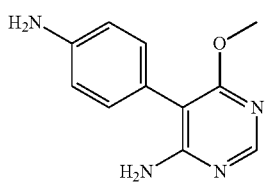 [SMILES: COc1ncnc(N)c1-c1ccc(N)cc1]

5-Bromo-6-methoxypyrimidin-4-amine (242 mg) and 4-(4,4,5,5-tetramethyl-1,3,2-dioxaborolan-2-yl)aniline (200 mg) yielded 121 mg of the title compound as a solid via by a reaction similar to that in Step 2 of Example 1.

MS (ESI) m/z: 217 (M+H)+.

[Step 2] N-[4-(4-Amino-6-methoxypyrimidin-5-yl)phenyl]-5-(4-fluorophenyl)-4-oxo-1-(2,2,2-trifluoroethyl)-1,4-dihydropyridine-3-carboxamide

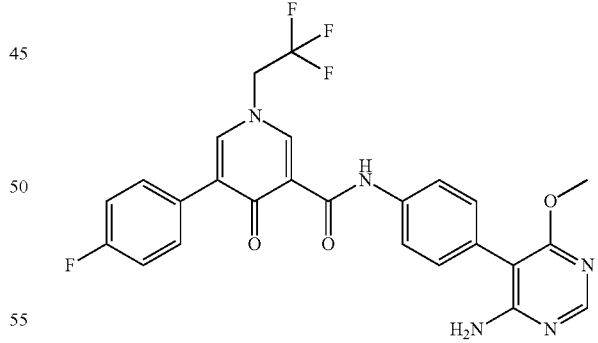

The compound obtained in Step 2 of Example 9 (60 mg) and the compound obtained in the above Step 1 (45 mg) yielded 15 mg of the title compound as a solid via a reaction similar to that in Step 2 of Example 47.

1H-NMR (CDCl3) δ: 3.89 (3H, s), 4.51 (2H, q, J=7.8 Hz), 4.72 (2H, s), 7.16-7.20 (2H, m), 7.34 (2H, d, J=8.7 Hz), 7.49-7.58 (3H, m), 7.83 (2H, d, J=8.3 Hz), 8.27 (1H, s), 8.63 (1H, d, J=2.8 Hz), 12.42 (1H, s).

MS (ESI) m/z: 514 (M+H)+.

Example 87

N-[2'-Amino-5'-(3,4-dimethoxyphenyl)-2,3'-bipyridin-5-yl]-5-(4-fluorophenyl)-4-oxo-1-(2,2,2-trifluoroethyl)-1,4-dihydropyridine-3-carboxamide

[Step 1] 5-Bromo-3-(4,4,5,5-tetramethyl-1,3,2-dioxaborolan-2-yl)pyridin-2-amine

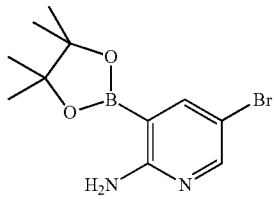 [SMILES: CC1(C)OB(c2cc(Br)cnc2N)OC1(C)C]

N-Bromosuccinimide (255 mg) was added to a solution of 3-(4,4,5,5-tetramethyl-1,3,2-dioxaborolan-2-yl)pyridin-2-amine (300 mg) in DMF (6.8 ml) at room temperature, and the mixture was stirred for four hours. Water was added and the precipitated solid was collected by filtration to give 210 mg of the title compound.

$^1$H-NMR (CDCl$_3$) δ: 1.31 (12H, s), 5.42 (2H, s), 7.88 (1H, d, J=2.93 Hz), 8.10 (1H, d, J=2.93 Hz).

[Step 2] 5'-Bromo-2,3'-bipyridine-2',5-diamine

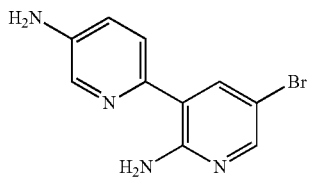

Tetrakis(triphenylphosphine)palladium (41 mg), 6-iodopyridin-3-amine (216 mg) and potassium carbonate (291 mg) were added to a solution of the compound obtained in the above Step 1 (210 mg) in dioxane (3.5 ml) and water (0.3 ml). The mixture was stirred at 80° C. for four hours. The reaction solution was further stirred at 90° C. for four hours and then diluted with ethyl acetate. The organic layer was washed with water and brine. After drying over sodium sulfate, the solvent was distilled off under reduced pressure, and the residue was purified by silica gel column chromatography [n-hexane:ethyl acetate=19:1->1:1 (v/v)] to give 136 mg of the title compound as a solid.

$^1$H-NMR (CDCl$_3$) δ: 3.83 (2H, s), 6.64 (2H, s), 7.10 (1H, dd, J=8.54, 3.05 Hz), 7.45-7.51 (1H, m), 7.78-7.83 (1H, m), 8.03-8.12 (2H, m).

MS (ESI) m/z: 265 (M+H)$^+$.

[Step 3] N-(2'-Amino-5'-bromo-2,3'-bipyridin-5-yl)-5-(4-fluorophenyl)-4-oxo-1-(2,2,2-trifluoroethyl)-1,4-dihydropyridine-3-carboxamide

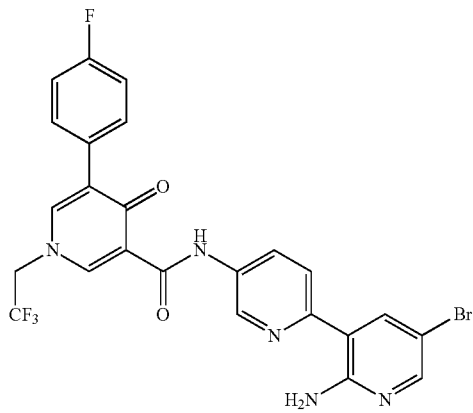 [SMILES: Nc1ncc(Br)cc1-c1ccc(NC(=O)c2cn(CC(F)(F)F)cc(-c3ccc(F)cc3)c2=O)cn1]

The compound obtained in Step 2 of Example 9 (140 mg) and the compound obtained in the above Step 2 (130 mg) yielded 179 mg of the title compound via a reaction similar to that in Step 1 of Example 31.

$^1$H-NMR (DMSO-D$_6$) δ: 5.23-5.33 (2H, m), 7.29-7.37 (2H, m), 7.58 (2H, s), 7.65-7.72 (2H, m), 8.03-8.09 (2H, m), 8.17 (1H, d, J=2.44 Hz), 8.28-8.35 (2H, m), 8.88-8.92 (1H, m), 8.97 (1H, d, J=2.44 Hz), 12.85 (1H, s).

MS (ESI) m/z: 562 (M+H)$^+$.

[Step 4] N-[2'-Amino-5'-(3,4-dimethoxyphenyl)-2,3'-bipyridin-5-yl]-5-(4-fluorophenyl)-4-oxo-1-(2,2,2-trifluoroethyl)-1,4-dihydropyridine-3-carboxamide

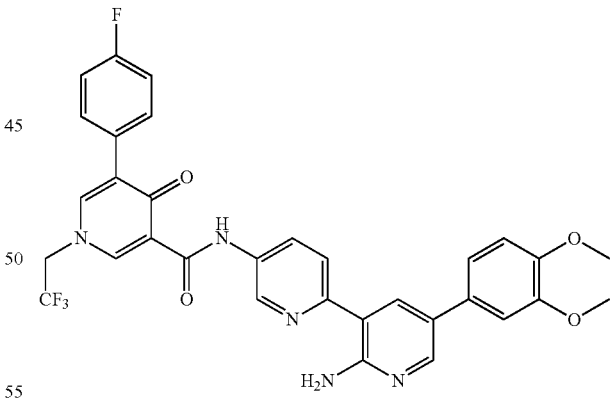

The compound obtained in the above Step 3 (95 mg) and 3,4-dimethoxyphenylboronic acid (37 mg) yielded 38 mg of the title compound as a solid via a reaction similar to that in Step 2 of Example 31.

$^1$H-NMR (CDCl$_3$) δ: 3.91 (3H, s), 3.94 (3H, s), 4.50 (2H, q, J=7.65 Hz), 6.58-6.73 (2H, m), 6.93 (1H, d, J=8.30 Hz), 7.01-7.10 (2H, m), 7.13-7.20 (2H, m), 7.48-7.55 (3H, m), 7.73-7.78 (1H, m), 7.94-7.98 (1H, m), 8.26-8.32 (2H, m), 8.59-8.63 (1H, m), 8.92 (1H, d, J=2.44 Hz), 12.58 (1H, s).

MS (ESI) m/z: 620 (M+H)$^+$.

Example 88

N-{4-[2-Amino-5-(3-hydroxy-4-methoxyphenyl)pyridin-3-yl]phenyl}-5-(4-fluorophenyl)-4-oxo-1-(2,2,2-trifluoroethyl)-1,4-dihydropyridine-3-carboxamide

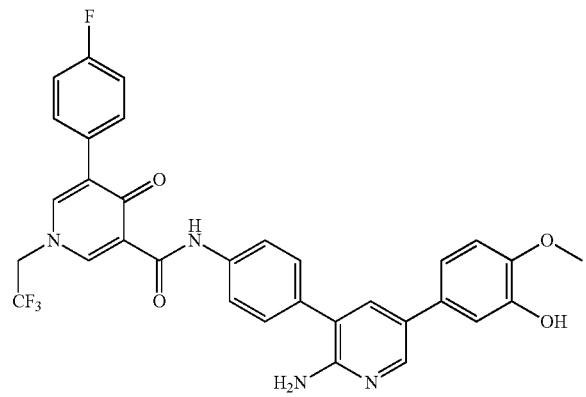 [SMILES: COc1ccc(-c2cnc(N)c(-c3ccc(NC(=O)c4cn(CC(F)(F)F)cc(-c5ccc(F)cc5)c4=O)cc3)c2)cc1O]

The compound obtained in Step 1 of Example 31 (95 mg) and 2-methoxy-5-(4,4,5,5-tetramethyl-1,3,2-dioxaborolan-2-yl)phenol (51 mg) yielded 58 mg of the title compound via a reaction similar to that in Step 2 of Example 31.

$^1$H-NMR (CDCl$_3$) δ: 3.93 (3H, s), 4.51 (2H, q, J=7.53 Hz), 4.57-4.66 (2H, m), 5.70 (1H, s), 6.88-6.93 (1H, m), 7.00-7.05 (1H, m), 7.11-7.22 (3H, m), 7.46-7.59 (6H, m), 7.81-7.88 (2H, m), 8.27 (1H, d, J=2.44 Hz), 8.64 (1H, d, J=2.44 Hz), 12.45 (1H, s).

MS (ESI) m/z: 605 (M+H)$^+$.

Example 89

N-{4-[2-Amino-5-(3,4-dimethoxyphenyl)pyridin-3-yl]phenyl}-5-(4-fluoro-3-bromophenyl)-4-oxo-1-(2,2,2-trifluoroethyl)-1,4-dihydropyridine-3-carboxamide

[Step 1] Ethyl 4-(3-bromo-4-fluorophenyl)-3-oxobutanoate

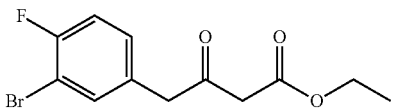 [SMILES: CCOC(=O)CC(=O)Cc1ccc(F)c(Br)c1]

Magnesium chloride (3.7 g) was added to a suspension of 3-ethoxy-3-oxopropanoic acid potassium salt (5.5 g) in THF (100 ml), and the mixture was stirred at room temperature for 2.5 hours (Reaction Solution 1). In another vessel, carbonyldiimidazole (4.2 g) was added in small portions to a solution of 2-(3-bromo-4-fluorophenyl)acetic acid (5 g) in THF (50 ml) at room temperature, and the mixture was stirred for 30 minutes (Reaction Solution 2). Reaction Solution 2 was added to Reaction Solution 1 at room temperature, and the mixture was stirred at 60° C. for three hours. Hydrochloric acid (1 N aqueous solution, 200 ml) was added, followed by extraction with ethyl acetate. The resulting organic layer was sequentially washed with water, a saturated aqueous sodium bicarbonate solution and brine, and then dried over anhydrous sodium sulfate. The solvent was distilled off under reduced pressure to give 7 g of the title compound as an oily substance.

MS (ESI) m/z: 305 (M+H)$^+$.

[Step 2] Ethyl 5-(3-bromo-4-fluorophenyl)-4-oxo-1,4-dihydropyridine-3-carboxylate

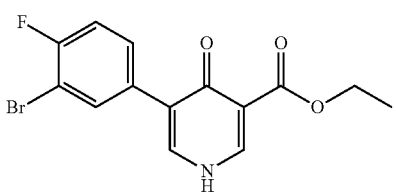 [SMILES: CCOC(=O)c1c[nH]cc(-c2ccc(F)c(Br)c2)c1=O]

1,3,5-Triazine (2.1 g) and sodium ethoxide (20% solution in ethanol, 9.4 ml) were added to a solution of the compound obtained in the above Step 1 (7 g) in ethanol (70 ml), and the mixture was stirred at 85° C. for five hours. The reaction solution was distilled off under reduced pressure, and the residue was diluted with water and then neutralized by adding hydrochloric acid (1 N solution). The precipitated solid was collected by filtration and sequentially washed with water and ethyl acetate to give 5.4 g of the title compound as a solid.

MS (ESI) m/z: 342 (M+H)$^+$.

[Step 3] Ethyl 5-(3-bromo-4-fluorophenyl)-4-oxo-1-(2,2,2-trifluoroethyl)-1,4-dihydropyridine-3-carboxylate

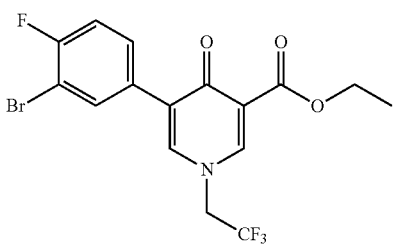 [SMILES: CCOC(=O)c1cn(CC(F)(F)F)cc(-c2ccc(F)c(Br)c2)c1=O]

The compound obtained in the above Step 2 (5.4 g) and 2,2,2-trifluoroethyl trifluoromethanesulfonate (5.2 g) yielded 6.0 g of the title compound as an oily substance via a reaction similar to that in Step 1 of Example 20.

MS (ESI) m/z: 424 (M+H)$^+$.

[Step 4] 5-(3-Bromo-4-fluorophenyl)-4-oxo-1-(2,2,2-trifluoroethyl)-1,4-dihydropyridine-3-carboxylic acid

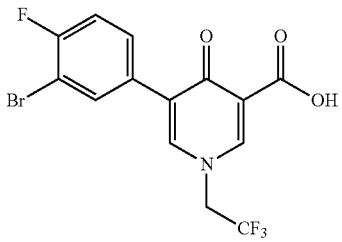 [SMILES: O=C(O)c1cn(CC(F)(F)F)cc(-c2ccc(F)c(Br)c2)c1=O]

The compound obtained in the above Step 3 (6.0 g) yielded 5.3 g of the title compound as a solid via a reaction similar to that in Step 2 of Example 20.

MS (ESI) m/z: 396 (M+H)+.

[Step 5] N-{4-[2-Amino-5-(3,4-dimethoxyphenyl)pyridin-3-yl]phenyl}-5-(4-fluoro-3-bromophenyl)-4-oxo-1-(2,2,2-trifluoroethyl)-1,4-dihydropyridine-3-carboxamide

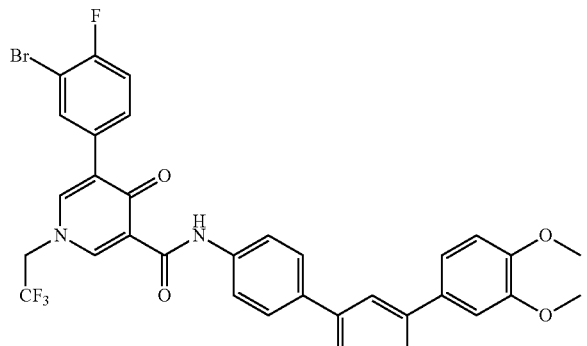

The compound obtained in the above Step 4 (1.6 g) and the compound obtained in Step 2 of Example 1 (1.6 g) yielded 2.5 g of the title compound as a solid via a reaction similar to that in Step 3 of Example 20.

1H-NMR (CDCl3) δ: 3.92 (3H, s), 3.94 (3H, s), 4.50-4.62 (4H, m), 6.93-6.95 (1H, m), 7.04 (1H, d, J=1.8 Hz), 7.09 (1H, d, J=8.5 Hz), 7.22-7.26 (1H, m), 7.49-7.53 (4H, m), 7.57 (1H, d, J=2.4 Hz), 7.78 (1H, dd, J=6.7, 1.8 Hz), 7.85 (2H, d, J=8.5 Hz), 8.28 (1H, d, J=2.4 Hz), 8.65 (1H, d, J=2.4 Hz), 12.37 (1H, s).

MS (ESI) m/z: 699 [M+H]+.

Reference Example 1

Ethyl 5-(2-fluorophenyl)-4-oxo-1,4-dihydropyridine-3-carboxylate

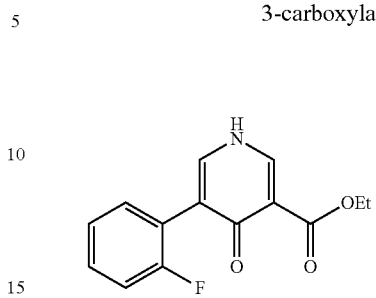

A solution of sodium ethoxide in ethanol (20%, 1270 μl) was added to a solution of ethyl 4-(2-fluorophenyl)-3-oxobutanoate (697 mg) and 1,3,5-triazine (277 mg) in ethanol (8.0 ml) at room temperature, and the mixture was stirred at 85° C. for four hours. The solvent was distilled off under reduced pressure, followed by dilution with water. A 1 N aqueous hydrochloric acid solution was added, and the precipitated solid was collected by filtration and washed with ethyl acetate to give 406 mg of the title compound as a solid.

1H-NMR (DMSO-D6) δ: 1.25 (3H, t, J=7.20 Hz), 4.19 (2H, q, J=7.20 Hz), 7.18-7.25 (2H, m), 7.36-7.42 (2H, m), 7.81 (1H, s), 8.25 (1H, s).

Reference Example 2

Ethyl 5-(3-fluorophenyl)-4-oxo-1,4-dihydropyridine-3-carboxylate

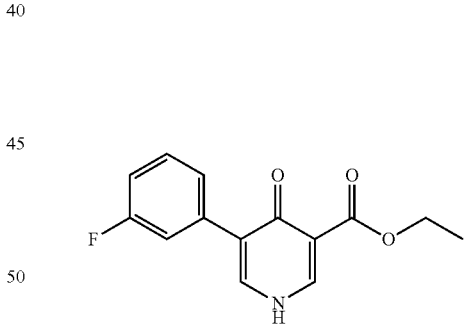

4-(3-Fluoro-phenyl)-3-oxobutyric acid ethyl ester (4.40 g) and 1,3,5-triazine (1.75 g) yielded 2.97 g of the title compound as a solid via a reaction similar to that in Reference Example 1.

1H-NMR (DMSO-D6) δ: 1.26 (3H, t, J=7.1 Hz), 4.19 (2H, q, J=7.1 Hz), 7.10-7.19 (1H, m), 7.38-7.55 (3H, m), 7.89-7.96 (1H, m), 8.16-8.23 (1H, m), 12.0 (1H, br s).

MS (ESI) m/z: 262 (M+H)+

Reference Example 3

Ethyl 5-(4-methylphenyl)-4-oxo-1,4-dihydropyridine-3-carboxylate

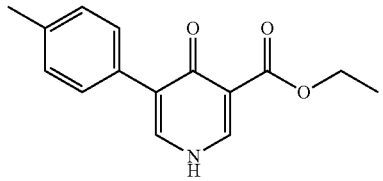 [SMILES: CCOC(=O)c1c[nH]cc(-c2ccc(C)cc2)c1=O]

4-(4-Methylphenyl)-3-oxobutyric acid ethyl ester (2.97 g) and 1,3,5-triazine (1.20 g) yielded 1.86 g of the title compound as a solid via a reaction similar to that in Reference Example 1.

$^1$H-NMR (DMSO-D$_6$) δ: 1.26 (3H, t, J=7.1 Hz), 2.32 (3H, s), 4.19 (2H, q, J=7.1 Hz), 7.16-7.21 (2H, m), 7.46-7.50 (2H, m), 7.79 (1H, br s), 8.17 (1H, br s), 11.9 (1H, br s).

MS (ESI) m/z: 258 (M+H)$^+$

Reference Example 4

Ethyl 5-(4-chlorophenyl)-4-oxo-1,4-dihydropyridine-3-carboxylate

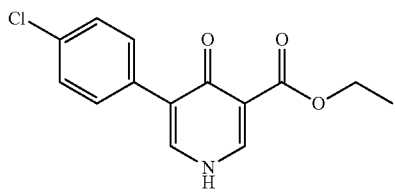 [SMILES: CCOC(=O)c1c[nH]cc(-c2ccc(Cl)cc2)c1=O]

4-(4-Chlorophenyl)-3-oxobutyric acid ethyl ester (2.97 g) and 1,3,5-triazine (1.10 g) yielded 1.87 g of the title compound as a solid via a reaction similar to that in Reference Example 1.

MS (ESI) m/z: 278 (M+H)$^+$

Reference Example 5

Ethyl 5-methyl-4-oxo-1,4-dihydropyridine-3-carboxylate

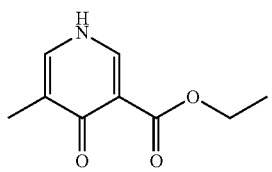

Ethyl 3-oxopentanoate (1.4 ml) and 1,3,5-triazine (930 mg) yielded 928 mg of the title compound as a solid via a reaction similar to that in Reference Example 1.

$^1$H-NMR (DMSO-D$_6$) δ: 1.24 (3H, t, J=7.1 Hz), 1.84 (3H, s), 4.16 (2H, q, J=7.2 Hz), 7.61 (1H, s), 8.15 (1H, d, J=3.2 Hz), 11.58 (1H, s).

Reference Example 6

Ethyl 5-methoxy-4-oxo-1,4-dihydropyridine-3-carboxylate

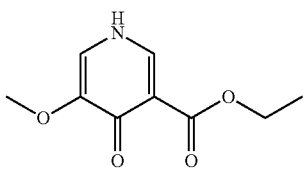

Ethyl 4-methoxy-3-oxobutanoate (1.3 ml) and 1,3,5-triazine (920 mg) yielded 92 mg of the title compound as a solid via a reaction similar to that in Reference Example 1.

$^1$H-NMR (DMSO-D$_6$) δ: 1.24 (3H, t, J=7.1 Hz), 3.66 (3H, s), 4.17 (2H, q, J=7.2 Hz), 7.35 (1H, s), 8.10 (1H, s), 11.67 (1H, s).

Reference Example 7

2-(4-{[(2R)-1,4-dioxan-2-yl]methoxy}-3-methoxyphenyl)-4,4,5,5-tetramethyl-1,3,2-dioxaborolane amine

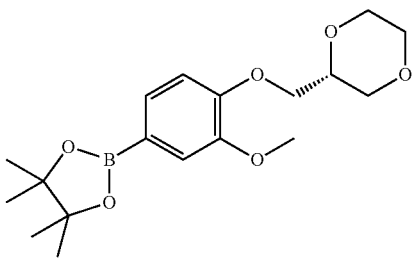 [SMILES: COc1cc(B2OC(C)(C)C(C)(C)O2)ccc1OC[C@H]1COCCO1]

2-Methoxy-4-(4,4,5,5-tetramethyl-1,3,2-dioxaborolan-2-yl)phenol (10.2 g), (2R)-1,4-dioxan-2-ylmethyl methanesulfonate (8.0 g) and potassium carbonate (11.2 g) were suspended in DMF (200 ml), and the suspension was stirred at 90° C. for 16 hours. After leaving to cool, the insoluble matter was removed and the solvent was distilled off under reduced pressure. The residue was purified by silica gel column chromatography [hexane:ethyl acetate=2:1 (v/v)] to give 14.3 g of the title compound.

MS (ESI) m/z: 351 (M+H)$^+$

Reference Example 8

1-[(2S)-1,4-Dioxan-2-ylmethyl]-4-(4,4,5,5-tetramethyl-1,3,2-dioxaborolan-2-yl)-1H-pyrazole

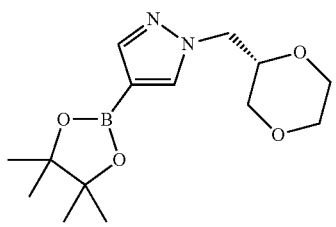 [SMILES: CC1(C)OB(c2cnn(C[C@H]3COCCO3)c2)OC1(C)C]

4-(4,4,5,5-Tetramethyl-1,3,2-dioxaborolan-2-yl)-1H-pyrazole (2.5 g) was added to a suspension of cesium carbonate (2.50 g) in 1,4-dioxane (30 ml). After stirring, (2R)-1,4-dioxan-2-ylmethyl methanesulfonate (2.78 g) was added and the mixture was stirred at 90° C. for four hours. After leaving to cool, the reaction solution was filtered, and the filtrate was concentrated. The residue was purified by silica gel column chromatography [chloroform:methanol=19:1 (v/v)] to give 3.79 g of the title compound.
MS (ESI) m/z: 295 (M+H)+

Reference Example 9

Methyl 5-(4-fluorophenyl)-4-oxo-1,4-dihydropyridine-3-carboxylate

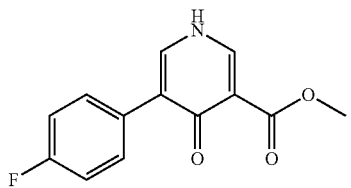 [SMILES: COC(=O)c1c[nH]cc(-c2ccc(F)cc2)c1=O]

Thionyl chloride (0.8 ml) was added to a suspension of 5-(4-fluorophenyl)-4-oxo-1,4-dihydropyridine-3-carboxylic acid (400 mg) in methanol (9 ml) at 0° C. The reaction mixture was stirred at 70° C. overnight. The reaction mixture was returned to room temperature and concentrated under reduced pressure. The resulting residue was washed with saturated aqueous sodium bicarbonate and water, and then further washed with diethyl ether to give 304 mg of the title compound as a solid.
$^1$H-NMR (DMSO-D$_6$) δ: 3.72 (3H, s), 7.17-7.24 (2H, m), 7.61-7.65 (2H, m), 7.85 (1H, s), 8.21 (1H, s), 11.96 (1H, s).
MS (ESI) m/z: 248 (M+H)$^{1-}$.

In Examples of the present invention, X-ray diffraction data were measured using the following instrument and measurement conditions.
Instrument manufacturer: Rigaku Co., Ltd.
Instrument: RINT TTR-III
Radiation source: Cu—Kα radiation
Wavelength (Å): 1.54
Detector: Scintillation counter
Optical system: Parallel beam method
Tube voltage (kV): 50
Tube current (mA): 300
Scanning field 2θ (deg): 2 to 40
Sampling step (deg): 0.02
Scanning speed (deg/min): 20 or 2
Sample holder: Nonreflective sample holder

Example 90

N-{4-[2-Amino-5-(3,4-dimethoxyphenyl)pyridin-3-yl]phenyl}-5-(4-fluorophenyl)-4-oxo-1-(2,2,2-trifluoroethyl)-1,4-dihydropyridine-3-carboxamide hydrochloride Acetonitrile (383 μl), a 5.788 mol/L aqueous hydrochloric acid solution (5.67 μl, 1.05 eq.) and water (4.15 μl) were added to N-{4-[2-amino-5-(3,4-dimethoxyphenyl)pyridin-3-yl]phenyl}-5-(4-fluorophenyl)-4-oxo-1-(2,2,2-trifluoroethyl)-1,4-dihydropyridine-3-carboxamide (19.64 mg, 31.75 μmol) at room temperature. After stirring at 40° C. for about 24 hours, the precipitated solid was collected by filtration. The solid was then dried at room temperature to give the title compound (12.42 mg). Yield: 60%.

For the powder X-ray diffraction (CuKα, λ=1.54 Å, scanning speed=20°/min) of the resulting crystals, the diffraction pattern is shown in FIG. 1. Peaks in FIG. 1 having a relative intensity of 28 or more, based on 100 as the maximum peak intensity, are shown in Table 1.

TABLE 1

| Peak No. | 2θ | d value | Relative intensity |
|---|---|---|---|
| 1 | 7.44 | 11.87 | 31 |
| 2 | 10.00 | 8.84 | 28 |
| 3 | 13.48 | 6.56 | 42 |
| 4 | 14.86 | 5.96 | 37 |
| 5 | 16.10 | 5.50 | 32 |
| 6 | 19.30 | 4.60 | 40 |
| 7 | 20.30 | 4.37 | 100 |
| 8 | 22.62 | 3.93 | 37 |
| 9 | 23.02 | 3.86 | 34 |
| 10 | 23.70 | 3.75 | 92 |
| 11 | 24.54 | 3.62 | 37 |
| 12 | 25.92 | 3.43 | 28 |
| 13 | 28.46 | 3.13 | 32 |

Example 91

N-{4-[2-Amino-5-(3,4-dimethoxyphenyl)pyridin-3-yl]phenyl}-5-(4-fluorophenyl)-4-oxo-1-(2,2,2-trifluoroethyl)-1,4-dihydropyridine-3-carboxamide monohydrochloride The compound of Step 3 of Example 9 (15.7 g) was suspended in ethanol (50 ml), and 4 N hydrochloric acid-dioxane (12.69 ml) was added at room temperature. After stirring at room temperature, the solvent was distilled off under reduced pressure. The residue was suspended in acetonitrile, and the suspension was stirred overnight. The resulting solid was collected by filtration, and the solid was then suspended in hexane, followed by stirring for three days. The resulting solid was collected by filtration and then dried under reduced pressure to give 15.7 g of the title compound as a solid.
MS (ESI) m/z: 619 (M+H)+.
Elemental analysis for $C_{33}H_{26}F_4N_4O_4 \cdot 1HCl \cdot 1.75H_2O$
Calculated: C, 57.73; H, 4.33; F, 11.06; N, 8.16; Cl, 5.16.
Found: C, 57.71; H, 4.15; F, 11.89; N, 8.18; Cl, 5.12.
For the powder X-ray diffraction (CuKα, λ=1.54 Å, scanning speed=2°/min), the diffraction pattern is shown in FIG.

2. Peaks in FIG. 2 having a relative intensity of 31 or more, based on 100 as the maximum peak intensity, are shown in Table 2.

TABLE 2

| Peak No. | 2θ | d value | Relative intensity |
|---|---|---|---|
| 1 | 4.32 | 20.44 | 52 |
| 2 | 9.10 | 9.71 | 100 |
| 3 | 15.52 | 5.70 | 41 |
| 4 | 18.32 | 4.84 | 40 |
| 5 | 18.54 | 4.78 | 41 |
| 6 | 19.22 | 4.61 | 43 |
| 7 | 20.54 | 4.32 | 64 |
| 8 | 20.70 | 4.29 | 76 |
| 9 | 23.54 | 3.78 | 82 |
| 10 | 24.14 | 3.68 | 80 |
| 11 | 25.34 | 3.51 | 47 |
| 12 | 27.02 | 3.30 | 42 |

Example 92

N-{4-[2-Amino-5-(3,4-dimethoxyphenyl)pyridin-3-yl]phenyl}-5-(4-fluorophenyl)-4-oxo-1-(2,2,2-trifluoroethyl)-1,4-dihydropyridine-3-carboxamide hydrochloride hydrate Water (36 ml) and a 1.004 mol/L aqueous hydrochloric acid solution (3.54 ml, 1.10 eq.) were added to N-{4-[2-amino-5-(3,4-dimethoxyphenyl)pyridin-3-yl]phenyl}-5-(4-fluorophenyl)-4-oxo-1-(2,2,2-trifluoroethyl)-1,4-dihydropyridine-3-carboxamide (2.00 g, 3.23 mmol) at room temperature. The mixture was stirred at 40° C. for six days and then stirred at room temperature for 30 minutes. The precipitated solid was collected by filtration and dried at room temperature. Water (38 ml) and a 1.004 mol/L aqueous hydrochloric acid solution (1.61 ml, 0.50 eq.) were added to the collected solid at room temperature. The mixture was stirred at 40° C. for about 12 hours and then stirred at room temperature for 30 minutes. The precipitated solid was collected by filtration and then dried under reduced pressure at room temperature for three hours to give the title compound (2.19 g). Yield: 100%.

For the powder X-ray diffraction (CuKα, λ=1.54 Å, scanning speed=2°/min) of the resulting crystals, the diffraction pattern is shown in FIG. 3. Peaks in FIG. 3 having a relative intensity of 51 or more, based on 100 as the maximum peak intensity, are shown in Table 3.

TABLE 3

| Peak No. | 2θ | d value | Relative intensity |
|---|---|---|---|
| 1 | 13.86 | 6.38 | 51 |
| 2 | 15.04 | 5.89 | 64 |
| 3 | 19.76 | 4.49 | 58 |
| 4 | 20.58 | 4.31 | 100 |
| 5 | 22.26 | 3.99 | 51 |
| 6 | 22.58 | 3.93 | 51 |
| 7 | 23.82 | 3.73 | 54 |
| 8 | 24.10 | 3.69 | 62 |
| 9 | 24.36 | 3.65 | 76 |
| 10 | 24.88 | 3.58 | 69 |

Example 93

N-{4-[2-Amino-5-(3,4-dimethoxyphenyl)pyridin-3-yl]phenyl}-5-(4-fluorophenyl)-4-oxo-1-(2,2,2-trifluoroethyl)-1,4-dihydropyridine-3-carboxamide monohydrochloride The compound of Step 3 of Example 9 (28.91 g) was suspended in ethanol (100 ml), and 4 N hydrochloric acid-dioxane (23.37 ml) was added at room temperature. After stirring at room temperature for two hours, the solvent was distilled off under reduced pressure, and the residue was recrystallized from ethanol/isopropyl ether (50 ml/150 ml). The resulting solid was collected by filtration, washed with isopropyl ether and then dried under reduced pressure to give 30.83 g of the title compound as a solid.

$^1$H-NMR (CDCl$_3$) δ: 3.93 (3H, s), 3.94 (3H, s), 4.66-4.73 (2H, m), 6.92-7.05 (3H, m), 7.18 (2H, t, J=8.5 Hz), 7.44 (2H, d, J=8.5 Hz), 7.51-7.58 (3H, m), 7.90-7.96 (4H, m), 8.72 (1H, d, J=1.8 Hz), 12.65 (1H, s).

MS (ESI) m/z: 619 (M+H)$^+$.

Elemental analysis for C$_{33}$H$_{26}$F$_4$N$_4$O$_4$.1HCl.0.05 isopropyl ether.1.25H$_2$O Calculated: C, 58.59; H, 4.46; F, 11.13; N, 8.21; Cl, 5.19.
Found: C, 58.43; H, 4.16; F, 11.19; N, 8.11; Cl, 5.24.

For the powder X-ray diffraction (CuKα, λ=1.54 Å, scanning speed=2°/min), the diffraction pattern is shown in FIG. 4. Peaks in FIG. 4 having a relative intensity of 31 or more, based on 100 as the maximum peak intensity, are shown in Table 4.

TABLE 4

| Peak No. | 2θ | d value | Relative intensity |
|---|---|---|---|
| 1 | 5.34 | 16.54 | 100 |
| 2 | 7.22 | 12.23 | 31 |
| 3 | 8.20 | 10.77 | 35 |
| 4 | 11.68 | 7.57 | 33 |
| 5 | 14.54 | 6.09 | 30 |
| 6 | 15.74 | 5.63 | 32 |
| 7 | 17.54 | 5.05 | 33 |
| 8 | 23.24 | 3.82 | 44 |
| 9 | 23.72 | 3.75 | 35 |
| 10 | 25.12 | 3.54 | 31 |
| 11 | 26.16 | 3.40 | 31 |

Example 94

N-{4-[2-Amino-5-(3,4-dimethoxyphenyl)pyridin-3-yl]phenyl}-5-(4-fluorophenyl)-4-oxo-1-(2,2,2-trifluoroethyl)-1,4-dihydropyridine-3-carboxamide monohydrochloride dihydrate Acetone (3.0 ml), water (1.87 ml) and a 1.004 mol/L aqueous hydrochloric acid solution (2.70 ml, 1.10 eq.) were added to N-{4-[2-amino-5-(3,4-dimethoxyphenyl)pyridin-3-yl]phenyl}-5-(4-fluorophenyl)-4-oxo-1-(2,2,2-trifluoroethyl)-1,4-dihydropyridine-3-carboxamide (1.52 g, 2.46 mmol) at room temperature. The mixture was stirred at 40° C. for about 11 hours and then stirred at room temperature for about 30 minutes, and the precipitated solid was collected by filtration. The solid was then dried under reduced pressure at room temperature for about three hours to give the title compound (1.60 g). Yield: 94%.

N-{4-[2-Amino-5-(3,4-dimethoxyphenyl)pyridin-3-yl]phenyl}-5-(4-fluorophenyl)-4-oxo-1-(2,2,2-trifluoroethyl)-

1,4-dihydropyridine-3-carboxamide monohydrochloride dihydrate is represented as elements; analytical values (theoretical values): C, 57.15% (57.35%); H, 4.46% (4.52%); N, 7.99% (8.11%); F; 11.23% (11.00%); Cl, 5.11% (5.13%).

For the powder X-ray diffraction (CuKα, λ=1.54 Å, scanning speed=20°/min), the diffraction pattern is shown in FIG. 5. Peaks in FIG. 5 having a relative intensity of 33 or more, based on 100 as the maximum peak intensity, are shown in Table 5.

TABLE 5

| Peak No. | 2θ | d value | Relative intensity |
|---|---|---|---|
| 1 | 11.02 | 8.02 | 59 |
| 2 | 11.86 | 7.46 | 66 |
| 3 | 15.56 | 5.69 | 44 |
| 4 | 18.20 | 4.87 | 60 |
| 5 | 22.12 | 4.02 | 41 |
| 6 | 24.70 | 3.60 | 100 |
| 7 | 25.80 | 3.45 | 45 |
| 8 | 26.04 | 3.42 | 40 |
| 9 | 26.26 | 3.39 | 33 |
| 10 | 28.62 | 3.12 | 43 |

Example 95

N-{4-[2-Amino-5-(3,4-dimethoxyphenyl)pyridin-3-yl]phenyl}-5-(4-fluorophenyl)-4-oxo-1-(2,2,2-trifluoroethyl)-1,4-dihydropyridine-3-carboxamide hydrochloride Acetone (200 μl) was added to N-{4-[2-amino-5-(3,4-dimethoxyphenyl)pyridin-3-yl]phenyl}-5-(4-fluorophenyl)-4-oxo-1-(2,2,2-trifluoroethyl)-1,4-dihydropyridine-3-carboxamide hydrochloride hydrate described in Example 92 (22.72 mg) at room temperature, and the mixture was stirred at 40° C. for about 24 hours. After leaving to stand at room temperature for about 30 minutes, the precipitated solid was collected by filtration. The solid was then dried at room temperature to give the title compound (21.11 mg). Yield: 89%.

For the powder X-ray diffraction (CuKα, λ=1.54 Å, scanning speed=20°/min) of the resulting crystals, the diffraction pattern is shown in FIG. 6. Peaks in FIG. 6 having a relative intensity of 17 or more, based on 100 as the maximum peak intensity, are shown in Table 6.

TABLE 6

| Peak No. | 2θ | d value | Relative intensity |
|---|---|---|---|
| 1 | 3.58 | 24.66 | 100 |
| 2 | 4.56 | 19.36 | 28 |
| 3 | 6.60 | 13.38 | 22 |
| 4 | 6.72 | 13.14 | 27 |
| 5 | 7.20 | 12.27 | 17 |
| 6 | 9.62 | 9.19 | 44 |
| 7 | 10.28 | 8.60 | 20 |
| 8 | 13.06 | 6.77 | 27 |
| 9 | 24.52 | 3.63 | 21 |

Example 96

N-{4-[2-Amino-5-(3,4-dimethoxyphenyl)pyridin-3-yl]phenyl}-5-(4-fluorophenyl)-4-oxo-1-(2,2,2-trifluoroethyl)-1,4-dihydropyridine-3-carboxamide hydrochloride Tetrahydrofuran (200 μl) was added to N-{4-[2-amino-5-(3,4-dimethoxyphenyl)pyridin-3-yl]phenyl}-5-(4-fluorophenyl)-4-oxo-1-(2,2,2-trifluoroethyl)-1,4-dihydropyridine-3-carboxamide hydrochloride hydrate described in Example 92 (21.27 mg) at room temperature, and the mixture was stirred at 40° C. for about 24 hours. After leaving to stand at room temperature for about 30 minutes, the precipitated solid was collected by filtration. The solid was then dried at room temperature to give the title compound (18.37 mg). Yield: 86%.

For the powder X-ray diffraction (CuKα, λ=1.54 Å, scanning speed=20°/min) of the resulting crystals, the diffraction pattern is shown in FIG. 7. Peaks in FIG. 7 having a relative intensity of 31 or more, based on 100 as the maximum peak intensity, are shown in Table 7.

TABLE 7

| Peak No. | 2θ | d value | Relative intensity |
|---|---|---|---|
| 1 | 7.78 | 11.35 | 94 |
| 2 | 8.14 | 10.85 | 34 |
| 3 | 8.88 | 9.95 | 40 |
| 4 | 12.54 | 7.05 | 33 |
| 5 | 15.68 | 5.65 | 31 |
| 6 | 16.36 | 5.41 | 37 |
| 7 | 18.76 | 4.73 | 47 |
| 8 | 19.34 | 4.59 | 100 |
| 9 | 20.08 | 4.42 | 47 |
| 10 | 22.36 | 3.97 | 40 |
| 11 | 24.66 | 3.61 | 66 |
| 12 | 25.74 | 3.46 | 39 |
| 13 | 26.70 | 3.34 | 44 |
| 14 | 28.02 | 3.18 | 34 |

Example 97

N-{4-[2-Amino-5-(3,4-dimethoxyphenyl)pyridin-3-yl]phenyl}-5-(4-fluorophenyl)-4-oxo-1-(2,2,2-trifluoroethyl)-1,4-dihydropyridine-3-carboxamide hydrochloride Ethanol (14.8 ml), concentrated hydrochloric acid (as 12 mol/L) (219 μl, 1.05 eq.) and water (6 μl) were added to N-{4-[2-amino-5-(3,4-dimethoxyphenyl)pyridin-3-yl]phenyl}-5-(4-fluorophenyl)-4-oxo-1-(2,2,2-trifluoroethyl)-1,4-dihydropyridine-3-carboxamide (1.50 g, 2.43 mmol) at room temperature. The mixture was stirred at 40° C. for about 11 hours and then at room temperature for one hour, and the precipitated solid was collected by filtration. The solid was then dried under reduced pressure at room temperature for three hours to give the title compound (1.54 g). Yield: 97%.

N-{4-[2-Amino-5-(3,4-dimethoxyphenyl)pyridin-3-yl]phenyl}-5-(4-fluorophenyl)-4-oxo-1-(2,2,2-trifluoroethyl)-1,4-dihydropyridine-3-carboxamide hydrochloride is represented as elements; analytical values (theoretical values): C, 60.41% (60.51%); H, 4.20% (4.15%); N, 8.48% (8.55%); F, 11.89% (11.60%); Cl, 5.26% (5.41%).

For the powder X-ray diffraction (CuKα, λ=1.54 Å, scanning speed=2°/min), the diffraction pattern is shown in FIG. 8. Peaks in FIG. 8 having a relative intensity of 30 or more, based on 100 as the maximum peak intensity, are shown in Table 8.

TABLE 8

| Peak No. | 2θ | d value | Relative intensity |
|---|---|---|---|
| 1 | 5.78 | 15.28 | 38 |
| 2 | 8.90 | 9.93 | 40 |

TABLE 8-continued

| Peak No. | 2θ | d value | Relative intensity |
|---|---|---|---|
| 3 | 13.66 | 6.48 | 66 |
| 4 | 14.42 | 6.14 | 88 |
| 5 | 16.84 | 5.26 | 57 |
| 6 | 17.56 | 5.05 | 100 |
| 7 | 19.26 | 4.60 | 36 |
| 8 | 20.74 | 4.28 | 35 |
| 9 | 22.42 | 3.96 | 31 |
| 10 | 24.66 | 3.61 | 68 |
| 11 | 25.12 | 3.54 | 66 |
| 12 | 25.60 | 3.48 | 34 |
| 13 | 26.96 | 3.30 | 30 |

Example 98

N-{4-[2-Amino-5-(3,4-dimethoxyphenyl)pyridin-3-yl]phenyl}-5-(4-fluorophenyl)-4-oxo-1-(2,2,2-trifluoroethyl)-1,4-dihydropyridine-3-carboxamide hydrochloride 1-Propanol (401 μl), a 5.877 mmol/L aqueous hydrochloric acid solution (6.22 μl, 1.10 eq.) and water (4.1 μl) were added to N-{4-[2-amino-5-(3,4-dimethoxyphenyl)pyridin-3-yl]phenyl}-5-(4-fluorophenyl)-4-oxo-1-(2,2,2-trifluoroethyl)-1,4-dihydropyridine-3-carboxamide (20.55 mg, 33.22 μmol) at room temperature, and the mixture was stirred at 40° C. for about 24 hours. After leaving to stand at room temperature for about 30 minutes, the precipitated solid was collected by filtration. The solid was then dried at room temperature to give the title compound (19.65 mg). Yield: 90%.

For the powder X-ray diffraction (CuKα, λ=1.54 Å, scanning speed=20°/min) of the resulting crystals, the diffraction pattern is shown in FIG. 9. Peaks in FIG. 9 having a relative intensity of 38 or more, based on 100 as the maximum peak intensity, are shown in Table 9.

TABLE 9

| Peak No. | 2θ | d value | Relative intensity |
|---|---|---|---|
| 1 | 11.12 | 7.95 | 93 |
| 2 | 14.82 | 5.97 | 49 |
| 3 | 18.86 | 4.70 | 51 |
| 4 | 20.32 | 4.37 | 44 |
| 5 | 20.66 | 4.30 | 38 |
| 6 | 21.64 | 4.10 | 48 |
| 7 | 22.36 | 3.97 | 38 |
| 8 | 22.68 | 3.92 | 80 |
| 9 | 23.00 | 3.86 | 67 |
| 10 | 24.10 | 3.69 | 48 |
| 11 | 25.26 | 3.52 | 45 |
| 12 | 27.00 | 3.30 | 100 |

Example 99

N-{4-[2-Amino-5-(3,4-dimethoxyphenyl)pyridin-3-yl]phenyl}-5-(4-fluorophenyl)-4-oxo-1-(2,2,2-trifluoroethyl)-1,4-dihydropyridine-3-carboxamide hydrochloride Acetone (400 μl) was added to a mixture of the three crystal forms of N-{4-[2-amino-5-(3,4-dimethoxyphenyl)pyridin-3-yl]phenyl}-5-(4-fluorophenyl)-4-oxo-1-(2,2,2-trifluoroethyl)-1,4-dihydropyridine-3-carboxamide hydrochloride described in Examples 92, 93 and 94 (22.15 mg) at room temperature, and the mixture was stirred for about 24 hours. The precipitated crystals were collected by filtration and dried at room temperature to give the title compound (19.45 mg). Yield: 88%.

For the powder X-ray diffraction (CuKα, λ=1.54 Å, scanning speed=20°/min) of the resulting crystals, the diffraction pattern is shown in FIG. 10. Peaks in FIG. 10 having a relative intensity of 38 or more, based on 100 as the maximum peak intensity, are shown in Table 10.

TABLE 10

| Peak No. | 2θ | d value | Relative intensity |
|---|---|---|---|
| 1 | 7.80 | 11.33 | 60 |
| 2 | 12.18 | 7.26 | 93 |
| 3 | 12.78 | 6.92 | 38 |
| 4 | 16.20 | 5.47 | 58 |
| 5 | 16.82 | 5.27 | 47 |
| 6 | 19.20 | 4.62 | 48 |
| 7 | 19.66 | 4.51 | 52 |
| 8 | 20.20 | 4.39 | 61 |
| 9 | 21.20 | 4.23 | 100 |
| 10 | 24.52 | 3.63 | 41 |
| 11 | 25.68 | 3.47 | 47 |
| 12 | 26.78 | 3.33 | 43 |

Example 100

N-{4-[2-Amino-5-(3,4-dimethoxyphenyl)pyridin-3-yl]phenyl}-5-(4-fluorophenyl)-4-oxo-1-(2,2,2-trifluoroethyl)-1,4-dihydropyridine-3-carboxamide monohydrochloride hydrate Water (60 ml), 1-propanol (90 ml) and concentrated hydrochloric acid (as 36%, d=1.18) (0.17 ml, 0.1 eq.) were added to the compound of Example 94 (14.00 g, 20 mmol) at room temperature. After heating to 90° C., the insoluble matter was collected by filtration and the mother liquor was cooled to room temperature. After stirring at the same temperature for about three hours and then stirring at 0° C. for about 27 hours, the precipitated solid was collected by filtration. The solid was then dried under reduced pressure at 40° C. and 50° C. overnight to give the title compound (12.10 g). Yield: 88%. The obtained crystals were used as seed crystals.

1-Propanol (144 ml), water (96 ml) and concentrated hydrochloric acid (as 36%, d=1.18) (3.1 ml, 1.1 eq.) were added to the compound of Step 3 of Example 9 (20.00 g, 32.33 mmol) at room temperature. The mixture was warmed to 83° C. After confirming dissolution, the solution was cooled to 0° C. The seed crystals obtained above (20 mg) were then seeded, and the mixture was stirred for about 17 hours. The precipitated solid was then collected by filtration. The solid was then dried under reduced pressure at 40° C. overnight to give the title compound (18.26 g). Yield: 82%.

N-{4-[2-Amino-5-(3,4-dimethoxyphenyl)pyridin-3-yl]phenyl}-5-(4-fluorophenyl)-4-oxo-1-(2,2,2-trifluoroethyl)-1,4-dihydropyridine-3-carboxamide hydrochloride dihydrate is represented as: C, 57.84% (57.35%); H, 4.23% (4.52%); N, 8.17% (8.11%); F, 11.44% (11.00%); Cl, 5.23% (5.13%).

For the powder X-ray diffraction (CuKα, λ=1.54 Å, scanning speed=2°/min), the diffraction pattern is shown in FIG. 11. Peaks in FIG. 11 having a relative intensity of 37 or more, based on 100 as the maximum peak intensity, are shown in Table 11.

TABLE 11

| Peak No. | 2θ | d value | Relative intensity |
|---|---|---|---|
| 1 | 2.80 | 31.53 | 73 |
| 2 | 6.86 | 12.87 | 39 |
| 3 | 7.88 | 11.21 | 57 |
| 4 | 11.60 | 7.62 | 100 |
| 5 | 13.68 | 6.47 | 54 |
| 6 | 14.86 | 5.96 | 69 |
| 7 | 17.40 | 5.09 | 44 |
| 8 | 22.40 | 3.97 | 37 |
| 9 | 23.78 | 3.74 | 38 |
| 10 | 25.74 | 3.46 | 40 |

Example 101

N-{4-[2-Amino-5-(3,4-dimethoxyphenyl)pyridin-3-yl]phenyl}-5-(4-fluorophenyl)-4-oxo-1-(2,2,2-trifluoroethyl)-1,4-dihydropyridine-3-carboxamide monohydrochloride hydrate 2-Propanol (50 ml), concentrated hydrochloric acid (as 36%, d=1.18) (0.76 ml, 1.1 eq.) and 1.5% aqueous 2-propanol (50 ml) were added to the compound of Step 3 of Example 9 (5.00 g, 8.08 mmol) at room temperature. After warming to 40° C., the compound of Example 93 (10 mg) was seeded. The mixture was stirred at 40° C. for about two hours and then stirred at room temperature for 30 minutes, and the precipitated solid was collected by filtration. The solid was then dried under reduced pressure at 40° C. overnight to give the title compound (5.02 g). Yield: 92%.

N-{4-[2-Amino-5-(3,4-dimethoxyphenyl)pyridin-3-yl]phenyl}-5-(4-fluorophenyl)-4-oxo-1-(2,2,2-trifluoroethyl)-1,4-dihydropyridine-3-carboxamide hydrochloride monohydrate is represented as: C, 59.07% (58.89%); H, 4.06% (4.34%); N, 8.31% (8.32%); F, 11.58% (11.29%); Cl, 5.27% (5.27%).

For the powder X-ray diffraction (CuKα, λ=1.54 Å, scanning speed=2°/min), the diffraction pattern is shown in FIG. 12. Peaks in FIG. 12 having a relative intensity of 17 or more, based on 100 as the maximum peak intensity, are shown in Table 12.

TABLE 12

| Peak No. | 2θ | d value | Relative intensity |
|---|---|---|---|
| 1 | 5.32 | 16.60 | 23 |
| 2 | 7.98 | 11.07 | 69 |
| 3 | 10.68 | 8.28 | 100 |
| 4 | 11.70 | 7.56 | 19 |
| 5 | 14.84 | 5.96 | 43 |
| 6 | 16.02 | 5.53 | 25 |
| 7 | 19.78 | 4.48 | 17 |
| 8 | 21.76 | 4.08 | 17 |
| 9 | 23.08 | 3.85 | 29 |
| 10 | 25.30 | 3.52 | 25 |
| 11 | 25.68 | 3.47 | 17 |

Example 102

N-{4-[2-Amino-5-(3,4-dimethoxyphenyl)pyridin-3-yl]phenyl}-5-(4-fluorophenyl)-4-oxo-1-(2,2,2-trifluoroethyl)-1,4-dihydropyridine-3-carboxamide monohydrochloride Ethanol (40 ml) was added to the compound of Example 96 (2.00 g, 3.05 mmol as hydrochloride anhydride) at room temperature. The mixture was stirred at room temperature for about 19 hours and then stirred at 40° C. for about 33 hours, and the precipitated solid was collected by filtration. The solid was then dried under reduced pressure at 40° C. overnight to give the title compound (1.62 g).

Yield: 81%.

N-{4-[2-Amino-5-(3,4-dimethoxyphenyl)pyridin-3-yl]phenyl}-5-(4-fluorophenyl)-4-oxo-1-(2,2,2-trifluoroethyl)-1,4-dihydropyridine-3-carboxamide hydrochloride is represented as: C, 60.34% (60.51%); H, 4.11% (4.15%); N, 8.47% (8.55%); F, 11.77% (11.60%); Cl, 5.35% (5.41%).

For the powder X-ray diffraction (CuKα, λ=1.54 Å, scanning speed=2°/min), the diffraction pattern is shown in FIG. 13. Peaks in FIG. 13 having a relative intensity of 49 or more, based on 100 as the maximum peak intensity, are shown in Table 13.

TABLE 13

| Peak No. | 2θ | d value | Relative intensity |
|---|---|---|---|
| 1 | 8.10 | 10.91 | 67 |
| 2 | 10.60 | 8.34 | 49 |
| 3 | 12.06 | 7.33 | 50 |
| 4 | 14.16 | 6.25 | 56 |
| 5 | 14.58 | 6.07 | 70 |
| 6 | 15.60 | 5.68 | 76 |
| 7 | 18.16 | 4.88 | 71 |
| 8 | 20.72 | 4.28 | 81 |
| 9 | 20.94 | 4.24 | 75 |
| 10 | 22.86 | 3.89 | 78 |
| 11 | 23.90 | 3.72 | 100 |
| 12 | 24.32 | 3.66 | 97 |
| 13 | 27.14 | 3.28 | 51 |

Example 103

N-{4-[2-Amino-5-(3,4-dimethoxyphenyl)pyridin-3-yl]phenyl}-5-(4-fluorophenyl)-4-oxo-1-(2,2,2-trifluoroethyl)-1,4-dihydropyridine-3-carboxamide monohydrochloride hydrate Acetonitrile (39 ml), 6 N hydrochloric acid (565 μl, 1.05 eq.) and water (420 μl) were added to the compound of Step 3 of Example 9 (2.00 g, 3.23 mmol) at room temperature. The mixture was stirred at 40° C. for about seven hours, followed by the addition of water (8.75 ml). After confirming dissolution, the solution was stirred at 0° C. for about 10 hours and then allowed to stand at room temperature for about three days, and the precipitated solid was collected by filtration. The solid was then dried at room temperature to give the title compound (0.54 g). Yield: 24%.

N-{4-[2-Amino-5-(3,4-dimethoxyphenyl)pyridin-3-yl]phenyl}-5-(4-fluorophenyl)-4-oxo-1-(2,2,2-trifluoroethyl)-1,4-dihydropyridine-3-carboxamide hydrochloride trihydrate is represented as: C, 55.73% (55.90%); H, 4.37% (4.69%); N, 8.07% (7.90%); F, 10.85% (10.72%); Cl, 4.98% (5.00%).

For the powder X-ray diffraction (CuKα, λ=1.54 Å, scanning speed=2°/min), the diffraction pattern is shown in FIG. 14. Peaks in FIG. 14 having a relative intensity of 17 or more, based on 100 as the maximum peak intensity, are shown in Table 14.

TABLE 14

| Peak No. | 2θ | d value | Relative intensity |
|---|---|---|---|
| 1 | 3.60 | 24.52 | 69 |
| 2 | 6.22 | 14.20 | 100 |
| 3 | 9.56 | 9.24 | 71 |
| 4 | 10.42 | 8.48 | 18 |
| 5 | 14.04 | 6.30 | 18 |
| 6 | 14.66 | 6.04 | 23 |
| 7 | 15.30 | 5.79 | 23 |
| 8 | 16.40 | 5.40 | 20 |
| 9 | 19.52 | 4.54 | 19 |
| 10 | 22.12 | 4.02 | 18 |
| 11 | 26.42 | 3.37 | 17 |

Example 104

N-{4-[2-Amino-5-(3,4-dimethoxyphenyl)pyridin-3-yl]phenyl}-5-(4-fluorophenyl)-4-oxo-1-(2,2,2-trifluoroethyl)-1,4-dihydropyridine-3-carboxamide monohydrochloride hydrate Forty percent aqueous 1-propanol (28 ml) and concentrated hydrochloric acid (36%, d=1.18) (0.14 ml, 0.56 eq.) were added to the compound of Example 100 (2.00 g, 2.89 mmol) at room temperature. The mixture was stirred at 0° C. for about 21 hours, and the precipitated solid was then collected by filtration. The solid was then dried at room temperature to give the title compound (1.89 g). Yield: 88%.

N-{4-[2-Amino-5-(3,4-dimethoxyphenyl)pyridin-3-yl]phenyl}-5-(4-fluorophenyl)-4-oxo-1-(2,2,2-trifluoroethyl)-1,4-dihydropyridine-3-carboxamide hydrochloride pentahydrate is represented as: C, 53.06% (53.19%); H, 4.78% (5.01%); N, 7.46% (7.52%); F, 10.46% (10.20%); Cl, 5.01% (4.76%).

For the powder X-ray diffraction (CuKα, λ=1.54 Å, scanning speed=2°/min), the diffraction pattern is shown in FIG. 15. Peaks in FIG. 15 having a relative intensity of 42 or more, based on 100 as the maximum peak intensity, are shown in Table 15.

TABLE 15

| Peak No. | 2θ | d value | Relative intensity |
|---|---|---|---|
| 1 | 5.46 | 16.17 | 88 |
| 2 | 7.98 | 11.07 | 50 |
| 3 | 9.54 | 9.26 | 45 |
| 4 | 11.00 | 8.04 | 81 |
| 5 | 14.00 | 6.32 | 56 |
| 6 | 15.36 | 5.76 | 49 |
| 7 | 16.56 | 5.35 | 100 |
| 8 | 22.00 | 4.04 | 59 |
| 9 | 23.54 | 3.78 | 63 |
| 10 | 24.00 | 3.70 | 48 |
| 11 | 26.56 | 3.35 | 42 |

Example 105

N-{4-[2-Amino-5-(3,4-dimethoxyphenyl)pyridin-3-yl]phenyl}-5-(4-fluorophenyl)-4-oxo-1-(2,2,2-trifluoroethyl)-1,4-dihydropyridine-3-carboxamide monohydrochloride 1 N aqueous hydrochloric acid (400 μl) was added to a suspension of the compound of Step 3 of Example 9 (50 mg) in ethanol (400 μl) at room temperature, and ethanol (300 μl) was then further added to form a solution. After stirring at room temperature for 30 minutes, the solid was precipitated, and the mixture was allowed to stand overnight. The reaction solution was added dropwise to water (7 ml), and the mixture was stirred for five days. The precipitate was collected by filtration and air-dried to give 52 mg of the title compound as a solid.

$^1$H-NMR (CDCl$_3$) δ: 3.93 (3H, s), 3.94 (3H, s), 4.66-4.73 (2H, m), 6.92-7.05 (3H, m), 7.18 (2H, t, J=8.5 Hz), 7.44 (2H, d, J=8.5 Hz), 7.51-7.58 (3H, m), 7.90-7.96 (4H, m), 8.72 (1H, d, J=1.8 Hz), 12.65 (1H, s).

MS (ESI) m/z: 619 (M+H)$^+$.

For the powder X-ray diffraction (CuKα, λ=1.54 Å, scanning speed=2°/min), the diffraction pattern is shown in FIG. 16. Peaks in FIG. 16 having a relative intensity of 12 or more, based on 100 as the maximum peak intensity, are shown in Table 16.

TABLE 16

| Peak No. | 2θ | d value | Relative intensity |
|---|---|---|---|
| 1 | 5.64 | 15.66 | 28 |
| 2 | 6.92 | 12.76 | 24 |
| 3 | 8.06 | 10.96 | 100 |
| 4 | 11.32 | 7.81 | 42 |
| 5 | 13.92 | 6.36 | 14 |
| 6 | 14.40 | 6.15 | 55 |
| 7 | 16.18 | 5.47 | 28 |
| 8 | 17.04 | 5.20 | 70 |
| 9 | 21.84 | 4.07 | 12 |
| 10 | 22.50 | 3.95 | 12 |
| 11 | 23.82 | 3.73 | 12 |
| 12 | 24.28 | 3.66 | 18 |

Test Example 1

Cell-Free Axl Kinase Inhibitory Activity

A kinase dilution solution containing 170 ng/ml of AXL (a fusion protein of amino acids 464-885 of the intracellular domain of human AXL with glutathione transferase, expressed using the baculovirus expression system and purified by glutathione sepharose chromatography; Carna Biosciences, Inc., catalog No. 08-107) was prepared using a kinase reaction buffer (100 mM HEPES (pH 7.4), 0.003% Brij-35, 0.004% Tween-20, 1 mM DTT, 10 mM MgCl$_2$), and added at 19 μl to each well of a 384-well plate.

Next, the test compound was diluted with DMSO, and 1 μl of this diluted solution was added to each well.

After preincubation at room temperature for 30 minutes, a solution containing 1.5 μM of a substrate peptide (FL-Peptide 30 (5FAM-KKKKEEIYFFF-CONH$_2$), Caliper Life Sciences, catalog No. 760430) and 10 μM of ATP was prepared. Five microliters of this solution were added to each well to initiate a kinase reaction. The plate was incubated at 28° C. for 1.5 hours, and 40 μl of a termination buffer (100 mM HEPES (pH 7.4), 0.015% Brij-35, 40 mM EDTA, 0.1% Coating Reagent 3) was added to each well to terminate the reaction.

The substrate peptide and the phosphorylated peptide in the reaction solution were separated and quantified by EZ Reader II (Caliper Life Sciences).

The kinase reaction was evaluated by the product ratio (P/(P+S)) calculated from the peak height of the substrate peptide (S) and the peak height of the phosphorylated peptide (P).

The inhibition was determined by the following formula (automatically calculated by software of the EZ Reader II system):

$$\text{Inhibition}(\%) = 100 \times (1 - C_i/C_0)$$

where $C_i$ represents the product ratio when the test compound is added, and $C_0$ represents the product ratio when DMSO is added in place of the test compound.

$IC_{50}$ was determined from inhibition data for 12 test compound concentrations by nonlinear regression (four-parameter logistic regression) using the following formula.

$$\text{Inhibition}(\%) = \text{Bottom} + (\text{Top} - \text{Bottom})/(1 + ([\text{Compound}]/IC_{50})^{slope})$$

The compounds of Examples 3, 5, 9, 11, 12, 13, 15, 17, 24, 26 to 29, 38, 39, 40, 42, 50, 51, 62, 64, 71, 74, 76, 77, 80 and 85 had an inhibitory activity of 0.1 nM≤$IC_{50}$<1 nM. The compounds of Examples 1, 2, 4, 6, 7, 8, 10, 14, 16, 18 to 23, 25, 30, 31, 33, 34, 37, 41, 43 to 49, 52 to 58, 60, 61, 63, 65, 66, 67, 69, 70, 72, 75, 78, 79, 82, 86, 87, 88 and 89 had an inhibitory activity of 1 nM≤$IC_{50}$<10 nM. The compounds of Examples 32, 35, 36, 59, 68, 73, 83 and 84 had an inhibitory activity of 10 nM≤$IC_{50}$<20 nM. The compound of Example 81 had an inhibitory activity of $IC_{50}$=23 nM.

Test Example 2

Intracellular Axl Phosphorylation Inhibitory Activity

A phosphorylated Axl (hereinafter pAxl) inhibitory test was performed using the human non-small-cell lung cancer-derived cell strain NCI-H1299.

NCI-H1299 cells were suspended in medium (RPMI 1640 medium containing 10% fetal bovine serum), inoculated into a 96-well multiwell plate at 15000 cells/100 μl/well, and cultured at 37° C. in the presence of 5% $CO_2$ for one day. On the following day, the medium was removed, 100 μl of fresh medium were added, and the cells were cultured at 37° C. in the presence of 5% $CO_2$ for one day.

The test compound was dissolved in DMSO and diluted with medium to prepare a sample solution (DMSO concentration: 2%). Twenty-five microliters of medium or sample-added medium was added to each well (DMSO concentration: 0.4%), and the plate was incubated at 37° C. in the presence of 5% $CO_2$ for one hour.

GAS6 (R&D, catalog No.: 885-GS) was diluted to 6 μg/ml with medium, and 25 μl of the diluted solution was added to each well. After stirring, the plate was incubated at 37° C. in the presence of 5% $CO_2$ for 10 minutes.

The supernatant was discarded, and 0.1 ml of a 37% formalin solution diluted to 4% with phosphate buffer (PBS) (hereinafter "4% formalin solution") was added to each well. The plate was allowed to stand at room temperature for 10 minutes.

Next, the 4% formalin solution was discarded, and 0.2 ml of a solution of Triton X-100 diluted to 0.1% with PBS (hereinafter "wash buffer") was added. The wash buffer was discarded using a decanter, and excess moisture in the plate was removed on a paper towel.

Subsequently, 110 μl of $NaN_3$ and $H_2O_2$ were added to the wash buffer at 0.1% (hereinafter "quenching buffer"), and 0.1 ml of the quenching buffer was added to each well. The plate was allowed to stand at room temperature for 15 minutes.

The quenching buffer was discarded, and 0.2 ml of wash buffer was added. The wash buffer was discarded using a decanter, and excess moisture in the plate was removed on a paper towel.

Skim milk (Nacalai Tesque) was added to the wash buffer at a final concentration of 5% (hereinafter "blocking buffer"), and 0.25 ml of the blocking buffer was added to each well. The plate was allowed to stand at room temperature for one hour.

The blocking buffer was discarded, anti-phospho-Axl (Y702) (D12B2) rabbit monoclonal antibody (Cell Signaling, catalog No. 5724) was reacted at a concentration of 1/1000, and the plate was allowed to stand at 4° C. overnight.

A washing operation with wash buffer was repeated five times, and Peroxidase AffiniPure Donkey Anti-Rabbit IgG (H+L) (Jackson ImmunoResearch, catalog No. 711-035-152) was reacted at a concentration of 1/2000 at room temperature for one hour.

Another washing operation was performed, and 0.05 ml of Super Signal ELISA Pico Chemiluminescent Substrate (Thermo Scientific, catalog No. 37069) was added. After light stirring, the plate was incubated for 20 minutes. Luminescence was then measured by ARVO sx (PerkinElmer), and the pAxl (Y702) level was measured.

pAxl Inhibitory activity was determined by the following formula.

$$\text{Inhibition }\% = 100 - (A-B) \times 100/(T-B)$$

A: Measurement of the test compound
B: Luminescence value of the reaction solution with a positive control compound added at a concentration that inhibits phosphorylation at almost 100% (e.g., the luminescence value of the reaction solution with 1 μM BMS-777607 added)
T: Luminescence value of the reaction solution with a compound not added The 50% inhibitory concentration ($IC_{50}$) was determined from pAxl inhibitory activity data at multiple concentrations by GraphPad Prism 4.

The compounds of Examples 2 to 5, 8 to 13, 15 to 17, 19 to 21, 23 to 29, 37 to 67, 70, 71, 73 to 78, 80, 82, 83, 85, 86, 87 and 88 had an inhibitory activity of 0 nM<$IC_{50}$<50 nM. The compounds of Examples 1, 7, 14, 18, 22, 30, 33, 34, 72, 79 and 89 had an inhibitory activity of 50 nM≤$IC_{50}$<100 nM. The compounds of Examples 6, 31, 32, 35, 36, 68, 69, 81 and 84 had an inhibitory activity of 100 nM≤$IC_{50}$<500 nM.

What is claimed is:
1. A compound of formula (1):

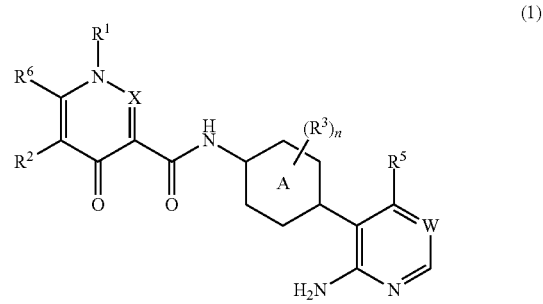

or a pharmaceutically acceptable salt thereof,
wherein,
A is selected from a phenylene group, a pyridylene group, a pyrimidylene group, a pyrazylene group, a pyridazylene group and a triazylene group,
where the amino group bonded to A and the nitrogen-containing heterocycle bonded to A are para-positioned relative to each other;

$R^1$ is
- a $C_1$-$C_6$ alkyl group which may have one or more substituents selected from Group 1,
- an aryl group which may have one or more substituents selected from Group 2,
- a heteroaryl group which may have one or more substituents selected from Group 2, or
- a hydrogen atom;

$R^2$ is
- a $C_1$-$C_6$ alkyl group which may have one or more substituents selected from Group 1,
- a $C_1$-$C_6$ alkoxy group which may have one or more substituents selected from a halogen atom and a hydroxyl group,
- —CONR$^A$R$^B$, a cycloalkyl group which may have one or more substituents selected from Group 2,
- a phenyl group which may have one or more substituents selected from Group 2,
- a heteroaryl group which may have one or more substituents selected from Group 2, or
- a hydrogen atom;

$R^3$ is
- a $C_1$-$C_6$ alkyl group which may have one or more substituents selected from Group 1,
- a $C_1$-$C_6$ alkoxy group which may have one or more substituents selected from a halogen atom and a hydroxyl group,
- a $C_1$-$C_6$ alkylthio group which may have one or more substituents selected from a halogen atom and a hydroxyl group,
- a halogen atom, or
- a hydroxyl group;

$R^5$ is
- a $C_1$-$C_6$ alkyl group which may have one or more substituents selected from Group 1,
- —OR$^C$,
- a $C_1$-$C_6$ alkylthio group which may have one or more substituents selected from a halogen atom and a hydroxyl group, or
- a hydrogen atom;

$R^6$ is
- a hydrogen atom, or
- a $C_1$-$C_6$ alkyl group which may have one or more substituents selected from Group 1;

W is
- C—$R^4$, or
- a nitrogen atom;

X is
- CH, or
- a nitrogen atom;

$R^A$ and $R^B$ are each independently
- a $C_1$-$C_6$ alkyl group which may have one or more substituents selected from a halogen atom, a $C_1$-$C_6$ alkoxy group, and a hydroxyl group, or
- a hydrogen atom; or
- $R^A$ and $R^B$ together with the nitrogen atom to which they are bonded may form a three- to seven-membered heterocycloalkyl group which may have one or more substituents selected from a halogen atom, a $C_1$-$C_6$ alkyl group, a $C_1$-$C_6$ alkoxy group, and a hydroxyl group;

n is an integer of 0 to 4;

each $R^3$ may be identical to or different from one another when n is two or more;

$R^C$ is
- a $C_1$-$C_6$ alkyl group which may have one or more substituents selected from a $C_1$-$C_6$ alkoxy group, a halogen atom, a three- to seven-membered heterocycloalkyl group and a hydroxyl group,
- a three- to seven-membered heterocycloalkyl group which may have one or more substituents selected from a halogen atom, a $C_1$-$C_6$ alkyl group, and a hydroxyl group, or
- a hydrogen atom;

$R^4$ is
- a $C_1$-$C_6$ alkyl group which may have one or more substituents selected from Group 1,
- a $C_1$-$C_6$ alkoxy group which may have one or more substituents selected from a $C_1$-$C_6$ alkoxy group, a heterocycloalkyl group, a halogen atom, and a hydroxyl group;
- a cycloalkyl group which may have one or more substituents selected from Group 3,
- a cycloalkenyl group which may have one or more substituents selected from Group 3,
- a heterocycloalkyl group which may have one or more substituents selected from Group 3,
- a heterocycloalkenyl group which may have one or more substituents selected from Group 3,
- an aryl group which may have one or more substituents selected from Group 3,
- a heteroaryl group which may have one or more substituents selected from Group 3,
- a halogen atom, or
- a hydrogen atom;

Group 1 is
- a halogen atom,
- —NR$^A$R$^B$,
- —CONR$^A$R$^B$,
- —OR$^C$,
- an aryl group which may have one or more substituents selected from
  - a $C_1$-$C_6$ alkyl group which may have one or more substituents selected from a halogen atom and a hydroxyl group,
  - a $C_1$-$C_6$ alkoxy group,
  - an oxo group, and
  - a halogen atom,
- a heteroaryl group which may have one or more substituents selected from
  - a $C_1$-$C_6$ alkyl group which may have one or more substituents selected from a halogen atom and a hydroxyl group,
  - a $C_1$-$C_6$ alkoxy group,
  - an oxo group,
  - a hydroxyl group, and
  - a halogen atom,
- a three- to seven-membered cycloalkyl group which may have one or more substituents selected from
  - a $C_1$-$C_6$ alkyl group which may have one or more substituents selected from a halogen atom and a hydroxyl group,
  - a $C_1$-$C_6$ alkoxy group,
  - an oxo group,
  - a hydroxyl group, and
  - a halogen atom, and
- a three- to seven-membered heterocycloalkyl group which may have one or more substituents selected from
  - a $C_1$-$C_6$ alkyl group which may have one or more substituents selected from a halogen atom and a hydroxyl group,
  - a $C_1$-$C_6$ alkoxy group,
  - an oxo group, a hydroxyl group, and
a halogen atom;
Group 2 is
  a $C_1$-$C_6$ alkyl group which may have one or more substituents selected from a halogen atom and a hydroxyl group,
  a $C_1$-$C_6$ alkoxy group,
  an oxo group,
  a hydroxyl group, and
  a halogen atom;
Group 3 is
  a $C_1$-$C_6$ alkyl group which may have one or more substituents selected from Group 1,
  a $C_1$-$C_6$ acyl group,
  a $C_1$-$C_6$ alkylthio group which may have one or more substituents selected from a halogen atom and a hydroxyl group,
  —CONR$^A$R$^B$,
  —OR$^C$, and
  a heterocycloalkyl group which may have one or more substituents selected from Group 2;
each heteroaryl group is independently selected from a pyrrolyl group, a pyrazolyl group, a triazolyl group, an oxazolyl group, an oxadiazolyl group, a thiophenyl group, a thiazolyl group, a thiadiazolyl group, a pyridinyl group, a pyrimidinyl group, a pyridazinyl group, a pyrazinyl group, a benzimidazolyl group, a benzotriazolyl group, a benzofuranyl group, a benzothiophenyl group, a quinolyl group, a carbazolyl group, and a dibenzofuranyl group;
each heterocycloalkyl group is independently selected from pyrrolidinyl, imidazolidinyl, piperidino, piperazinyl, azetidinyl, morpholino, dioxanyl, oxetanyl, tetrahydropyranyl, and quinuclidinyl; and
each heterocycloalkenyl group is independently selected from a tetrahydropyridinyl group and a dihydropyranyl group.

2. The compound or pharmaceutically acceptable salt thereof of claim 1, wherein A is a phenylene group.

3. The compound or pharmaceutically acceptable salt thereof of claim 1, wherein W is C—R$^4$.

4. The compound or pharmaceutically acceptable salt thereof of claim 1, wherein n is 0.

5. The compound or pharmaceutically acceptable salt thereof of claim 1, wherein R$^5$ is a hydrogen atom.

6. A compound selected from:

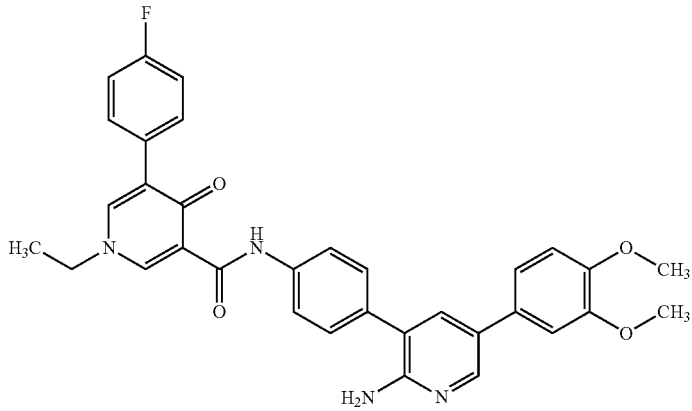

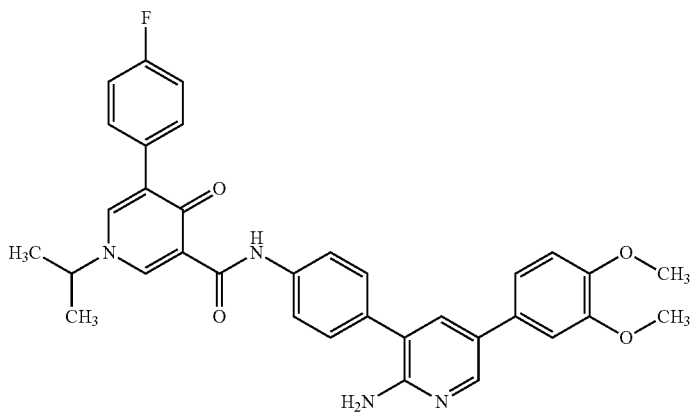

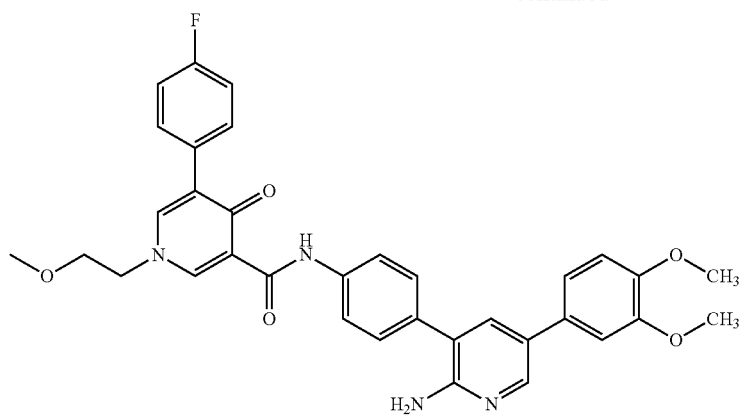
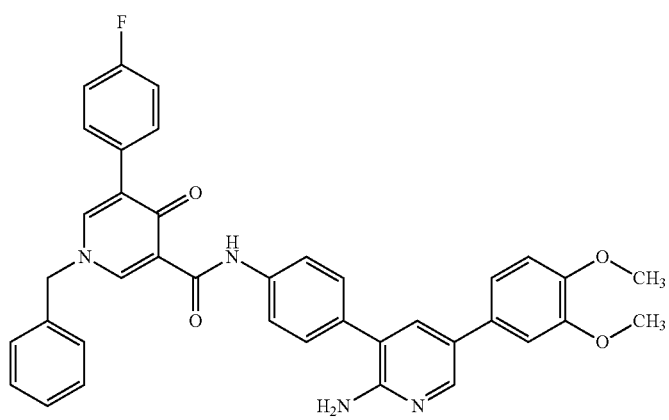
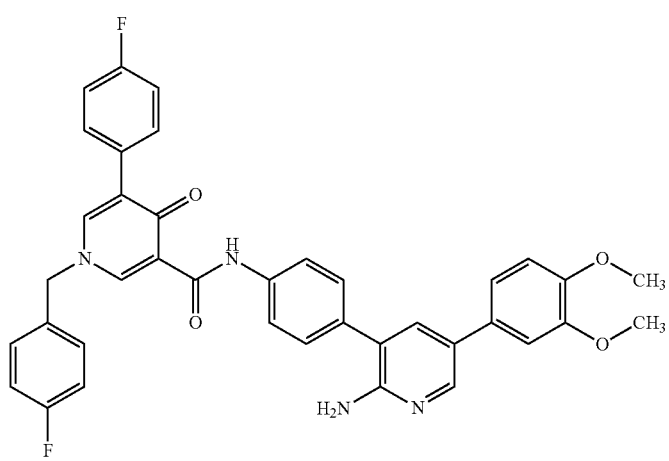
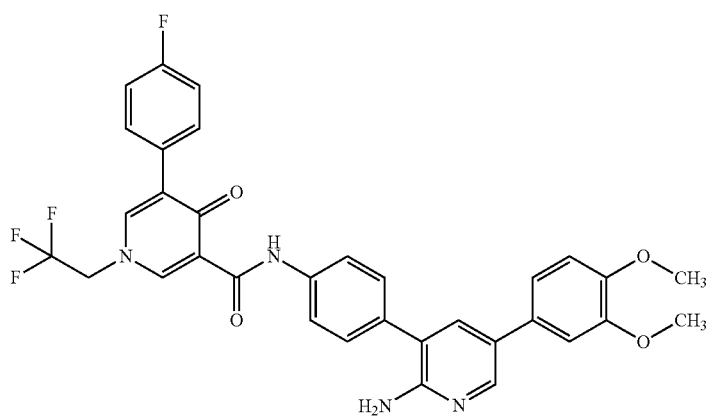

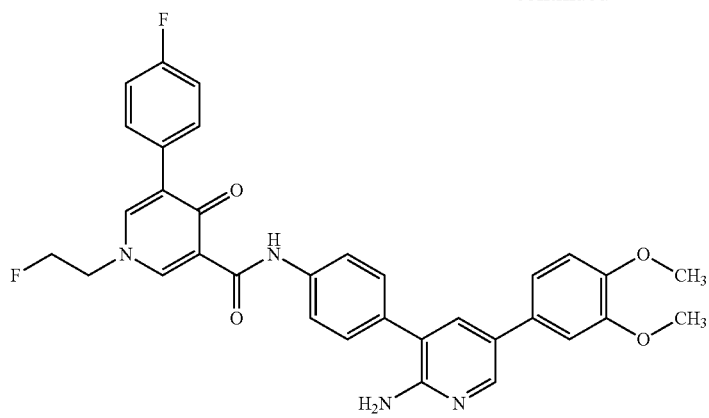
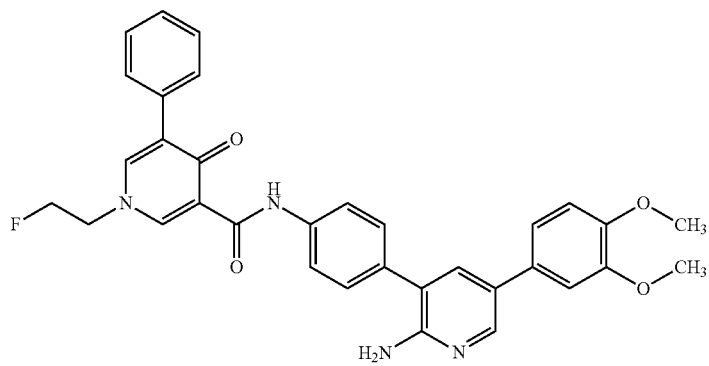
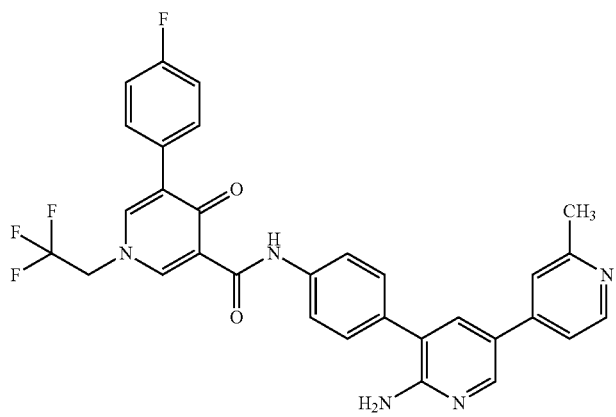
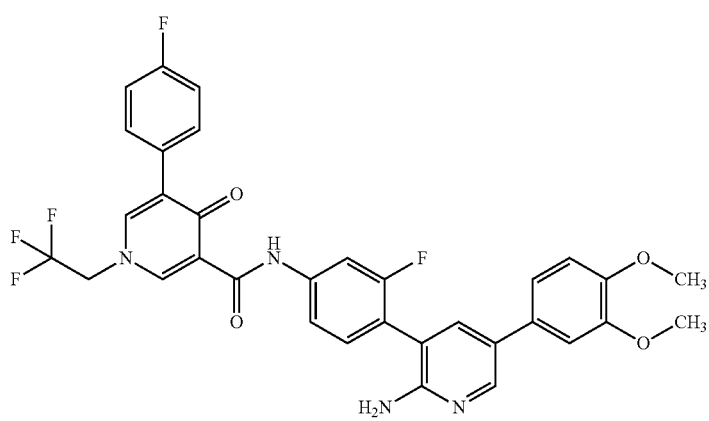

-continued
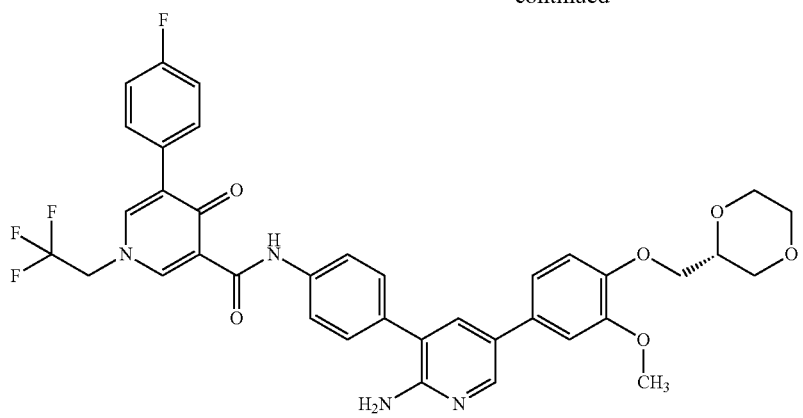
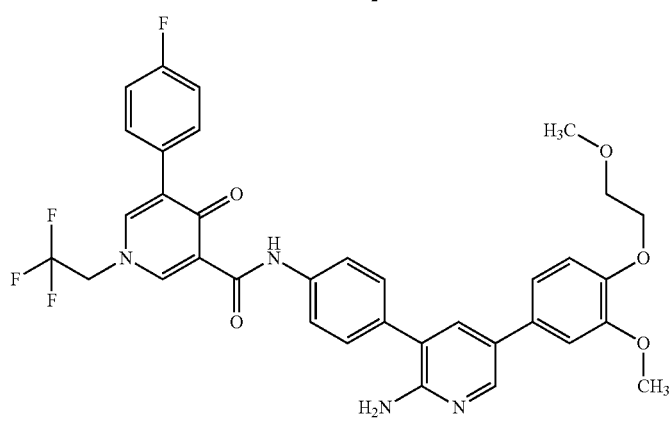
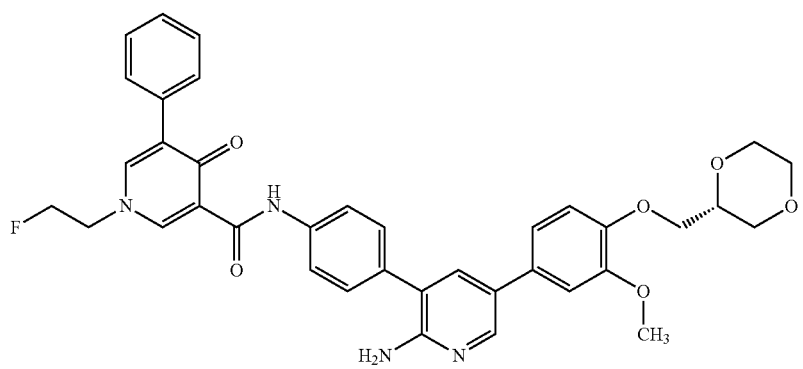
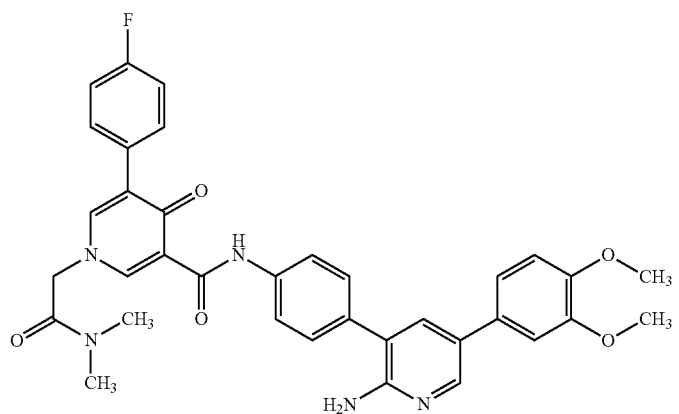

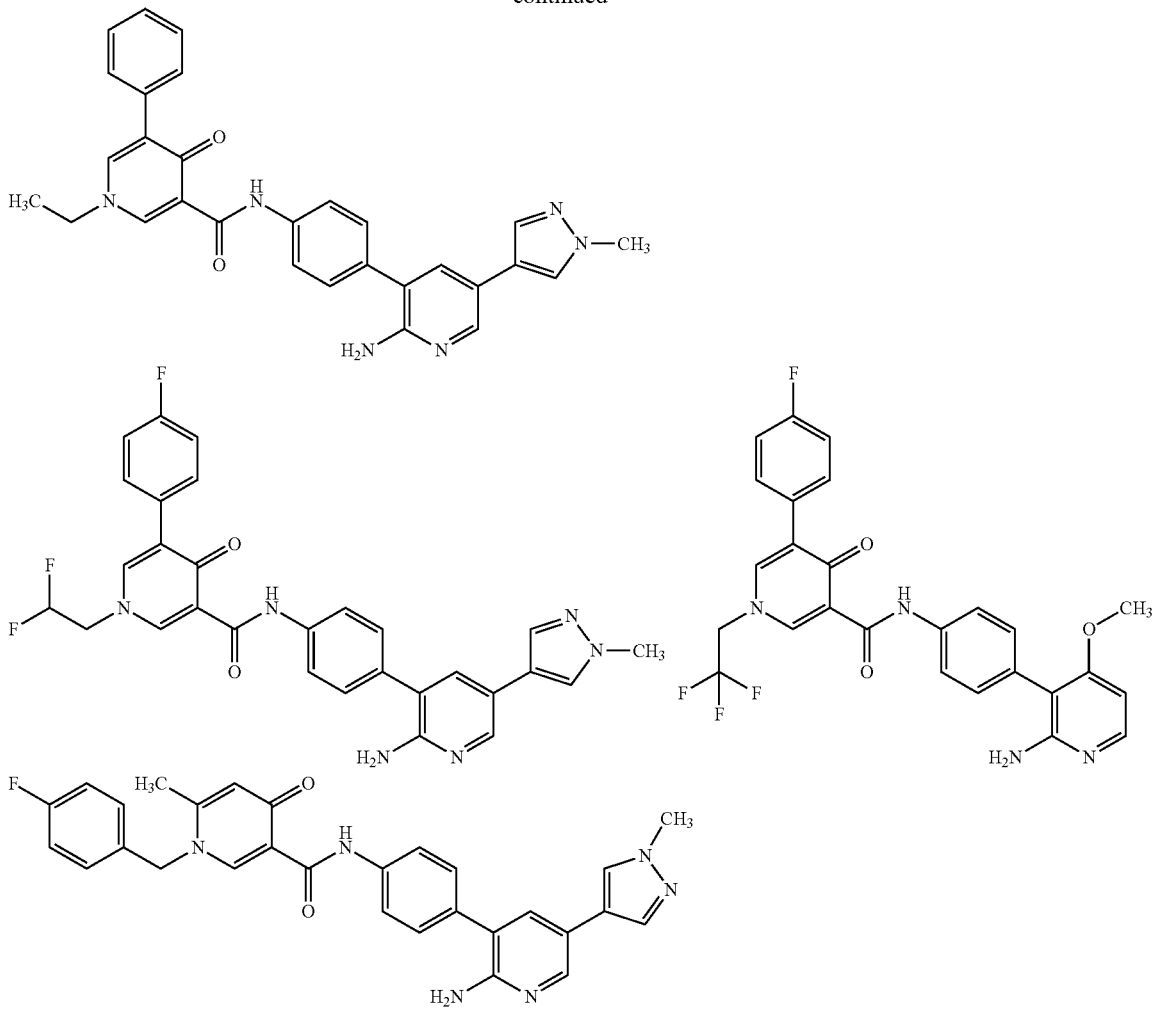

or a pharmaceutically acceptable salt of any of the foregoing.

7. The compound N-{4-[2-Amino-5-(3,4-dimethoxyphenyl)pyridin-3-yl]phenyl}-5-(4-fluorophenyl)-4-oxo-1-(2,2,2-trifluoroethyl)-1,4-dihydropyridine-3-carboxamide or a pharmaceutically acceptable salt thereof.

8. The compound N-{4-[2-Amino-5-(3,4-dimethoxyphenyl)pyridin-3-yl]phenyl}-5-(4-fluorophenyl)-4-oxo-1-(2,2,2-trifluoroethyl)-1,4-dihydropyridine-3-carboxamide hydrochloride.

9. A crystalline form of the N-{4-[2-amino-5-(3,4-dimethoxyphenyl)pyridin-3-yl]phenyl}-5-(4-fluorophenyl)-4-oxo-1-(2,2,2-trifluoroethyl)-1,4-dihydropyridine-3-carboxamide hydrochloride of claim 8, which has characteristic peaks at diffraction angles 2θ of 7.44, 10.00, 13.48, 14.86, 16.10, 19.30, 20.30, 22.62, 23.02, 23.70, 24.54, 25.92 and 28.46 in a powder X-ray diffraction diagram obtained by irradiation with copper Kα radiation (wavelength λ=1.54 Å).

10. A crystalline form of the N-{4-[2-amino-5-(3,4-dimethoxyphenyl)pyridin-3-yl]phenyl}-5-(4-fluorophenyl)-4-oxo-1-(2,2,2-trifluoroethyl)-1,4-dihydropyridine-3-carboxamide hydrochloride of claim 8, which has characteristic peaks at diffraction angles 2θ of 4.32, 9.10, 15.52, 18.32, 18.54, 19.22, 20.54, 20.70, 23.54, 24.14, 25.34 and 27.02 in a powder X-ray diffraction diagram obtained by irradiation with copper Kα radiation (wavelength λ=1.54 Å).

11. A crystalline form of the N-{4-[2-amino-5-(3,4-dimethoxyphenyl)pyridin-3-yl]phenyl}-5-(4-fluorophenyl)-4-oxo-1-(2,2,2-trifluoroethyl)-1,4-dihydropyridine-3-carboxamide hydrochloride of claim 8, which has characteristic peaks at diffraction angles 2θ of 13.86, 15.04, 19.76, 20.58, 22.26, 22.58, 23.82, 24.10, 24.36 and 24.88 in a powder X-ray diffraction diagram obtained by irradiation with copper Kα radiation (wavelength λ=1.54 Å).

12. A crystalline form of the N-{4-[2-amino-5-(3,4-dimethoxyphenyl)pyridin-3-yl]phenyl}-5-(4-fluorophenyl)-4-oxo-1-(2,2,2-trifluoroethyl)-1,4-dihydropyridine-3-carboxamide hydrochloride of claim 8, which has characteristic peaks at diffraction angles 2θ of 5.34, 7.22, 8.20, 11.68, 14.54, 15.74, 17.54, 23.24, 23.72, 25.12 and 26.16 in a powder X-ray diffraction diagram obtained by irradiation with copper Kα radiation (wavelength λ=1.54 Å).

13. A crystalline form of the N-{4-[2-amino-5-(3,4-dimethoxyphenyl)pyridin-3-yl]phenyl}-5-(4-fluorophenyl)-4-oxo-1-(2,2,2-trifluoroethyl)-1,4-dihydropyridine-3-carboxamide hydrochloride of claim 8, which has characteristic peaks at diffraction angles 2θ of 11.02, 11.86, 15.56, 18.20, 22.12, 24.70, 25.80, 26.04, 26.26 and 28.62 in a powder X-ray diffraction diagram obtained by irradiation with copper Kα radiation (wavelength λ=1.54 Å).

14. A crystalline form of the N-{4-[2-amino-5-(3,4-dimethoxyphenyl)pyridin-3-yl]phenyl}-5-(4-fluorophenyl)-

4-oxo-1-(2,2,2-trifluoroethyl)-1,4-dihydropyridine-3-carboxamide hydrochloride of claim 8, which has characteristic peaks at diffraction angles 2θ of 3.58, 4.56, 6.60, 6.72, 7.20, 9.62, 10.28, 13.06 and 24.52 in a powder X-ray diffraction diagram obtained by irradiation with copper Kα radiation (wavelength λ=1.54 Å).

15. A crystalline form of the N-{4-[2-amino-5-(3,4-dimethoxyphenyl)pyridin-3-yl]phenyl}-5-(4-fluorophenyl)-4-oxo-1-(2,2,2-trifluoroethyl)-1,4-dihydropyridine-3-carboxamide hydrochloride of claim 8, which has characteristic peaks at diffraction angles 2θ of 7.78, 8.14, 8.88, 12.54, 15.68, 16.36, 18.76, 19.34, 20.08, 22.36, 24.66, 25.74, 26.70 and 28.02 in a powder X-ray diffraction diagram obtained by irradiation with copper Kα radiation (wavelength λ=1.54 Å).

16. A crystalline form of the N-{4-[2-amino-5-(3,4-dimethoxyphenyl)pyridin-3-yl]phenyl}-5-(4-fluorophenyl)-4-oxo-1-(2,2,2-trifluoroethyl)-1,4-dihydropyridine-3-carboxamide hydrochloride of claim 8, which has characteristic peaks at diffraction angles 2θ of 5.78, 8.90, 13.66, 14.42, 16.84, 17.56, 19.26, 20.74, 22.42, 24.66, 25.12, 25.60 and 26.96 in a powder X-ray diffraction diagram obtained by irradiation with copper Kα radiation (wavelength λ=1.54 Å).

17. A crystalline form of the N-{4-[2-amino-5-(3,4-dimethoxyphenyl)pyridin-3-yl]phenyl}-5-(4-fluorophenyl)-4-oxo-1-(2,2,2-trifluoroethyl)-1,4-dihydropyridine-3-carboxamide hydrochloride of claim 8, which has characteristic peaks at diffraction angles 2θ of 11.12, 14.82, 18.86, 20.32, 20.66, 21.64, 22.36, 22.68, 23.00, 24.10, 25.26 and 27.00 in a powder X-ray diffraction diagram obtained by irradiation with copper Kα radiation (wavelength λ=1.54 Å).

18. A crystalline form of the N-{4-[2-amino-5-(3,4-dimethoxyphenyl)pyridin-3-yl]phenyl}-5-(4-fluorophenyl)-4-oxo-1-(2,2,2-trifluoroethyl)-1,4-dihydropyridine-3-carboxamide hydrochloride of claim 8, which has characteristic peaks at diffraction angles 2θ of 7.80, 12.18, 12.78, 16.20, 16.82, 19.20, 19.66, 20.20, 21.20, 24.52, 25.68 and 26.78 in a powder X-ray diffraction diagram obtained by irradiation with copper Kα radiation (wavelength λ=1.54 Å).

19. A crystalline form of the N-{4-[2-amino-5-(3,4-dimethoxyphenyl)pyridin-3-yl]phenyl}-5-(4-fluorophenyl)-4-oxo-1-(2,2,2-trifluoroethyl)-1,4-dihydropyridine-3-carboxamide hydrochloride of claim 8, which has characteristic peaks at diffraction angles 2θ of 2.80, 6.86, 7.88, 11.60, 13.68, 14.86, 17.40, 22.40, 23.78 and 25.74 in a powder X-ray diffraction diagram obtained by irradiation with copper Kα radiation (wavelength λ=1.54 Å).

20. A crystalline form of the N-{4-[2-amino-5-(3,4-dimethoxyphenyl)pyridin-3-yl]phenyl}-5-(4-fluorophenyl)-4-oxo-1-(2,2,2-trifluoroethyl)-1,4-dihydropyridine-3-carboxamide hydrochloride of claim 8, which has characteristic peaks at diffraction angles 2θ of 5.32, 7.98, 10.68, 11.70, 14.84, 16.02, 19.78, 21.76, 23.08, 25.30 and 25.68 in a powder X-ray diffraction diagram obtained by irradiation with copper Kα radiation (wavelength λ=1.54 Å).

21. A crystalline form of the N-{4-[2-amino-5-(3,4-dimethoxyphenyl)pyridin-3-yl]phenyl}-5-(4-fluorophenyl)-4-oxo-1-(2,2,2-trifluoroethyl)-1,4-dihydropyridine-3-carboxamide hydrochloride of claim 8, which has characteristic peaks at diffraction angles 2θ of 8.10, 10.60, 12.06, 14.16, 14.58, 15.60, 18.16, 20.72, 20.94, 22.86, 23.90, 24.32 and 27.14 in a powder X-ray diffraction diagram obtained by irradiation with copper Kα radiation (wavelength λ=1.54 Å).

22. A crystalline form of the N-{4-[2-amino-5-(3,4-dimethoxyphenyl)pyridin-3-yl]phenyl}-5-(4-fluorophenyl)-4-oxo-1-(2,2,2-trifluoroethyl)-1,4-dihydropyridine-3-carboxamide hydrochloride of claim 8, which has characteristic peaks at diffraction angles 2θ of 3.60, 6.22, 9.56, 10.42, 14.04, 14.66, 15.30, 16.40, 19.52, 22.12 and 26.42 in a powder X-ray diffraction diagram obtained by irradiation with copper Kα radiation (wavelength λ=1.54 Å).

23. A crystalline form of the N-{4-[2-amino-5-(3,4-dimethoxyphenyl)pyridin-3-yl]phenyl}-5-(4-fluorophenyl)-4-oxo-1-(2,2,2-trifluoroethyl)-1,4-dihydropyridine-3-carboxamide hydrochloride of claim 8, which has characteristic peaks at diffraction angles 2θ of 5.46, 7.98, 9.54, 11.00, 14.00, 15.36, 16.56, 22.00, 23.54, 24.00 and 26.56 in a powder X-ray diffraction diagram obtained by irradiation with copper Kα radiation (wavelength λ=1.54 Å).

24. A crystalline form of the N-{4-[2-amino-5-(3,4-dimethoxyphenyl)pyridin-3-yl]phenyl}-5-(4-fluorophenyl)-4-oxo-1-(2,2,2-trifluoroethyl)-1,4-dihydropyridine-3-carboxamide hydrochloride of claim 8, which has characteristic peaks at diffraction angles 2θ of 5.64, 6.92, 8.06, 11.32, 14.40, 16.18, 17.04, 21.84, 22.50, 23.82 and 24.28 in a powder X-ray diffraction diagram obtained by irradiation with copper Kα radiation (wavelength λ=1.54 Å).

25. A pharmaceutical composition comprising the compound of claim 1, or a pharmaceutically acceptable salt thereof, and a pharmaceutically acceptable carrier.

26. A method of treating endometrial hyperplasia, thrombin-induced vascular smooth muscle cell (VSMC) growth, benign tumor, brain cancer, breast cancer, prostate cancer, splenic cancer, ovarian cancer, thymic cancer, gastric cancer, acute myeloid leukemia, glioblastoma, acute and chronic glomerulonephritis, or diabetic nephropathy, comprising administering the compound of claim 1, or a pharmaceutically acceptable salt thereof, to a mammal.

27. A method of treating cancer, comprising administering the compound of claim 1, or a pharmaceutically acceptable salt thereof, to a mammal,
  wherein the cancer is selected from brain cancer, breast cancer, prostate cancer, splenic cancer, ovarian cancer, thymic cancer, gastric cancer, acute myeloid leukemia and glioblastoma.

28. A method of overcoming resistance to imatinib, doxorubicin, VP16, cisplatin, lapatinib, vemurafenib, temozolomode, carboplatin, or vincristine, comprising administering the compound of claim 1, or a pharmaceutically acceptable salt thereof, to a mammal.

* * * * *